US008273755B2

(12) United States Patent
Cheng et al.

(10) Patent No.: US 8,273,755 B2
(45) Date of Patent: Sep. 25, 2012

(54) 4-METHYLPYRIDOPYRIMIDINONE COMPOUNDS

(75) Inventors: Hengmiao Cheng, San Diego, CA (US); Dilip Bhumralkar, Valencia, CA (US); Klaus Ruprecht Dress, San Diego, CA (US); Jacqui Elizabeth Hoffman, San Diego, CA (US); Mary Catherine Johnson, San Diego, CA (US); Robert Steven Kania, San Diego, CA (US); Phuong Thi Quy Le, San Diego, CA (US); Mitchell David Nambu, San Diego, CA (US); Mason Alan Pairish, San Diego, CA (US); Michael Bruno Plewe, San Diego, CA (US); Khanh Tuan Tran, San Diego, CA (US)

(73) Assignee: Pfizer Inc, New York, NY (US)

( * ) Notice: Subject to any disclaimer, the term of this patent is extended or adjusted under 35 U.S.C. 154(b) by 430 days.

(21) Appl. No.: 12/702,937

(22) Filed: Feb. 9, 2010

(65) Prior Publication Data

US 2010/0137279 A1    Jun. 3, 2010

Related U.S. Application Data

(63) Continuation of application No. 11/854,999, filed on Sep. 13, 2007, now Pat. No. 7,696,213.

(60) Provisional application No. 60/845,065, filed on Sep. 15, 2006, provisional application No. 60/947,852, filed on Jul. 3, 2007, provisional application No. 60/952,628, filed on Jul. 30, 2007.

(51) Int. Cl.
*C07D 471/04* (2006.01)
*A61K 31/519* (2006.01)
*A61P 35/00* (2006.01)

(52) U.S. Cl. .................... 514/264.11; 544/279
(58) Field of Classification Search ............. 514/264.11; 544/279
See application file for complete search history.

(56) References Cited

U.S. PATENT DOCUMENTS

| 6,498,163 | B1 | 12/2002 | Boschelli et al. |
| 7,696,213 | B2 | 4/2010 | Cheng et al. |
| 2004/0009993 | A1 | 1/2004 | Angiolini et al. |
| 2004/0122029 | A1 | 6/2004 | Liu et al. |
| 2005/0043309 | A1 | 2/2005 | Clark et al. |
| 2005/0182078 | A1 | 8/2005 | Barvian et al. |
| 2006/0142312 | A1 | 6/2006 | Flamme et al. |
| 2010/0087456 | A1 | 4/2010 | Baik et al. |
| 2010/0209340 | A1 | 8/2010 | Buhr et al. |

FOREIGN PATENT DOCUMENTS

| EP | 1 277 738 | 1/2003 |
| EP | 1 364 950 A1 | 11/2003 |
| JP | 2003-321472 | 11/2003 |
| JP | 2004-83587 | 3/2004 |
| JP | 2004-203751 | 7/2004 |
| WO | WO 96/15128 | 5/1996 |
| WO | WO 96/34867 | 11/1996 |
| WO | WO 98/33789 | 8/1998 |
| WO | WO 98/33798 A2 | 8/1998 |
| WO | WO 00/78299 A2 | 12/2000 |
| WO | WO 01/55148 | 8/2001 |
| WO | WO 01/70741 A1 | 9/2001 |
| WO | WO 02/068419 | 9/2002 |
| WO | WO 03/062236 A1 | 7/2003 |
| WO | WO 03/088972 | 10/2003 |
| WO | WO 03/093290 A2 | 11/2003 |
| WO | WO 2004/063195 A1 | 7/2004 |
| WO | WO 2004/089930 A1 | 10/2004 |
| WO | WO 2005/005426 A1 | 1/2005 |
| WO | WO 2005/009967 | 2/2005 |
| WO | WO 2005/040337 | 5/2005 |
| WO | WO 2005/080393 | 9/2005 |
| WO | WO 2005/082903 A1 | 9/2005 |
| WO | WO 2005/094830 A1 | 10/2005 |
| WO | WO 2005/105097 | 11/2005 |
| WO | WO 2005/105801 | 11/2005 |
| WO | WO 2005/117980 A1 | 12/2005 |
| WO | WO 2006/021547 A1 | 3/2006 |
| WO | WO 2006/050501 A2 | 5/2006 |
| WO | WO 2006/065703 A1 | 6/2006 |
| WO | WO 2007/044698 | 4/2007 |
| WO | WO 2007/044813 | 4/2007 |
| WO | WO 2008/021389 | 2/2008 |

OTHER PUBLICATIONS

Barvian, M., et al., "Pyrido[2,3-d]pyrimidin-7-one Inhibitors of Cyclin-Dependent Kinases," *Journal of Medicinal Chemistry*, Jun. 22, 2000, pp. 4606-4616, vol. 43.

Boschelli, D.H., et al., "Synthesis and Tyrosine Kinase Inhibitory Activity of a Series of 2- amino-8H-pyrido[2,3-d]pyrimidines: Identification of Potent, Selective Platelet-derived Growth Factor Receptor Tyrosine Kinase Inhibitors," *Journal of Medicinal Chemistry*, Jul. 6, 1998, pp. 4365-4377, vol. 41.

Database Registry, CAS registration No. 294874-94-5 (date of publication Oct. 12, 2000), Chemical Abstracts Service, STN North America, Columbus, Ohio, www.cas.org.stn.html.

Database Registry, CAS Registry Nos. 364741-74-2; Database Registry, date of publication STN is Oct. 26, 2001, Chemical Abstracts Service, STN North America, Columbus, Ohio, www.cas.org/stn.html.

(Continued)

*Primary Examiner* — James O Wilson
*Assistant Examiner* — Cecilia M Jaisle
(74) *Attorney, Agent, or Firm* — David Rubin

(57) ABSTRACT

The present invention is directed to novel 4-methylpyridopyrimidinone compounds of Formula (I), (I)

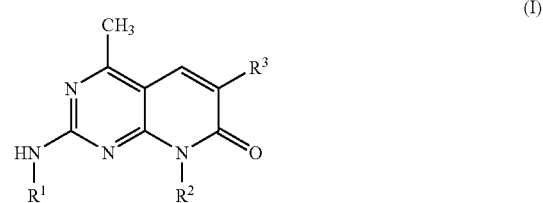

and to salts thereof, their synthesis, and their use as inhibitors of phosphoinositide 3-kinase alpha (PI3-Kα).

15 Claims, 3 Drawing Sheets

OTHER PUBLICATIONS

Database Registry, CAS Registry Nos. 371782-11-5; Database Registry, date of publication STN is Nov. 12, 2001, Chemical Abstracts Service, STN North America, Columbus, Ohio, www.cas.org/stn.html.

Database Registry, CAS registration No. 374910-33-5 (date of publication Dec. 13, 2001), Chemical Abstracts Service, STN North America, Columbus, Ohio, www.cas.org/stn.html.

Database Registry, CAS registration No. 400878-58-2, (date of publication Mar. 14, 2002), Chemical Abstracts Service, STN North America, Columbus, Ohio www.cas.org/stn.html.

Database Registry, CAS registration No. 400881-06-3, (date of publication Mar. 14, 2002), Chemical Abstracts Service, STN North America, Columbus, Ohio, www.cas.org/stn.html.

Database Registry, CAS registration No. 405295-77-4 (date of publication Apr. 16, 2002), Chemical Abstracts Service, STN North America, Columbus, Ohio, www.cas.org/stn.html.

Database Registry, CAS registration No. 443903-90-0 (date of publication Aug. 14, 2002), Chemical Abstracts Service, STN North America, Columbus, Ohio, www.cas.org/stn.html.

Fry, D. W. et al., "Cell Cycle and Biochemical Effects of PD 0183812", *The Journal of Biological Chemistry*, May 18, 2001, pp. 16617-16623, vol. 276, No. 20.

Fry, et al, "Specific Inhibition of Cyclin-dependent Kinase 4/6 by PD 0332991 and Associated Antitumor Activity in Human Tumor Xenografts," *Molecular Cancer Therapeutics*, Nov. 12, 2004 pp. 1427-1438, vol. 3.

Griesser, U.J.,(2006) "The Importance of Solvates" *Polymorphism: In the Pharmaceutical Industry*, pp. 211-233 Chapter 8.

Hamby, J.M., et al., "Structure-Activity Relationships for a Novel Series of Pyrido[2,3-d]pyrimidine Tyrosine Kinase Inhibitors," *Journal of Medicinal Chemistry*, Mar. 6, 1997, pp. 2296-2303, vol. 40.

Klutchko, S.R., et al., "2-Substituted Aminopyrido[2,3-d]pyrimidin-7(8H)-ones. Structure-Activity Relationships Against Selected Tyrosine Kinases and In Vitro and In Vivo Anticancer Activity," *Journal of Medicinal Chemistry*, Apr. 13, 1998, pp. 3276-3292, vol. 41.

Panek, et al., "In Vitro Pharmacological Characterization of PD 166285, a New Nanomolar Potent and Broadly Active Protein Tyrosine Kinase Inhibitor," *Journal of Pharmacology and Experimental Therapeutics*, Aug. 4, 1997, 1423-1444, vol. 283, No. 3.

Toogood, P.L. et al., "Discovery of a Patent and Selective Inhibitor of Cyclin-Dependent Kinase 4/6," *Journal of Medicinal Chemistry*, Aug. 6, 2004, pp. 2388-2406, vol. 28.

Trumpp-Kallmeyer, S., et al., "Development of a Binding Model to Protein Tyrosine Kinases for Substituted Pyrido[2,3-d]pyrimidine Inhibitors," *Journal of Medicinal Chemistry*, Sep. 19, 1997, pp. 1752-1763, vol. 41.

Vanderwel, et al., "Pyrido[2,3-d]Pyrimidin-7-ones as Specific Inhibitors of Cyclin-Dependent Kinase 4," *Journal of Medicinal Chemistry*, Aug. 6, 2004, pp. 2371-2387, vol. 48.

Wikipedia, Acyl, last modified Mar. 11, 2010, http://en.wikipedia.org/wiki/Acyl.

Angiolini, M., et al., "Solid-Phase Synthesis of Pyrido[2,3-d]pyrimidin-7-ones," *Tetrahedron Letters*, 2005, 8749-8752, vol. 46, No. 50.

IPCOM000009511D, "Pyridopyrimidionone Derivatives as Telomerase Inhibitors," The IP.com Journal, 2002, 227, vol. 2, No. 9.

4-METHYLPYRIDOPYRIMIDINONE COMPOUNDS

This application is a continuation of U.S. patent application Ser. No. 11/854,999, filed Sep. 13, 2007, now U.S. Pat. No. 7,696,213, which claims the benefit of U.S. Provisional Application No. 60/845,065 filed Sep. 15, 2006, U.S. Provisional Application No. 60/947,852 filed Jul. 3, 2007, and U.S. Provisional Application No. 60/952,628 filed Jul. 30, 2007, the contents of which are hereby incorporated by reference in their entireties.

FIELD OF THE INVENTION

The present invention is directed to novel 4-methylpyridopyrimidinone compounds, and salts thereof, their synthesis, and their use as modulators or inhibitors of the phosphoinositide 3-kinase alpha (PI3-Kα) enzyme. The compounds of the present invention are useful for modulating (e.g. inhibiting) PI3-Kα activity and for treating diseases or conditions mediated by PI3-Kα, such as for example, disease states associated with abnormal cell growth such as cancer.

BACKGROUND

Phosphoinositide 3-kinases (PI3-Ks) catalyze the synthesis of the phosphatidylinositol (PI) second messengers PI(3)P, PI(3,4)P$_2$, and PI(3,4,5)P$_3$ (PIP$_3$). (Fruman et al., Phosphoinositide kinases, *Annu. Rev. Biochem.* 67 (1998), pp. 481~507; Knight et al., A Pharmacological Map of the PI3-K Family Defines a Role for p110α in Insulin Signaling, *Cell* 125 (2006), pp. 733-747.) In the appropriate cellular context, these three lipids control diverse physiological processes including cell growth, survival, differentiation, and chemotaxis. (Katso et al., Cellular function of phosphoinositide 3-kinases: implications for development, homeostasis, and cancer, *Annu. Rev. Cell Dev. Biol.* 17 (2001), pp. 615-675.) The PI3-K family comprises at least 15 different enzymes, sub-classified by structural homology, with distinct substrate specificities, expression patterns, and modes of regulation. The main PI3-kinase isoform in cancer is the Class I PI3-Kα, consisting of catalytic (p110α) and adapter (p85) subunits. (Stirdivant et al., Cloning and mutagenesis of the p110α subunit of human phosphoinositide 3'-hydroxykinase, *Bioorg. Med. Chem.* 5 (1997), pp. 65-74.)

The 3-phosphorylated phospholipids (PIP$_3$s) generated by PI3-Ks act as second messengers recruiting kinases with lipid binding domains (including plekstrin homology (PH) regions), such as Akt and phosphoinositide-dependent kinase-1 (PDK1). (Vivanco & Sawyers, The Phosphatidylinositol 3-Kinase-Akt Pathway In Human Cancer, *Nature Reviews Cancer* 2 (2002), pp. 489-501.) Binding of Akt to membrane PIP$_3$s causes the translocation of Akt to the plasma membrane, bringing Akt into contact with PDK1, which is responsible for activating Akt. The tumour-suppressor phosphatase, PTEN, dephosphorylates PIP$_3$ and therefore acts as a negative regulator of Akt activation. The PI3-Ks, Akt and PDK1 are important in the regulation of many cellular processes including cell cycle regulation, proliferation, survival, apoptosis and motility and are significant components of the molecular mechanisms of diseases such as cancer, diabetes and immune inflammation. Several components of the PI3-K/Akt/PTEN pathway are implicated in oncogenesis. In addition to growth factor receptor tyrosine kinases, integrin-dependent cell adhesion and G-protein coupled receptors activate PI3-K both directly and indirectly through adaptor molecules. Functional loss of PTEN (the most commonly mutated tumour-suppressor gene in cancer after p53), oncogenic mutations in the PIK3CA gene encoding PI3-Kα, amplification of the PIK3CA gene and overexpression of Akt have been established in many malignancies. (see, for example, Samuels, et al., High frequency of mutations of the PIK3CA gene in human cancers, *Science* 304 (2004), p. 554; Broderick et al., Mutations in PIK3CA in anaplastic oligodendrogliomas, high-grade astrocytomas, and medulloblastomas, *Cancer Research* 64 (2004), pp. 5048-5050.)

PI3-Kα is thus an attractive target for cancer drug development since such agents would be expected to inhibit proliferation and surmount resistance to cytotoxic agents in cancer cells. There is a need to provide new PI3-Kα inhibitors that are good drug candidates. They should be bioavailable, be metabolically stable and possess favorable pharmacokinetic properties.

SUMMARY

In one embodiment of the present invention is a compound of Formula (I)

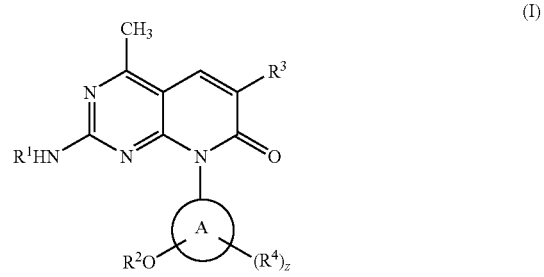

(I)

or a salt thereof,
wherein:
$R^1$ is H or ($C_1$ to $C_6$) alkyl optionally substituted with at least one $R^5$ group;
A is a 3 to 10 membered cycloalkyl group;
$R^2$ is ($C_1$ to $C_6$) alkyl substituted with at least one $R^6$ group, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —NR$^{7a}$R$^{7b}$, or —N=CR$^{8a}$R$^{8b}$ wherein each of the said ($C_3$ to $C_{10}$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^9$ group;
$R^3$ is ($C_1$ to $C_6$) alkyl, ($C_3$ to $C_{10}$) cycloalkyl, ($C_2$ to $C_9$) cycloheteroalkyl, ($C_2$ to $C_8$) alkenyl, ($C_2$ to $C_8$) alkynyl, halogen, cyano, —(CH$_2$)$_n$C(O)OR$^{10}$, —(CH$_2$)$_n$C(O)N(R$^{11a}$R$^{11b}$), COR$^{12}$, ($C_6$ to $C_{14}$) aryl, or ($C_2$ to $C_9$) heteroaryl, wherein said ($C_1$ to $C_6$) alkyl, ($C_3$ to $C_{10}$) cycloalkyl, ($C_2$ to $C_9$) cycloheteroalkyl, ($C_2$ to $C_8$) alkenyl, ($C_2$ to $C_8$) alkynyl, ($C_6$ to $C_{14}$) aryl and ($C_2$ to $C_9$) heteroaryl is optionally substituted with at least one $R^9$ group;
each $R^4$ is independently —OH, halogen, CF$_3$, —NR$^{11a}$R$^{11b}$($C_1$ to $C_6$) alkyl, ($C_1$ to $C_6$) alkenyl, ($C_1$ to $C_6$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —C(O)R$^{12}$—C(O)NR$^{11a}$R$^{11b}$, —S(O)$_m$R$^{12}$, —S(O)$_m$NR$^{11a}$R$^{11b}$, —NR$^{11a}$S(O)$_m$R$^{12}$—(CH$_2$)$_n$C(O)OR$^{10}$, —(CH$_2$)$_n$C(O)N(R$^{11a}$R$^{11b}$), —OC(O)R$^{12}$, —NR$^{11a}$C(O)R$^{12}$ or —NR$^{11a}$C(O)N(R$^{11a}$R$^{11b}$) wherein each of the said ($C_1$ to $C_6$) alkyl, ($C_1$ to $C_6$) alkenyl, ($C_1$ to $C_6$) alkynyl, ($C_1$ to $C_6$) alkoxy, ($C_3$ to $C_{10}$) cycloalkyl, ($C_2$ to $C_9$) cycloheteroalkyl, ($C_6$ to $C_{12}$) aryl, and ($C_2$ to $C_9$) heteroaryl is optionally substituted with at least one $R^{13}$ group;

each $R^5$ is independently —OH, halogen, $CF_3$, —$NR^{11a}R^{11b}$, ($C_1$ to $C_6$) alkyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —S(O)$_m$R$^{12}$, —S(O)$_m$NR$^{11a}$R$^{11b}$, —C(O)R$^{12}$ or —C(O)NR$^{11a}$R$^{11b}$ wherein each of the said ($C_1$ to $C_6$) alkyl, ($C_1$ to $C_6$) alkoxy, ($C_3$ to $C_{10}$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^9$ group;

each $R^6$ is independently —OH, ($C_1$ to $C_6$) alkynyl, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —C(O)R$^{12}$—C(O)NR$^{11a}$R$^{11b}$, —S(O)$_m$R$^{12}$, —S(O)$_m$NR$^{11a}$R$^{11b}$, —NR$^{11a}$S(O)$_m$R$^{12}$—(CH$_2$)$_n$C(O)OR$^{10}$, —(CH$_2$)$_n$C(O)N(R$^{11a}$R$^{11b}$), —OC(O)R$^{12}$, —NR$^{11a}$C(O)R$^{12}$ or —NR$^{11a}$C(O)N(R$^{11a}$R$^{11b}$) wherein each of the said ($C_1$ to $C_6$) alkynyl, ($C_3$ to $C_{10}$) cycloalkyl, ($C_2$ to $C_9$) cycloheteroalkyl, ($C_6$ to $C_{12}$) aryl, and ($C_2$ to $C_9$) heteroaryl is optionally substituted with at least one $R^{13}$ group;

$R^{7a}$ and $R^{7b}$ are each independently H, ($C_1$ to $C_6$) alkyl, ($C_2$ to $C_6$)alkenyl, ($C_2$ to $C_6$)alkynyl, ($C_3$ to $C_{10}$) cycloalkyl, or ($C_6$ to $C_{10}$)aryl, wherein each of the said ($C_1$ to $C_6$) alkyl, ($C_2$ to $C_6$)alkenyl, ($C_2$ to $C_6$)alkynyl, ($C_3$ to $C_{10}$) cycloalkyl, and ($C_6$ to $C_{10}$)aryl is optionally substituted with at least one $R^9$ group; or $R^{7a}$ and $R^{7b}$ may be taken together with the nitrogen atom to form a 5 to 8 membered heterocyclyl ring, wherein said heterocyclyl ring has 1 to 3 ring heteroatoms selected from the group consisting of N, O, and S and wherein the said 5 to 8 membered cycloheteroalkyl ring is optionally substituted with at least one $R^9$ group;

$R^{8a}$ and $R^{8b}$ are each independently H, ($C_1$ to $C_6$) alkyl, or ($C_3$ to $C_{10}$) cycloalkyl wherein each of the said ($C_1$ to $C_6$) alkyl, and ($C_3$ to $C_{10}$) cycloalkyl, is optionally substituted with at least one $R^9$ group;

each $R^9$ is independently —OH, halogen, $CF_3$, —NR$^{11a}$R$^{11b}$, ($C_1$ to $C_6$) alkyl, ($C_1$ to $C_6$) alkenyl, ($C_1$ to $C_6$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —C(O)R$^{12}$—C(O)NR$^{11a}$R$^{11b}$, —S(O)$_m$R$^{12}$, —S(O)$_m$NR$^{11a}$R$^{11b}$, —NR$^{11a}$S(O)$_m$R$^{12}$—(CH$_2$)$_n$C(O)OR$^{10}$, —(CH$_2$)$_n$C(O)N(R$^{11a}$R$^{11b}$), —OC(O)R$^{12}$, —NR$^{11a}$C(O)R$^{12}$ or —NR$^{11a}$C(O)N(R$^{11a}$R$^{11b}$) wherein each of the said ($C_1$ to $C_6$) alkyl, ($C_1$ to $C_6$) alkenyl, ($C_1$ to $C_6$) alkynyl, ($C_1$ to $C_6$) alkoxy, ($C_3$ to $C_{10}$) cycloalkyl, ($C_2$ to $C_9$) cycloheteroalkyl, ($C_6$ to $C_{12}$) aryl, and ($C_2$ to $C_9$) heteroaryl is optionally substituted with at least one $R^{13}$ group;

each $R^{10}$ is independently H, or ($C_1$ to $C_6$) alkyl;

$R^{11a}$ and $R^{11b}$ are each independently H, ($C_1$ to $C_6$) alkyl, ($C_2$ to $C_9$) cycloheteroalkyl, ($C_2$ to $C_9$) heteroaryl, or ($C_6$ to $C_{12}$) aryl wherein each of the said ($C_1$ to $C_6$) alkyl, ($C_2$ to $C_9$) cycloheteroalkyl, ($C_2$ to $C_9$) heteroaryl, and ($C_6$ to $C_{12}$) aryl is optionally substituted with at least one $R^{13}$ group;

each of the $R^{12}$ is independently ($C_1$ to $C_6$) alkyl, ($C_3$ to $C_{10}$) cycloalkyl, ($C_2$ to $C_9$) cycloheteroalkyl, ($C_2$ to $C_9$) heteroaryl, or ($C_6$ to $C_{14}$) aryl wherein each of the said ($C_1$ to $C_6$) alkyl, ($C_3$ to $C_{10}$) cycloalkyl, ($C_2$ to $C_9$) cycloheteroalkyl, ($C_2$ to $C_9$) heteroaryl, and ($C_6$ to $C_{14}$) aryl is optionally substituted with at least one $R^{13}$ group;

each of the $R^{13}$ is independently —OH, halogen, $CF_3$, ($C_1$ to $C_6$) alkyl, ($C_1$ to $C_6$) alkenyl, ($C_1$ to $C_6$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, amino, carbonyl, C-amido, sulfinyl, S-sulfonamido, C-carboxyl, N-amido, or N-carbamyl;

each m is independently 1 or 2;

each n is independently 0, 1, 2, 3, or 4; and each z is an integer independently selected from 0, 1, 2, 3, 4, 5, 6, 7, or 8.

One aspect of this embodiment is a compound according to Formula (I), as described above, wherein A is selected from the group consisting of cyclobutyl, cyclopentyl, and cyclohexyl.

A further aspect of this embodiment is a compound according to Formula (I), as described above, wherein $R^3$ is ($C_6$ to $C_{14}$) aryl or ($C_2$ to $C_9$) heteroaryl, wherein said ($C_6$ to $C_{14}$) aryl or ($C_2$ to $C_9$) heteroaryl is optionally substituted with at least one $R^9$ group.

A further aspect of this embodiment is a compound according to Formula (I), as described above, which is selected from the group consisting of: 2-amino-6-(5-fluoro-6-methoxypyridin-3-yl)-8-[trans-4-(2-hydroxyethoxy)cyclohexyl]-4-methylpyrido[2,3-d]pyrimidin-7(8H)-one; 2-amino-8-[trans-4-(2-hydroxyethoxy)cyclohexyl]-6-(6-methoxypyridin-3-yl)-4-methylpyrido[2,3-d]pyrimidin-7(8H)-one; 2-amino-8-[trans-4-(2-hydroxyethoxy)cyclohexyl]-4-methyl-6-quinolin-3-ylpyrido[2,3-d]pyrimidin-7(8H)-one; 2-amino-8-[trans-4-(2-hydroxyethoxy)cyclohexyl]-6-(2-methoxypyrimidin-5-yl)-4-methyl pyrido[2,3-d]pyrimidin-7(8H)-one; 2-amino-8-[trans-4-(2-hydroxyethoxy)cyclohexyl]-4-methyl-6-(1H-pyrazol-4-yl)pyrido[2,3-d]pyrimidin-7(8H)-one; 2-amino-6-bromo-8-[trans-4-(2-hydroxyethoxy)cyclohexyl]-4-methylpyrido[2,3-d]pyrimidin-7(8H)-one; 2-amino-8-[cis-4-(2-hydroxyethoxy)cyclohexyl]-4-methyl-6-(1H-pyrazol-4-yl)pyrido[2,3-d]pyrimidin-7(8H)-one; 2-amino-8-(trans-4-{[(2S)-2,3-dihydroxypropyl]oxy}cyclohexyl)-6-(6-methoxypyridin-3-yl)-4-methyl pyrido[2,3-d]pyrimidin-7(8H)-one; 2-amino-8-[cis-4-(2-hydroxyethoxy)cyclohexyl]-4-methyl-6-quinolin-3-ylpyrido[2,3-d]pyrimidin-7(8H)-one; 2-amino-6-(5-fluoro-6-methoxypyridin-3-yl)-8-[cis-4-(2-hydroxyethoxy)cyclohexyl]-4-methylpyrido[2,3-d]pyrimidin-7(8H)-one; 2-amino-8-[cis-4-(2-hydroxyethoxy)cyclohexyl]-6-(2-methoxypyrimidin-5-yl)-4-methylpyrido[2,3-d]pyrimidin-7(8H)-one; 2-amino-8-[cis-4-(2-hydroxyethoxy)cyclohexyl]-6-(6-methoxypyridin-3-yl)-4-methylpyrido[2,3-d]pyrimidin-7(8H)-one; 2-amino-6-bromo-8-[cis-4-(2-hydroxyethoxy)cyclohexyl]-4-methylpyrido[2,3-d]pyrimidin-7(8H)-one; 2-amino-6-[6-(dimethylamino)pyridin-3-yl]-8-[trans-4-(2-hydroxyethoxy)cyclohexyl]-4-methyl pyrido[2,3-d]pyrimidin-7(8H)-one; 2-({trans-4-[2-amino-6-(5-fluoro-6-methoxypyridin-3-yl)-4-methyl-7-oxopyrido[2,3-d]pyrimidin-8(7H)-yl]cyclohexyl}oxy)acetamide; methyl ({trans-4-[2-amino-6-(5-fluoro-6-methoxypyridin-3-yl)-4-methyl-7-oxopyrido[2,3-d]pyrimidin-8(7H)-yl]cyclohexyl}oxy)acetate; 2-amino-8-[trans-4-(2-hydroxyethoxy)cyclohexyl]-4-methyl-6-(1H-pyrazol-3-yl)pyrido[2,3-d]pyrimidin-7(8H)-one, 2-amino-8-[trans-4-(2-hydroxyethoxy)cyclohexyl]-4-methyl-6-(1-methyl-1H-pyrazol-4-yl)pyrido[2,3-d]pyrimidin-7(8H)-one, 2-({cis-4-[2-amino-6-(6-methoxypyridin-3-yl)-4-methyl-7-oxopyrido[2,3-d]pyrimidin-8(7H)-yl]cyclohexyl}oxy)acetamide, 2-({cis-4-[2-amino-6-(5-fluoro-6-methoxypyridin-3-yl)-4-methyl-7-oxopyrido[2,3-d]pyrimidin-8(7H)-yl]cyclohexyl}oxy)acetamide, 2-({cis-4-[2-amino-4-methyl-7-oxo-6-(1H-pyrazol-4-yl)pyrido[2,3-d]pyrimidin-8(7H)-yl]cyclohexyl}oxy)acetamide, 2-({cis-4-[2-amino-4-methyl-6-(1-methyl-1H-pyrazol-4-yl)-7-oxopyrido[2,3-d]pyrimidin-8(7H)-yl]cyclohexyl}oxy)acetamide, 2-({cis-4-[2-amino-6-(2-methoxypyrimidin-5-yl)-4-methyl-7-oxopyrido[2,3-d]pyrimidin-8(7H)-yl]cyclohexyl}oxy)acetamide, 2-{[cis-4-(2-amino-4-methyl-7-oxo-6-quinolin-3-ylpyrido[2,3-d]pyrimidin-8(7H)-yl]cyclohexyl]oxy}acetamide, 2-({trans-4-[2-amino-6-(6-methoxypyridin-3-yl)-4-methyl-7-oxopyrido[2,3-d]pyrimidin-8(7H)-yl]cyclohexyl}oxy)acetamide, 2-{[trans-4-(2-amino-4-methyl-7-oxo-6-quinolin-3-yl pyrido[2,3-d]pyrimidin-8(7H)-yl)cyclohexyl]oxy}acetamide, 2-({trans-4-[2-amino-6-(2-methoxypyrimidin-5-yl)-4-methyl-7-oxopyrido[2,3-d]pyrimidin-8(7H)-yl]cyclohexyl}oxy)acetamide, 2-({trans-4-[2-amino-4-methyl- 7-oxo-6-(1H-pyrazol-4-yl)pyrido[2,3-d]pyrimidin-8(7H)-yl]cyclohexyl}oxy)acetamide, 2-({trans-4-[2-amino-4-methyl-6-(1-methyl-1H-pyrazol-4-yl)-7-oxopyrido[2,3-d]pyrimidin-8(7H)-yl]cyclohexyl}oxy)acetamide, 2-amino-8-[trans-3-(2-hydroxyethoxy)cyclobutyl]-6-(6-methoxypyridin-3-yl)-4-methylpyrido[2,3-d]pyrimidin-7(8H)-one, 2-amino-6-(5-fluoro-6-methoxypyridin-3-yl)-8-[trans-3-(2-hydroxyethoxy)cyclobutyl]-4-methylpyrido[2,3-d]pyrimidin-7(8H)-one, 2-amino-8-[trans-3-(2-hydroxyethoxy)cyclobutyl]-6-(2-methoxypyrimidin-5-yl)-4-methylpyrido[2,3-d]pyrimidin-7(8H)-one, 2-({trans-3-[2-amino-6-(6-methoxypyridin-3-yl)-4-methyl-7-oxopyrido[2,3-d]pyrimidin-8(7H)-yl]cyclobutyl}oxy)acetamide, 2-({trans-3-[2-amino-6-(5-fluoro-6-methoxypyridin-3-yl)-4-methyl-7-oxopyrido[2,3-d]pyrimidin-8(7H)-yl]cyclobutyl}oxy)acetamide, 2-({trans-3-[2-amino-6-(2-methoxypyrimidin-5-yl)-4-methyl-7-oxopyrido[2,3-d]pyrimidin-8(7H)-yl]cyclobutyl}oxy)acetamide, or the salt thereof.

A further aspect of the present invention is a compound of Formula (II)

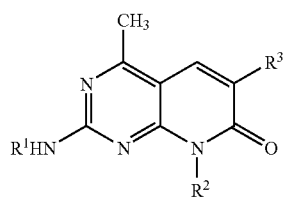

(II)

or a salt thereof,
wherein:
R$^1$ is H or (C$_1$ to C$_6$) alkyl optionally substituted with at least one R$^4$ group;
R$^2$ is (C$_1$ to C$_6$) alkyl, (C$_2$ to C$_8$) alkenyl, (C$_3$ to C$_{10}$) cycloalkyl, (C$_5$ to C$_8$) cycloalkenyl, (C$_2$ to C$_9$) cycloheteroalkyl, or —(CH$_2$)$_n$(C$_6$ to C$_{14}$) aryl, wherein said (C$_1$ to C$_6$) alkyl, (C$_2$ to C$_8$) alkenyl, (C$_3$ to C$_{10}$) cycloalkyl, (C$_5$ to C$_8$) cycloalkenyl, (C$_2$ to C$_9$) cycloheteroalkyl, and —(CH$_2$)$_n$(C$_6$ to C$_{14}$) aryl is optionally substituted with at least one R$^4$ group;
R$^3$ is (C$_1$ to C$_6$) alkyl, (C$_2$ to C$_8$) alkenyl, cyano, —(CH$_2$)$_n$C(O)OR$^{5a}$ or —(CH$_2$)$_n$C(O)N(R$^{5a}$R$^{5b}$), wherein said (C$_1$ to C$_6$) alkyl or (C$_2$ to C$_8$) alkenyl is optionally substituted with at least one R$^4$ group;
each R$^4$ is independently —OH, halogen, CF$_3$, —NR$^{5a}$R$^{5b}$, (C$_1$ to C$_6$) alkyl, (C$_1$ to C$_6$) alkoxy, cyano, (C$_3$ to C$_{10}$) cycloalkyl, —S(O)$_m$R$^{5a}$, —S(O)$_m$NR$^{5a}$R$^{5b}$, —C(O)R$^{5a}$ or —C(O)NR$^{5a}$R$^{5b}$;
R$^{5a}$ and R$^{5b}$ are each independently H, (C$_1$ to C$_6$) alkyl, (C$_2$ to C$_9$) cycloheteroalkyl, (C$_2$ to C$_9$) heteroaryl, or (C$_6$ to C$_{14}$) aryl;
each m is independently 1 or 2; and
each n is independently 0, 1, 2, 3, or 4.

A further aspect of this embodiment is a compound of Formula (II), wherein R$^3$ is —(CH$_2$)$_n$C(O)N(R$^{5a}$R$^{5b}$).

A further aspect of this embodiment is a compound of Formula (II), wherein R$^2$ is selected from the group consisting of isopropyl, allyl, cyclopentyl, cyclobutyl, hydroxycyclohexyl, hydroxycyclopentyl, hydroxycyclobutyl, hydroxycycloheptyl, methoxyethyl, methoxypropyl, ethyl, methyl, cyclopropyl, cyclopropylmethyl, cyclopropylethyl, 2-methyl-2-hydroxypropyl, 3-methyl-3-hydroxylbutyl, methoxybenzyl, and chlorobenzyl.

A further aspect of the present invention is a compound according to Formula (II), as described above, which is selected from the group consisting of: 2-Amino-8-(trans-4-hydroxycyclohexyl)-4-methyl-7-oxo-N-1H-pyrazol-5-yl-78-dihydropyrido[23-d]pyrimidine-6-carboxamide; 2-amino-N-(1-ethyl-1H-pyrazol-5-yl)-8-(trans-4-hydroxy-cyclohexyl)-4-methyl-7-oxo-7,8-dihydropyrido[23-d]pyrimidine-6-carboxamide; 8-Cyclopentyl-4-methyl-2-methylamino-7-oxo-7,8-dihydro-pyrido[2,3-d]pyrimidine-6-carboxylic acid (1H-pyrazol-3-yl)-amide; 2-amino-8-isopropyl-4-methyl-7-oxo-N-1H-pyrazol-5-yl-7,8-dihydropyrido[2,3-d]pyrimidine-6-carboxamide; 2-amino-N-(1-ethyl-1H-pyrazol-5-yl)-8-isopropyl-4-methyl-7-oxo-7,8-dihydropyrido[2,3-d]pyrimidine-6-carboxamide; 8-cyclopentyl-N-[(1-ethyl-1H-pyrazol-4-yl)methyl]-4-methyl-2-(methylamino)-7-oxo-7,8-dihydropyrido[2,3-d]pyrimidine-6-carboxamide; 8-cyclopentyl-4-methyl-2-(methylamino)-7-oxo-N-pyridin-2-yl-7,8-dihydropyrido[2,3-d]pyrimidine-6-carboxamide; and 8-cyclopentyl-N-isoxazol-3-yl-4-methyl-2-(methylamino)-7-oxo-7,8-dihydropyrido[2,3-d]pyrimidine-6-carboxamide, or the salt thereof.

A further aspect of the present invention is a compound of Formula (III)

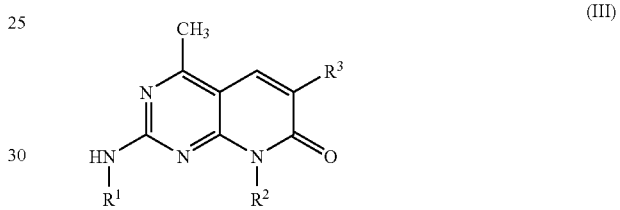

(III)

or a salt thereof,
wherein:
R$^1$ is H or (C$_1$ to C$_6$) alkyl optionally substituted with at least one R$^4$ group;
R$^2$ is a spirocyclyl group optionally substituted with at least one R$^4$ group;
R$^3$ is (C$_1$ to C$_6$) alkyl, (C$_2$ to C$_8$) alkenyl, cyano, —(CH$_2$)$_n$C(O)OR$^5$, —(CH$_2$)$_n$C(O)N(R$^{6a}$R$^{6b}$), (C$_6$ to C$_{14}$) aryl, or (C$_2$ to C$_9$) heteroaryl, wherein said (C$_1$ to C$_6$) alkyl or (C$_2$ to C$_8$) alkenyl is optionally substituted with at least one R$^4$ group, and wherein said (C$_6$ to C$_{14}$) aryl or (C$_2$ to C$_9$) heteroaryl is optionally substituted with at least one R$^7$ group;
each R$^4$ is independently —OH, halogen, CF$_3$, —NR$^{6a}$R$^{6b}$, (C$_1$ to C$_6$) alkyl, (C$_1$ to C$_6$) alkoxy, cyano, (C$_3$ to C$_8$) cycloalkyl, —S(O)$_m$R$^{6a}$, —S(O)$_m$NR$^{6a}$R$^{6b}$, —C(O)R$^{6a}$ or —C(O)NR$^{6a}$R$^{6b}$;
each R$^5$ is independently H, or (C$_1$ to C$_6$) alkyl;
R$^{6a}$ and R$^{6b}$ are each independently H, (C$_1$ to C$_6$) alkyl, (C$_2$ to C$_9$) cycloheteroalkyl, (C$_2$ to C$_9$) heteroaryl, or (C$_6$ to C$_{14}$) aryl;
each of R$^7$ is independently —OH, halogen, —NR$^{6a}$R$^{6b}$, cyano, (C$_1$ to C$_6$) alkyl, (C$_1$ to C$_6$) alkoxy, (C$_3$ to C$_{10}$) cycloalkyl, (C$_2$ to C$_9$) cycloheteroalkyl, —S(O)$_m$R$^{6a}$, —S(O)$_m$NR$^{6a}$R$^{6b}$, —(CH$_2$)$_n$C(O)OR$^5$, —(CH$_2$)$_n$C(O)N(R$^{6a}$R$^{6b}$), —OC(O)R$^{6a}$, or —NR$^{6a}$C(O)R$^{6b}$ wherein each of said (C$_1$ to C$_6$) alkyl, (C$_1$ to C$_6$) alkoxy, (C$_2$ to C$_9$) cycloheteroalkyl, and (C$_3$ to C$_{10}$) cycloalkyl is optionally substituted with at least one R$^4$ group;
each m is independently 1 or 2; and
each n is independently 0, 1, 2, 3, or 4.

A further aspect of the present invention is a compound selected from the group consisting of: 2-amino-8-(trans-4-hydroxycyclohexyl)-6-(6-methoxypyridin-3-yl)-4-methylpyrido[2,3-d]pyrimidin-7(8H)-one; 2-amino-8-(cis-4-hydroxycyclohexyl)-6-(6-methoxypyridin-3-yl)-4-methyl pyrido[2,3-d]pyrimidin-7(8H)-one; 2-amino-6-[6-(dimethylamino)pyridin-3-yl]-8-(trans-4-hydroxycyclohexyl)-4-methylpyrido[2,3-d]pyrimidin-7(8H)-one; 2-amino-8-(trans-4-hydroxycyclohexyl)-4-methyl-6-quinolin-3-yl pyrido[2,3-d]pyrimidin-7(8H)-one; 2-amino-6-(2,3-dihydro-1,4-benzodioxin-6-yl)-8-(trans-4-hydroxycyclohexyl)-4-methyl pyrido[2,3-d]pyrimidin-7(8H)-one; 2-amino-6-(5-fluoro-6-methoxypyridin-3-yl)-8-(trans-4-hydroxycyclohexyl)-4-methylpyrido[2,3-d]pyrimidin-7(8H)-one; 2-amino-8-(trans-4-hydroxycyclohexyl)-4-methyl-6-(6-pyrrolidin-1-yl pyridin-3-yl)pyrido[2,3-d]pyrimidin-7(8H)-one; 2-amino-6-(5-fluoro-6-methoxypyridin-3-yl)-8-(cis-4-hydroxycyclohexyl)-4-methylpyrido[2,3-d]pyrimidin-7(8H)-one; 2-amino-6-(6-ethoxypyridin-3-yl)-8-(trans-4-hydroxycyclohexyl)-4-methyl pyrido[2,3-d]pyrimidin-7(8H)-one; 2-amino-6-[6-(dimethylamino)pyridin-3-yl]-8-(cis-4-hydroxycyclohexyl)-4-methylpyrido[2,3-d]pyrimidin-7(8H)-one; 2-amino-8-(trans-4-methoxycyclohexyl)-4-methyl-6-(1H-pyrazol-4-yl)pyrido[2,3-d]pyrimidin-7(8H)-one; 2-amino-8-(cis-4-hydroxy-4-methylcyclohexyl)-4-methyl-6-(1H-pyrazol-4-yl)pyrido[2,3-d]pyrimidin-7(8H)-one; 2-amino-8-(trans-4-hydroxycyclohexyl)-4-methyl-6-(1H-pyrazol-3-yl)pyrido[2,3-d]pyrimidin-7(8H)-one; 2-amino-8-(cis-4-hydroxycyclohexyl)-6-(2-methoxypyrimidin-5-yl)-4-methylpyrido[2,3-d]pyrimidin-7(8H)-one; 2-amino-8-(trans-4-hydroxycyclohexyl)-6-(2-methoxypyrimidin-5-yl)-4-methylpyrido[2,3-d]pyrimidin-7(8H)-one; 8-(trans-4-hydroxycyclohexyl)-6-(6-methoxypyridin-3-yl)-4-methyl-2-(methylamino)pyrido[2,3-d]pyrimidin-7(8H)-one; 2-(ethylamino)-6-(5-fluoro-6-methoxypyridin-3-yl)-8-(trans-4-hydroxycyclohexyl)-4-methylpyrido[2,3-d]pyrimidin-7(8H)-one; 2-(ethylamino)-8-(trans-4-hydroxycyclohexyl)-6-(2-methoxypyrimidin-5-yl)-4-methylpyrido[2,3-d]pyrimidin-7(8H)-one; 2-amino-8-(trans-4-hydroxycyclohexyl)-4-methyl-6-(1-methyl-1H-pyrazol-4-yl)pyrido[2,3-d]pyrimidin-7(8H)-one; 2-amino-8-(trans-4-hydroxycyclohexyl)-4-methyl-6-(1H-pyrazol-4-yl)pyrido[2,3-d]pyrimidin-7(8H)-one; 2-[(2,2-difluoroethyl)amino]-8-(trans-4-hydroxycyclohexyl)-6-(6-methoxypyridin-3-yl)-4-methylpyrido[2,3-d]pyrimidin-7(8H)-one, or the salt thereof.

In a further embodiment is any of the aspects described above in combination with any of the other aspects described above which is not inconsistent therewith.

The present invention also relates to a pharmaceutical composition, comprising at least one compound as described herein, or a salt thereof, and a pharmaceutically acceptable carrier or diluent.

The present invention also relates to a method of treating abnormal cell growth, or any PI3-Kα-mediated disease or condition, in a mammal in need thereof, comprising the step of administering to said mammal a therapeutically effective amount of at least one compound as described herein, or a salt thereof. For example, in one embodiment the abnormal cell growth is cancerous. In a further embodiment, the abnormal cell growth is non-cancerous.

The present invention further relates to a method of inhibiting PI3-Kα enzymatic activity, comprising contacting a PI3-Kα enzyme with a PI3-Kα-inhibiting amount of at least one compound as described herein, or a salt thereof.

The present invention further relates to the use of any of the compounds as described herein, or a salt thereof, in the manufacture of a medicament for the treatment of abnormal cell growth in a mammal.

The present invention further relates to methods of making the compounds as described herein using the methods as shown in the specific examples herein and in the general synthetic methods A, B, C, D, E, F, H and I as described herein.

The present invention further relates to any of the compounds described above, or salts thereof, for use as a medicament. The present invention further relates to the use of any of the compounds described above, or salts thereof, for the manufacture of a medicament for the treatment of abnormal cell growth.

DETAILED DESCRIPTION

Figure 1:
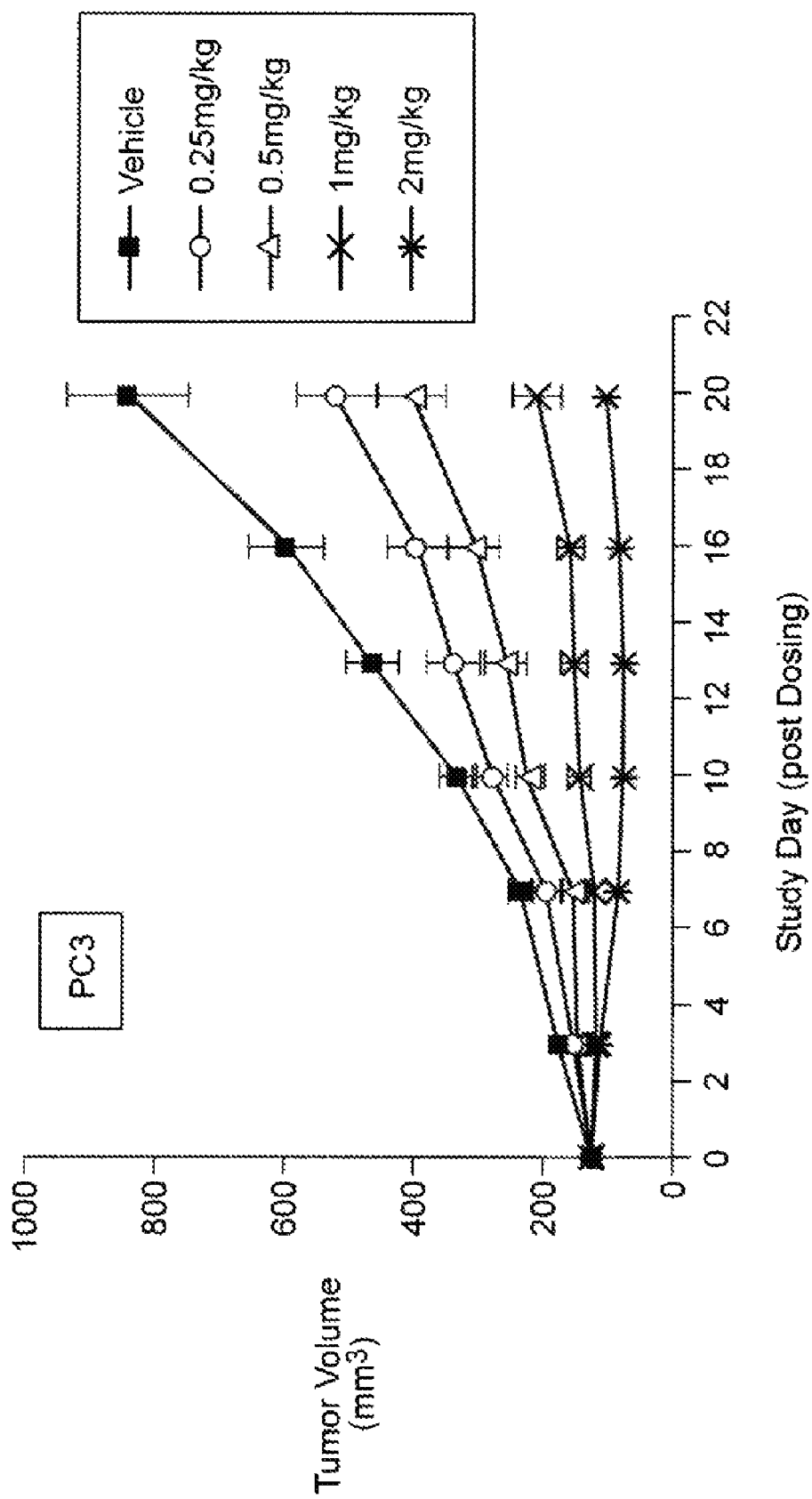
FIG. 1 shows an example of dose-dependent anti-tumor efficacy of 2-amino-8-(trans-4-hydroxycyclohexyl)-6-(6-methoxypyridin-3-yl)-4-methylpyrido[2,3-d]pyrimidin-7(8H)-one (Compound 152) in the PC3 tumor model.

As used herein, the terms "comprising" and "including" are used in their open, non-limiting sense.

The terms "halo" and/or "halogen" refer to fluorine, chlorine, bromine or iodine.

The term "($C_1$ to $C_6$)" alkyl refers to a saturated aliphatic hydrocarbon radical including straight chain and branched chain groups of 1 to 6 carbon atoms. Examples of ($C_1$ to $C_6$) alkyl groups include methyl, ethyl, propyl, 2-propyl, n-butyl, iso-butyl, tert-butyl, pentyl, and the like. The terms "Me" and "methyl," as used herein, mean a —$CH_3$ group. The terms "Et" and "ethyl," as used herein, mean a —$C_2H_5$ group.

The term "($C_2$ to $C_8$) alkenyl", as used herein, means an alkyl moiety comprising 2 to 8 carbons having at least one carbon-carbon double bond. The carbon-carbon double bond in such a group may be anywhere along the 2 to 8 carbon chain that will result in a stable compound. Such groups include both the E and Z isomers of said alkenyl moiety. Examples of such groups include, but are not limited to, ethenyl, propenyl, butenyl, allyl, and pentenyl. The term "allyl," as used herein, means a —$CH_2CH=CH_2$ group. The term, "C(R)=C(R)," as used herein, represents a carbon-carbon double bond in which each carbon is substituted by an R group.

As used herein, the term "($C_2$ to $C_8$) alkynyl" means an alkyl moiety comprising from 2 to 8 carbon atoms and having at least one carbon-carbon triple bond. The carbon-carbon triple bond in such a group may be anywhere along the 2 to 8 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

The term "($C_1$ to $C_8$) alkoxy", as used herein, means an O-alkyl group wherein said alkyl group contains from 1 to 8 carbon atoms and is straight, branched, or cyclic. Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The term "($C_6$ to $C_{14}$) aryl", as used herein, means a group derived from an aromatic hydrocarbon containing from 6 to 14 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

"($C_2$ to $C_9$) heteroaryl", as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The $C_2$ to $C_9$ heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

"($C_2$ to $C_9$) cycloheteroalkyl", as used herein, means a non-aromatic, monocyclic, bicyclic, tricyclic, spirocyclic, or tetracyclic group having a total of from 4 to 13 atoms in its ring system, and containing from 2 to 9 carbon atoms and from 1 to 4 heteroatoms each independently selected from O, S and N, and with the proviso that the ring of said group does not contain two adjacent O atoms or two adjacent S atoms. Furthermore, such $C_2$ to $C_9$ cycloheteroalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a $C_2$ to $C_9$ cycloheteroalkyl group contains a sulfur atom, said sulfur atom may be oxidized with one or two oxygen atoms to afford either a sulfoxide or sulfone. An example of a 4 membered cycloheteroalkyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such $C_2$ to $C_9$ cycloheteroalkyl groups include, but are not limited to, tetrahydrofuranyl, dihydrofuranyl, tetrahydrothienyl, tetrahydropyranyl, dihydropyranyl, tetrahydrothiopyranyl, piperidino, morpholine, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, azabicyclo[4.1.0]heptanyl, 3H-indolyl quinolizinyl, 3-oxopiperazinyl, 4-methylpiperazinyl, 4-ethyl piperazinyl, and 1-oxo-2,8,diazaspiro[4.5]dec-8-yl.

The term "($C_3$ to $C_{10}$) cycloalkyl group" means a saturated, monocyclic, fused, spirocyclic, or polycyclic ring structure having a total of from 3 to 10 carbon ring atoms. Examples of such groups include, but are not limited to, cyclopropyl, cyclobutyl, cyclopentyl, cyclopentenyl, cyclohexyl, cycloheptyl, and adamantyl.

The term "spirocyclic" as used herein has its conventional meaning, that is, any compound containing two or more rings wherein two of the rings have one ring carbon in common. The rings of a spirocyclic compound, as herein defined, independently have 3 to 20 ring atoms. Preferably, they have 3 to 10 ring atoms. Non-limiting examples of a spirocyclic compound include spiro[3.3]heptane, spiro[3.4]octane, and spiro[4.5]decane.

The term "($C_5$ to $C_8$) cycloalkenyl" means an unsaturated, monocyclic, fused, spirocyclic ring structures having a total of from 5 to 8 carbon ring atoms. Examples of such groups include, but not limited to, cyclopentenyl, cyclohexenyl.

The term cyano" refers to a —C≡N group.

An "aldehyde" group refers to a carbonyl group where R is hydrogen.

An "alkoxy" group refers to both an —O-alkyl and an —O-cycloalkyl group, as defined herein.

An "alkoxycarbonyl" refers to a —C(O)OR.

An "alkylaminoalkyl" group refers to an -alkyl-NR-alkyl group.

An "alkylsulfonyl" group refer to a —SO$_2$alkyl.

An "amino" group refers to an —NH$_2$ or an —NRR'group.

An "aminoalkyl" group refers to an -alky-NRR' group.

An "aminocarbonyl" refers to a —C(O)NRR'.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)Oaryl.

An "arylsulfonyl" group refers to a —SO$_2$aryl.

A "C-amido" group refers to a —C(O)NRR' group.

A "carbonyl" group refers to a —C(O)R.

A "C-carboxyl" group refers to a —C(O)OR groups.

A "carboxylic acid" group refers to a C-carboxyl group in which R is hydrogen.

A "cyano" group refers to a —CN group.

A "dialkylamionalkyl" group refers to an -(alkyl)N(alkyl)$_2$ group.

A "halo" or "halogen" group refers to fluorine, chlorine, bromine or iodine.

A "heteroalicycloxy" group refers to a heteroalicyclic-O group with heteroalicyclic as defined herein.

A "heteroaryloxyl" group refers to a heteroaryl-O group with heteroaryl as defined herein.

A "hydroxy" group refers to an —OH group.

An "N-amido" group refers to a —R'C(O)NR group.

An "N-carbamyl" group refers to a —ROC(O)NR-group.

A "nitro" group refers to a —NO$_2$ group.

An "N-Sulfonamido" group refers to a —NR—S(O)$_2$R group.

An "N-thiocarbamyl" group refers to a ROC(S)NR' group.

An "O-carbamyl" group refers to a —OC(O)NRR' group.

An "O-carboxyl" group refers to a RC(O)O group.

An "O-thiocarbamyl" group refers to a —OC(S)NRR' group.

An "oxo" group refers to a carbonyl moiety such that alkyl substituted by oxo refers to a ketone group.

A "perfluoroalkyl group" refers to an alkyl group where all of the hydrogen atoms have been replaced with fluorine atoms.

A "phosphonyl" group refers to a —P(O)(OR)$_2$ group.

A "silyl" group refers to a —Si(R)$_3$ group.

An "S-sulfonamido" group refers to a —S(O)$_2$NR-group.

A "sulfinyl" group refers to a —S(O)R group.

A "sulfonyl" group refers to a —S(O)$_2$R group.

A "thiocarbonyl" group refers to a —C(=S)—R group.

A "trihalomethanecarbonyl" group refers to a Z$_3$CC(O) group, where Z is halogen.

A "trihalomethanesulfonamido" group refers to a Z$_3$CS(O)$_2$NR-group.

A "trihalomethanesulfonyl" group refers to a Z$_3$CS(O)$_2$ group.

A "trihalomethyl" group refers to a —CZ$_3$ group.

A "C-carboxyl" group refers to a —C(O)OR groups.

The term "substituted," means that the specified group or moiety bears one or more substituents. The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

The term "solvate," is used to describe a molecular complex between compounds of the present invention and solvent molecules. Examples of solvates include, but are not limited to, compounds of the invention in combination water, isopropanol, ethanol, methanol, dimethylsulfoxide (DMSO), ethyl acetate, acetic acid, ethanolamine, or mixtures thereof. The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The term "pharmaceutically acceptable formulation," as used herein, means a combination of a compound of the invention, or a salt or solvate thereof, and a carrier, diluent, and/or excipient(s) that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional agents that reduce abnormal cell growth.

The term "PI3-Kα-inhibiting amount" as used herein, refers to the amount of a compound of the present invention, or a salt or solvate thereof, required to inhibit the enzymatic activity of PI3-Kα in vivo, such as in a mammal, or in vitro. The amount of such compounds required to cause such inhibition can be determined without undue experimentation using methods described herein and those known to those of ordinary skill in the art.

The term "inhibiting PI3-Kα enzyme activity," as used herein, means decreasing the activity or functioning of the PI3-Kα enzyme either in vitro or in vivo, such as in a mammal, such as a human, by contacting the enzyme with a compound of the present invention.

The term "PI3-Kα" as used herein means PI3-Kα, or mutants thereof, or any of the known PI3-Kα isoformic splice variants.

The term "therapeutically effective amount," as used herein, means an amount of a compound of the present invention, or a salt thereof, that, when administered to a mammal in need of such treatment, is sufficient to effect treatment, as defined herein. Thus, a therapeutically effective amount of a compound of the present invention, or a salt thereof, is a quantity sufficient to modulate or inhibit the activity of the PI3-Kα enzyme such that a disease condition that is mediated by activity of the PI3-Kα enzyme is reduced or alleviated.

The terms "treat", "treating", and "treatment" with reference to abnormal cell growth, or to any PI3-Kα mediated disease or condition, in a mammal, particularly a human, include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition. With regard to abnormal cell growth, such as cancer, these terms simply mean that the life expectancy of an individual affected with abnormal cell growth will be increased or that one or more of the symptoms of the disease will be reduced.

Unless indicated otherwise, all references herein to the inventive compounds include references to salts, solvates, and complexes thereof, including polymorphs, stereoisomers, tautomers, and isotopically labeled versions thereof. For example, compounds of the present invention can be pharmaceutically acceptable salts and/or pharmaceutically acceptable solvates.

"Abnormal cell growth", as used herein, unless otherwise indicated, refers to cell growth that is independent of normal regulatory mechanisms (e.g., loss of contact inhibition), including the abnormal growth of normal cells and the growth of abnormal cells. This includes, but is not limited to, the abnormal growth of: tumor cells (tumors) that proliferate by expressing a mutated tyrosine kinase or overexpression of a receptor tyrosine kinase; benign and malignant cells of other proliferative diseases in which aberrant tyrosine kinase activation occurs; any tumors that proliferate by receptor tyrosine kinases; any tumors that proliferate by aberrant serine/threonine kinase activation; benign and malignant cells of other proliferative diseases in which aberrant serine/threonine kinase activation occurs; tumors, both benign and malignant, expressing an activated Ras oncogene; tumor cells, both benign and malignant, in which the Ras protein is activated as a result of oncogenic mutation in another gene; benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The terms "abnormal cell growth" and "hyperproliferative disorder" are used interchangeably in this application.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

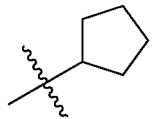

represents a cyclopentyl group, etc.

The compounds of the present invention may have asymmetric carbon atoms. The carbon-carbon bonds of the compounds of the present invention may be depicted herein using a solid line (( —— )), a solid wedge ( ◢ ), or a dotted wedge ( ⋯⋯ⅢⅢ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

If a group, as for example, "R" is depicted as "floating" on a ring system A in the formula:

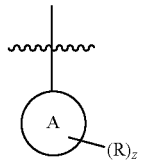

then, unless otherwise defined, a substituent "R" may reside on any atom of the ring system, assuming replacement of a depicted, implied, or expressly defined hydrogen from one of the ring atoms, so long as a stable structure is formed. A ring system A may be, for example, but not limited to aryl, heteroaryl, cycloalkyl, cycloheteroalkyl, spirocyclyl or a fused ring system.

If a group "R" is depicted as "floating" on a ring system A containing saturated carbons, than "z" can be more than one, assuming each replaces a currently depicted, implied, or expressly defined hydrogen the ring A; then, unless otherwise defined, where the resulting structure is stable, two "R's" may reside on the same carbon. For example, when R is a methyl group, there can exist a germinal dimethyl on a carbon of the ring A. In another example, two "R's" on the same carbon, including that carbon, may form a ring, thus creating a spirocyclic ring (a "spirocyclyl group").

Conventional techniques for the preparation/isolation of individual enantiomers include chiral synthesis from a suitable optically pure precursor or resolution of the reacemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E L Eliel (Wiley, New York, 1994), the disclosure of which is incorporated herein by reference in its entirety.

Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. Examples of tautomerism include keto and enol tautomers. A single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof. Cis/trans isomers may be separated by conventional techniques well known to those skilled in the art, for example, chromatography and fractional crystallization.

The compounds of the present invention may be administered as prodrugs. Thus certain derivatives of compounds of Formula (I), which may have little or no pharmacological activity themselves can, when administered to a mammal, be converted into a compound of Formula (I) having the desired activity, for example, by hydrolytic cleavage. Such derivatives are referred to as "prodrugs". Prodrugs can, for example, be produced by replacing appropriate functionalities present in the compound of Formula (I) with certain moieties known to those skilled in the art. See, e.g. "Pro-drugs as Novel Delivery Systems", Vol. 14, ACS Symposium Series (T Higuchi and W Stella) and "Bioreversible Carriers in Drug Design", Pergamon Press, 1987 (ed. E B Roche, American Pharmaceutical Association), the disclosures of which are incorporated herein by reference in their entireties. Some examples of such prodrugs include: an ester moiety in the place of a carboxylic acid functional group; an ether moiety or an amide moiety in place of an alcohol functional group; and an amide moiety in place of a primary or secondary amino functional group. For example, the compound shown as Example 31 below is one example of where the hydrogen in an alcohol moiety is replaced by an amide functional group. Further examples of replacement groups are known to those of skill in the art. See, e.g. "Design of Prodrugs" by H Bundgaard (Elsevier, 1985), the disclosure of which is incorporated herein by reference in its entirety. It is also possible that certain compounds of Formula (I) may themselves act as prodrugs of other compounds of Formula (I).

Salts of the present invention can be prepared according to methods known to those of skill in the art. Examples of salts include, but are not limited to, acetate, acrylate, benzenesulfonate, benzoate (such as chlorobenzoate, methyl benzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenyl butyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

To treat or prevent diseases or conditions mediated by PI3-Kα, a pharmaceutical composition of the invention is administered in a suitable formulation prepared by combining a therapeutically effective amount (i.e., a PI3-Kα modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringers solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal suffering from abnormal cell growth, such as a human, either alone or as part of a pharmaceutically acceptable formulation, once a day, twice a day, three times a day, or four times a day, or even more frequently.

Those of ordinary skill in the art will understand that with respect to the compounds of the present invention, the particular pharmaceutical formulation, the dosage, and the number of doses given per day to a mammal requiring such treatment, are all choices within the knowledge of one of ordinary skill in the art and can be determined without undue experimentation.

The compounds of the present invention are useful for modulating or inhibiting PI3-Kα activity. Accordingly, these compounds are useful for the prevention and/or treatment of disease states associated with abnormal cell growth such as cancer, alone or in combination with other anti-cancer agents.

This invention also relates to a method for the treatment of abnormal cell growth in a mammal, including a human, comprising administering to said mammal an amount of a compound of the Formula (I), as defined above, or a salt or solvate thereof, that is effective in treating abnormal cell growth.

In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In one embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkins's lymphoma, spinal axis tumors, or a combination of one or more of the foregoing cancers.

In another embodiment of the present invention the cancer is selected from lung cancer (NSCLC and SCLC), ovarian cancer, colon cancer, rectal cancer, cancer of the anal region, or a combination of one or more of the foregoing cancers.

In another embodiment of the present invention the cancer is selected from lung cancer (NSCLC and SCLC), ovarian cancer, colon cancer, rectal cancer, or a combination of one or more of the foregoing cancers.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a compound of the present invention, or a salt or solvate thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

In one embodiment of the present invention the anti-tumor agent used in conjunction with a compound of the present invention and pharmaceutical compositions described herein is an anti-angiogenesis agent, kinase inhibitor, pan kinase inhibitor or growth factor inhibitor. Preferred pan kinase inhibitors include Sutent™ (sunitinib), described in U.S. Pat. No. 6,573,293 (Pfizer, Inc, NY, USA). Anti-angiogenesis agents, include but are not limited to the following agents, such as EGF inhibitors, EGFR inhibitors, VEGF inhibitors, VEGFR inhibitors, TIE2 inhibitors, IGF1R inhibitors, COX-II (cyclooxygenase II) inhibitors, MMP-2 (matrix-metalloprotienase 2) inhibitors, and MMP-9 (matrix-metalloprotienase 9) inhibitors.

Preferred VEGF inhibitors, include for example, Avastin (bevacizumab), an anti-VEGF monoclonal antibody of Genentech, Inc. of South San Francisco, Calif. Additional VEGF inhibitors include CP-547,632 (Pfizer Inc., NY, USA), AG13736 (Pfizer Inc.), ZD-6474 (AstraZeneca), AEE788 (Novartis), AZD-2171, VEGF Trap (Regeneron/Aventis), Vatalanib (also known as PTK-787, ZK-222584: Novartis & Schering AG), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof.

VEGF inhibitors useful in the practice of the present invention are described in U.S. Pat. Nos. 6,534,524 and 6,235,764, both of which are incorporated in their entirety for all purposes. Additional VEGF inhibitors are described in, for example in WO 99/24440, in WO 95/21613, WO 99/61422, U.S. Pat. No. 5,834,504, WO 98/50356, U.S. Pat. No. 5,883, 113 U.S. Pat. No. 5,886,020, U.S. Pat. No. 5,792,783, U.S. Pat. No. 6,653,308, WO 99/10349, WO 97/32856, WO 97/22596, WO 98/54093, WO 98/02438, WO 99/16755, and WO 98/02437, all of which are herein incorporated by reference in their entirety.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain, Vitaxin and combinations thereof.

Other antiproliferative agents that may be used in combination with the compounds of the present invention include inhibitors of the enzyme farnesyl protein transferase and inhibitors of the receptor tyrosine kinase PDGFr, including the compounds disclosed and claimed in the following: U.S. Pat. No. 6,080,769; U.S. Pat. No. 6,194,438; U.S. Pat. No. 6,258,824; U.S. Pat. No. 6,586,447; U.S. Pat. No. 6,071,935; U.S. Pat. No. 6,495,564; and U.S. Pat. No. 6,150,377; U.S. Pat. No. 6,596,735; U.S. Pat. No. 6,479,513; WO 01/40217; U.S. 2003-0166675. Each of the foregoing patents and patent applications is herein incorporated by reference in their entirety.

PDGRr inhibitors include but are not limited to those disclosed in international patent application publication numbers WO01/40217 and WO2004/020431, the contents of which are incorporated in their entirety for all purposes. Preferred PDGFr inhibitors include Pfizer's CP-673,451 and CP-868,596 and its salts.

Preferred GARF inhibitors include Pfizer's AG-2037 (pelitrexol and its salts). GARF inhibitors useful in the practice of the present invention are disclosed in U.S. Pat. No. 5,608,082 which is incorporated in its entirety for all purposes.

Examples of useful COX-II inhibitors which can be used in conjunction with a compound of Formula (I) and pharmaceutical compositions disclosed herein include CELEBREX™ (celecoxib), parecoxib, deracoxib, ABT-963, MK-663 (etoricoxib), COX-189 (Lumiracoxib), BMS 347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoyl phenyl)-1H-pyrrole, T-614, JTE-522, S-2474, SVT-2016, CT-3, SC-58125 and Arcoxia (etoricoxib). Additionally, COX-II inhibitors are disclosed in U.S. Patent Applications US 2005-0148627 and US 2005-0148777, the contents of which are incorporated in their entirety for all purposes.

In a particular embodiment the anti-tumor agent is celecoxib (U.S. Pat. No. 5,466,823), valdecoxib (U.S. Pat. No. 5,633,272), parecoxib (U.S. Pat. No. 5,932,598), deracoxib (U.S. Pat. No. 5,521,207), SD-8381 (U.S. Pat. No. 6,034,256, Example 175), ABT-963 (WO 2002/24719), rofecoxib (CAS No. 162011-90-7), MK-663 (or etoricoxib) as disclosed in WO 1998/03484, COX-189 (Lumiracoxib) as disclosed in WO 1999/11605, BMS-347070 (U.S. Pat. No. 6,180,651), NS-398 (CAS 123653-11-2), RS 57067 (CAS 17932-91-3), 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, or meloxicam.

Other useful inhibitors as anti-tumor agents used in combination with a compound of the present invention and pharmaceutical compositions disclosed herein include aspirin, and non-steroidal anti-inflammatory drugs (NSAIDs) which inhibit the enzyme that makes prostaglandins (cyclooxygenase I and II), resulting in lower levels of prostaglandins, include but are not limited to the following, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol), Oxaprozin (Daypro) and combinations thereof.

Preferred COX-I inhibitors include ibuprofen (Motrin), nuprin, naproxen (Aleve), indomethacin (Indocin), nabumetone (Relafen) and combinations thereof.

Targeted agents used in combination with a compound of the present invention and pharmaceutical compositions disclosed herein include EGFr inhibitors such as Iressa (gefitinib, AstraZeneca), Tarceva (erlotinib or OSI-774, OSI Pharmaceuticals Inc.), Erbitux (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof. Preferred EGFr inhibitors include Iressa, Erbitux, Tarceva and combinations thereof.

Other anti-tumor agents include those selected from pan erb receptor inhibitors or ErbB2 receptor inhibitors, such as CP-724,714 (Pfizer, Inc.), CI-1033 (canertinib, Pfizer, Inc.), Herceptin (trastuzumab, Genentech Inc.), Omitarg (2C4, pertuzumab, Genentech Inc.), TAK-165 (Takeda), GW-572016 (Ionafarnib, GlaxoSmithKline), GW-282974 (GlaxoSmithKline), EKB-569 (Wyeth), PKI-166 (Novartis), dHER2 (HER2 Vaccine, Corixa and GlaxoSmithKline), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifunctional bispecific antibodies (University of Munich) and mAB AR-209 (Aronex Pharmaceuticals Inc) and mAB 2B-1 (Chiron) and combinations thereof.

Preferred erb selective anti-tumor agents include Herceptin, TAK-165, CP-724,714, ABX-EGF, HER3 and combinations thereof. Preferred pan erbb receptor inhibitors include GW572016, CI-1033, EKB-569, and Omitarg and combinations thereof.

Additional erbB2 inhibitors include those disclosed in WO 98/02434, WO 99/35146, WO 99/35132, WO 98/02437, WO 97/13760, WO 95/19970, U.S. Pat. No. 5,587,458, and U.S. Pat. No. 5,877,305, each of which is herein incorporated by reference in its entirety. ErbB2 receptor inhibitors useful in the present invention are also disclosed in U.S. Pat. Nos. 6,465,449, and 6,284,764, and in WO 2001/98277 each of which are herein incorporated by reference in their entirety.

Additionally, other anti-tumor agents may be selected from the following agents, BAY-43-9006 (Onyx Pharmaceuticals Inc.), Genasense (augmerosen, Genta), Panitumumab (Abgenix/Amgen), Zevalin (Schering), Bexxar (Corixa/GlaxoSmithKline), Abarelix, Alimta, EPO 906 (Novartis), discodermolide (XAA-296), ABT-510 (Abbott), Neovastat (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antisoma), Thymitaq (Eximias), Temodar (temozolomide, Schering Plough) and Revilimd (Celegene) and combinations thereof.

Other anti-tumor agents may be selected from the following agents, CyPat (cyproterone acetate), Histerelin (histrelin acetate), Plenaixis (abarelix depot), Atrasentan (ABT-627), Satraplatin (JM-216), thalomid (Thalidomide), Theratope, Temilifene (DPPE), ABI-007 (paclitaxel), Evista (raloxifene), Atamestane (Biomed-777), Xyotax (polyglutamate paclitaxel), Targetin (bexarotine) and combinations thereof.

Additionally, other anti-tumor agents may be selected from the following agents, Trizaone (tirapazamine), Aposyn (exisulind), Nevastat (AE-941), Ceplene (histamine dihydrochloride), Orathecin (rubitecan), Virulizin, Gastrimmune (G17DT), DX-8951f (exatecan mesylate), Onconase (ranpirnase), BEC2 (mitumoab), Xcytrin (motexafin gadolinium) and combinations thereof.

Further anti-tumor agents may be selected from the following agents, CeaVac (CEA), NeuTrexin (trimetresate glucuronate) and combinations thereof. Additional anti-tumor agents may be selected from the following agents, OvaRex (oregovomab), Osidem (IDM-1), and combinations thereof. Additional anti-tumor agents may be selected from the following agents, Advexin (ING 201), Tirazone (tirapazamine), and combinations thereof. Additional anti-tumor agents may be selected from the following agents, RSR13 (efaproxiral), Cotara (131 I chTNT 1/b), NBI-3001 (IL-4) and combinations thereof. Additional anti-tumor agents may be selected from the following agents, Canvaxin, GMK vaccine, PEG Interon A, Taxoprexin (DHA/paciltaxel), and combinations thereof.

Other anti-tumor agents include Pfizer's MEK1/2 inhibitor PD325901, Array Biopharm's MEK inhibitor ARRY-142886, Bristol Myers' CDK2 inhibitor BMS-387,032, Pfizer's CDK inhibitor PD0332991 and AstraZeneca's AXD-5438, and combinations thereof.

Additionally, mTOR inhibitors may also be utilized such as CCI-779 (Wyeth) and rapamycin derivatives RAD001 (Novartis) and AP-23573 (Ariad), HDAC inhibitors, SAHA (Merck Inc./Aton Pharmaceuticals) and combinations thereof. Additional anti-tumor agents include aurora 2 inhibitor VX-680 (Vertex), and Chk1/2 inhibitor XL844 (Exilixis).

The following cytotoxic agents, e.g., one or more selected from the group consisting of epirubicin (Ellence), docetaxel (Taxotere), paclitaxel, Zinecard (dexrazoxane), rituximab (Rituxan) imatinib mesylate (Gleevec), and combinations thereof, may be used in combination with a compound of the present invention and pharmaceutical compositions disclosed herein.

The invention also contemplates the use of the compounds of the present invention together with hormonal therapy, including but not limited to, exemestane (Aromasin, Pfizer Inc.), leuprorelin (Lupron or Leuplin, TAP/Abbott/Takeda), anastrozole (Arimidex, Astrazeneca), gosrelin (Zoladex, AstraZeneca), doxercalciferol, fadrozole, formestane, tamoxifen citrate (tamoxifen, Nolvadex, AstraZeneca), Casodex (AstraZeneca), Abarelix (Praecis), Trelstar, and combinations thereof.

The invention also relates to the use of the compounds of the present invention together with hormonal therapy agents such as anti-estrogens including, but not limited to fulvestrant, toremifene, raloxifene, lasofoxifene, letrozole (Femara, Novartis), anti-androgens such as bicalutamide, flutamide, mifepristone, nilutamide, Casodex™ (4'-cyano-3-(4-fluorophenylsulphonyl)-2-hydroxy-2-methyl-3'-(trifluoromethyl)propionanilide, bicalutamide) and combinations thereof.

Further, the invention provides a compound of the present invention alone or in combination with one or more supportive care products, e.g., a product selected from the group consisting of Filgrastim (Neupogen), ondansetron (Zofran), Fragmin, Procrit, Aloxi, Emend, or combinations thereof.

Particularly preferred cytotoxic agents include Camptosar, Erbitux, Iressa, Gleevec, Taxotere and combinations thereof.

The following topoisomerase I inhibitors may be utilized as anti-tumor agents: camptothecin; irinotecan HCl (Camptosar); edotecarin; orathecin (Supergen); exatecan (Daiichi); BN-80915 (Roche); and combinations thereof. Particularly preferred toposimerase II inhibitors include epirubicin (Ellence).

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, Paraplatin (carboplatin), eptaplatin, lobaplatin, nedaplatin, Eloxatin (oxaliplatin, Sanofi) or satrplatin and combinations thereof. Particularly preferred alkylating agents include Eloxatin (oxaliplatin).

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof.

Antibiotics include intercalating antibiotics and include, but are not limited to: aclarubicin, actinomycin D, amrubicin, annamycin, adriamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin, zinostatin and combinations thereof.

Plant derived anti-tumor substances include for example those selected from mitotic inhibitors, for example vinblastine, docetaxel (Taxotere), paclitaxel and combinations thereof.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, topotecan, and combinations thereof.

Preferred cytotoxic topoisomerase inhibiting agents include one or more agents selected from the group consisting of camptothecin, 10-hydroxycamptothecin, 9-aminocamptothecin, irinotecan HCl (Camptosar), edotecarin, epirubicin (Ellence), etoposide, SN-38, topotecan, and combinations thereof.

Immunologicals include interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-n1 and combinations thereof. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab (Y-muHMFG1), Provenge (Dendreon) and combinations thereof.

Biological response modifiers are agents that modify defense mechanisms of living organisms or biological responses, such as survival, growth, or differentiation of tissue cells to direct them to have anti-tumor activity. Such agents include krestin, lentinan, sizofuran, picibanil, ubenimex and combinations thereof.

Other anticancer agents that can be used in combination with a compound of the present invention include alitretinoin, ampligen, atrasentan bexarotene, bortezomib. Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, Telcyta (TLK-286, Telik Inc.), Velcade (bortemazib, Millenium), tretinoin, and combinations thereof.

Platinum-coordinated compounds include but are not limited to, cisplatin, carboplatin, nedaplatin, oxaliplatin, and combinations thereof.

Camptothecin derivatives include but are not limited to camptothecin, 10-hydroxycamptothecin, 9-aminocamptothecin, irinotecan, SN-38, edotecarin, topotecan and combinations thereof. Other antitumor agents include mitoxantrone, 1-asparaginase, procarbazine, dacarbazine, hydroxycarbamide, pentostatin, tretinoin and combinations thereof.

Anti-tumor agents capable of enhancing antitumor immune responses, such as CTLA4 (cytotoxic lymphocyte antigen 4) antibodies, and other agents capable of blocking CTLA4 may also be utilized, such as MDX-010 (Medarex) and CTLA4 compounds disclosed in U.S. Pat. No. 6,682,736; and anti-proliferative agents such as other farnesyl protein transferase inhibitors, for example the farnesyl protein transferase inhibitors. Additionally, specific CTLA4 antibodies that can be used in combination with compounds of the present invention include those disclosed in U.S. Pat. Nos. 6,682,736 and 6,682,736 both of which are herein incorporated by reference in their entirety.

Specific IGF1R antibodies that can be used in the combination methods of the present invention include those disclosed in WO 2002/053596, which is herein incorporated by reference in its entirety.

Specific CD40 antibodies that can be used in the present invention include those disclosed in WO 2003/040170 which is herein incorporated by reference in its entirety. Gene therapy agents may also be employed as anti-tumor agents such as TNFerade (GeneVec), which express TNFalpha in response to radiotherapy.

In one embodiment of the present invention statins may be used in combination with a compound of the present invention and pharmaceutical compositions thereof. Statins (HMG-CoA reducatase inhibitors) may be selected from the group consisting of Atorvastatin (Lipitor™, Pfizer Inc.), Provastatin (Pravachol™, Bristol-Myers Squibb), Lovastatin (Mevacor™, Merck Inc.), Simvastatin (Zocor™, Merck Inc.), Fluvastatin (Lescol™, Novartis), Cerivastatin (Baycol™, Bayer), Rosuvastatin (Crestor™, AstraZeneca), Lovostatin and Niacin (Advicor™, Kos Pharmaceuticals), derivatives and combinations thereof.

In a preferred embodiment the statin is selected from the group consisting of Atovorstatin and Lovastatin, derivatives and combinations thereof. Other agents useful as anti-tumor agents include Caduet.

In the following Preparations and Examples, "Ac" means acetyl, "Me" means methyl, "Et" means ethyl, "Ph" means phenyl, "BOC", "Boc" or "boc" means N-tert-butoxycarbonyl, "DCM" (CH$_2$Cl$_2$) means methylene chloride, "DIPEA" or "DIEA" means diisopropyl ethyl amine, "DMA" means N,N-dimethylacetamide, "DMF" means N—N-dimethyl formamide, "DMSO" means dimethylsulfoxide, "DPPP" means 1,3-bis(diphenylphosphino)propane, "HOAc" means acetic acid, "IPA" means isopropyl alcohol, "NMP" means 1-methyl 2-pyrrolidinone, "TEA" means triethyl amine, "TFA" means trifluoroacetic acid, "DCM" means dichloromethane, "EtOAc" means ethyl acetate, "MgSO$_4$" means magnesium sulphate, "Na$_2$SO$_4$" means sodium sulphate, "MeOH" means methanol, "Et$_2$O" means diethyl ether, "EtOH" means ethanol, "H$_2$O" means water, "HCl" means hydrochloric acid, "POCl$_3$" means phosphorus oxychloride, "K$_2$CO$_3$" means potassium carbonate, "THF" means tetrahydrofuran, "DBU" means 1,8-diazabicyclo[5.4.0]undec-7-ene, "LiHMDS" or "LHMDS" means lithium hexamethyldisilazide, "TBME" or "MTBE" means tert-butyl methyl ether, "LDA" means lithium diisopropylamide, "N" means Normal, "M" means molar, "mL" means millilitre, "mmol" means millimoles, "µmol" means micromoles, "eq." means equivalent, "° C." means degrees Celsius, "Pa" means pascals.

Methods of Preparation

Compounds of the present invention may be prepared using the reaction routes and synthetic schemes described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

In one general synthetic process, compounds of the general structure represented by 3 are prepared according to Method A.

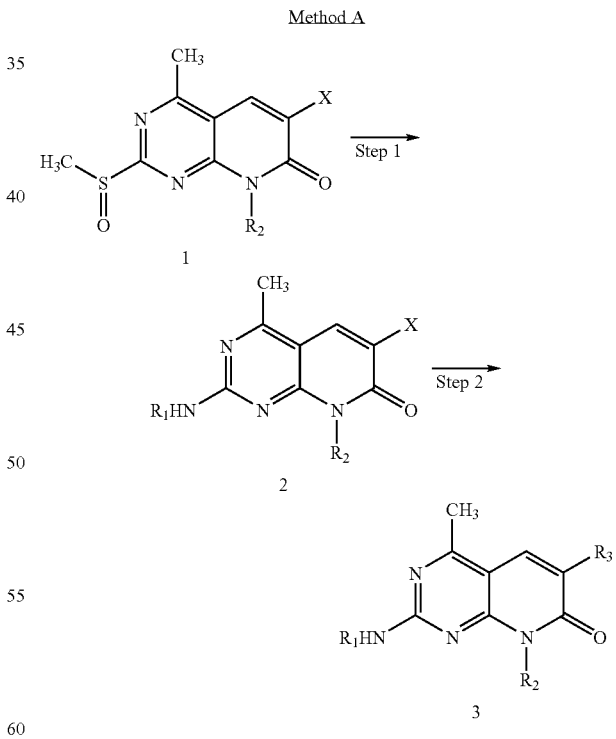

Compound 1, wherein X is Cl, Br or I and the preparation was described in WO2005105801, is converted to compound 2 by treatment with an amine of the formula R$_1$NH$_2$ in a suitable solvent, for example, dioxane, in the presence of a base, for example, triethyl amine, at an elevated temperature ranging from 40° C. to 220° C. for a period of time ranging from a few hours to a few days. Compound 2 is converted to compound 3 by treatment with boronic acid of the formula $R_3$—$B(OH)_2$ or a corresponding boronic ester, following modified Suzuki reaction conditions known to those skilled in the art.

In another general synthetic process, compounds of the general structure represented by 8 are prepared according to Method B.

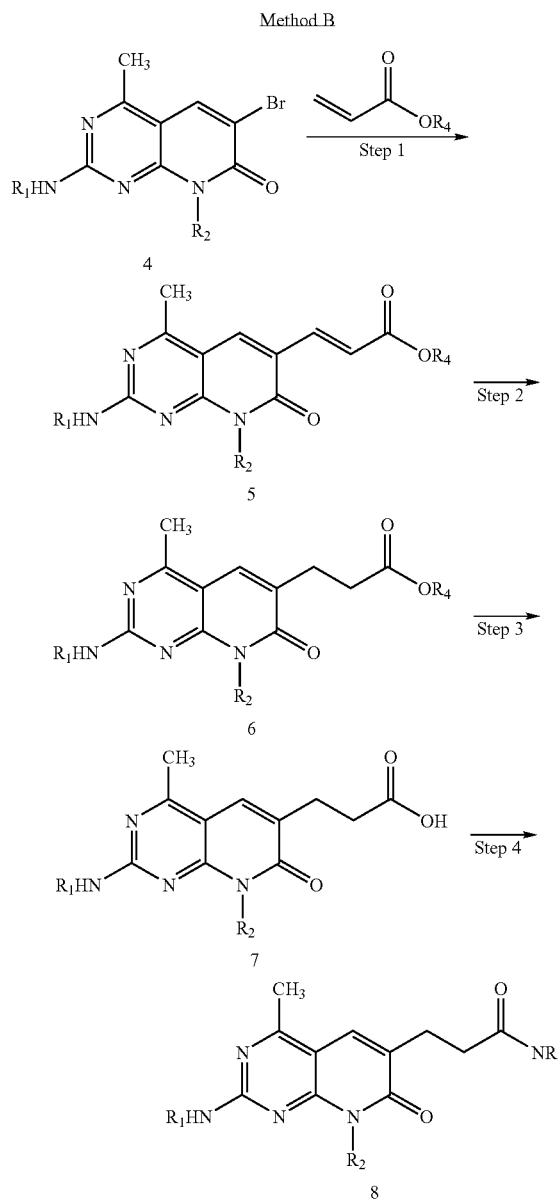

In another general synthetic process, compounds of the general structure represented by 11 are prepared according to Method C.

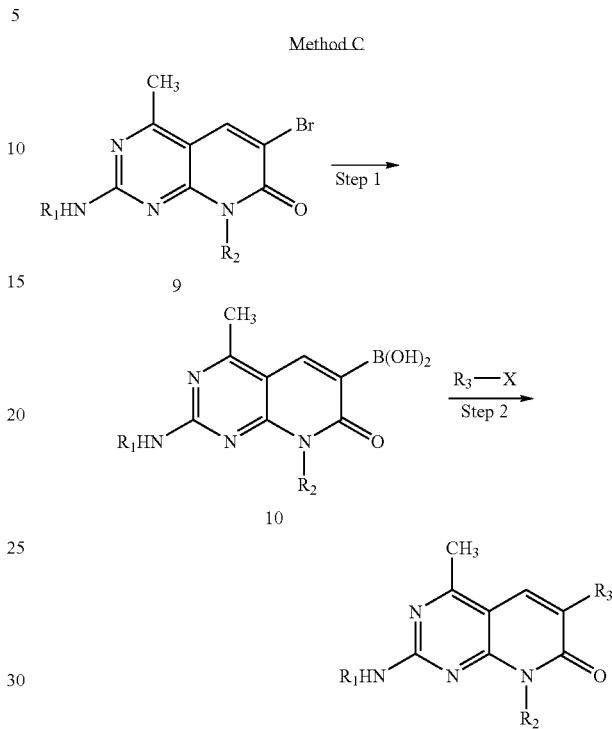

Compound 9 is converted to compound 10 by treatment with trimethylborate and butyl lithium in a suitable solvent, for example, THF at low temperature ranging from −40° C. to −90° C. Compound 10 is converted to compound 11 by reacting with $R_3$—X following Suzuki reaction conditions known to those skilled in the art.

In another general synthetic process, compounds of the general structure represented by 16 are prepared according to Method D.

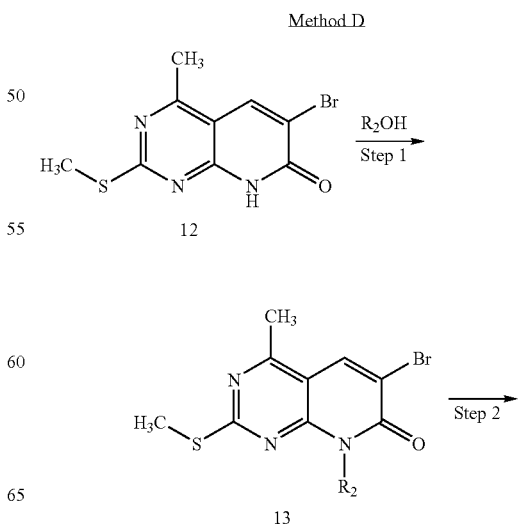

Compound 4 is converted to compound 5 by reacting with an acrylate ester in the presence of N-cyclohexyl-N-methyl-cyclohexanamine, tri-tert-butylphosphonium tetrafluoroborate, lithium chloride and tris(dibenzylldeneacetone)dipalladium(0), in a suitable solvent, for example, 1,4-dioxane at a temperature ranging from 50° C. to 75° C. for half of an hour to several days. Compound 5 is converted to compound 6 by hydrogenation. Hydrolysis of the ester derivative 6, followed by amide formation, yields compound of formula 8.

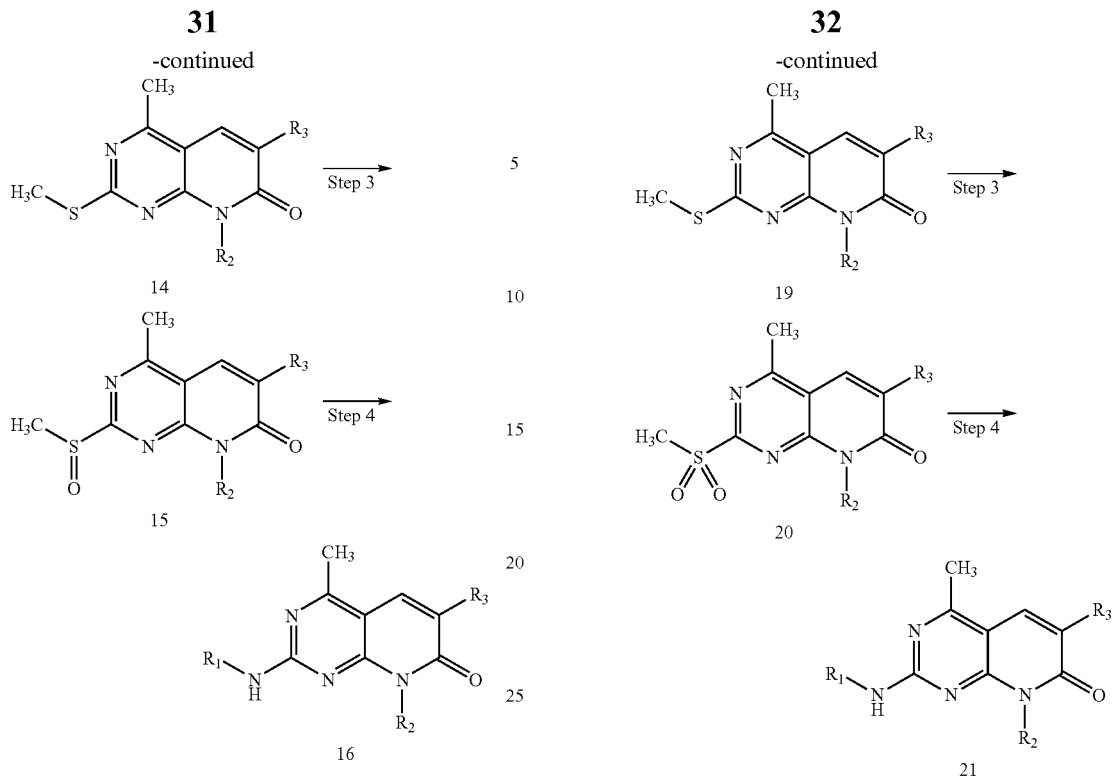

Compound 12 is reacted with an alcohol of the formula R$_2$OH in the presence of triphenylphosphine and diethyl azodicarboxylate (DEAD) in a suitable solvent, for example, THF at a temperature ranging from room 0° C. to 60° C. to afford compound of formula 13. Compound 13 is converted to compound 14 by treatment with boronic acid of the formula R$_3$—B(OH)$_2$ or a corresponding boronic ester, following modified Suzuki reaction conditions known to those skilled in the art. Compound 14 is oxidized to afford compound 15 using reagents such as, for example, m-chloroperbenzoic acid (MCPBA). Treatment of compound 15 with an amine of formula R$_1$NH$_2$ affords compound 16.

In another general synthetic process, compounds represented by 21 are prepared according to Method E.

Compound 17 is converted to compound 18 by treatment with R$_2$X, wherein X is Cl, Br or I, in the presence of a base, for example, sodium hydride, in a suitable solvent such as, for example, DMF, at a temperature ranging from 25° C. to 100° C. Compound 18 is converted to compound 19 by treatment with boronic acid of the formula R$_3$—B(OH)$_2$ or a corresponding boronic ester, following Suzuki reaction conditions known to those skilled in the art. Compound 19 is oxidized to afford compound 20 using reagents such as, for example, MCPBA. Treatment of compound 20 with an amine of formula R$_1$NH$_2$ in a suitable solvent such as, for example, THF under reflux conditions affords compound of formula 21.

In another general synthetic process, compounds of the general structure represented by 28 are prepared according to Method F.

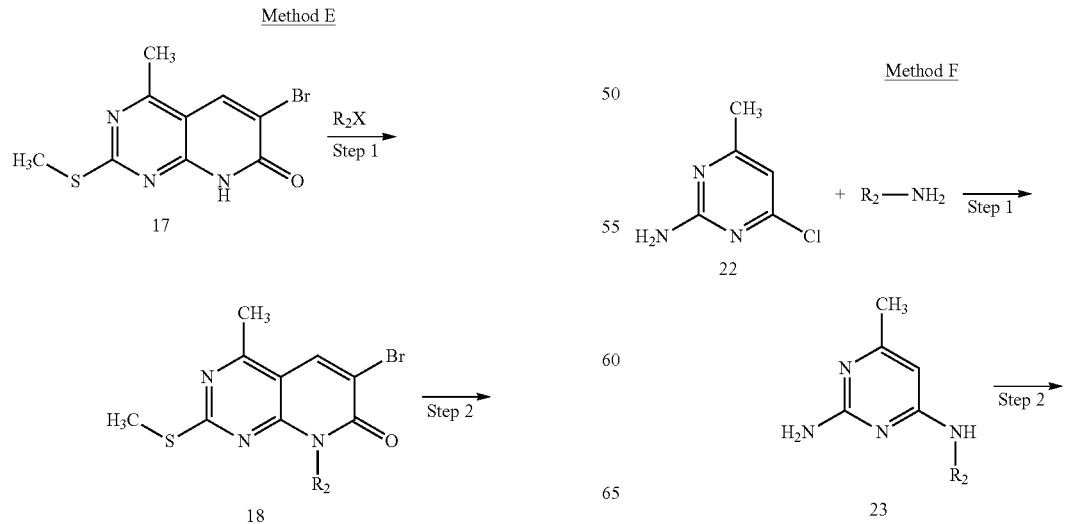

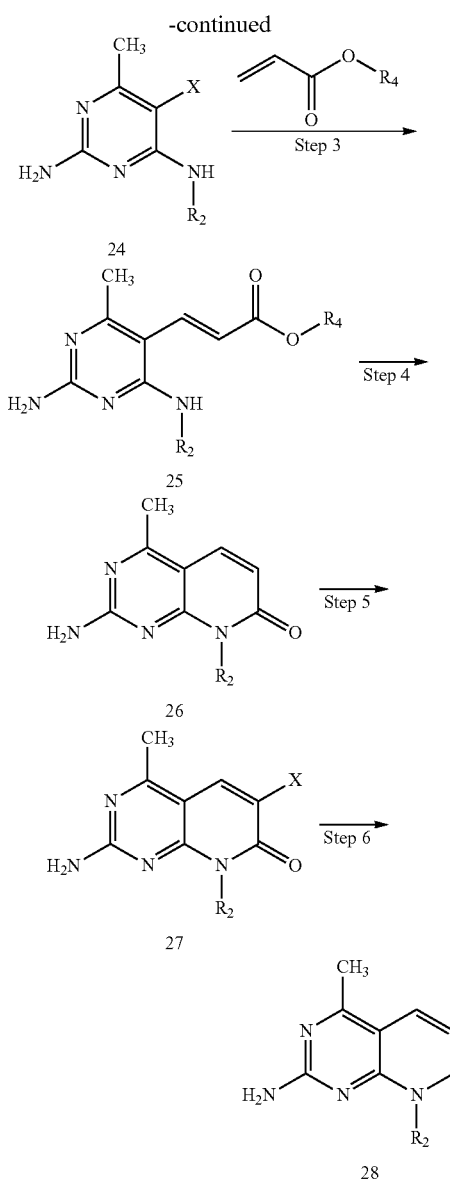

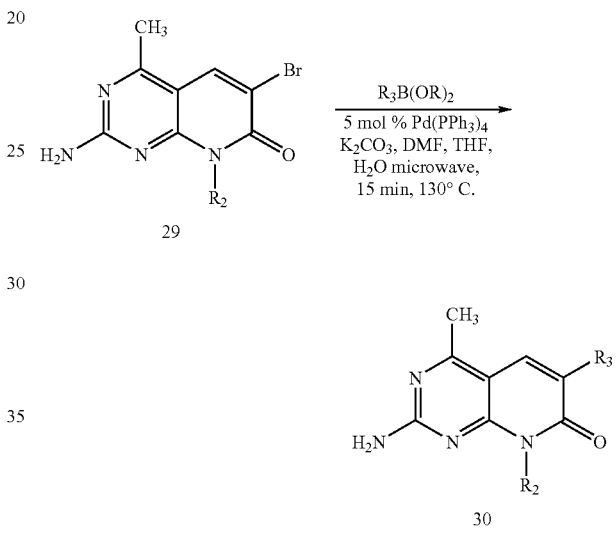

Compound 26 is converted to compound 27 by treatment with N-halosuccinamide in a suitable solvent such as DMF at ambient temperature for a period of time ranging from 30 min to a few hours. Compound 27 is then converted to compound 28 by reacting with boronic acid of the formula $R_3$—$B(OH)_2$ or a corresponding boronic ester, in the presence of a base, for example, potassium carbonate, and bis(triphenylphosphine) palladium (II) chloride, in a suitable solvent such as DMF and water solution, at an elevated temperature ranging from 70° C. to 120° C., for a period of time from several hours to a few days.

Method F can be used, for example, for preparing compound 28 wherein $R_2$ is an optionally substituted spirocyclic group.

In a glove box, the following was added to a 2.0 mL Personal Chemistry Microwave reaction tube: one triangular stir bar, the appropriate aryl halide 29 solution in DMF (300 µL, 75 µmol, 1.0 eq., 0.25 M), the appropriate boronic acid or boronic ester in DMF (300 µL, 75 µmol, 1.0 eq., 0.25 M), catalyst $Pd(PPh_3)_4$ in anhydrous THF (300 µL, 3.75 µmol, 0.05 eq., 0.0125 M) and $K_2CO_3$ in degassed DI water (94 µL, 188 µmol, 2.5 eq., 2.0 M). The microwave tube was sealed with a septum cap, and outside the glove box, the reaction mixtures were heated in a Personal Chemistry Microwave Synthesizer for 15 minutes at 130° C. The reaction mixtures were transferred into a 13×100 mm test tube. The microwave tubes were washed with DMF (1.0 mL), and the wash DMF was combined with the originally transferred material. The solvents were removed, and EtOAc (1 mL) and DI water (1 mL) were added to each tube. After agitation and centrifugation, the supernatant was transferred to a new 13×100 mm test tube. The aqueous phase was extracted two more times with fresh EtOAc (1 mL). The combined organic phases were back extracted with DI water (1 mL) and aq. NaCl (1 mL). The organic phase was filtered through a syringe filter, and the filtrate was evaporated. The residues were reconstituted in DMSO, and the crude material was subjected to HPLC purification using acetonitrile/water with 0.05% TFA as the mobile phase on an Agilent Zorbax Extend C18 column.

Commercially available compound 22 is converted to compound 23 by reacting with amine of the formula $R_2$—$NH_2$ in a suitable solvent such as, for example, dimethylacetamide, in the presence of bases such as potassium carbonate and diisopropylethyl amine, at elevated temperature ranging from 40° C. to 220° C. for a period of time ranging from a few hours to a few days. Compound 23 is converted to compound 24 wherein X is Cl, Br or I by treatment with N-halosuccinamide in a suitable solvent such as chloroform or carbon tetrachloride, at ambient temperature for a period of time ranging from 30 min to a few hours. Compound 24 is converted to compound 25 by reacting with an acrylate ester in the presence of tri-o-tolylphosphine, palladium (II) acetate and triethylamine at an elevated temperature. Compound 25 is converted to compound 26 by heating the solution of compound 25, thiophenol or KOtBu, and organic bases such as triethylamine and DBU, in a suitable solvent such as dimethylacetamide at an elevated temperature ranging from 40° C. to 220° C. for a period of time ranging from a few hours to a few days.

Method H

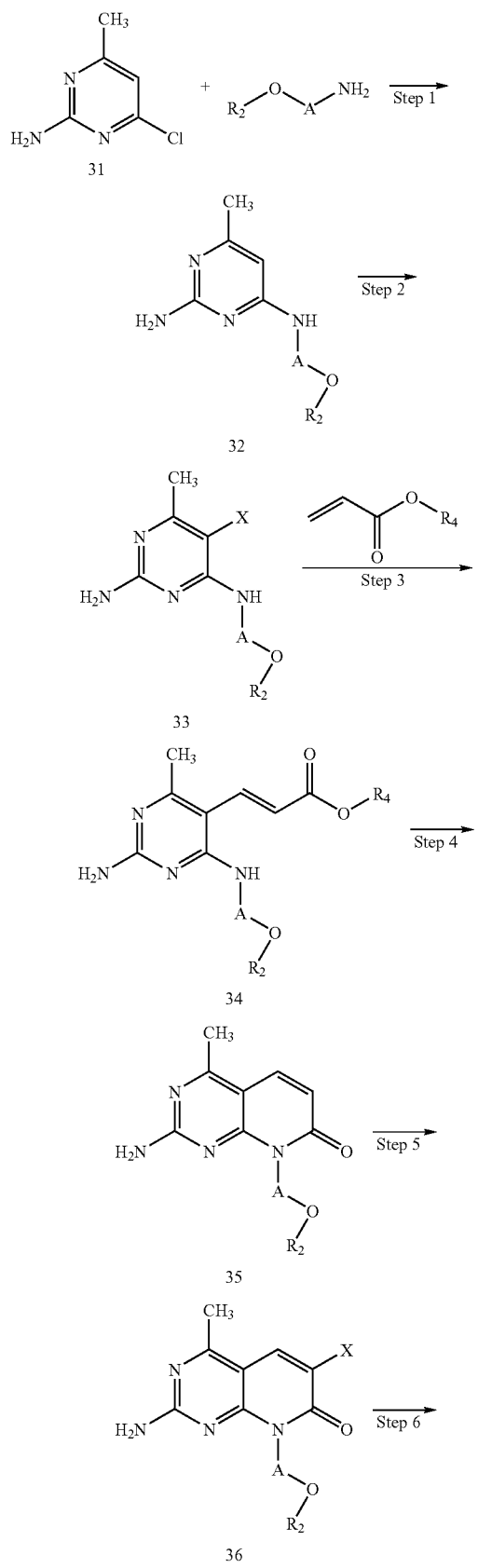

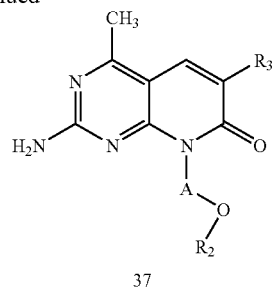

Commercially available compound 31 is converted to compound 32 by reacting with amine of the formula $R_2$—O-A-$NH_2$, wherein A is optionally substituted $C_{3-10}$ cycloalkyl, in a suitable solvent such as, for example, dimethylacetamide, in the presence of bases such as potassium carbonate and diisopropylethyl amine, at elevated temperature ranging from 40° C. to 220° C. for a period of time ranging from a few hours to a few days. Compound 32 is converted to compound 33 wherein X is Cl, Br or I by treatment with N-halosuccinamide in a suitable solvent such as chloroform or carbon tetrachloride, at ambient temperature for a period of time ranging from 30 min to a few hours. Compound 33 is converted to compound 34 by reacting with an acrylate ester in the presence of tri-o-tolylphosphine, palladium (II) acetate and triethylamine at an elevated temperature. Compound 34 is converted to compound 35 by heating a solution of compound 34, thiophenol or KOtBu, and organic bases such as triethylamine and DBU, in a suitable solvent such as dimethylacetamide at an elevated temperature ranging from 40° C. to 220° C. for a period of time ranging from a few hours to a few days. Compound 35 is converted to compound 36 by treatment with N-halosuccinamide in a suitable solvent such as DMF at ambient temperature for a period of time ranging from 30 min to a few hours. Compound 36 is then converted to compound 37 by reacting with boronic acid of the formula $R_3$—$B(OH)_2$ or a corresponding boronic ester, in the presence of a base, for example, potassium carbonate, and bis(triphenylphosphine) palladium (II) chloride, in a suitable solvent such as DMF and water solution, at an elevated temperature ranging from 70° C. to 150° C., for a period of time from several hours to a few days.

Method I

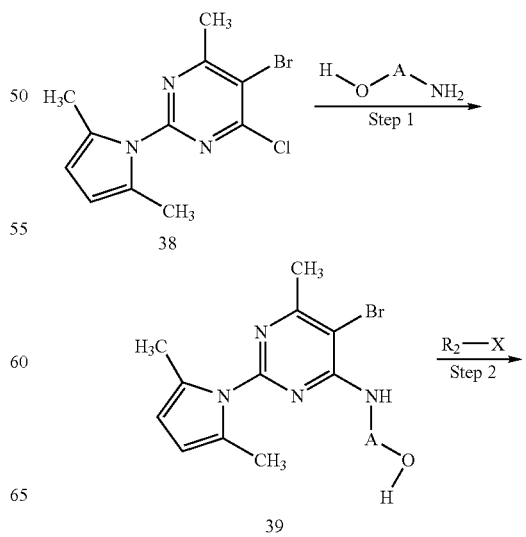

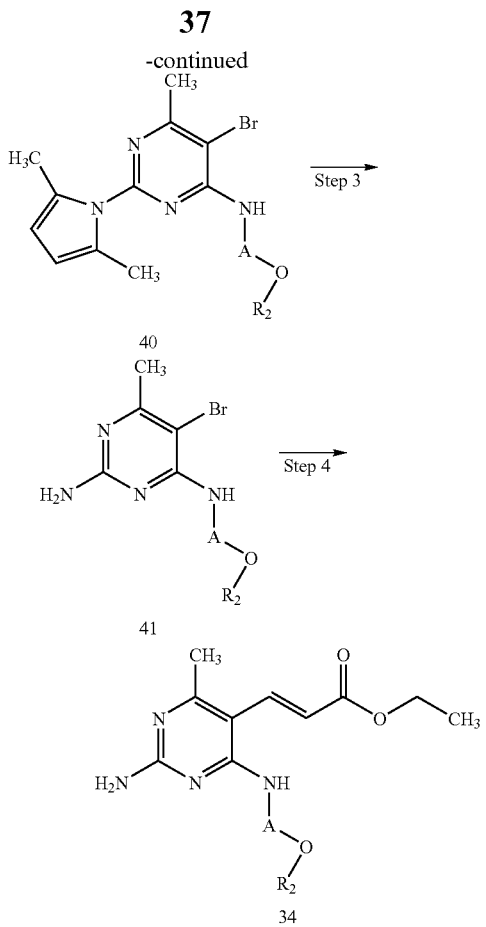

Compound of the formula 34 can also be prepared as described in Method I. Compound 38 is converted to compound 39 by reacting with amine of the formula HO-A-NH$_2$ in a suitable solvent such as, for example, dimethylacetamide, in the presence of bases such as potassium carbonate and diisopropylethyl amine, at elevated temperature ranging from 40° C. to 220° C. for a period of time ranging from a few hours to a few days. Compound 39 is converted to compound 40 by reacting with R$_2$X in a suitable solvent such as DMF in the presence of a base such as sodium hydride at temperature ranging from room temperature to 100° C. Compound 40 is converted to compound 41 by treating with hydroxylamine in aqueous ethanol at temperature ranging from room temperature to 80° C. Compound 41 is converted to compound 34 by reacting with an acrylate ester in the presence of tri-o-tolylphosphine, palladium (II) acetate and triethylamine at an elevated temperature. Compound 34 is then converted to compound of formula 37 following the procedures described in Method H.

EXAMPLES

The examples and preparations provided below further illustrate and exemplify the compounds of the present invention and methods of preparing such compounds. Examples 1 to 100 provide detailed synthetic steps for preparing Compounds 101, 104-107, 109, 113-114, 116, 120-121, 123, 129-130, 132-133, 147-152, 179, 192, 193, 247-252, 263-264, 267-270, 275, 284, and 285 of the present invention. Table 1 shows compounds of the present invention that were prepared using the general methods A-I described herein. Table 2 shows the biochemical and cellular data for the compounds of the present invention. Table 3 shows mouse xenograft efficacy data for a representative Compound 152 of the present invention. Table 4 shows data on pharmacokinetic and pharmacodynamic (PK-PD) correlation in xenograft models.

It is to be understood that the scope of the present invention is not limited in any way by the scope of the following examples and preparations. In the following examples molecules with a single chiral center, unless otherwise noted or indicated by the structural formula or chemical name, exist as a racemic mixture. Those molecules with two or more chiral centers, unless otherwise noted or indicated by the structural formula or chemical name, exist as a racemic mixture of diastereomers. Single enantiomers/diastereomers may be obtained by methods known to those skilled in the art.

Various starting materials and other reagents were purchased from commercial suppliers, such as Aldrich Chemical Company, and used without further purification, unless indicated otherwise. $^1$H-NMR spectra were recorded on a Bruker instrument operating either at 300 MHz, or 400 MHz and $^{13}$C-NMR spectra were recorded operating at 75 MHz. NMR spectra were obtained as CDCl$_3$ solutions (reported in ppm), using chloroform as the reference standard (7.25 ppm and 77.00 ppm) or DMSO-D$_6$ (2.50 ppm and 39.51 ppm) or CD$_3$OD (3.4 ppm and 4.8 ppm and 49.3 ppm), or internal tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

2-Amino-8-cyclopentyl-6-(3-hydroxyphenyl)-4-methylpyrido[2,3-d]pyrimidin-7(8H)-one (Compound 147)

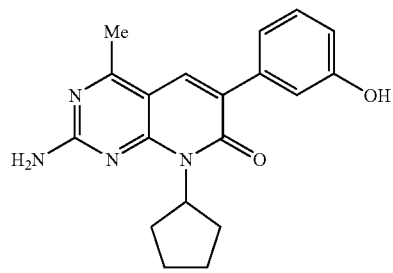

To a solution of 2-amino-6-bromo-8-cyclopentyl-4-methylpyrido[2,3-d]pyrimidin-7(8H)-one (100 mg, 0.31 mmol), 3-hydroxyphenylboronic acid (50 mg, 1.2 equiv), dichlorobis (triphenylphosphine)palladium(II) (6.5 mg, 009 mmol), DMF (2 mL) in a 10 mL microwave vial was added potassium carbonate (3 M, 0.8 mL). The solution was degassed with N$_2$ for 10 min before being capped and heated in the microwave reactor for 10 min at 120° C. Once complete, the reaction was diluted with 1 N NaOH (10 mL) and EtOAc (50 mL). The EtOAc layer was separated, dried over MgSO$_4$, filtered, and concentrated under reduced pressure. The crude product was submitted for chromatography purification. The title compound was obtained in (82.1 mg, 79% yield).

LRMS: 337 (M+H)$^+$.

$^1$H NMR (DMSO-d$_6$, 400 MHz): 9.37 (1H, s), 7.87 (1H, s), 7.19 (3H, m), 7.11 (1H, s), 7.03 (1H, d), 6.74-6.71 (1H, m), 6.04-5.99 (1H, m), 2.55 (3H, s), 2.24-2.22 (2H, m), 2.02 (2H, m), 1.77-1.75 (2H, m), 1.60-1.58 (2H, m).

Example 2

2-Amino-6-bromo-8-cyclopentyl-4-methylpyrido[2,3-d]pyrimidin-7(8H)-one

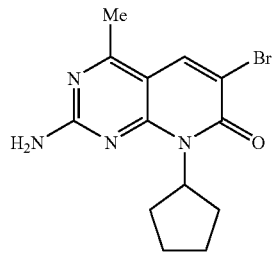

To a solution of 6-bromo-8-cyclopentyl-4-methyl-2-(methylsulfinyl)pyrido[2,3-d]pyrimidin-7(8H)-one (0.80 g, 2.16 mmol) in dioxane (5 mL) was added ammonium hydroxide (30%, 2.6 mL). The mixture was then heated at 110° C. in a sealed tube for 30 minutes. The solution was concentrated in vacuo and extracted with ethyl acetate (3×30 mL). The combined organics were washed with saturated aqueous sodium chloride, dried (anhydrous sodium sulfate), filtered and concentrated to dryness to give the title compound as a brown crystalline solid (0.65 g, 93%).

LRMS: 324 (M+H)+.

1H NMR (DMSO-d6, 400 MHz): 8.34 (1H, s), 7.27 (2H, bs), 6.01-5.93 (1H, m), 2.51 (3H, s), 2.16-2.13 (2H, m), 2.00-1.98 (2H, m), 1.75-1.72 (2H, m), 1.57-1.54 (2H, m).

Example 3

6-Bromo-8-cyclopentyl-4-methyl-2-(methylamino)pyrido[2,3-d]pyrimidin-7(8H)-one

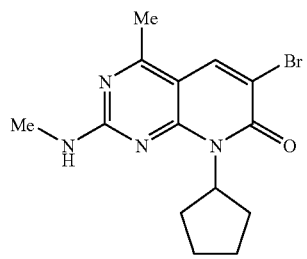

Following the procedure described in Example 2, using methylamine (2M in THF) in place of ammonium hydroxide, the title compound was obtained in 90% yield.

LRMS: 338 (M+H)+.

1H NMR (DMSO-d6, 400 MHz): 8.36 (1H, s), 7.82 (1H, bs), 5.98-5.94 (1H, m), 2.86 (3H, s), 2.51 (3H, s), 2.28 (2H, m), 1.99-1.97 (2H, m), 1.75-1.72 (2H, m), 1.62 (2H, m).

Example 4

6-Bromo-8-cyclopentyl-4-methyl-2-(ethylamino)pyrido[2,3-d]pyrimidin-7(8H)-one

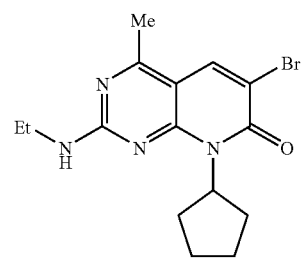

Following the procedure described in Example 2, using ethylamine (2M in THF) in place of ammonium hydroxide, the title compound was obtained in 93% yield.

LRMS: 352 (M+H)+.

1H NMR (DMSO-d6, 400 MHz): 8.35 (1H, s), 7.90 (1H, bs), 6.01-5.93 (1H, m), 3.34 (2H, m), 2.51 (3H, s), 2.27 (2H, m), 1.96 (2H, m), 1.75 (2H, m), 1.62 (2H, m), 1.15 (3H, m).

Example 5

Preparation of 2-amino-8-cyclopentyl-6-(1H-pyrazol-4-yl)-4-methylpyrido[2,3-d]pyrimidin-7(8H)-one (Compound 101)

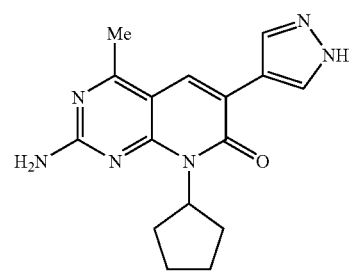

To a solution of 2-amino-6-bromo-8-cyclopentyl-4-methylpyrido[2,3-d]pyrimidin-7(8H)-one (100 mg, 0.31 mmol), tert-butyl 4-(4,4,5,5-tetramethyl-1,3,2-dioxaborolan-2-yl)-1H-pyrazole-1-carboxy late 110 mg, 1.2 equiv), dichlorobis(triphenylphosphine)palladium(II) (6.5 mg, 009 mmol), DMF (2 mL) in a 10 mL microwave vial was added potassium carbonate (3 M, 0.8 mL). The solution was degassed with N2 for 10 min before being capped and heated in the microwave reactor for 10 min at 120° C. Once complete, the reaction was diluted with 1 N NaOH (10 mL) and EtOAc (50 mL). The EtOAc layer was washed with 3N HCl, dried over MgSO4, filtered, and concentrated under reduced pressure. The crude product was submitted for chromatography purification. the title compound was obtained in (62.5 mg, 65% yield).

LRMS: 311 (M+H)+.

1H NMR (DMSO-d6, 400 MHz): 8.26 (2H, bs), 8.13 (1H, s), 7.09 (2H, bs), 6.04-5.99 (1H, m), 2.59 (3H, s), 2.27-2.23 (2H, bm), 2.04 (2H, bm), 1.77-1.74 (2H, bm), 1.62 (2H, bm).

Example 6

2-Methylamino-6-carbonitrile-8-cyclopentyl-4-methylpyrido[2,3-d]pyrimidin-7(8H)-one (Compound 133)

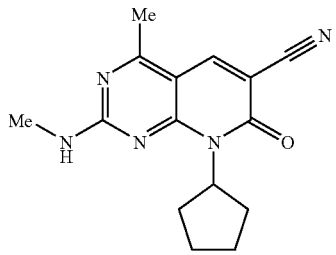

A solution of 6-Bromo-8-cyclopentyl-4-methyl-2-methylamino-8H-pyrido[2,3-d]pyrimidin-7-one (150 mg, 0.15 mmol) and tetraethylammonium cyanide 946 mg, 0.30 mmol); DABCO (33 mg, 0.30 mmol) in acetonitrile (2 mL) was stirred at 22° C. for 3 days. The reaction appears completed by LCMS and the mixture was evaporated and sent for chromatography. (70.6 mg, 61% yield).

LRMS: 284 (M+H)+.

$^1$H NMR (CDCl$_3$, 400 MHz): 8.68 (1H, s), 8.31 (1H, m), 5.90-5.85 (1H, m), 2.91 (3H, m), 2.51 (3H, s), 2.28 (2H, bm), 1.96 (2H, bm), 1.77 (2H, bm), 1.62 (2H, bm).

Example 7

8-Cyclopentyl-4-methyl-2-(methylamino)-7-oxo-7,8-dihydropyrido[2,3-d]pyrimidine-6-carboxamide (Compound 123)

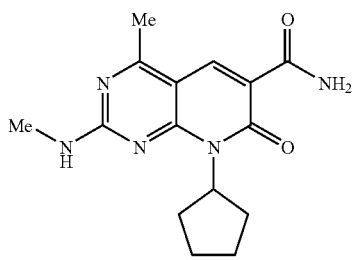

A solution of 2-methylamino-6-carbonitrile-8-cyclopentyl-4-methylpyrido[2,3-d]pyrimidin-7(8H)-one (90 mg, 3.20 mmol) in 3M HCl (10 mL) was stirred at 110° C. for 24 h. The reaction appears completed by LCMS and the mixture was evaporated and sent for chromatography. (32.2 mg, 45% yield).

LRMS: 302 (M+H)+.

$^1$H NMR (CDCl$_3$, 400 MHz): 8.80 (1H, bs), 8.68 (1H, s), 8.13 (1H, m), 7.62 (1H, bs), 5.98-5.96 (1H, m), 2.91 (3H, m), 2.51 (3H, s), 2.33 (2H, bm), 1.99 (2H, bm), 1.78 (2H, bm), 1.65 (2H, bm).

Example 8

(E)-8-cyclopentyl-6-(2-hydroxyvinyl)-4-methyl-2-(methylamino)pyrido[2,3-d]pyrimidin-7(8H)-one (Compound 120)

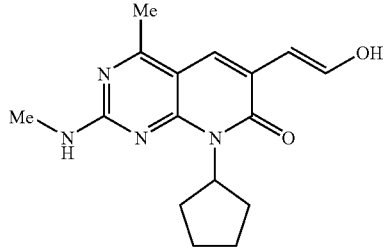

6-bromo-8-cyclopentyl-4-methyl-2-(methylamino)pyrido[2,3-d]pyrimidin-7(8H)-one (336 mg, 1.0 mmole), 1-(vinyloxy)butane (501 mg, 5.0 mmole), N-cyclohexyl-N-methylcyclohexanamine (254 mg, 1.3 mmole), tri-tert-butylphosphonium tetrafluoroborate (8.70 mg, 0.03 mmole), lithium chloride (127 mg, 3.0 mmole), tris(dibenzylideneacetone)dipalladium(0)) (27.5 mg, 0.03 mmole) and 1,4-dioxane (10 ml) were added to a reaction vial equipped with a stir bar. The reaction vial was flushed with nitrogen, capped, and heated at 75° C. for 75 min. LCMS data indicated that both the intermediate vinyl ether and the product were obtained (4:6). The reaction mixture was cooled to ambient temperature, filtered through Celite™ and washed with dioxane (10 ml). The filtrate and washing were combined, and para-toluene sulfonic acid monohydrate (761 mg, 4.0 mmole) was added. The reaction was stirred at ambient temperature for 1 h. At this point LCMS data indicated that all of the intermediate vinyl ether hydrolyzed to the desired product. The solvent was removed under reduced pressure to a residue, and ethyl acetate (120 ml) was added, and washed with aqueous potassium carbonate solution (5 wt/v %), water, and brine. The organic layer was dried over sodium sulfate, and the solvent was removed under reduced pressure to a yellow solid residue, which was crystallized from boiling heptane. Upon cooling to ambient temperature, yellow crystals formed and collected by filtration to give the title compound (190 mg, 62% yield) after two steps.

LCMS: 301 (M+H)+.

$^1$H NMR (CDCl$_3$, 400 MHz) 8.49 (s, 1H) 5.79-6.19 (m, 1H) 5.23-5.76 (m, 1H) 3.10 (d, J=4.78 Hz, 3H) 2.72 (s, 3H) 2.60 (s, 3H) 2.34-2.54 (m, 2H) 1.98-2.15 (m, 2H) 1.80-1.94 (m, 2H) 1.65-1.78 (m, 2H).

$^1$H NMR (DMSO-d6, 400 MHz) 8.35 (s, 1H) 7.81-8.21 (m, 1H) 5.75-6.05 (m, 1H) 2.90 (t, J=5.41 Hz, 3H) 2.60 (s, 1H) 2.53-2.57 (m, 5H) 2.20-2.42 (m, 2H) 1.91-2.11 (m, 2H) 1.70-1.85 (m, 2H) 1.52-1.69 (m, 2H).

Example 9

(E)-Ethyl 3-(8-cyclopentyl-4-methyl-2-(methylamino)-7-oxo-7,8-dihydropyrido[2,3-d]pyrimidin-6-yl)acrylate

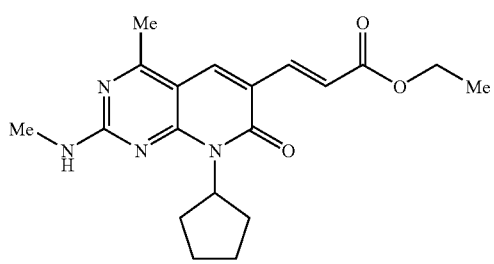

6-bromo-8-cyclopentyl-4-methyl-2-(methylamino)pyrido[2,3-d]pyrimidin-7(8H)-one (375 mg, 1.1 mmole), ethyl acrylate (442 mg, 4.42 mmole), N-cyclohexyl-N-methylcyclohexanamine (280 mg, 1.43 mmole), tri-tert-butylphosphonium tetrafluoroborate (9.61 mg, 0.03 mmole), lithium chloride (42.4 mg, 3.3 mmole), tris(dibenzylideneacetone)dipalladium(0)) (30.3 mg, 0.03 mmole) and 1,4-dioxane (10 ml) were added to a reaction vial equipped with a stir bar. The reaction vial was flushed with nitrogen, capped, and heated at 75° C. for 75 min. The reaction mixture was cooled to ambient temperature, filtered through Celite™, and washed with ethyl acetate. The filtrate and washing were combined, and the volatiles were removed under reduced pressure to a yellow solid residue. This solid residue was crystallized from boiling heptane:ethyl acetate (50 ml: 50 ml). Upon cooling to ambient temperature, needle-liked yellow crystals formed and collected by filtration to give the title compound as a beta-trans isomer (356 mg, 90% yield).

LCMS: 357 (M+H)+.

$^1$H NMR (CDCl$_3$, 400 MHz) 7.88 (s, 1H) 7.71 (d, J=15.86 Hz, 1H) 6.96 (d, J=15.86 Hz, 1H) 6.03 (s, 1H) 5.46 (s, 1H) 4.25 (q, J=7.22 Hz, 2H) 3.09 (d, J=5.04 Hz, 3H) 2.58 (s, 3H) 2.42 (s, 2H) 1.91-2.19 (m, 3H) 1.86 (s, 2H) 1.28-1.37 (m, 3H).

Example 10

Ethyl 3-(8-cyclopentyl-2-(ethylamino)-4-methyl-7-oxo-7,8-dihydropyrido[2,3-d]pyrimidin-6-yl)propanoate (Compound 132)

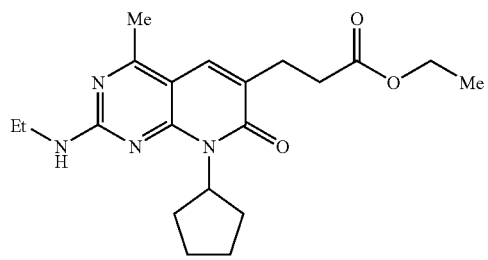

(E)-ethyl 3-(8-cyclopentyl-2-(ethylamino)-4-methyl-7-oxo-7,8-dihydropyrido[2,3-d]pyrimidin-6-yl)acrylate (525 mg, 1.4 mmole) obtained in an analogous manner to Example 9 was dissolved in ethanol (150 ml) in a 500 ml-Parr™ reaction bottle, and the solution was degassed with nitrogen for 5 min. Pd/C (450.0 mg) (Aldrich 330108-50G, batch 08331KC, Palladium, 10 wt % dry basis on activated carbon, wet, Degussa type E101 NE/W, water ca. 50%) was added. The reaction was hydrogenated at 50 psi hydrogen at ambient temperature for 18 h. The catalyst was filtered and washed with ethanol (20 ml). The filtrate and washing were combined and the volatiles were removed under reduced pressure to a solid residue. The residue was crystallized from boiling heptane (30 ml). Upon cooling to ambient temperature, white needle-liked crystals formed, and collected by filtration to give the title compound (338 mg, 64% yield).

LCMS: 373 (M+H)+.

$^1$H NMR (CDCl$_3$, 400 MHz) 7.55 (s, 1H) 5.83-6.12 (m, J=17.88, 8.81, 8.56 Hz, 1H) 5.21 (s, 1H) 4.12 (q, J=7.13 Hz, 2H) 3.38-3.63 (m, 2H) 2.87 (t, J=7.30 Hz, 2H) 2.67 (t, J=7.30 Hz, 2H) 2.53 (s, 3H) 2.31-2.46 (m, 2H) 1.99-2.10 (m, 2H) 1.77-1.91 (m, 2H) 1.63-1.74 (m, 2H) 1.19-1.31 (m, 6H).

Example 11

3-(8-Cyclopentyl-2-(ethylamino)-4-methyl-7-oxo-7,8-dihydropyrido[2,3-d]pyrimidin-6-yl)propanoic acid (Compound 130)

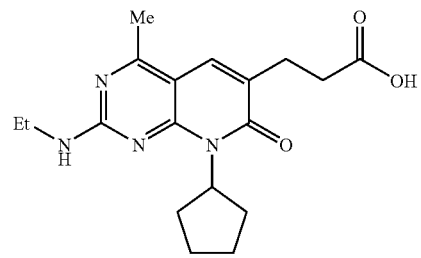

Ethyl 3-(8-cyclopentyl-2-(ethylamino)-4-methyl-7-oxo-7,8-dihydropyrido[2,3-d]pyrimidin-6-yl)propanoate (167 mg, 0.45 mmole) was dissolved in THF (5 ml) in a reaction vial equipped with a stir bar. Lithium hydroxide (35 mg, 1.46 mmole) was dissolved in water (5 ml) and then added to the reaction vial. The reaction mixture was stirred at ambient temperature for 3 h. The volatiles were removed under reduced pressure to a white solid residue. Aqueous hydrochloric acid (3.26 mmole, 3.26 ml of 1.0 M solution) was added. The white solid was collected by filtration as the title compound (125 mg, 81% yield).

LCMS: 345 (M+H)+.

$^1$H NMR (D$_2$O, 400 MHz) 7.54 (s, 1H) 5.56-5.81 (m, 1H) 3.22 (q, J=7.22 Hz, 2H) 2.60 (t, J=7.55 Hz, 2H) 2.31-2.38 (m, 5H) 1.91-2.05 (m, 2H) 1.77-1.90 (m, 2H) 1.58-1.71 (m, 2H) 1.46-1.58 (m, 2H) 1.06 (t, J=7.30 Hz, 3H).

Example 12

3-(8-Cyclopentyl-2-(ethylamino)-4-methyl-7-oxo-7,8-dihydropyrido[2,3-d]pyrimidin-6-yl)-N,N-dimethylpropanamide (Compound 121)

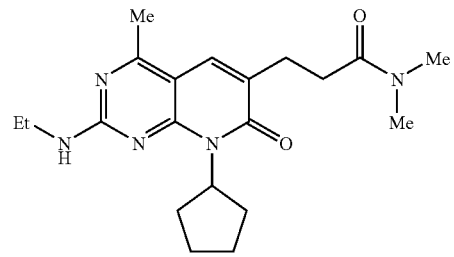

3-(8-cyclopentyl-2-(ethylamino)-4-methyl-7-oxo-7,8-dihydropyrido[2,3-d]pyrimidin-6-yl)propanoic acid (94 mg, 0.27 mmole), dimethylamine (1.09 mmole, 0.55 ml of 2.0 M solution in THF), triethylamine (27.6 mg, 0.27 mmole), O-(7-Azabenzotriazol-1-yl)-N,N,N'N'-tetramethyluronium hexafluorophosphate (HATU, 104 mg, 0.27 mmole) and DMF (3.0 ml) were added to a reaction vial equipped with a stir bar. The reaction mixture was heated at 50° C. for 26 h. The reaction was quenched with water (2 ml), and the volatiles were removed under reduced pressure to a residue. Ethyl acetate (70 ml) and water (30 ml) were added and shaken well. The organic layer was separated, washed with water (2×30 ml), brine (30 ml), and dried over sodium sulfate. The solvent was removed under reduced pressure to a residue, which was purified using silica (100% petroleum ether to 100% ethyl acetate). The fractions were combined, and the volatiles were removed to a colorless oil as the title compound (55 mg, 54% yield).

LCMS: 372 (M+H)+.

1H NMR (CDCl3, 400 MHz) 7.66 (s, 1H) 5.85-6.07 (m, 1H) 3.38-3.60 (m, 2H) 3.03 (s, 3H) 2.94 (s, 3H) 2.88 (t, J=7.30 Hz, 2H) 2.68 (t, J=7.43 Hz, 2H) 2.54 (s, 3H) 2.34-2.48 (m, 2H) 1.97-2.14 (m, 2H) 1.78-1.91 (m, 2H) 1.62-1.75 (m, 3H) 1.27 (t, J=7.18 Hz, 3H).

Example 13

8-Cyclopentyl-2-(ethylamino)-6-(3-hydroxypropyl)-4-methylpyrido[2,3-d]pyrimidin-7(8H)-one (Compound 129)

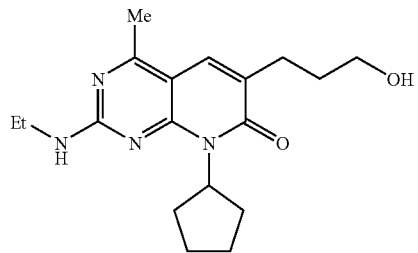

Ethyl-3-(8-cyclopentyl-2-(ethylamino)-4-methyl-7-oxo-7,8-dihydropyrido[2,3-d]pyrimidin-6-yl) propanoate (60 mg, 0.16 mmole) was dissolved in ethanol (5 ml) and methanol (2 ml). Sodium borohydride (18 mg, 0.48 mmole) was slowly added to the reaction solution. The reaction progress was monitored by LCMS. More sodium borohydride was added in portions to push the reaction to completion after 20 h at ambient temperature. The reaction was quenched with water, and the solvents were removed under reduced pressure to dryness. Water (15 ml) was added, and the product was extracted with ethyl acetate (3×30 ml). The organic layer was dried over sodium sulfate, and the solvent was removed under reduced pressure to a residue, which was purified by HPLC. The TFA salt form of product was free-based to give the title compound (34 mg, 61% yield).

LCMS: 331 (M+H)+.

1H NMR (CDCl3, 400 MHz) 7.53 (s, 1H) 5.85-6.12 (m, 1H) 3.57-3.65 (m, 2H) 3.51-3.57 (m, 2H) 2.96 (s, 1H) 2.71 (t, J=7.05 Hz, 2H) 2.58 (s, 3H) 2.35 (s, 2H) 1.99-2.12 (m, 2H) 1.79-1.91 (m, 4H) 1.61-1.77 (m, 3H) 1.28 (t, J=7.18 Hz, 3H).

Example 14

8-Cyclopentyl-2-(2-hydroxy-2-methylpropylamino)-6-(3-hydroxyphenyl)-4-methylpyrido[2,3-d]-pyrimidin-7(8H)-one (Compound 114)

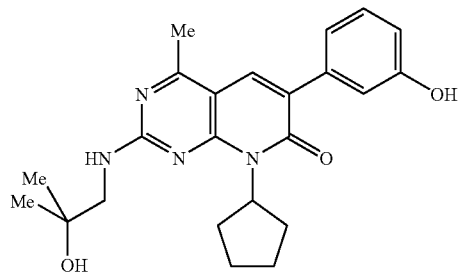

To a solution of 6-bromo-8-cyclopentyl-2-(2-hydroxy-2-methylpropylamino)-4-methylpyrido[2,3-d]pyrimidin-7(8H)-one (52.5 mg, 0.133 mmol), 3-hydroxyphenylboronic acid (20.5 mg, 0.149 mmol), potassium carbonate (3 M, 0.06 mL) in DMF (1.2 mL) was added dichlorobis(triphenylphosphine)palladium(II) (5 mg, 0.007 mmol). The mixture was degassed with N2, sealed and heated for 30 min at 110° C. The mixture was poured into brine and extracted with EtOAc. The EtOAc layer was dried (anhydrous sodium sulfate), filtered, and concentrated under reduced pressure. The crude product was purified by chromatography to give the title compound (12 mg, 22%).

LRMS: 409 (M+H)+.

1H NMR (CDCl3, 400 MHz): 7.73 (1H, s), 7.28-7.33 (1H, m), 7.09-7.20 (2H, m), 6.79-6.89 (1H, m), 5.90-6.10 (1H, m), 5.13-5.88 (1H, m), 3.54 (2H, d, J=6.32 Hz), 2.58 (3H, s), 2.25-2.49 (2H, m), 1.96-2.18 (2H, m), 1.79-1.95 (2H, m), 1.63-1.77 (4H, m), 1.31 (6H, s).

Example 15

6-Bromo-8-cyclopentyl-2-(2-hydroxy-2-methylpropylamino)-4-methylpyrido[2,3-d]pyrimidin-7(8H)-one

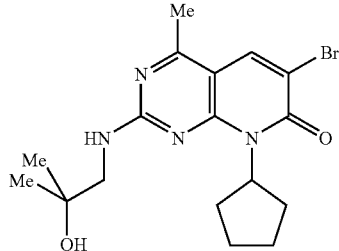

To a solution of 6-bromo-8-cyclopentyl-4-methyl-2-(methylsulfinyl)pyrido[2,3-d]pyrimidin-7(8H)-one (600 mg, 1.62 mmol) and 1-amino-2-methylpropan-2-ol (294 mg, 2.34 mmol) in dioxane (6 mL) was added triethylamine (1.2 mL, 8.6 mmol). The mixture was then heated at 110° C. in a sealed tube for 1 h. The solution was poured into brine and extracted with ethyl acetate. The organic was dried (anhydrous sodium sulfate), filtered and concentrated to dryness. The crude product was purified by silica gel flash chromatography to give the title compound as a solid (565 mg, 88%).

LRMS: 395, 397 (M+H)+.

1H NMR (CDCl3, 400 MHz): 8.07 (1H, s), 5.91-6.13 (1H, m), 5.46-5.90 (1H, m), 3.52 (2H, d, J=6.32 Hz), 2.54 (3H, s), 2.17-2.43 (2H, m), 1.95-2.16 (2H, m), 1.76-1.95 (2H, m), 1.56-1.74 (3H, m), 1.30 (6H, s).

Example 16

8-Cyclopentyl-2-(2-hydroxy-2-methylpropylamino)-6-(6-methoxypyridin-3-yl)-4-methylpyrido[2,3-d]pyrimidin-7(8H)-one (Compound 116)

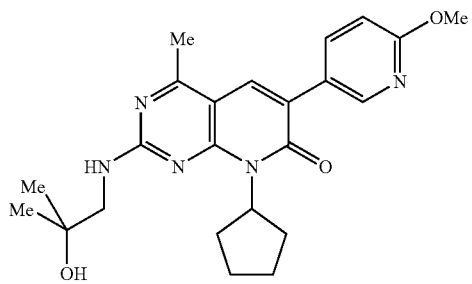

To a solution of 6-bromo-8-cyclopentyl-2-(2-hydroxy-2-methylpropylamino)-4-methyl-pyrido[2,3-d]pyrimidin-7(8H)-one (50 mg, 0.126 mmol), 6-methoxypyridin-3-ylboronic acid (21 mg, 0.137 mmol), potassium carbonate (3 M, 0.06 mL) in DMF (1.2 mL) was added dichlorobis(triphenylphosphine)palladium(II) (4.5 mg, 0.0064 mmol). The mixture was degassed with $N_2$, sealed and heated for 30 min at 110° C. The solvent was removed under reduced pressure. The crude mixture was purified by chromatography to give the title compound (23.6 mg, 44%).

LRMS: 424 (M+H)+.

$^1$H NMR (CDCl$_3$, 400 MHz): 8.31 (1H, d, J=2.27 Hz), 7.97 (1H, dd, J=8.59, 2.53 Hz), 7.72 (1H, s), 6.81 (1H, d, J=8.59 Hz), 5.88-6.12 (1H, m), 5.28-5.86 (1H, m), 3.97 (3H, s), 3.55 (2H, d, J=6.32 Hz), 2.59 (3H, s), 2.26-2.47 (2H, m), 1.98-2.17 (2H, m), 1.79-1.98 (2H, m), 1.65-1.77 (3H, m), 1.32 (6H, s).

Example 17

8-Cyclopentyl-4-methyl-2-(methylamino)-6-(pyrimidin-5-yl)pyrido[2,3-d]pyrimidin-7(8H)-one (Compound 107)

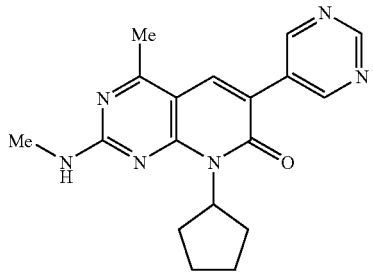

Following the procedure described in Preparation of Example 14, using 6-bromo-8-cyclopentyl-4-methyl-2-(methylamino)pyrido[2,3-d]pyrimidin-7(8H)-one in place of 6-bromo-8-cyclopentyl-2-(2-hydroxy-2-methylpropylamino)-4-methylpyrido[2,3-d]pyrimidin-7(8H)-one, pyrimidin-5-ylboronic acid in place of 3-hydroxyphenylboronic acid, the title compound was obtained in 10% yield.

LRMS: 337 (M+H)+.

$^1$H NMR (CDCl$_3$, 400 MHz): 9.19 (1H, s), 9.03 (1H, s), 7.80 (1H, s), 5.69-6.29 (1H, m), 3.11 (3H, d, J=5.05 Hz), 2.65 (3H, s), 2.27-2.54 (2H, m), 1.97-2.25 (4H, m), 1.82-1.97 (2H, m), 1.51-1.80 (2H, m).

Example 18

8-Isopropyl-6-(6-methoxypyridin-3-yl)-4-methyl-2-(methylamino)pyrido[2,3-d]pyrimidin-7(8H)-one (Compound 113)

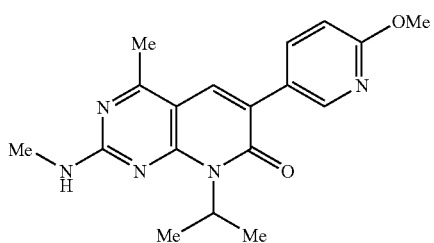

Following the procedure described in Preparation of Example 14, using 6-bromo-8-isopropyl-4-methyl-2-(methylamino)pyrido[2,3-d]pyrimidin-7(8H)-one in place of 6-bromo-8-cyclopentyl-2-(2-hydroxy-2-methylpropylamino)-4-methylpyrido[2,3-d]pyrimidin-7(8H)-one, the title compound was obtained in 11% yield.

LRMS: 340 (M+H)+.

$^1$H NMR (CDCl$_3$, 400 MHz) 8.31 (1H, d, J=2.02 Hz), 7.99 (1H, dd, J=8.72, 2.40 Hz), 7.71 (1H, s), 6.80 (1H, d, J=8.59 Hz), 5.72-6.03 (1H, m), 3.97 (3H, s), 3.09 (3H, d, J=5.05 Hz), 2.58 (3H, s), 1.65 (6H, d, J=6.82 Hz).

Example 19

6-Bromo-8-isopropyl-4-methyl-2-(methylamino)pyrido[2,3-d]pyrimidin-7(8H)-one

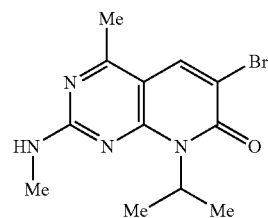

To a stirred solution of 6-bromo-8-isopropyl-4-methyl-2-(methylsulfinyl)pyrido[2,3-d]pyrimidin-7(8H)-one (175 mg, 0.508 mmol) in 1,4-dioxane (2.5 mL) was added methyl amine (0.80 mL, 2.0 M in THF, 1.6 mmol). The mixture was sealed and heated at 110° C. microwave for 15 min. The solvent was evaporated and the crude product was washed with EtOAc/Hexane to give the title compound (158 mg, 76%).

LRMS: 311, 313 (M+H)+.

$^1$H NMR (CDCl$_3$, 400 MHz): 8.06 (1H, s), 5.55-6.19 (1H, m), 5.19-5.46 (1H, m), 3.07 (3H, d, J=5.05 Hz), 2.52 (3H, s), 1.62 (6H, d, J=6.32 Hz).

Example 20

6-Bromo-8-isopropyl-4-methyl-2-(methylsulfinyl)pyrido[2,3-d]pyrimidin-7(8H)-one

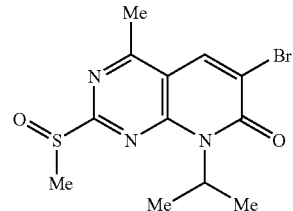

To a stirred and cooled (−20° C.) solution of 6-bromo-8-isopropyl-4-methyl-2-(methylthio)-pyrido[2,3-d]pyrimidin-7(8H)-one (380 mg, 1.16 mmol) in CH$_2$Cl$_2$ (25 mL) was added MCPBA (340 mg, 77%, 1.52 mmol). After stirring for 30 min (−20° C. to 0° C.), the mixture was quenched with saturated aqueous NaHCO$_3$, extracted with EtOAc, dried and evaporated. The crude product was washed with EtOAc/Hexane to give the title compound (190 mg, 48%).

LRMS: 344, 346 (M+H)+.

$^1$H NMR (DMSO-d6, 400 MHz): 8.78 (1H, s), 5.60-5.97 (1H, m), 2.92 (3H, s), 2.79 (3H, s), 1.56 (6H, d, J=6.82 Hz).

Example 21

6-Bromo-8-isopropyl-4-methyl-2-(methylthio)pyrido[2,3-d]pyrimidin-7(8H)-one

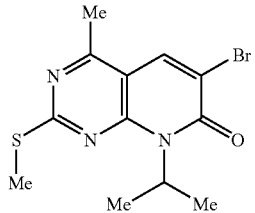

To a suspension of NaH (120 mg, 5.00 mmol) in DMF (15 mL) was added 6-bromo-4-methyl-2-(methylthio)pyrido[2,3-d]pyrimidin-7(8H)-one (572 mg, 2 mmol). The mixture was heated to 46° C. The solution was cooled down slightly and 2-iodopropane (0.30 mL, 3.0 mmol) was added. The mixture was heated at 46° C. for 30 min and then cooled to room temperature and partitioned between water and ethyl acetate. The organic phase was dried (MgSO$_4$) and concentrated. The crude product was purified by silica gel flash chromatography, using EtOAc/Hexane, to give the title compound (390 mg, 59%).

LRMS: 328, 330 (M+H)$^+$.

$^1$H NMR (DMSO-d6, 400 MHz): 8.60 (1H, s), 5.45-5.99 (1H, m), 2.64 (3H, s), 2.58 (3H, s), 1.54 (6H, d, J=6.82 Hz).

Example 22

6-(5-(Aminomethyl)-2-fluorophenyl)-8-cyclopentyl-4-methyl-2-(methylamino)pyrido[2,3-d]pyrimidin-7(8H)-one (Compound 104)

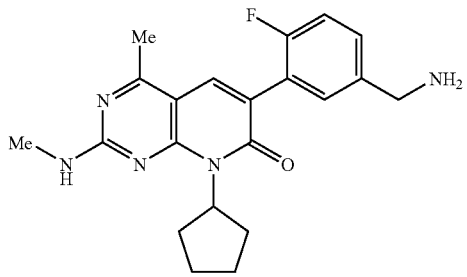

To a solution of 8-cyclopentyl-4-methyl-2-(methylamino)-7-oxo-7,8-dihydropyrido[2,3-d]pyrimidin-6-ylboronic acid (30 mg, 0.099 mmol), 3-bromo-4-fluorobenzylamine hydrochloride (28.7 mg, 0.119 mmol), potassium carbonate (3 M, 0.10 mL) in DME (0.5 mL) and EtOH (0.5 mL) was added tetrakis(triphenylphosphine) palladium(0) (6 mg, 0.005 mmol). The mixture was degassed with N$_2$, sealed and heated for 1 h at 100° C. in microwave. The mixture was removed under reduced pressure. The crude product was purified by chromatography to give the title compound (16.4 mg, 43.3%).

LRMS: 382 (M+H)$^+$.

$^1$H NMR (CDCl$_3$, 400 MHz): 7.73 (1H, s), 7.46 (1H, d, J=6.06 Hz), 7.29-7.40 (1H, m), 7.07 (1H, t, J=8.84 Hz), 6.14-6.73 (1H, m), 5.78-6.12 (1H, m), 3.84-4.11 (2H, m), 3.08 (3H, d, J=4.80 Hz), 2.48-2.67 (4H, m), 2.32 (3H, d, J=6.57 Hz), 1.91-2.06 (2H, m), 1.75-1.91 (2H, m), 1.51-1.72 (2H, m).

Example 23

8-Cyclopentyl-4-methyl-2-(methylamino)-7-oxo-7,8-dihydropyrido[2,3-d]pyrimidin-6-ylboronic acid

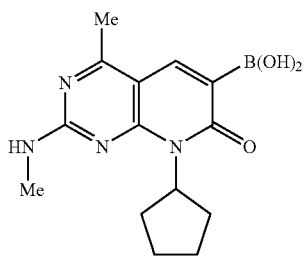

To a stirred and cooled (−78° C.) solution of 6-bromo-8-cyclopentyl-4-methyl-2-(methylamino)-pyrido[2,3-d]pyrimidin-7(8H)-one (1.00 g, 2.94 mmol) and trimethylborate (1.40 mL, 12.6 mmol) in THF (60 mL) was added BuLi (9.5 mL, 1.6 M, 15.2 mmol). After stirring for 20 min, the mixture was quenched with small amount of 2 N HCl and water, extracted with EtOAc (3 times), dried and evaporated. The crude mixture was purified by silica gel chromatography to give the title compound (157.2 mg, 18%).

LRMS: 303 (M+H)$^+$.

$^1$H NMR (DMSO-d6, 400 MHz): 8.58 (1H, s), 8.57 (1H, s), 8.36 (1H, s), 7.58-8.03 (1H, m), 5.64-6.14 (1H, m), 2.79-2.98 (3H, m), 2.52-2.62 (3H, m), 2.12-2.41 (2H, m), 1.87-2.12 (2H, m), 1.44-1.86 (4H, m).

Example 24

6-(6-Methoxypyridin-3-yl)-4-methyl-2-(methylamino)pyrido[2,3-d]pyrimidin-7(8H)-one (Compound 153)

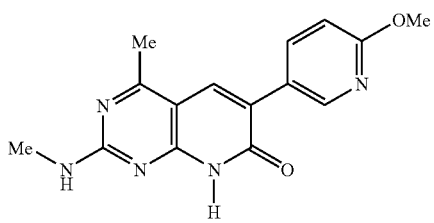

To a solution of 6-(6-methoxypyridin-3-yl)-4-methyl-2-(methylsulfinyl)pyrido[2,3-d]pyrimidin-7(8H)-one (147 mg, 0.445 mmol) in 1,4-dioxane (2.5 mL) was added methylamine (1.1 mL, 2.0 M in THF, 2.2 mmol). The mixture was sealed and heated at 110° C. microwave for 10 min. The mixture was concentrated under reduced pressure to give a solid. The crude solid was washed with water and EtOAc, recrystallized from DMSO/EtOAc to give the title compound (80 mg, 61%).

LRMS: 298 (M+H)$^+$.

$^1$H NMR (DMSO-d6, 400 MHz): 11.68-12.05 (1H, m), 8.50 (1H, d, J=1.77 Hz), 8.05 (1H, dd, J=8.59, 2.53 Hz), 8.02 (1H, s), 7.23-7.71 (1H, m), 6.86 (1H, d, J=8.59 Hz), 3.89 (3H, s), 2.86 (3H, d, J=4.29 Hz), 2.54 (3H, s).

Example 25

6-(6-Methoxypyridin-3-yl)-4-methyl-2-(methylamino)pyrido[2,3-d]pyrimidin-7(8H)-one

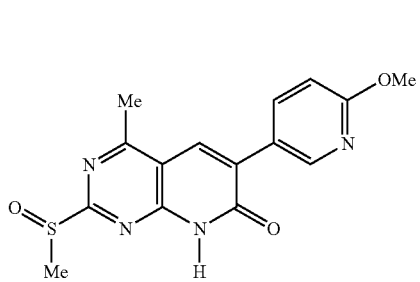

Following the procedure described in Example 20, using 6-(6-methoxypyridin-3-yl)-4-methyl-2-(methylthio)pyrido[2,3-d]pyrimidin-7(8H)-one in place of 6-bromo-8-isopropyl-4-methyl-2-(methylthio)-pyrido[2,3-d]pyrimidin-7(8H)-one, the title compound was used as crude to the next step.

LRMS: 331 (M+H)$^+$.

Example 26

6-(6-Methoxypyridin-3-yl)-4-methyl-2-(methylthio)pyrido[2,3-d]pyrimidin-7(8H)-one

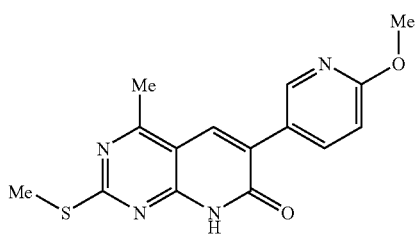

To a solution of 6-bromo-4-methyl-2-(methylthio)pyrido[2,3-d]pyrimidin-7(8H)-one (50 mg, 0.17 mmol), 6-methoxypyridin-3-ylboronic acid (40.1 mg, 1.1 equiv), dichlorobis(triphenylphosphine) palladium(II) (6.13 mg, 0.008 mmol), DMF (2 mL) in a 5 mL microwave vial was added potassium carbonate (3 M, 1.1 equiv). The solution was degassed with N$_2$ for 10 min before being capped and heated in the microwave reactor for 1 h. at 100° C. The reaction was poured into 20 ml brine and the precipitate was collected by filtration. It was further purified by chromatography (80% thylacetate/hexane). The title compound was obtained as a solid (30 mg, 55% yield).

LRMS: 315.0 (ES+)

$^1$H NMR (DMSO-d6, 400 MHz): 12.54 (1H, s), 8.56 (1H, d, J=2.27 Hz), 8.20 (1H, s), 8.10 (1H, dd, J=8.72, 2.40 Hz), 6.90 (1H, d, J=8.59 Hz), 3.90 (3H, s), 2.70 (3H, s), 2.57 (3H, s).

Example 27

8-Cyclobutyl-6-(6-methoxypyridin-3-yl)-4-methyl-2-(methylamino)pyrido[2,3-d]pyrimidin-7(8H)-one (Compound 109)

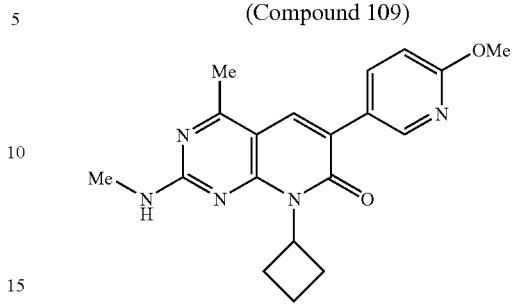

Following the procedure described in Example 22, using 8-cyclobutyl-6-(6-methoxypyridin-3-yl)-4-methyl-2-(methylsulfinyl)pyrido[2,3-d]pyrimidin-7(8H)-one in place of 6-(6-methoxypyridin-3-yl)-4-methyl-2-(methylsulfinyl)pyrido[2,3-d]pyrimidin-7(8H)-one, the title compound was obtained in 35% yield.

LRMS: 352 (M+H)$^+$.

$^1$H NMR (CDCl$_3$, 400 MHz): 8.31 (1H, d, J=2.02 Hz), 7.98 (1H, dd, J=8.72, 2.40 Hz), 7.71 (1H, s), 6.80 (1H, d, J=8.59 Hz), 5.76-6.10 (1H, m), 5.41 (1H, s), 3.97 (1H, s), 3.18-3.44 (2H, m), 3.12 (3H, d, J=5.05 Hz), 2.56 (3H, s), 2.24-2.46 (2H, m), 2.01 (1H, q, J=10.36 Hz), 1.78-1.93 (1H, m).

Example 28

8-Cyclobutyl-6-(6-methoxypyridin-3-yl)-4-methyl-2-(methylsulfinyl)pyrido[2,3-d]pyrimidin-7(8H)-one

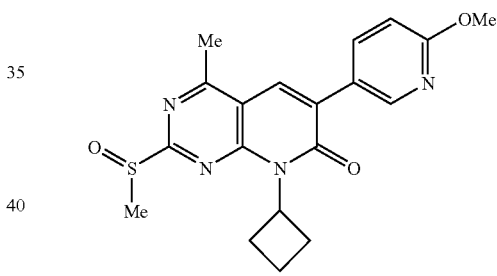

Following the procedure described in Example 24, using 8-cyclobutyl-6-(6-methoxypyridin-3-yl)-4-methyl-2-(methylthio)pyrido[2,3-d]pyrimidin-7(8H)-one in place of 6-bromo-8-isopropyl-4-methyl-2-(methylthio)-pyrido[2,3-d]pyrimidin-7(8H)-one, the title compound was used as crude to the next step.

LRMS: 385 (M+H)$^+$.

Example 29

8-Cyclobutyl-6-(6-methoxypyridin-3-yl)-4-methyl-2-(methylthio)pyrido[2,3-d]pyrimidin-7(8H)-one

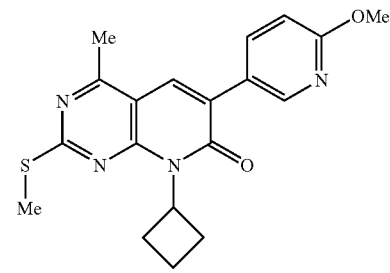

Following the procedure described in Example 12, using 6-bromo-8-cyclobutyl-4-methyl-2-(methylthio)pyrido[2,3-d]pyrimidin-7(8H)-one in place of 6-bromo-8-cyclopentyl-2-(2-hydroxy-2-methylpropylamino)-4-methylpyrido[2,3-d]pyrimidin-7(8H)-one, the title compound was obtained in 78% yield.

LRMS: 369 (M+H)$^+$.

$^1$H NMR (CDCl$_3$, 400 MHz): 8.35 (1H, d, J=2.53 Hz), 7.99 (1H, dd, J=8.59, 2.53 Hz), 7.79 (1H, s), 6.82 (1H, d, J=8.59 Hz), 5.80-6.13 (1H, m), 3.98 (3H, s), 3.07-3.41 (2H, m), 2.69 (3H, s), 2.68 (3H, s), 2.29-2.52 (2H, m), 1.78-2.11 (2H, m).

Example 30

6-Bromo-8-cyclobutyl-4-methyl-2-(methylthio)pyrido[2,3-d]pyrimidin-7(8H)-one (Compound 100); 6-bromo-7-cyclobutoxy-4-methyl-2-(methylthio)pyrido[2,3-d]pyrimidine (Compound 99)

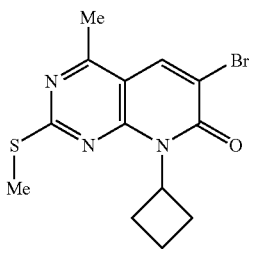

100

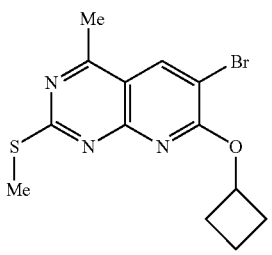

99

To a solution of 6-bromo-4-methyl-2-(methylthio)pyrido[2,3-d]pyrimidin-7(8H)-one (500 mg, 1.75 mmol) and cyclobutanol (164 mg, 2.27 mmol) in THF (40 mL) was added triphenylphosphine (917 mg, 3.49 mmol) and DEAD (852 mg, 4.89 mmol). After 2 h, the mixture was poured into brine, extracted with ethyl acetate, dried (anhydrous Na$_2$SO$_4$) and evaporated. The mixture was purified by chromatography to give Compound 100 (97 mg, 16%) and Compound 99 (180 mg, 30%).

LRMS: 340, 342 (M+H)$^+$.

Compound 100:

$^1$H NMR (CDCl$_3$, 400 MHz): 8.18 (1H, s), 5.78-6.12 (1H, m), 3.03-3.34 (2H, m), 2.66 (3H, s), 2.65 (3H, s), 2.25-2.48 (2H, m), 1.95-2.18 (1H, m), 1.71-1.95 (1H, m).

Compound 99:

$^1$H NMR (CDCl$_3$, 400 MHz): 8.38 (1H, s), 5.45-5.74 (1H, m), 2.77 (3H, s), 2.69 (3H, s), 2.53-2.66 (2H, m), 2.17-2.37 (2H, m), 1.81-1.98 (1H, m), 1.65-1.81 (1H, m).

Example 31

2-Amino-8-cyclopentyl-6-(1-(2-hydroxyethyl)-1H-pyrazol-4-yl)-4-methylpyrido[2,3-d]pyrimidin-7(8H)-one (Compound 106)

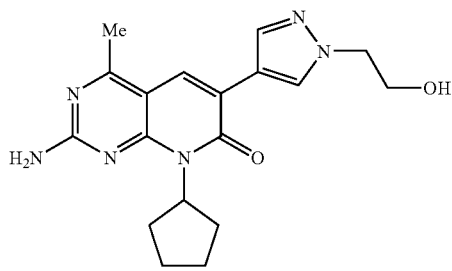

To the solution of 8-cyclopentyl-6-(1-(2-(methoxymethoxy)ethyl)-1H-pyrazol-4-yl)-4-methyl-2-(methylsulfonyl)pyrido[2,3-d]pyrimidin-7(8H)-one (80 mg, 0.17 mmol) in 5 ml 1,4-dioxane was babbled through ammonium gas for 10 minutes. The reaction tube was sealed and heated to 100° C. for 30 minutes. The reaction mixture was poured into brine and the precipitate was collected via filtration. The solid was then re-dissolved in 5 ml methanol and a few drop of concentrated HCl was added and the mixture was heated to 50° C. for 5 hours. The reaction mixture was cooled down to room temperature. Solvent was removed via rot vap and the residue was triturated with ethylacetate/hexane to give the title compound (33 mg, 54% yield).

LCMS: 355.20 (ES+)

$^1$H NMR (DMSO-d$_6$, 400 MHz): 8.44 (s, 1H), 8.17 (d, J=4.29 Hz, 2H), 7.11 (s, 2H), 6.21-6.02 (m, 1H), 4.96 (s, 1H), 4.23 (t, J=5.56 Hz, 2H), 3.81 (t, J=5.18 Hz, 2H), 2.64 (s, 3H), 2.39-2.22 (m, 2H), 2.19-2.06 (m, 2H), 1.88-1.74 (m, 2H), 1.74-1.56 (m, 2H).

Example 32

8-Cyclopentyl-6-(1-(2-(methoxymethoxy)ethyl)-1H-pyrazol-4-yl)-4-methyl-2-(methylsulfonyl)pyrido[2,3-d]pyrimidin-7(8H)-one

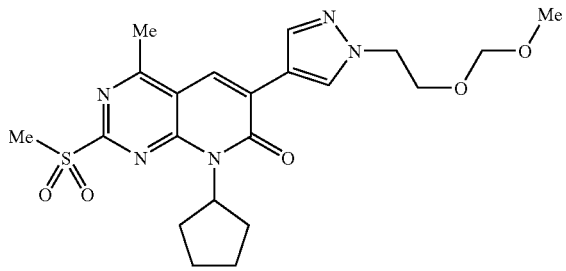

m-CPBA (209 mg, 2.0 equiv.) was added into the solution of 8-cyclopentyl-6-(1-(2-(methoxymethoxy)ethyl)-1H-pyrazol-4-yl)-4-methyl-2-(methylthio)pyrido[2,3-d]pyrimidin-7(8H)-one (200 mg, 0.46 mmol) in 10 ml methylene chloride at room temperature. It was stirred at room temperature for 2 hour. The solvent was removed via rot vap and the residue was purified by chromatography (30 to 80% ethylacetate/hexane) to give the title compound (166 mg, 77% yield).

LCMS: 462.1 (ES+)

¹H NMR (CDCl₃, 400 MHz): 8.51 (s, 1H), 8.04 (s, 1H), 8.01 (s, 1H), 6.13-6.00 (m, 1H), 4.61 (s, 2H), 4.40 (t, J=5.31 Hz, 2H), 3.97 (t, J=5.31 Hz, 2H), 3.39 (s, 3H), 3.30 (s, 3H), 2.91 (s, 3H), 2.40-2.28 (m, 2H), 2.24-2.12 (m, 2H), 2.03-1.91 (m, 2H), 1.81-1.70 (m, 2H).

Example 33

8-Cyclopentyl-6-(1-(2-(methoxymethoxy)ethyl)-1H-pyrazol-4-yl)-4-methyl-2-(methylthio)pyrido[2,3-d]pyrimidin-7(8H)-one

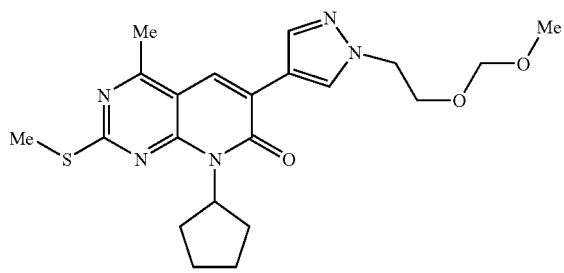

To a solution of 6-bromo-8-cyclopentyl-4-methyl-2-(methylthio)pyrido[2,3-d]pyrimidin-7(8H)-one (200 mg, 0.56 mmol), 1-(2-(methoxymethoxy)ethyl)-4-(4,4,5,5-tetramethyl-1,3,2-dioxaborolan-2-yl)-1H-pyrazole (239 mg, 1.5 equiv), palladium (0) tetrakis(triphenylphosphine) (6.13 mg, 0.05 equiv.), DMF (2 mL) in a 5 mL microwave vial was added potassium carbonate (3 M, 3.0 equiv). The solution was degassed with N₂ for 10 min before being capped and heated in the microwave reactor for 30 min. at 100° C. The reaction was poured into 20 ml brine and the precipitate was collected by filtration. The title compound was obtained as a solid (208 mg, 86% yield). It was used for next step without further purification.

LRMS: 430.0 (ES+).

Example 34

8-Cyclopentyl-6-(1-(2-hydroxyethyl)-1H-pyrazol-4-yl)-4-methyl-2-(methylamino)pyrido[2,3-d]pyrimidin-7(8H)-one (Compound 105)

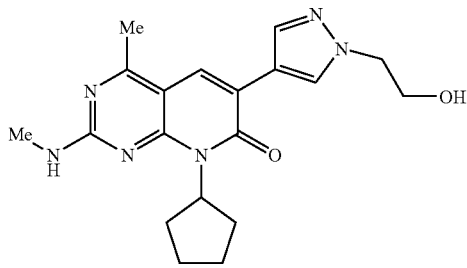

8-cyclopentyl-6-(1-(2-(methoxymethoxy)ethyl)-1H-pyrazol-4-yl)-4-methyl-2-(methylsulfonyl)pyrido[2,3-d]pyrimidin-7(8H)-one (80 mg, 0.17 mmol) was dissolved into 3 ml methylamine in THF (1.0 M). The reaction mixture was then heated to 100° C. in microwave for 30 minutes. The solvent was removed via rot vap and the residue was re-dissolved in 5 ml methanol. A few drop of concentrated HCl was added the mixture was heated to 50° C. for 5 hours. The reaction mixture was cooled down to room temperature. Solvent was removed via rot vap and the residue was triturated with ethylacetate/hexane to give the title compound (45 mg, 70% yield).

LRMS: 369.20 (ES+)

¹H NMR (CDCl₃, 400 MHz): 8.33 (s, 1H), 7.91 (s, 1H), 7.84 (s, 1H), 6.11-5.98 (m, 1H), 4.34-4.24 (m, 2H), 4.08-4.00 (m, 2H), 3.09 (d, J=5.05 Hz, 3H), 2.65 (s, 3H) 2.50-2.37 (m, 2H) 2.15-2.04 (m, 2H) 1.94-1.83 (m, 2H) 1.79-1.64 (m, 2H).

Example 35

8-Cyclopentyl-6-(3-(hydroxymethyl)phenyl)-4-methyl-2-(methylamino)pyrido[2,3-d]pyrimidin-7(8H)-one (Compound 148)

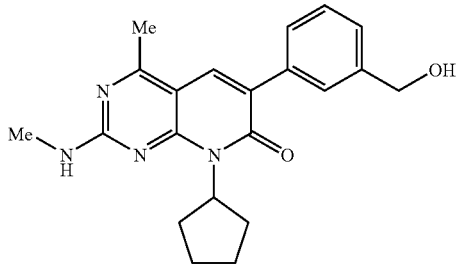

6-Bromo-8-cyclopentyl-4-methyl-2-methylamino-8H-pyrido[2,3-d]pyrimidin-7-one (5.00 g, 14.83 mmol), 3-(hydroxymethyl)phenylboronic acid (3.38 g, 22.24 mmol) and Pd(PPh₃)₄ (0.685 g, 0.593 mmol) were suspended in Toluene (20 mL), MeOH (10 mL) and sat. NaHCO₃ (10 mL) and then heated to 100° C. overnight. The reaction was deemed complete by MS and TLC. The organic layer was injected directly onto a column, eluting with CH₂Cl₂ then 4% MeOH in CH₂Cl₂. The fractions containing the desired material, as deemed by MS, were combined and evaporated in vacuo to give a greenish beige solid. This was triturated with MeCN and filtered to give crop one, 4.7 g. A second crop was obtained of 0.25 g. A third crop was obtained of 0.10 g. The three crops were deemed to be of sufficient purity based on NMR's and were combined and washed again with MeCN to give a solid (4.39 g, 81.24%).

Elemental Analysis: Calcd for C₂₁H₂₄N₄O₂, C, 69.21/69.00; H, 6.64/6.65; N, 15.37/15.16.

LRMS (M+H)⁺: 365.1

¹H NMR (CDCl₃, 400 MHz): 7.73 (1H, s) 7.61 (1H, s), 7.53 (1H, d, J=7.57 Hz), 7.40 (1H, t, J=7.69 Hz), 7.34 (1H, d, J=7.57 Hz), 6.04 (1H, m), 5.27 (1H, s), 4.74 (2H, d, J=6.11 Hz), 3.06 (3H, d, J=5.13 Hz), 2.56 (3H, s), 2.40 (2H, m), 2.05 (2H, m), 1.66 (2H, m).

Example 36

6-Bromo-8-cyclopentyl-4-methyl-2-(methylamino)pyrido[2,3-d]pyrimidin-7(8H)-one

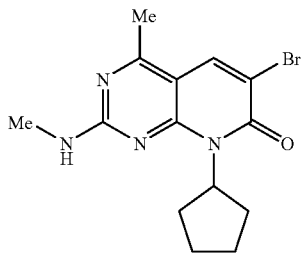

6-Bromo-8-cyclopentyl-2-methanesulfinyl-4-methyl-8H-pyrido[2,3-d]pyrimidin-7-one (8.00 g, 22.04 mmol) was dissolved in 100 mL of CH$_2$Cl$_2$, then NH$_2$Me was bubbled in for 3 minutes. The reaction was diluted with CH$_2$Cl$_2$ and washed with water. The organic layer was dried over Na$_2$SO$_4$ and the solvent evaporated in vacuo to give an off white solid. The material was diluted with CH$_2$Cl$_2$ and purified by silica gel chromatography to give an off white solid (7.33 g, 98.42%).

LRMS: 337.1, 339.1 (M+H)$^+$.

$^1$H NMR (CDCl$_3$, 400 MHz): 8.06 (1H, s), 6.04 (1H, s), 5.31 (1H, br s), 3.04 (3H, d, J=4.88 Hz), 2.51 (3H, s), 2.29-2.36 (2H, m), 2.03-2.13 (2H, m), 1.80-1.89 (2H, m), 1.61-1.68 (2H, m).

Example 37

8-(4-Methoxybenzyl)-6-bromo-4-methyl-2-(methylthio)pyrido[2,3-d]pyrimidin-7(8H)-one

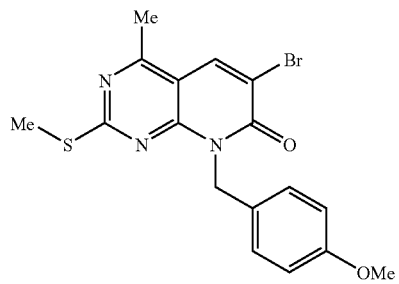

To a mixture of sodium hydride (60% dispersion in mineral oil) (90 mg, 1.5 equiv.) and anhydrous DMF (5 mL) was added 6-bromo-4-methyl-2-(methylthio)pyrido[2,3-d]pyrimidin-7(8H)-one (429 mg, 1.5 mmol) and the mixture stirred for 30 minutes at 50° C. Solution was then cooled a little and p-methoxybenzylchloride (281 mg, 1.2 equiv) in 1 mL DMF was then added dropwise. Heated to 50° C. for 3 hours and then stirred at rt overnight. Cooled to rt, partitioned between water and AcOEt, water further washed with AcOEt, pooled organic extracts washed with saturated sodium bicarbonate, brine and dried over MgSO4. Filtration and solvent removal afforded crude material which was used without further purification. Yield 675 mg.

LRMS (APCI) 406.3/408.3 (M+H)$^+$.

$^1$H NMR (CDCl$_3$, 400 MHz) 8.19 (s, 1H), 7.45 (d, 2H), 6.79 (d, J=8.72 Hz, 2H), 5.62 (s, 2H), 3.75 (s, 3H), 2.64 (s, 3H), 2.63 (s, 3H).

Example 38

8-(4-Methoxybenzyl)-4-methyl-2-(methylthio)-6-phenylpyrido[2,3-d]pyrimidin-7(8H)-one

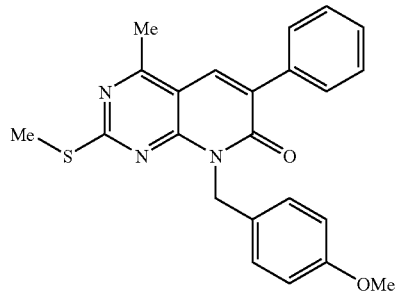

Ref. JMC 2004, 47 (16), p. 4097

To a mixture of bromoolefin (203 mg, 0.5 mmol) in toluene (5 mL) and ethanol (5 mL) was added saturated sodium bicarbonate (5 mL), palladium tetrakis(triphenylphosphine) (29 mg, 5 mol. %), followed by phenylboronic acid (73 mg, 1.2 equiv.). Mixture was heated to 100° C. for 3 hours. Cooled to room temperature, diluted with EA and water, phases separated, aqueous phase washed 2× with 10 mL of EA, combined organic phases washed with brine and dried over MgSO$_4$. Filtered and stripped to give light brown solid (166 mg, 82%). Used without purification.

$^1$H NMR (CDCl$_3$, 400 MHz) 7.87 (s, 1H), 7.65 (d, J=7.89 Hz, 2H), 7.38-7.48 (m, 5H), 7.11-7.20 (m, 2H), 2.70 (s, 3H), 2.60 (s, 3H), 2.35 (s, 3H).

Example 39

8-(4-Methoxybenzyl)-4-methyl-2-(methylsulfonyl)-6-phenylpyrido[2,3-d]pyrimidin-7(8H)-one

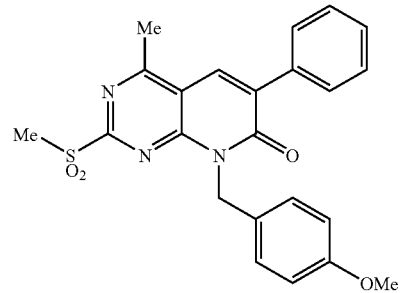

A mixture of methyl sulfide (150 mg, 0.372 mmol), m-chloroperbenzoic acid (129 mg, 2 equiv.) in dichloromethane (5 mL) was stirred at rt for 4 hours. Solvent was then removed and crude material (232 mg) used for next step without purification.

Example 40

8-(4-Methoxybenzyl)-2-amino-4-methyl-6-phenylpyrido[2,3-d]pyrimidin-7(8H)-one (Compound 149)

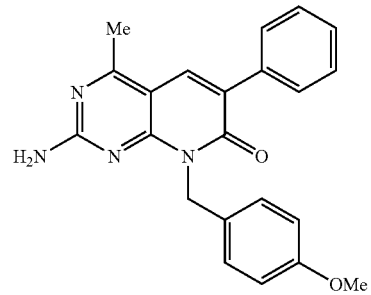

The crude sulfone compound (220 mg) was dissolved in freshly prepared saturated ammonia/THF solution and the mixture heated to reflux overnight. Stripped, partitioned between EA and aqueous saturated sodium bicarbonate, organic portion washed with brine, dried over MgSO₄, filtered and stripped. Purified on Biotage flash column using 1:2 hexane/EA. Yellow foam, 55 mg (76%).

LRMS (APCI): 373.4 (M+H)⁺.

¹H NMR (CDCl₃, 400 MHz) 7.77 (s, 1H), 7.62 (d, J=7.06 Hz, 2H), 7.51 (d, J=8.72 Hz, 2H), 7.32-7.43 (m, 3H), 6.79 (d, J=8.72 Hz, 2H), 5.55 (s, 2H), 5.31 (s, 2H), 3.74 (s, 3H), 2.59 (s, 3H)

Example 41

8-(4-Chlorobenzyl)-6-bromo-4-methyl-2-(methylthio)pyrido[2,3-d]pyrimidin-7(8H)-one

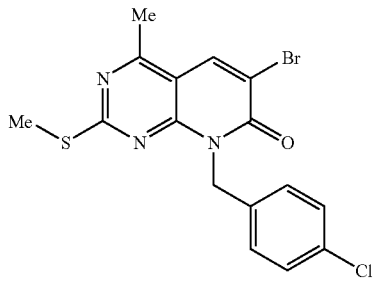

To the solution of NaH (90 mg, 2.25 mmol, 1.5 equiv.) in DMF (5 mL) was at rt added lactam compound (429 mg, 1.5 mmol) and the mixture heated to 50° C. for 30 minutes. Cooled to rt, added p-chlorobenzyl bromide (370 mg, 1.8 mmol, 1.2 equiv.) as a solution in DMF (1 mL). Heated to 50° C. for 3 hours. Cooled, diluted with water, extracted 3× with. Organic portions combined and washed with brine and dried over MgSO4, filtered and stripped. Orange-brown solid (605 mg, 98% (crude). Used without further purification.

LRMS (APCI) 410.3/412.3 (M+H)⁺

¹H NMR (CDCl₃) 8.22 (s, 1H), 7.40 (d, J=8.72 Hz, 2H), 7.22-7.31 (m, 2H), 5.63 (s, 2H), 2.65 (s, 3H), 2.58 (s, 3H).

Example 42

8-(4-Chlorobenzyl)-4-methyl-2-(methylthio)-6-phenylpyrido[2,3-d]pyrimidin-7(8H)-one

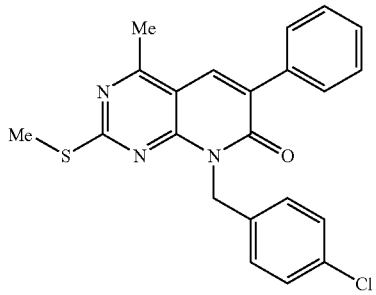

To the solution of bromo compound (205 mg, 0.5 mmol) in toluene/EtOH (5 and 5 mL) was added saturated aqueous sodium bicarbonate (3 mL), palladium tetrakis(triphenylphosphine (29 mg, 5 mol %) and phenylboronic acid (73, 0.6 mmol, 1.2 equiv.). Heated to 100° C. for 2 hours and then allowed to stand at rt for 72 hours. Diluted with EA and water, phases separated, organic phase washed with brine and dried over MgSO4. Filtered and stripped to give light yellow solid, 162 mg (80%). Crude material used without further purification.

LRMS (M+H)⁺: 408.5

Example 43

8-(4-Chlorobenzyl)-4-methyl-2-(methylsulfonyl)-6-phenylpyrido[2,3-d]pyrimidin-7(8H)-one

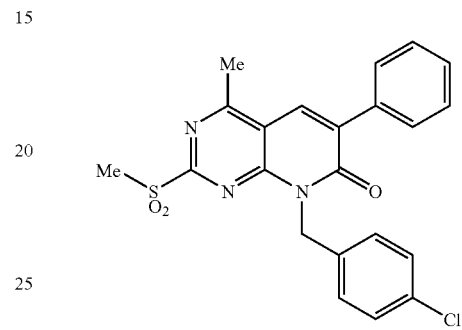

To the solution of methylsulfide (160 mg, 0.39 mmol) in dichloromethane (5 mL) was added m-chloroperbenzoic acid (203 mg, 3 equiv.) in several small portions and the resulting reaction allowed to stir overnight. The reaction mixture was then washed with saturated aqueous sodium bicarbonate (2×), brine and dried over MgSO4. Filtration and concentration gave material as white glassy solid (185 mg) which was used immediately without purification. Product is likely a mixture of sulfoxide and sulfone (LC MS).

LRMS (APCI) (M+H)⁺: 440.5.

Example 44

8-(4-Chlorobenzyl)-2-amino-4-methyl-6-phenylpyrido[2,3-d]pyrimidin-7(8H)-one (Compound 150)

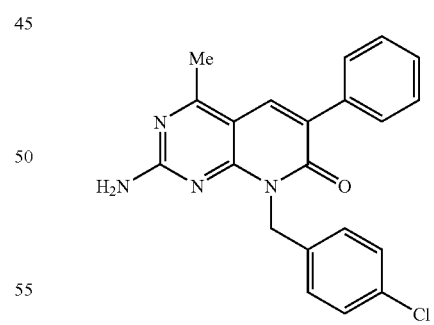

The crude material from previous experiment (150 mg, 0.35 mmol) was dissolved in a freshly prepared ammonia/THF solution and heated to reflux. After 3 hours, the solvent removed under reduced pressure, the product isolated on SCX cartridge and purified on Biotage flash column using EA/hexane 1:1. Light yellow foam (90 mg, 70%).

LRMS (APCI) 377.4 (M+H)⁺,

¹H NMR (400 MHz, CDCl₃): 7.80 (s, 1H), 7.62 (d, 2H), 7.33-7.46 (m, 5H), 7.22 (d, 2H), 5.57 (s, 2H), 5.27 (bs, 2H, NH2), 2.60 (s, 3H).

Example 45

8-(4-Chlorobenzyl)-4-methyl-2-(methylthio)-6-(pyridin-4-yl)pyrido[2,3-d]pyrimidin-7(8H)-one

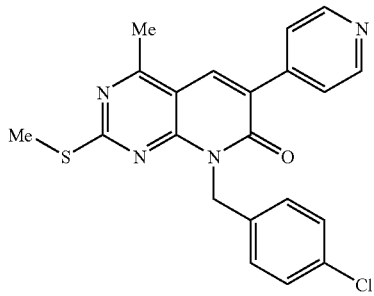

To the solution of bromo compound (150 mg, 0.366 mmol), prepared as described in Example 41, in toluene/EtOH (2 and 2 mL) was added saturated aqueous sodium bicarbonate (1 mL), palladium tetrakis(triphenylphosphine (21 mg, 5 mol. %) and 4-pyridylboronic acid (54 mg, 1.2 equiv.). The reaction mixture was heated to 100° C. for 2 hours and then allowed to stand at rt for 72 hours. Diluted with EA and water, phases separated, organic phase washed with brine and dried over MgSO4. Crude material (148 mg, 96%) analyzed by TLC and LC MS and used without further purification.

LRMS (M+H)+: 409.2

Example 46

8-(4-Chlorobenzyl)-4-methyl-2-(methylsulfonyl)-6-(pyridin-4-yl)pyrido[2,3-d]pyrimidin-7(8H)-one

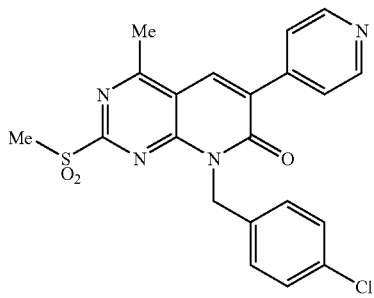

A mixture of starting material (100 mg, 0.244 mmol) and m-CPBA (84 mg, 2 equiv.) in dichloromethane was stirred at rt for 3 hours. Stripped to dryness and used without further purification for aminolysis. Yield 110 mg, 93%.

LRMS (APCI) (M+H)+: 441.2

Example 47

8-(4-Chlorobenzyl)-2-amino-4-methyl-6-(pyridin-4-yl)pyrido[2,3-d]pyrimidin-7(8H)-one (Compound 151)

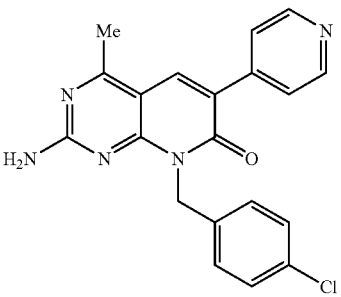

To a solution of crude product from previous experiment (sulfone, 80 mg, 0.181 mmol) in THF (4 mL) was bubbled ammonia for 2 minutes and solution allowed to stand capped at rt for 72 hours. Solvent removed under reduced pressure, residue partitioned between EA and saturated aqueous sodium bicarbonate (to remove PhCOOH from previous experiment). Organic phase washed with brined and dried over MgSO4. Material purified on flash column using 100% EA as eluent. Product obtained as yellow powder, 42 mg (61%).

LRMS (APCI) m/z 378.4 (M+H)+

$^1$H NMR (400 MHz, d6-DMSO 8.55 (bs, 2H), 8.23 (s, 1H), 7.75 (d, J=5.81 Hz, 2H), 7.33 (q, 4H), 5.73 (s, 2H), 5.45 (s, 2H), 2.58 (s, 3H).

$^1$H NMR (400 MHz, DMSO-$d_6$) d ppm 1.23-1.34 (m, 2H) 1.45-1.55 (m, 2H) 1.89-1.98 (m, 2H) 2.55 (s, 3H) 2.70-2.82 (m, 2H) 3.48-3.60 (m, 1H) 3.82-3.91 (m, 3H) 4.61 (d, J=4.29 Hz, 1H) 5.16-5.62 (m, 1H) 6.84 (d, J=8.59 Hz, 1H) 7.16 (s, 2H) 7.97 (s, 1H) 8.00 (dd, J=8.72, 2.40 Hz, 1H) 8.42 (d, J=2.53 Hz, 1H)

Example 48

Trans-4-(2-amino-6-methylpyrimidin-4-ylamino)cyclohexanol

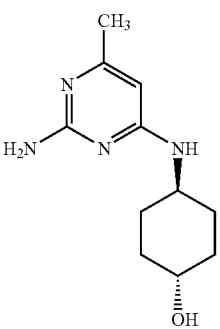

A mixture of 2-amino-4-chloro-6-methylpyrimidine (1.18 g, 8.24 mmol), trans-4-aminocyclohexanol (1.00 g, 6.60 mmol), potassium carbonate (1.82 g, 13.2 mmol), and diisopropylethyl amine (1.44 mL, 8.24 mmol) in dimethylacetamide (20.0 mL) was heated at 160° C. in a sealed tube overnight. The reaction mixture was diluted with ethyl acetate, filtered, and the filtrate was concentrated. The residue was purified by flash chromatography eluting with chloroform/7 N ammonia in methanol (0.5-5%) to afford the title compound as a foamy solid (1.47 g, 99%).

LRMS (M+H)$^+$: 223

$^1$H NMR (400 MHz, DMSO-d6) d ppm 1.14-1.24 (m, 4H) 1.77-1.86 (m, 4H) 1.97 (s, 3H) 3.35-3.40 (m, 1H) 3.57-3.69 (m, 1H) 4.52 (d, J=4.55 Hz, 1H) 5.53 (s, 1H) 5.73 (s, 2H) 6.43 (d, J=4.29 Hz, 1H)

Example 49

Trans-4-(2-amino-5-bromo-6-methylpyrimidin-4-ylamino)cyclohexanol

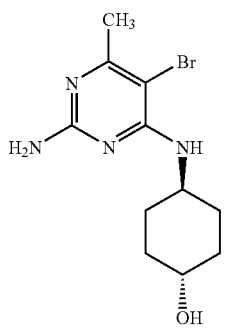

To a solution of (trans-4-(2-amino-6-methylpyrimidin-4-ylamino)cyclohexanol (1.33 g, 5.98 mmol) in chloroform (15 mL) was added N-bromosuccinamide (1.08 g, 6.04 mmol). After stirring at room temperature for 1.5 hr, the solution was concentrated. The residue was purified by flash chromatography eluting with chloroform/7 N ammonia in methanol (0.5-5%) to afford the title compound (1.14 g, 63%).

LRMS (M+H)$^+$: 301, 303

$^1$H NMR (400 MHz, DMSO-d6) d ppm 1.14-1.25 (m, 2H) 1.34-1.45 (m, 2H) 1.74-1.85 (m, 4H) 2.17 (s, 3H) 3.34-3.43 (m, 1H) 3.79-3.89 (m, 1H) 4.55 (d, J=4.55 Hz, 1H) 5.83 (d, J=8.34 Hz, 1H) 6.11 (s, 2H)

Example 50

(E)-ethyl 3-(2-amino-4-(trans-4-hydroxycyclohexylamino)-6-methylpyrimidin-5-yl)acrylate

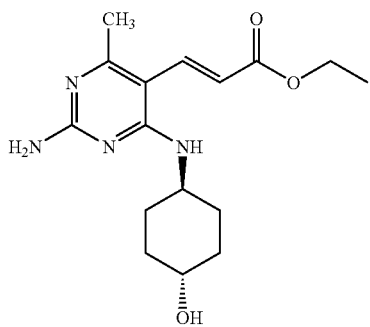

A sealed tube containing trans-4-(2-amino-5-bromo-6-methylpyrimidin-4-ylamino)cyclohexanol (655 mg, 2.17 mmol), tri-o-tolylphosphine (298 mg, 0.979 mmol), ethyl acrylate (355 uL, 3.26 mmol) and palladium (II) acetate (73 mg, 0.33 mmol) in triethylamine (20 mL) was evacuated and back-filled with nitrogen (3×). The reaction mixture was heated overnight at 130° C., filtered and concentrated. The residue was purified by flash chromatography eluting with chloroform/7 N ammonia in methanol (0.5-5%) to afford the title compound (364 mg, 52%).

LRMS (M+H)$^+$: 321

$^1$H NMR (400 MHz, DMSO-d6) d ppm 1.13-1.22 (m, 2H) 1.24 (t, J=7.07 Hz, 3H) 1.34-1.45 (m, 2H) 1.80 (m, 4H) 2.21 (s, 3H) 3.34-3.41 (m, 1H) 3.90-4.01 (m, 1H) 4.15 (q, J=7.07 Hz, 2H) 4.52 (d, J=4.55 Hz, 1H) 5.95 (d, J=15.92 Hz, 1H) 6.27 (d, J=8.08 Hz, 1H) 6.37 (s, 2H) 7.58 (d, J=15.92 Hz, 1H)

Example 51

2-Amino-8-(trans-4-hydroxycyclohexyl)-4-methylpyrido[2,3-d]pyrimidin-7(8H)-one (Compound 153)

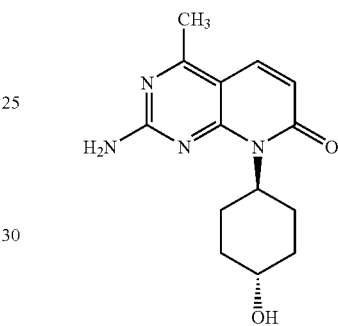

To a solution of (E)-ethyl 3-(2-amino-4-(trans-4-hydroxycyclohexylamino)-6-methylpyrimidin-5-yl)acrylate (233 mg, 0.727 mmol) in dimethylacetamide was added 1,5-diazbicyclo[5,4,0]undec-5-ene (544 uL, 3.64 mmol) followed by potassium tert-butoxide (1 M in THF, 364 uL, 364 mmol). The resulting solution was heated at 150° C. overnight then concentrated. The residue was purified by flash chromatography eluting with chloroform/7 N ammonia in methanol (0.5-5%). The product was then triturated with 1:1 chloroform:hexane to afford the title compound (119 mg, 60%).

LRMS (M+H)$^+$: 275

$^1$H NMR (400 MHz, DMSO-d6) d ppm 1.18-1.30 (m, 2H) 1.37-1.48 (m, 2H) 1.87-1.94 (m, 2H) 2.45 (s, 3H) 2.70 (m, 2H) 3.46-3.57 (m, 1H) 4.59 (d, J=4.29 Hz, 1H) 5.08-5.61 (m, 1H) 6.13 (d, J=9.60 Hz, 1H) 7.09 (s, 2H) 7.81 (d, J=9.35 Hz, 1H)

Example 52

2-Amino-6-bromo-8-(trans-4-hydroxycyclohexyl)-4-methylpyrido[2,3-d]pyrimidin-7(8H)-one

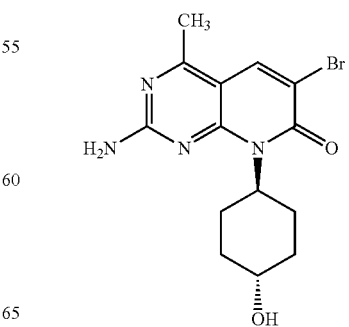

To a solution of 2-amino-8-(trans-4-hydroxycyclohexyl)-4-methylpyrido[2,3-d]pyrimidin-7(8H)-one (115 mg, 0.419 mmol) in dimethylformamide (2.0 mL) was added N-bromosuccinimide (75 mg, 0.42 mmol). After stirring for 1.5 hr at room temperature the solution was concentrated. The residue was slurried in methanol, filtered solids, and the filtrated was concentrated and purified by flash chromatography eluting with chloroform/7 N ammonia in methanol (0.5-3%). Combined solids to afford the title compound (120 mg, 81%).

LRMS (M+H)$^+$: 353/355

$^1$H NMR (400 MHz, DMSO-d6) d ppm 1.21-1.32 (m, 2H) 1.43-1.53 (m, 2H) 1.86-1.96 (m, 2H) 2.48 (s, 3H) 2.59-2.71 (m, 2H) 3.46-3.57 (m, 1H) 4.62 (d, J=3.03 Hz, 1H) 5.08-5.76 (m, 1H) 7.26 (s, 2H) 8.34 (s, 1H)

Example 53

2-Amino-8-(trans-4-hydroxycyclohexyl)-6-(6-methoxypyridin-3-yl)-4-methylpyrido[2,3-d]pyrimidin-7(8H)-one (Compound 152)

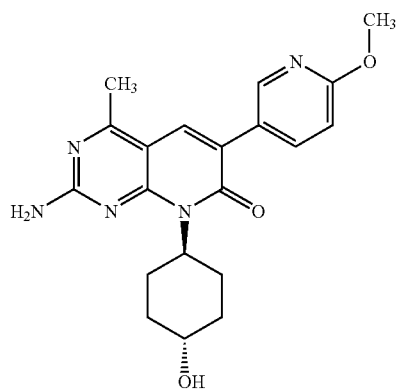

A flask containing 2-amino-6-bromo-8-(trans-4-hydroxycyclohexyl)-4-methylpyrido[2,3-d]pyrimidin-7(8H)-one (105 mg, 0.297 mmol), potassium carbonate (123 mg, 0.892 mmol), and 2-methoxy-5-pyridine boronic acid (52 mg, 0.34 mmol) was evacuated and back-filled with nitrogen (2×). A solution of 5:1 dimethylformade:water (1.8 mL) was bubbled with argon for 15 min then added to the flask followed by bis(tripehnylphosphine) palladium (II) chloride (10 mg, 0.015 mmol). The flask was fitted with a cold finger, evacuated and back filled with nitrogen (2×) then heated to 100° C. for 4 hr. The mixture was cooled overnight, diluted with methanol and chloroform then filtered through a glass fiber filter to filter out palladium. The filtrate was concentrated and the residue was purified by flash chromatography eluting with chloroform/7 N ammonia in methanol (0.5-6%) to afford the title compound (80, 71%).

LRMS (M+H)$^+$: 382

$^1$H NMR (400 MHz, DMSO-d6) d ppm 1.23-1.34 (m, 2H) 1.45-1.55 (m, 2H) 1.89-1.98 (m, 2H) 2.55 (s, 3H) 2.70-2.82 (m, 2H) 3.48-3.60 (m, 1H) 3.82-3.91 (m, 3H) 4.61 (d, J=4.29 Hz, 1H) 5.16-5.62 (m, 1H) 6.84 (d, J=8.59 Hz, 1H) 7.16 (s, 2H) 7.97 (s, 1H) 8.00 (dd, J=8.72, 2.40 Hz, 1H) 8.42 (d, J=2.53 Hz, 1H)

Example 54

6-Bromo-4-methyl-2-(methylthio)-8-((tetrahydrofuran-3-yl)methyl)pyrido[2,3-d]pyrimidin-7(8H)-one

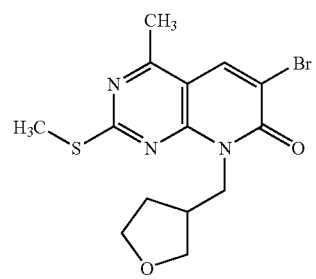

To a mixture of 6-bromo-4-methyl-2-(methylthio)pyrido[2,3-d]pyrimidin-7(8H)-one (900 mg, 3.15 mmol) and 3-(bromomethyl)-tetrahydrofuran (571 mg, 3.46 mmol) in DMF was added CsCO$_3$ (1.13 g, 3.46 mmol). After stirred at 70° C. for 7 h and the mixture was quenched with water and extracted with t-butyl ethyl ether (4 times) and concentrated. The crude mixture was purified by flash chromatography, using 0-2% MeOH/CHCl$_3$, to give the title compound (715 mg, 61%).

LRMS: 370, 372 (M+H)$^+$.

$^1$H NMR (400 MHz, CDCl$_3$) 8.25 (1H, s), 4.56 (2H, m), 3.96 (1H, dt, J=8.15, 5.68 Hz), 3.72-3.83 (2H, m), 3.66 (1H, dd, J=8.59, 5.81 Hz), 2.81-2.95 (1H, m), 2.68 (3H, s), 2.62 (3H, s), 1.91-2.04 (1H, m), 1.71-1.85 (1H, m).

Example 55

2-Amino-8-cyclobutyl-4-methyl-7-oxo-7,8-dihydropyrido[2,3-d]pyrimidine-6-carbonitrile (Compound 269)

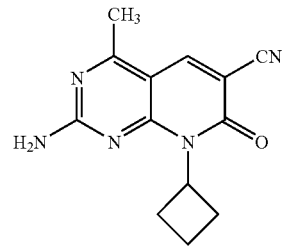

To a solution of 2-amino-6-bromo-8-cyclobutyl-4-methyl-8H-pyrido[2,3-d]pyrimidin-7-one (371 mg, 1.20 mmol) in NMP (4 mL) was added CuCN (480 mg, 5.36 mmol). The mixture was sealed and heated at 220° C. for 30 min using microwave irradiation. The mixture was poured into brine and filtered to give a solid. The aqueous phase was extracted with t-butyl methyl ether (3 times), dried and evaporated. The combined solid was purification by flash chromatography, using 0 to 3% MeOH/CHCl$_3$, to give the title compound (240 mg, 78%).

LRMS: 256 (M+H)+.

¹H NMR (400 MHz, DMSO-d6) 8.66 (1H, s), 7.77 (2H, d, J=21.47 Hz), 5.68-5.85 (1H, m), 2.90-3.11 (2H, m), 2.12-2.28 (2H, m), 1.85-2.02 (1H, m), 1.62-1.80 (1H, m).

Example 56

2-Amino-8-cyclobutyl-4-methyl-6-(2-(trimethylsilyl)ethynyl)pyrido[2,3-d]pyrimidin-7(8H)-one

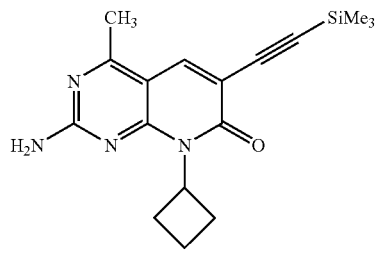

A flask was charged with Pd(PPh₃)₂Cl₂ (84.2 mg, 0.120 mmol) and copper iodide (34.3 mg, 0.180 mmol). To this were added 1,4-dioxane (12 mL) and diisopropylethylamine (0.84 mL, 4.8 mmol) via syringe. 2-Amino-6-bromo-8-cyclobutyl-4-methyl-8H-pyrido[2,3-d]pyrimidin-7-one (371 mg, 1.20 mmol) was introduced, and the resulting yellow solution was carefully sparged with nitrogen for 10 min. TMS-acetylene (0.50 mL, 3.6 mmol) was then added via syringe, and the resulting black solution was stirred at 70° C. for 1 h. Solvent was removed under reduced pressure. The crude solid was purified by flash chromatography on silica gel eluting with CHCl₃ then 3% MeOH in CHCl₃ to afford the title product (322 mg).

LRMS: 327 (M+H)+.

¹H NMR (400 MHz, DMSO-d6) 8.06 (1H, s), 7.39 (2H, s), 5.74-5.97 (1H, m), 2.92-3.13 (2H, m), 2.49 (3H, s), 2.09-2.23 (2H, m), 1.86-1.97 (1H, m), 1.63-1.81 (1H, m), 0.22 (9H, s).

Example 57

2-Amino-8-cyclobutyl-6-ethynyl-4-methylpyrido[2,3-d]pyrimidin-7(8H)-one (Compound 270)

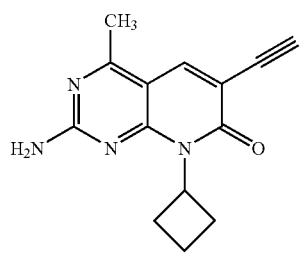

To a stirred solution of 2-amino-8-cyclobutyl-4-methyl-6-(2-(trimethylsilyl)ethynyl)pyrido[2,3-d]pyrimidin-7(8H)-one (105 mg, 0.322 mmol) in MeOH (7 mL) was added K₂CO₃ (50 mg, 0.36 mmol) and the mixture was stirred for 5 h. LC-MS indicated complete conversion. Solvent was evaporated and the residue was purified by flash chromatography, using CHCl₃, to give the title compound (81 mg, 99%).

LRMS: 255 (M+H)+.

¹H NMR (400 MHz, CDCl₃) 7.95 (1H, s), 5.78-5.98 (1H, m), 5.25 (2H, s), 3.31 (1H, s), 3.04-3.25 (2H, m), 2.56 (3H, s), 2.23-2.40 (2H, m), 1.96-2.13 (1H, m), 1.73-1.91 (1H, m).

Example 58

(4-(2-Amino-8-isopropyl-4-methyl-7-oxo-7,8-dihydropyrido[2,3-d]pyrimidin-6-yl)-1H-1,2,3-triazol-1-yl)methyl diethylcarbamate (Compound 263)

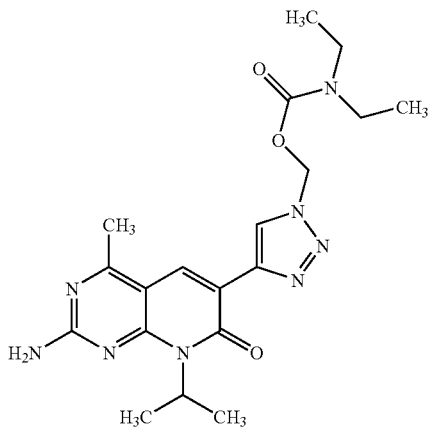

2-amino-6-ethynyl-8-isopropyl-4-methylpyrido[2,3-d]pyrimidin-7(8H)-one (75 mg, 0.31 mmol) and azidomethyl diethylcarbamate (80 mg, 0.46 mmol) was suspended in 1:1 t-BuOH/H₂O (4 mL). To this was added saturated copper sulfate solution (0.05 mL) and stirring was continued for 24 h. The mixture was concentrated and diluted with 5 mL water. The mixture was separated and the organic phase was washed with water and evaporated. Flash chromatography of the residue over silica gel, using 0-5% MeOH/CHCl₃, gave the title compound (88 mg, 69%).

LRMS: 415 (M+H)+.

¹H NMR (400 MHz, DMSO-d6) 8.67 (1H, s), 8.61 (1H, s), 7.28 (2H, br. s.), 6.34 (2H, s), 5.88 (1H, br. s.), 3.10-3.29 (4H, m), 2.60 (3H, s), 1.55 (6H, d, J=6.82 Hz), 1.05 (3H, t, J=6.95 Hz), 0.99 (3H, t, J=6.95 Hz).

Example 59

2-Amino-8-isopropyl-4-methyl-6-(1H-1,2,3-triazol-4-yl)pyrido[2,3-d]pyrimidin-7(8H)-one (Compound 264)

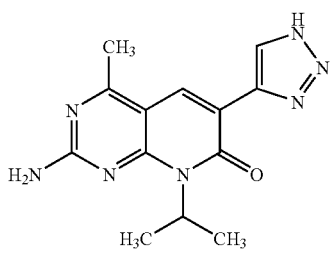

To a solution of (4-(2-amino-8-isopropyl-4-methyl-7-oxo-7,8-dihydropyrido[2,3-d]pyrimidin-6-yl)-1H-1,2,3-triazol-1-yl)methyl diethylcarbamate (38 mg, 0.092 mmol) in MeOH (0.5 mL) was added aqueous NaOH (1.0 M, 0.20 mL, 0.20 mmol) and the reaction mixture was stirred at 85° C. for 2 day. There is about 90% conversion from LCMS. Solvent was evaporated and the residue was purified by flash chromatography eluting with MeOH/CHCl$_3$ (0-5%) to give the title (8 mg, 30%).

LRMS: 286 (M+H)$^+$.

$^1$H NMR (400 MHz, DMSO-d6) 8.50 (1H, br. s.), 8.38 (1H, br. s.), 7.27 (2H, br. s.), 5.77-6.03 (1H, m), 2.59 (3H, s), 1.55 (6H, d, J=6.82 Hz).

Example 60

2-Amino-6-(2-hydroxypyrimidin-5-yl)-4-methyl-8-(tetrahydro-2H-pyran-4-yl)pyrido[2,3-d]pyrimidin-7(8H)-one (Compound 267)

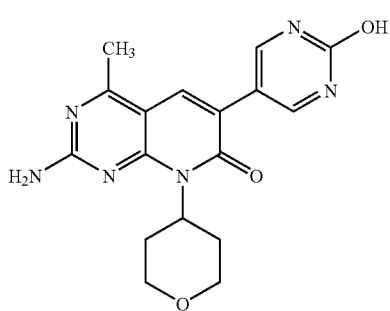

A mixture of 2-amino-6-(2-methoxypyrimidin-5-yl)-4-methyl-8-(tetrahydro-2H-pyran-4-yl)pyrido-[2,3-d]pyrimidin-7(8H)-one (42.2 mg, 0.115 mmol), TMSI (0.10 mL, 0.70 mmol), and dry acetonitrile (2.3 mL) was heated at 82° C. for 1 h. After being cooled to room temperature, the mixture was treated with 20% NH$_4$OH solution and concentrated. The mixture was purified by analytical group (HPLC) to give the title compound (12 mg, 30%).

LRMS: 355 (M+H)$^+$.

$^1$H NMR (400 MHz, DMSO-d6) 8.63 (2H, br. s.) 8.10 (1H, s) 7.23 (2H, br. s.) 5.54-5.84 (1H, m) 3.99 (2H, dd, J=11.12, 3.79 Hz) 3.36-3.53 (3H, m) 2.83-3.06 (2H, m) 2.56 (3H, s) 1.46 (2H, d, J=9.85 Hz).

Example 61

5-Bromo-4-chloro-6-methylpyrimidin-2-amine

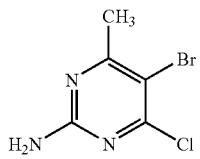

To a mixture of the 2-amino-4-chloro-6-methylpyrimidine (5.00 g, 34.8 mmol) in dichloromethane (240 mL) was added bromine (1.88 mL, 36.6 mmol). The resulting suspension was stirred at room temperature for 1.5 hours. The mixture was diluted with dichloromethane (1.3 L) and washed with saturated sodium bicarbonate (2×200 mL) and brine (200 mL), dried (MgSO$_4$), filtered and concentrated to afford 5-bromo-4-chloro-6-methylpyrimidin-2-amine (7.5 g, 97%).

LCMS (M+H): 223

1H NMR (400 MHz, CHLOROFORM-d) δ ppm 2.54 (s, 3H) 5.10 (s, 2H)

Example 62

5-Bromo-4-chloro-2-(2,5-dimethyl-1H-pyrrol-1-yl)-6-methylpyrimidine

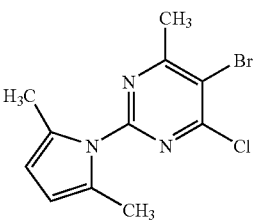

A flask containing a mixture of 5-bromo-4-chloro-6-methylpyrimidin-2-amine (34.8 mmol), 2,5-hexanedione (6.15 mL, 52.2 mmol), and p-toluenesulfonic acid (330 mg, 1.74 mmol) in toluene (100 mL) was fitted with a Dean-stark apparatus and condenser and the mixture was heated to reflux. After refluxing overnight the solution was cooled to room temperature and concentrated. The residue was slurried in hexanes, filtered and the filtrate was concentrated. The precipitate was purified by flash chromatography eluting with hexanes/chloroform (0-50%) to afford the 5-bromo-4-chloro-2-(2,5-dimethyl-1H-pyrrol-1-yl)-6-methylpyrimidine (1.60 g, 15%). The concentrated filtrate was purified by flash chromatography eluting with hexanes/chloroform (10-40%) to afford 5-bromo-4-chloro-2-(2,5-dimethyl-1H-pyrrol-1-yl)-6-methylpyrimidine (5.22 g, 50%).

LRMS (M+H)$^+$: 302

$^1$H NMR (400 MHz, CHLOROFORM-d) δ ppm 2.39 (s, 6H) 2.72 (s, 3H) 5.90 (s, 2H)

Example 63 trans-4-(5-bromo-2-(2,5-dimethyl-1H-pyrrol-1-yl)-6-methylpyrimidin-4-ylamino)cyclohexanol

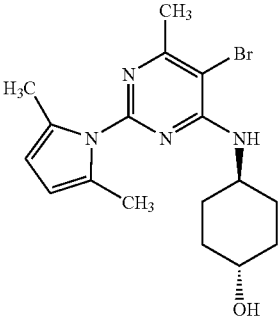

A mixture of 5-bromo-4-chloro-2-(2,5-dimethyl-1H-pyrrol-1-yl)-6-methyl pyrimidine (1.50 g, 4.99 mmol), trans-4-aminocyclohexanol hydrochloride (1.17 g, 6.24 mmol), and diisopropylethyl amine (2.61 mL, 15.0 mmol) in dimethylacetamide (25.0 mL) was heated at 160° C. in a sealed tube overnight. The reaction mixture was diluted with methyltertbutyl ether (400 mL), washed with saturated ammonia chloride (2×) and brine, dried (MgSO$_4$), filtered, and concentrated. The combined aqueous layers were extracted with dichloromethane (3×150 mL), dried (MgSO$_4$), filtered, and concentrated. The crude product was purified by flash chromatography eluting with chloroform/methanol (0.5-3%) to afford trans-4-(5-bromo-2-(2,5-dimethyl-1H-pyrrol-1-yl)-6-methylpyrimidin-4-ylamino)cyclohexanol (1.76 g, 93%).

LCMS LRMS (M+H)$^+$: 379/381

¹H NMR (400 MHz, DMSO-d6) δ ppm 1.15-1.26 (m, 2H) 1.46-1.57 (m, 2H) 1.74-1.80 (m, 2H) 1.81-1.87 (m, 2H) 2.26 (s, 6H) 2.41 (s, 3H) 3.35-3.45 (m, 1H) 3.86-3.96 (m, 1H) 4.57 (d, J=4.29 Hz, 1H) 5.76 (s, 2H) 6.82 (d, J=8.34 Hz, 1H)

Example 64

5-Bromo-2-(2,5-dimethyl-1H-pyrrol-1-yl)-N-(trans-4-methoxycyclohexyl)-6-methylpyrimidin-4-amine

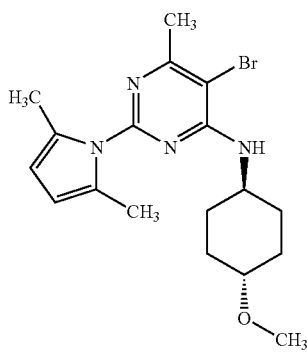

To a cooled (0° C.) solution of trans-4-(5-bromo-2-(2,5-dimethyl-1H-pyrrol-1-yl)-6-methylpyrimidin-4-ylamino)cyclohexanol (1.45 g, 3.82 mmol) in tetrahydrofuran (40 mL) was added sodium hydride (60% dispersion in oil, 459 mg, 11.5 mmol). After 40 minutes, methyl iodide was added (262 uL, 4.21 mmol) and the mixture was stirred at 0° C. for 2 hours. The ice bath was removed and continued to stir for 3 hours then quenched with methanol and concentrated. The residue was dissolved in ethyl acetate and washed with saturated ammonia chloride (2×), brine, dried (MgSO₄), filtered and concentrated. The crude product was purified by flash chromatography eluting with hexanes/methyltertbutyl ether (5-25%) to afford 5-bromo-2-(2,5-dimethyl-1H-pyrrol-1-yl)-N-(trans-4-methoxycyclohexyl)-6-methyl pyrimidin-4-amine (1.10 g, 73%).

LRMS (M+H)⁺: 293/295

¹H NMR (400 MHz, DMSO-d₆) δ ppm 1.11-1.22 (m, 2H) 1.47-1.58 (m, 2H) 1.78-1.87 (m, 2H) 1.97-2.07 (m, 2H) 2.26 (s, 6H) 2.41 (s, 3H) 3.04-3.14 (m, 1H) 3.23 (s, 3H) 3.90-4.00 (m, 1H) 5.76 (s, 2H) 6.87 (d, J=8.34 Hz, 1H)

Example 65

5-Bromo-N4-(trans-4-methoxycyclohexyl)-6-methylpyrimidine-2,4-diamine

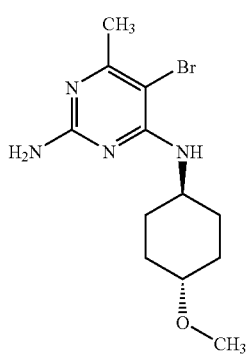

A solution of 5-bromo-2-(2,5-dimethyl-1H-pyrrol-1-yl)-N-(trans-4-methoxycyclohexyl)-6-methylpyrimidin-4-amine (1.07 g, 2.72 mmol) and hydroxylamine hydrochloride (945 mg, 13.6 mmol) in 10:1 ethanol:water (27.5 mL) was heated to reflux for 7 hours, then room temperature overnight. Another 0.5 eq of hydroxylamine hydrochloride was added and the solution was refluxed for another 4 hours, then cooled to room temperature and concentrated. The crude product was purified by flash chromatography eluting with chloroform/methanol (0.5-3%) to afford 5-bromo-N4-(trans-4-methoxycyclohexyl)-6-methylpyrimidine-2,4-diamine (767 mg, 89%).

LRMS (M+H)⁺: 315/317

¹H NMR (400 MHz, DMSO-d6) δ ppm 1.09-1.20 (m, 2H) 1.35-1.46 (m, 2H) 1.78-1.88 (m, 2H) 1.96-2.04 (m, 2H) 2.17 (s, 3H) 3.03-3.14 (m, 1H) 3.23 (s, 3H) 3.82-3.92 (m, 1H) 5.91 (d, J=8.34 Hz, 1H) 6.12 (s, 2H)

Example 66

(E)-ethyl 3-(2-amino-4-(trans-4-methoxycyclohexylamino)-6-methylpyrimidin-5-yl)acrylate

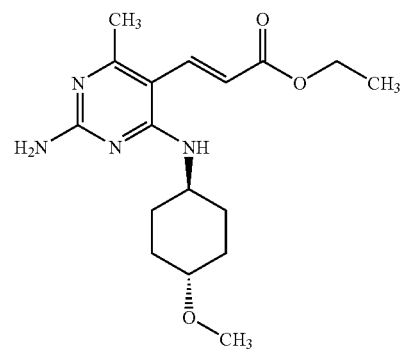

In a sealed tube a solution of 5-bromo-N4-(trans-4-methoxycyclohexyl)-6-methylpyrimidine-2,4-diamine (811 mg, 2.57 mmol) and ethyl acrylate (559 uL, 5.15 mmol) in triethylamine (25 mL) was bubbled with argon for ~10 minutes. Tetrakis(triphenylphosphin)-palladium (0) (297 mg, 0.257 mmol) was added, the vial was sealed, and the reaction was heated to 130° C. overnight. The reaction mixture was cooled to room temperature, diluted with ethyl acetate (450 mL), washed with water, 0.1 N hydrochloric acid, brine, dried (MgSO₄), filtered and concentrated. The crude product was purified by flash chromatography eluting with chloroform/methanol (0-10%) to afford (E)-ethyl 3-(2-amino-4-(trans-4-methoxycyclohexylamino)-6-methylpyrimidin-5-yl)acrylate (674 mg, 78%).

LRMS (M+H)⁺: 335

¹H NMR (400 MHz, DMSO-d6) δ ppm 1.09-1.20 (m, 2H) 1.24 (t, J=7.07 Hz, 3H) 1.34-1.46 (m, 2H) 1.79-1.89 (m, 2H) 1.96-2.05 (m, 2H) 2.21 (s, 3H) 3.03-3.12 (m, 1H) 3.23 (s, 3H) 3.92-4.03 (m, 1 H) 4.15 (q, J=7.07 Hz, 2H) 5.96 (d, J=15.92 Hz, 1H) 6.31 (d, J=8.08 Hz, 1H) 6.37 (s, 2H) 7.59 (d, J=15.92 Hz, 1H)

Example 67

2-Amino-8-(trans-4-methoxycyclohexyl)-4-methylpyrido[2,3-d]pyrimidin-7(8H)-one

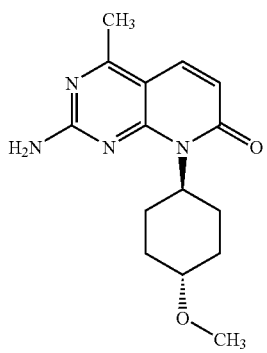

A solution of (E)-ethyl 3-(2-amino-4-(trans-4-methoxycyclohexylamino)-6-methylpyrimidin-5-yl)acrylate (674 mg, 2.02 mmol) thiophenol (621 ul, 6.05 mmol), 1,5-diazabicyclo5,4,0)undec-5-ene (1.81 mL, 12.1 mmol) and triethylamine (1.69 mL, 12.1 mmol) in N',N-dimethylformamide (15 mL) was heated in the microwave for 30 minutes at 100° C. then in an oil bath at 100° C. overnight. The reaction mixture was diluted with methyltertbutylether and washed with saturated sodium carbonate, brine, 0.1 N hydrochloric acid, brine, dried (MgSO$_4$), filtered and concentrated. The combined aqueous layer was extracted with dichloromethane (2×). The organic layer was dried (MgSO$_4$), filtered and concentrated. The crude product was purified by flash chromatography eluting with chloroform/methanol (0-5%) to afford 2-amino-8-(trans-4-methoxycyclohexyl)-4-methylpyrido[2,3-d]pyrimidin-7(8H)-one (482 mg, 83%).

LRMS (M+H)$^+$: 289

$^1$H NMR (400 MHz, DMSO-d6) δ ppm 1.14-1.25 (m, 2H) 1.45-1.55 (m, 2H) 2.05-2.14 (m, 2H) 2.46 (s, 3H) 2.66-2.77 (m, 2H) 3.26 (s, 3H) 3.29-3.33 (m, 1H) 4.97-5.61 (m, 1H) 6.14 (d, J=9.35 Hz, 1H) 7.11 (s, 2H) 7.82 (d, J=9.35 Hz, 1H)

Example 68

2-Amino-6-bromo-8-(trans-4-methoxycyclohexyl)-4-methylpyrido[2,3-d]pyrimidin-7(8H)-one

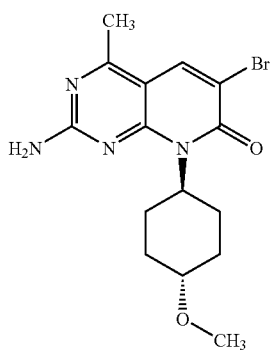

To a solution of 2-amino-8-(trans-4-methoxycyclohexyl)-4-methylpyrido[2,3-d]pyrimidin-7(8H)-one (482 mg, 0.1.67 mmol) in dimethylformamide (15 mL) was added N-bromosuccinimide (300 mg, 1.69 mmol). After stirring for 1 hour at room temperature the solution was diluted with methyltertbutylether and washed with 50% sodium carbonate (2×) and brine. The combined aqueous layers were extracted with dichloromethane. The combined organics were dried (MgSO$_4$) filtered and concentrated. The solids were triturated with diethyl ether to afford 2-amino-6-bromo-8-(trans-4-methoxycyclohexyl)-4-methylpyrido[2,3-d]pyrimidin-7(8H)-one (594 mg, 97%).

LRMS (M+H)$^+$: 367/369

$^1$H NMR (400 MHz, DMSO-d6) δ ppm 1.15-1.26 (m, 2H) 1.49-1.59 (m, 2H) 2.06-2.15 (m, 2H) 2.49 (s, 3H) 2.61-2.73 (m, 2H) 3.17-3.26 (m, 1H) 3.27 (s, 3H) 5.15-5.67 (m, 1H) 7.26 (s, 2H) 8.34 (s, 1H)

Example 69

2-Amino-8-(trans-4-methoxycyclohexyl)-6-(6-methoxypyridin-3-yl)-4-methylpyrido[2,3-d]pyrimidin-7(8H)-one (Compound 179)

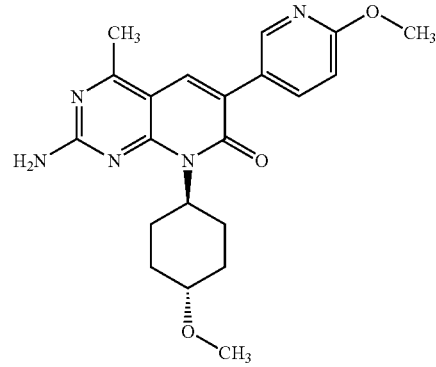

To a vial containing 2-amino-6-bromo-8-(trans-4-methoxycyclohexyl)-4-methylpyrido[2,3-d]pyrimidin-7(8H)-one (75 mg, 0.20 mmol), 2-methoxy-5-pyridineboronic acid (37.5 mg, 0.245 mmol) and cesium carbonate was added PdCl$_2$(dppf)1:1 w/CH$_2$Cl$_2$ followed by 5:1 dimethoxyethane:water (3 mL, degassed by bubbling with argon). The vial was capped and heated in the microwave for 30 minutes at 100° C. The reaction mixture was concentrated and the crude product was purified by flash chromatography eluting with chloroform/methanol (0-5%). The fractions containing the desired product were concentrated and the solids were triturated with methyltertbutyl ether to afford 2-amino-8-(trans-4-methoxycyclohexyl)-6-(6-methoxypyridin-3-yl)-4-methylpyrido[2,3-d]pyrimidin-7(8H)-one (33 mg, 40%).

LRMS (M+H)$^+$: 396

$^1$H NMR (400 MHz, DMSO-d6) δ ppm 1.16-1.28 (m, 2H) 1.52-1.62 (m, 2H) 2.07-2.17 (m, 2H) 2.55 (s, 3H) 2.72-2.83 (m, 2H) 3.26 (s, 3H) 3.30-3.33 (m, 1H) 3.88 (s, 3H) 5.30-5.63 (m, 1H) 6.84 (d, J=8.59 Hz, 1H) 7.17 (s, 2H) 7.98 (s, 1H) 8.00 (dd, J=8.59, 2.53 Hz, 1H) 8.42 (d, J=2.53 Hz, 1H)

Example 70

Potassium 1H-pryazole-5-trifluoroborate

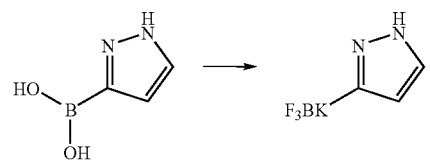

A mixture of 1H-pryazole-5-boronic acid (150 mg, 1.34 mmol) and potassium hydrogen fluoride (262 mg, 3.35 mmol) in 1:3 methanol/water (2 mL) was stirred at room temperature overnight. The mixture was transferred to a vial, the vial was sealed and the mixture was heated to 100° C. in an oil bath for 2 hours, resulting in a solution. The solution was cooled and concentrated. The solids were slurried in hot acetone, filtered, and the filtrate was concentrated to afford potassium 1H-pryazole-5-trifluoroborate (234 mg, 100%).

Example 71

2-Amino-8-((trans)-4-hydroxycyclohexyl)-4-methyl-6-(1H-pyrazol-3-yl)pyrido[2,3-d]pyrimidin-7(8H)-one (Compound 186)

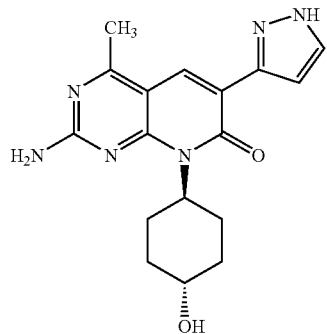

A mixture of 2-amino-6-bromo-8-((trans)-4-hydroxycyclohexyl)-4-methylpyrido[2,3-d]pyrimidin-7(8H)-one (100 mg, 0.283 mmol), potassium 1H-pryazole-5-trifluoroborate (98.5 mg, 0.566 mmol), and triethylamine (197 uL, 1.42 mmol) in ethanol (3.0 mL) was bubbled with argon. PdCl$_2$ (dppf)1:1 w/CH$_2$Cl$_2$ was added, the vial was sealed and the mixture was bubbled with argon again, then heated in the microwave for 30 minutes at 100° C., then 60 minutes at 150° C. The reaction mixture was concentrated and purified by flash chromatography eluting with 1:1 ethyl acetate:chloroform/7 N ammonia in methanol (0.5-7%). The fractions containing the desired product were combined and concentrated and the solids were recrystallized from methanol/chloroform to afford 2-amino-8-((trans)-4-hydroxycyclohexyl)-4-methyl-6-(1H-pyrazol-3-yl)pyrido[2,3-d]pyrimidin-7(8H)-one (32 mg, 33%).

LRMS (M+H)$^+$: 341

$^1$H NMR (400 MHz, DMSO-d6) δ ppm 1.24-1.35 (m, 2H) 1.44-1.55 (m, 2H) 1.90-1.99 (m, 2H) 2.56 (s, 3H) 2.73-2.84 (m, 2H) 3.50-3.62 (m, 1H) 4.62 (d, J=4.04 Hz, 1H) 5.12-5.74 (m, 1H) 6.93 (s, 1H) 7.14-7.26 (m, 2H) 7.62 (m, 1H) 8.34 (s, 1H) 12.97 (m, 1H)

Example 72

1-(5-Bromo-2-(2,5-dimethyl-1H-pyrrol-1-yl)-6-methylpyrimidin-4-yl)hydrazine

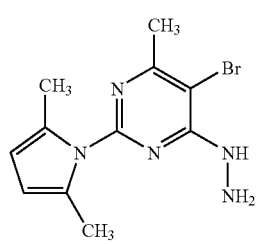

To a microwave vial was added 5-bromo-4-chloro-2-(2,5-dimethyl-1H-pyrrol-1-yl)-6-methylpyrimidine (4.95 g, 16.5 mmol) and hydrazine (0.57 ml, 18.1 mmol) hunig's base 95.74 ml, 32.9 mmol) and dimethyacetamide (24 ml) at R.T. After heating in the microwave for 30 mins at 100° C. The reaction mixture was concentrated under reduced pressure to dryness and the residue was trituarated with 1:1 ethyl acetate:methanol to obtain the desired product as a white solid weighted 2820 mg. The mother liquor was purified by column chromatography eluted with 30% EtOAc:hexane to give an additional batch of the desired product. Both lots were combined to give the titled compound as a white solid weighted 3620 mg 74%

$^1$H NMR (400 MHz, MeOD) δ ppm 2.30 (s, 6H) 2.51 (s, 3H) 5.79 (s, 2H)

Example 73

5-Bromo-2-(2,5-dimethyl-1H-pyrrol-1-yl)-6-methyl-N-(pyrrolidin-1-yl)pyrimidin-4-amine

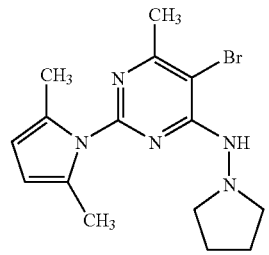

To a flask was added 1-(5-bromo-2-(2,5-dimethyl-1H-pyrrol-1-yl)-6-methylpyrimidin-4-yl)hydrazine (100 mg, 0.34 mmol) 1,4-dibromobutane (0.04 ml, 0.37 mmol) hunig's base (0.18 ml, 1.01 mmol) and DMAC (1.0 ml) at R.T. After heating at 60° C. over night, the reaction mixture was cooled to R.T. and diluted with EtOAc (2 ml) the white solid was filtered and the mother liquor was concentrated under reduced pressure. The resulting residue was purified by column chromatography eluted with 30% EtOAc:hex to give the titled compound weighted 76 mg 64%

$^1$H NMR (400 MHz, MeOD) δ ppm 1.78 (ddd, J=6.95, 3.41, 3.28 Hz, 4H) 2.15 (s, 6H) 2.41 (s, 3H) 2.85-2.92 (m, 4H) 5.67 (s, 2H)

Example 74

N-(5-Bromo-2-(2,5-dimethyl-1H-pyrrol-1-yl)-6-methylpyrimidin-4-yl)-N-(pyrrolidin-1-yl)acrylamide

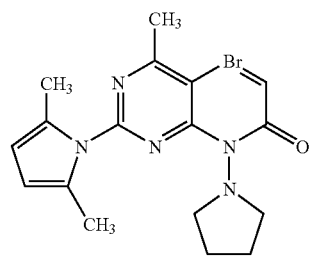

To a reaction solution of 5-bromo-2-(2,5-dimethyl-1H-pyrrol-1-yl)-6-methyl-N-(pyrrolidin-1-yl)pyrimidin-4-amine (3.14 g, 8.97 mmol) in anhyrous methylene chloride (120 ml) and hunig's base (4.68 ml) was added slowly a solution of acryloyl chloride (0.80 ml, 9.86 mmol) in methylene chloride (30 ml) dropwise at R.T. After stirring at R.T for 60 mins, the reaction mixture was concentrated under reduced pressure and the residue was purified by 120 g column eluted with 40% ethyl acetate:hexane to give the titled product weighted 3.5 g a white solid 97%

$^1$H NMR (400 MHz, DMSO-d6) δ ppm 1.72-1.77 (m, 4H) 2.28 (s, 6H) 2.70 (s, 3H) 3.17-3.20 (m, 4H) 5.79 (d, J=11.12 Hz, 1H) 5.85 (s, 2H) 6.30 (dd, J=17.18, 2.02 Hz, 1H) 6.75 (bs, 1H)

Example 75

2-(2,5-Dimethyl-1H-pyrrol-1-yl)-4-methyl-8-(pyrrolidin-1-yl)pyrido[2,3-d]pyrimidin-7(8H)-one

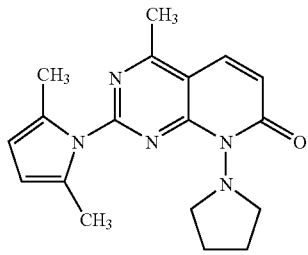

To a microwave vial was added N-(5-bromo-2-(2,5-dimethyl-1H-pyrrol-1-yl)-6-methylpyrimidin-4-yl)-N-(pyrrolidin-1-yl)acrylamide (2.0 g, 4.95 mmol) silver carbonate (2.73 g, 9.89 mmol) and anhydrous THF (100 ml). The reaction suspension was bubbled in nitrogen for 2 mins and then added the palladium tetrakis tert-(triphenylphosphine) (286 mg, 0.25 mmol). After stirring at 70° C. oil bath for 3 h, the reaction mixture was cooled to R.T. and diluted with 20 ml of brine. After stirring at R.T. for 5 mins, the reaction mixture was filtered through a celite pad. The cake was washed with ethyl acetate. The layers were separated. The organic layer was washed with brine 20 ml, dried with potassium carbonate, filtered and concentrated under reduced pressure. The resulting residue was purified by column chromatography eluted with 40% etoac:hex to give the titled compound weighted 480 mg 30%

$^1$H NMR (400 MHz, MeOD) δ ppm 2.01-2.13 (m, 4H) 2.39 (s, 6H) 2.80 (s, 3H) 3.32-3.39 (m, 4H) 5.86 (s, 2H) 6.72 (d, J=9.85 Hz, 1H) 8.15 (d, J=9.60 Hz, 1H)

Example 76

2-Amino-4-methyl-8-pyrrolidin-1-ylpyrido[2,3-d]pyrimidin-7(8H)-one

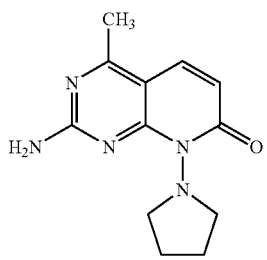

To a microwave vial was added 2-(2,5-dimethyl-1H-pyrrol-1-yl)-4-methyl-8-(pyrrolidin-1-yl)pyrido[2,3,d]pyrimidin-7(8H)-one (530 mg, 1.64 mmol) hydroxamine hydrochloride (1.14 g, 16.4 mmol) ethanol (20 ml) and water (2.92 ml). The vial was capped and refluxed at 100° C. After 3 h, the reaction mixture was concentrated to dryness under reduced pressure and the resulting residue was purified by column chromatography eluted with 10% 7N NH3 in MeOH:CHCl3 to give the desired product weighted 296 mg 74%

LRMS (M+H)$^+$: 246.1

$^1$H NMR (400 MHz, DMSO-d6) δ ppm 1.90-2.00 (m, 4H) 2.47 (s, 3H) 3.16-3.24 (m, 4H) 6.20 (d, J=9.60 Hz, 1H) 7.21 (br. s., 2H) 7.84 (d, J=9.60 Hz, 1H)

Example 77

2-Amino-6-bromo-4-methyl-8-(pyrrolidin-1-yl)pyrido[2,3-d]pyrimidin-7(8H)-one

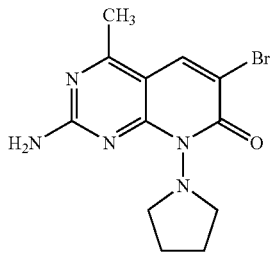

To a suspension of 2-amino-4-methyl-8-pyrrolidin-1-ylpyrido[2,3-d]pyrimidin-7(8H)-one (22.0 mg, 0.09 mmol) in anhydrous DMF (1.0 ml) and 0014 (1.0 ml) was added two drops of bromine via syringe at R.T. After stirring at R.T. for 3 mins to the reaction mixture, TEA (0.08 ml) was added. After stirring for 1.5 h at R.T., the reaction mixture was concentrated under reduced pressure and the resulting residue was purified by column chromatography eluted with 10% 7N NH3 in MeOH:CHCl3 to give the titled compound 13.0 mg 45% product weighted 25 mg 45%

LCMS (APCI+) 324.0

$^1$H NMR (400 MHz, MeOD) δ ppm 2.02-2.14 (m, 4H) 2.57 (s, 3H) 3.32-3.38 (m, 4H) 8.36 (s, 1H)

Example 78

2-Amino-4-methyl-6-(1H-pyrazol-4-yl)-8-(pyrrolidin-1-yl)pyrido[2,3-d]pyrimidin-7(8H)-one (Compound 193)

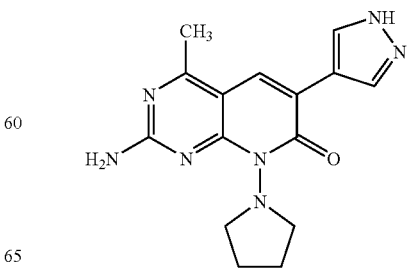

To a flask was added a 2-amino-6-bromo-4-methyl-8-(pyrrolidin-1-yl)pyrido[2,3-d]pyrimidin-7(8H)-one (21.0 mg, 0.06 mmol), tert-butyl 4-(4,4,5,5-tetramethyl-1,3,2-dioxaborolan-2-yl)-1H-pyrazole-1-carboxylate (20.9 mg, 0.07 mmol) potassium carbonate (25.6 mg, 0.19 mmol) in DMAC (1.20 ml):H2O (0.1 ml). The reaction mixture was degassed by alternating between N2 and vacuum. To the reaction mixture was added PdCl$_2$(PPh$_3$)$_2$ (4.3 mg). After heating in microwave for 60 min at 100° C., the reaction mixture was concentrated under reduced pressure and the resulting residue was purified by reversed phase column eluted with acetonitrile: 0.1% acetic acid in water to give the titled compound weighted 2.5 mg $^1$H NMR (400 MHz, MeOD): 2.07-2.18 (m, 4H) 2.66 (s, 3H) 3.35-3.46 (m, 4H) 8.18 (s, 1H) 8.28 (bs, 2H)

Example 79

Tert-butyl-4-(2-amino-4-methyl-7-oxo-8-(pyrrolidin-1-yl)-7,8-dihydropyrido[2,3-d]pyrimidin-6-yl)-1H-pyrazole-1-carboxylate (Compound 192)

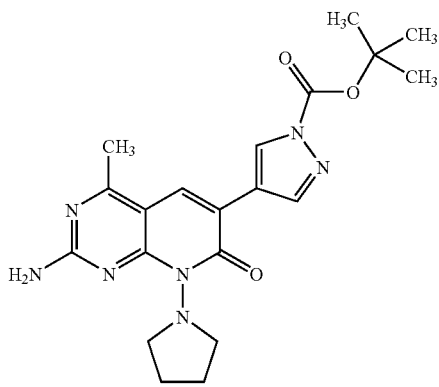

This titled compound was obtained from the reaction that produced example 78, weighted 3.1 mg.

$^1$H NMR (400 MHz, MeOD): 1.58 (s, 9H) 2.00-2.05 (m, 4H) 2.57 (s, 3H) 3.27-3.34 (m, 4H) 8.07 (s, 1H) 8.21 (s, 1H) 8.32 (s, 1H)

Example 80

8-Cyclopentyl-6-[1-(2-hydroxy-2-methyl-propyl)-1H-pyrazol-4-yl]-4-methyl-2-methylsulfanyl-8H-pyrido[2,3-d]pyrimidin-7-one

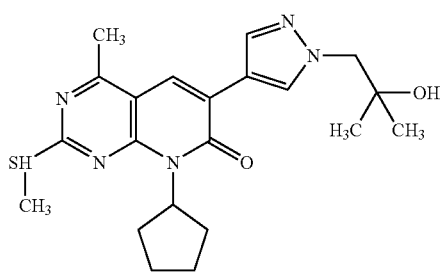

To the solution of 8-Cyclopentyl-4-methyl-2-methylsulfanyl-6-(1H-pyrazol-4-yl)-8H-pyrido[2,3-d]pyrimidin-7-one (100 mg, 0.29 mmol) in 5 ml of DMSO were added 2,2-Dimethyl-oxirane (0.03 ml, 1.20 eq.), and potassium carbonate (40.5 mg, 1.00 eq.) under nitrogen. The reaction mixture was stirred at room temperature. After two hours, no reaction. The reaction mixture was heated to 100° C. for 30 min. Some product was formed. It was continued heating for 1 hour. Starting material was gone. The reaction mixture was partitioned in EA/brine. EA layer was dried and concentrated. It was further purified by chromatography (10% MeOH/DCM). 15 mg of product was obtained at yield of 12%.

LCMS: 414.20 (ES+)

$^1$H NMR (400 MHz, CHLOROFORM-d) δ ppm 8.19 (1H, s) 7.77 (2H, d, J=20.72 Hz) 7.48 (1H, t) 5.78-5.96 (1H, m) 3.92 (2H, s) 2.54 (3H, s) 2.43 (3H, d, J=1.26 Hz) 2.21 (2H, s) 1.91 (2H, s) 1.70 (2H, s) 1.52 (2H, s) 1.01 (6H, s)

Example 81

2-Amino-6-(6-methoxy-pyridin-3-yl)-4-methyl-8-pyrrolidin-3-yl-8H-pyrido[2,3-d]pyrimidin-7-one (Compound 247)

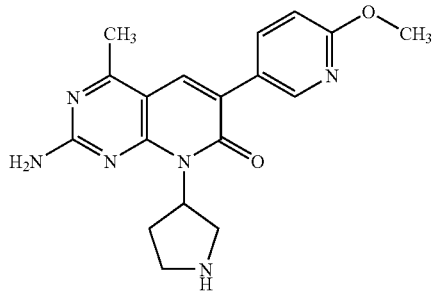

The TFA (0.56 ml, 10 eq.) was added into the solution of 3-[2-Amino-6-(6-methoxy-pyridin-3-yl)-4-methyl-7-oxo-7H-pyrido[2,3-d]pyrimidin-8-yl]pyrrolidine-1-carboxylic acid tert-butyl ester (328 mg, 0.725 mmol) in 2 ml dichloromethane at room temperature. The reaction mixture was stirred at room temperature overnight. The reaction was complete and the solvent was removed. The residue was partitioned in EA/sat. sodium bicarbonate. The EA layer was dried and concentrated to obtain the title compound as a solid (237 mg, 92.8% yield).

LCMS: 353.20 (ES+)

$^1$H NMR (400 MHz, DMSO-d6) δ ppm 8.46 (1H, d, J=2.53 Hz) 8.07 (1H, s) 8.02 (1H, dd, J=8.72, 2.40 Hz) 7.39 (2H, br. s.) 6.87 (1H, d, J=8.59 Hz) 6.23-6.43 (1H, m) 3.88 (3H, s) 3.63-3.77 (2H, m) 3.36-3.45 (2H, m) 3.14-3.26 (1H, m) 2.58 (3H, s) 2.24-2.37 (2H, m)

Example 82

8-(1-Acetyl-pyrrolidin-3-yl)-2-amin-6-(6-methoxy-pyridin-3-yl)-4-methyl-8H-pyrido[2,3-d]pyrimidin-7-one (Compound 248)

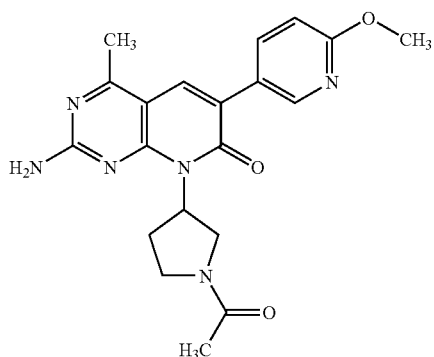

To the solution of 2-Amino-6-(6-methoxy-pyridin-3-yl)-4-methyl-8-pyrrolidin-3-yl-8H-pyrido[2,3-d]pyrimidin-7-one (100 mg, 0.284 mmol) in 5 ml DMF were added acetic acid (17 mg, 1.0 eq.), HATU (108 mg, 1.0 eq.), and TEA (0.04 ml, 1.0 eq.). The reaction mixture was stirred at room temperature overnight. The reaction mixture was partitioned in EA/brine. The EA layer was washed with sodium bicarbonate and brine, dried and concentrated. The residue was further purified by chromatography (10% MeOH/DCM and 0.5% TEA) to give the title compound (37 mg, 31% yield).

LCMS: 395.20 (ES+)

$^1$H NMR (400 MHz, DMSO-d6) δ ppm 8.44 (1H, s) 7.94-8.12 (2H, m) 7.23 (2H, br. s.) 6.85 (1H, d, J=8.59 Hz) 6.07-6.41 (1H, m) 3.83-4.08 (4H, m) 3.47-3.81 (3H, m) 2.62-2.82 (4H, m) 2.53-2.62 (3H, m) 2.02-2.23 (1H, m)

Example 83

Butyl-2-amino-8-(trans-4-hydroxycyclohexyl)-4-methyl-7-oxo-7,8-dihydropyrido[2,3-d]pyrimidine-6-carboxylate

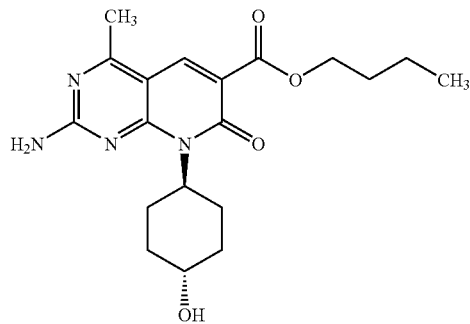

A microwave vial was charged with Mo(CO)6 (264 mg, 1.0 mmol), Herrmann's palladacycle (23 mg, 0.025 mmol), [(t-Bu)3PH]BF4 (15 mg, 0.050 mmol), 2-amino-6-bromo-8-(trans-4-hydroxycyclohexyl)-4-methylpyrido[2,3-d]pyrimidin-7(8H)-one (353 mg, 1.0 mmol), DMF (5 mL) and butanol (5 mL). DBU (412 ml, 3.0 mmol) was added, followed by rapid sealing of the vial under air. The vial was then heated to 120° C. by microwave irradiation for 30 minutes. After cooling, the reaction mixture was slurried with water and filtered. The precipitate was washed with ether and dried to afford 253 mg of butyl 2-amino-8-(trans-4-hydroxycyclohexyl)-4-methyl-7-oxo-7,8-dihydropyrido[2,3-d]pyrimidine-6-carboxylate.

LRMS (M+H)$^+$: 375

$^1$H NMR (400 MHz, DMSO-d6) δ ppm 0.93 (t, J=7.33 Hz, 3H) 1.24-1.33 (m, 2H) 1.37-1.49 (m, 4H) 1.58-1.69 (m, 3H) 1.92 (dd, J=10.74, 3.41 Hz, 3H) 2.52 (s, 3H) 3.47 (s, 1H) 3.54 (s, 1H) 4.18 (t, J=6.69 Hz, 2H) 4.61 (d, J=4.55 Hz, 1H) 7.51 (s, 2H) 8.31 (s, 1H)

Example 84

2-Amino-8-(trans-4-hydroxycyclohexyl)-4-methyl-7-oxo-7,8-dihydropyrido[2,3-d]pyrimidine-6-carboxylic acid

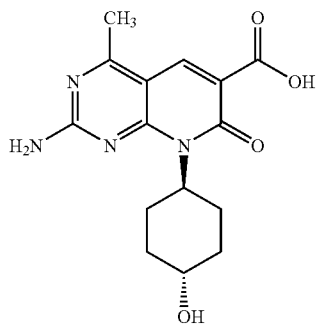

A 1M solution of LiOH in H2O (0.81 mL, 0.81 mmol) was added to a suspension of butyl 2-amino-8-(trans-4-hydroxycyclohexyl)-4-methyl-7-oxo-7,8-dihydropyrido[2,3-d]pyrimidine-6-carboxylate (0.25 g, 0.68 mmol) in THF (7 mL) and MeOH (2 mL). After 2.5 h, DCM, EtOH, water, brine, celite and 0.7 mL of 1 M HCl were added. The mixture was filtered. The organic layer was seperated and concentrated by rotary evaporation to afford 0.25 g of 2-amino-8-(trans-4-hydroxycyclohexyl)-4-methyl-7-oxo-7,8-dihydropyrido[2,3-d]pyrimidine-6-carboxylic acid.

LRMS (M+H)$^+$: 319

$^1$H NMR (400 MHz, DMSO-d6) δ ppm 1.15-1.36 (m, 3H) 1.57 (d, J=11.12 Hz, 2H) 1.56 (br. s., 1H) 1.94 (t, J=9.73 Hz, 2H) 2.62 (s, 3H) 2.67 (br. s., 1H) 3.55 (br. s., 1H) 4.69 (br. s., 1H) 7.92 (d, J=8.59 Hz, 1H) 7.89 (d, J=2.78 Hz, 1H) 8.68 (s, 1H) 14.14 (br. s., 1H)

Example 85

2-Amino-8-(trans-4-hydroxycyclohexyl)-4-methyl-7-oxo-N-1H-pyrazol-5-yl-7,8-dihydropyrido[2,3-d]pyrimidine-6-carboxamide (Compound 251)

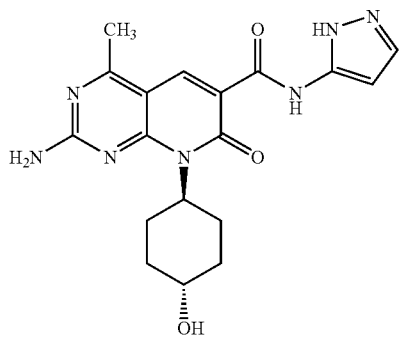

HATU (105 mg, 0.28 mmol) was added to a mixture of 2-amino-8-(trans-4-hydroxycyclohexyl)-4-methyl-7-oxo-7,8-dihydropyrido[2,3-d]pyrimidine-6-carboxylic acid (80 mg, 0.25 mmol), DMF (2.5 mL) and TEA (38 uL, 0.28 mmol). After 5 min. a solution of 1H-pyrazol-5-amine (46 mg, 0.55 mmol) in DMF (0.55 mL) was added. After 19 hours the mixture was diluted with water (~10 mL), centrifuged then decanted. More water was added to the precipitate and procedure was repeated. The resulting precipitate was suspended in a mixture of DCM and methanol and concentrated by rotary evaporation to afford 2-amino-8-(trans-4-hydroxy-cyclohexyl)-4-methyl-7-oxo-N-1H-pyrazol-5-yl-78-dihydropyrido[23-d]pyrimidine-6-carboxamide (35 mg, 37%).

LRMS (M+H)+: 384

$^1$H NMR (400 MHz, DMSO-d 6) δ ppm 1.31 (q, J=12.13 Hz, 2H) 1.56 (d, J=9.85 Hz, 2H) 1.96 (d, J=8.34 Hz, 2H) 2.61 (br. s., 3H) 2.64-2.84 (m, 2H) 3.58 (br. s., 1H) 4.66 (br. s., 1H) 5.54 (br. s., 1H) 6.65 (s, 1H) 7.71 (d, J=5.81 Hz, 1H) 7.67 (br. s., 2H) 8.79 (s, 1H) 11.90 (s, 1H)

Example 86

8-Cyclopentyl-4-methyl-2-methylsulfanyl-7-oxo-7,8-dihydro-pyrido[2,3-d]pyrimidine-6-carboxylic acid ethyl ester

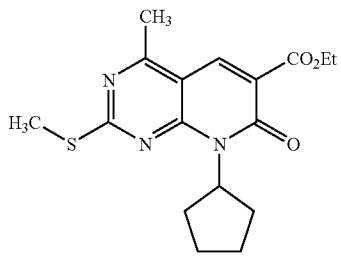

A solution of 4-cyclopentylamino-6-methyl-2-methylsulfanyl-pyrimidine-5-carbaldehyde (20.8 g, 0.083 mol), piperidine (8.2 mL) and AcOH (9.4 mL) in malonic acid diethyl ester (150 mL) was stirred at 130° C. for 72 hours. TLC (petroleum ether/EtOAc 4:1) indicated about half of the starting material was consumed. The reaction mixture was then concentrated in vacuo and the residue was purified by column chromatography (silica gel, petroleum ether/EtOAc 4:1) to yield the title compound (11.3 g, 39.4%) as a yellow solid.

LRMS: 348 (M+H)+.

$^1$H NMR (400 MHz, CDCl$_3$): 8.38 (s, 1H), 5.96-5.91 (m, 1H), 4.38-4.32 (q, 2H), 2.63 (s, 3H), 2.55 (s, 3H), 2.31-2.28 (m, 2H), 2.04-2.00 (m, 2H), 1.83-1.75 (m, 2H), 1.62-1.58 (m, 2H), 1.36-1.32 (t, 3H)

Example 87

8-Cyclopentyl-2-methanesulfinyl-4-methyl-7-oxo-7,8-dihydro-pyrido[2,3-d]pyrimidine-6-carboxylic acid ethyl ester

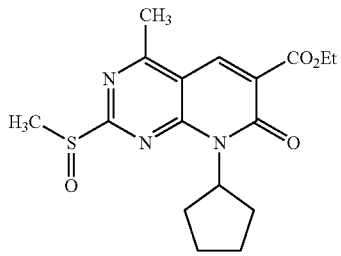

To a stirred solution of compound 86 (17.0 g, 0.049 mol) in CHCl$_3$ (200 mL) was added m-CPBA (11.0 g, 0.050 mol) portion wise at 10° C. After the addition, the resulting mixture was stirred at room temperature for 2 hours. TLC (petroleum ether/EtOAc 2:1) indicated complete consumption of starting material. The reaction mixture was then washed with saturated aqueous Na$_2$SO$_3$ (100 mL×3), saturated aqueous NaHCO$_3$ (100 mL) and brine (100 mL) in sequence, dried over Na$_2$SO$_4$ and concentrated in vacuo to give the title compound (16.0 g, 90.0%) as a yellow solid.

Example 88

8-Cyclopentyl-4-methyl-2-methylamino-7-oxo-7,8-dihydro-pyrido[2,3-d]pyrimidine-6-carboxylic acid ethyl ester

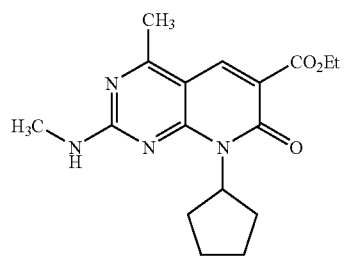

A solution of example 87 (16.0 g, 0.044 mol), methylamine (10.15 g, 0.088 mol, 27% in EtOH), Et$_3$N (8.9 g, 0.088 mol) and a catalytic amount of DMF in acetonitrile (60 mL) was refluxed for 48 hours under a N$_2$ balloon. TLC (petroleum ether/EtOAc 1:2) indicated the starting material was consumed completely. The reaction mixture was then concentrated in vacuo and the residue was purified by column chromatography (silica gel, petroleum ether/EtOAc from 15:1 to 4:1) to yield the crude product. Re-crystallization from CH$_2$Cl$_2$/petroleum ether (10 mL/150 mL) afforded pure title compound (10.5 g, 72.2%) as a white solid.

Example 89

8-Cyclopentyl-4-methyl-2-methylamino-7-oxo-7,8-dihydro-pyrido[2,3-d]pyrimidine-6-carboxylic acid

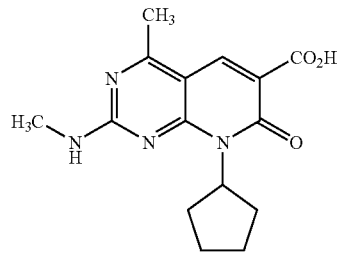

A solution of example 88 (10.5 g, 0.032 mol) and LiOH H$_2$O (2.67 g, 0.064 mol) in EtOH (350 mL) and water (50 mL) was stirred at room temperature overnight. TLC (petroleum ether/EtOAc 1:2) indicated complete consumption of starting material. EtOH was removed in vacuo and the residue was acidified to pH~5 by 1 N aqueous HCl (20 mL). The resulting mixture was filtered. The cake was washed with petroleum ether (100 mL×3) and dried in vacuo to give the title compound (6.53 g, 68.0%) as a white solid.

LRMS: 303 (M+H)+.

¹H NMR (400 MHz, DMSO): 8.59 (s, 1H), 8.12-7.87 (d, 1H), 6.00-5.97 (m, 1H), 2.89 (s, 3H), 2.61-2.56 (d, 3H), 2.31-2.17 (m, 2H), 2.05-1.90 (m, 2H), 1.83-1.70 (m, 2H), 1.70-1.52 (m, 2H)

Example 90

8-Cyclopentyl-4-methyl-2-methylamino-7-oxo-7,8-dihydro-pyrido[2,3-d]pyrimidine-6-carboxylic acid (1H-pyrazol-3-yl)-amide (Compound 250)

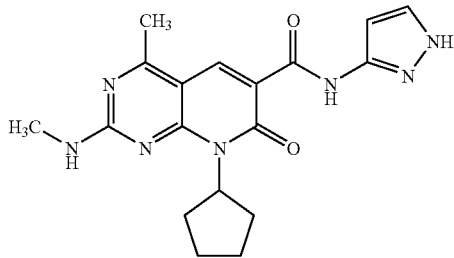

To 110 µL of 0.1 M solution of example 89 in DMF in a test tube (10×95 mm) was added 100 µL of 0.1 M solution of 3-aminopyrazole in DMF followed by 110 µL each of 0.1 M solution of HATU and triethylamine, respectively. The reaction mixture was stirred at 80° C. for 8 h. After the removal of the solvent in vacuo, the residue was reconstituted in 1.2 mL of DMSO and subjected to HPLC purification to obtain the title compound.

LRMS: 368 (M+H)⁺.

¹H NMR (500 MHz, DMSO-$d_6$): 11.89 (s, 1H) 8.78 (s, 1H) 8.11 (s, 1H) 7.63 (s, 1H) 6.64 (s, 1H) 5.95-6.05 (m, 1H) 2.92 (s, 3H) 1.96-2.14 (m, 2H) 1.74-1.94 (m, 2H) 1.54-1.74 (m, 2H).

Example 91

2-(2,2-Difluoroethylamino)-8-(4-hydroxycyclohexyl)-6-(6-methoxypyridin-3-yl)-4-methylpyrido[2,3-d]pyrimidin-7(8H)-one (Compound 275)

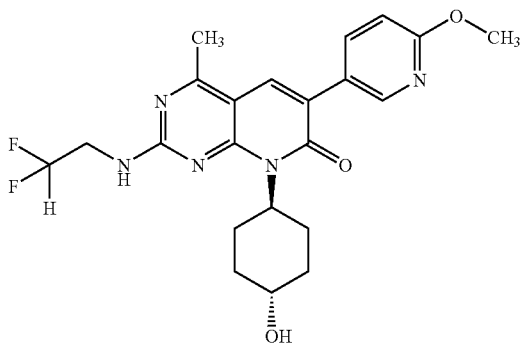

To a solution of 2-amino-8-(4-hydroxycyclohexyl)-6-(6-methoxypyridin-3-yl)-4-methylpyrido[2,3-d]pyrimidin-[7(8H)-one (50 mg, 0.13 mmol) in anhydrous DMA (1.0 ml) at room temperature was added a 1M solution of potassium tert-butoxide in THF (0.14 ml). After stirring at R.T. for 1 hour, to the reaction mixture was added 1-bromo-2,2-difluoroethane (20.9 mg, 0.14 mmol). After stirring at room temperature for 16 h and 4.5 h at 80° C. the reaction mixture was cooled to room temperature, and 1M solution of potassium tert-butoxide in THF (0.16 ml) and 1-bromo-2,2-difluoroethane (41.8 mg, 0.28 mmol) were added. After stirring at 80° C. for 16 h, to the reaction mixture was added another 1M solution of potassium tert-butoxide in THF (0.1 ml) and 1-bromo-2,2difluoroethane (62.7 mg, 0.42 mmol). After stirring at 80° C. for 16 h, to the reaction mixture another 3 eq of 1M solution of potassium tert-butoxide in THF and 3 eq of 1-bromo-2,2-difluoroethane were added. After heating in microwave for 20 mins at 120° C., the reaction mixture was cooled to room temperature and diluted with DMSO, the precipitate was removed by filtration. The filtrate was combined and purified using reversed phase column eluted with acetonitrile (0.1% acetic acid) and water (0.1% acetic acid) to give the titled compound as a solid weighted 14.6 mg.

LCMS (APCI+1) 446.3.

¹H NMR (400 MHz, MeOD): 1.38-1.54 (m, 2H) 1.61-1.76 (m, 2H) 2.04-2.15 (m, 2H) 2.84 (br. s., 2H) 3.63-3.72 (m, 1H) 3.86 (t, J=14.53 Hz, 2H) 3.94 (s, 3H) 5.58 (br. s., 1H) 6.05 (t, J=56.08 Hz, 1H) 6.82 (d, J=8.59 Hz, 1H) 7.91-7.99 (m, 2H) 8.33-8.41 (m, 1H).

Example 92 trans-4-(2-Amino-5-iodo-6-methylpyrimidin-4-ylamino)cyclohexanol

Step 1: Synthesis of trans-4-(2-amino-6-methylpyrimidin-4-ylamino)cyclohexanol

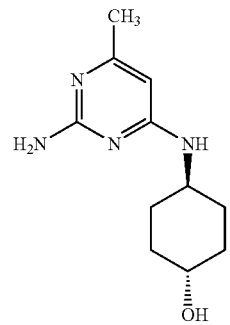

A suspension mixture of 2-amino-4-chloro-6-methylpyrimidine (144 g, 1.0 mol), trans-4-aminocyclohexanol (140 g, 1.2 mol), AcOH (5 mL) in water (0.6 L) was heated at 99° C. in a 3.0 L flask. After 6 h at same temperature, Sodium acetate (82.0 g, 1 mol) was added to the reaction mixture. After 48 h, at the same temperature aq NaOH (50 mL, 10 N) was added. The reaction mixture was heated to 99° C. for 2 additional days. The reaction can be stopped if 2-amino-4-chloro-6-methylpyrimidine is less than 2% by HPLC analysis. If the reaction is slow another portion of aq. NaOH can be added to the reaction mixture as long as the pH is ~7 to 8. The reaction mixture was then neutralized with Sodium bicarbonate and cooled to 0° C. Filtration gave trans-4-(2-amino-6-methylpyrimidin-4-ylamino)cyclohexanol (~85%). Wet material is used for next step.

¹H NMR (300 MHz, DMSO-d6) δ ppm 1.14-1.24 (m, 4H) 1.77-1.86 (m, 4H) 1.97 (s, 3H) 3.35-3.40 (m, 1H) 3.57-3.69

(m, 1H) 4.52 (d, J=4.55 Hz, 1H) 5.53 (s, 1H) 5.73 (s, 2H) 6.43 (d, J=4.29 Hz, 1H) (M+H)+223

Step 2: Synthesis of trans-4-(2-amino-5-iodo-6-methylpyrimidin-4-ylamino)cyclohexanol

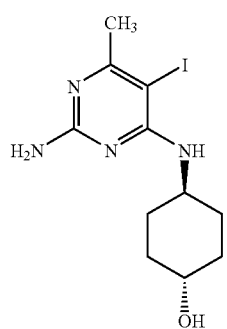

To a slurry of (1r,4r)-4-(2-amino-6-methylpyrimidin-4-ylamino)cyclohexanol (58 g, 0.26 mol) in water (0.5 L) was added slowly 1.0 equivalent of N-iodosuccinimide (59 g, 0.26 mol) at 10° C. over several hours. After stirring at 10° C. for 4 h, the reaction mixture was stirred overnight and heated to 40° C. for several hours. The suspension mixture was then cooled to rt, quenched with NaHSO₃. 0.8 Equivalent of NaOH was added (form the sodium succinimide) and the product was filtered to give 100 g of wet product. The product was purified by slurry with t-butylmethylether and recrystallization in 100 mL methanol and dried to provide pure trans-4-(2-amino-5-iodo-6-methylpyrimidin-4-ylamino)cyclohexanol (65 g, 72% yield).

$^1$H NMR (400 MHz, DMSO-d6) δ ppm 1.10-1.45 (m, 4H) 1.74-1.90 (m, 4H) 2.21 (s, 3H) 3.34-3.43 (m, 1H) 3.79-3.91 (m, 1H) 4.55 (d, J=4.55 Hz, 1H) 5.40 (d, J=8.34 Hz, 1H) 6.11 (s, 2H)

(M+H)+349

Example 93

2-amino-8-(trans-4-hydroxycyclohexyl)-6-(6-methoxypyridin-3-yl)-4-methylpyrido[2,3-d]pyrimidin-7(8H)-one (Compound 152)

Step 1: Preparation of (E)-ethyl 3-(2-amino-4-(trans-4-hydroxycyclohexylamino)-6-methylpyrimidin-5-yl)acrylate

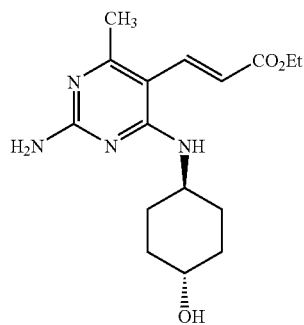

Materials:

| trans-4-(2-amino-5-iodo-6-methylpyrimidin-4-ylamino)cyclohexanol | 35 g, 0.1 mol, 1.0 eq. |
| Ethyl acrylate (FW = 100, d = 0.918) | 22 mL, 0.2 mol, 2.0 eq. |
| Palladium acetate (FW = 224.5) | 675 mg, 3 mmol, 0.03 eq. |
| Triethylamine (FW = 101, d = 0.726) | 28 mL, 0.2 mol, 2.0 eq. |
| DMF | 80 mL |

Procedure:

1. Equip a 500 mL, 3-neck round bottom flask into a heating mantle with a mechanical stirrer, additional funnel, thermocouple and nitrogen inlet.
2. Charge the flask with trans-4-(2-amino-5-iodo-6-methylpyrimidin-4-ylamino)cyclohexanol (35 g), DMF (80 mL), Palladium acetate (675 mg), ethyl acetate (22 mL), and triethylamine (28 mL) and the reaction was heated with stirring at ~90° C. for 6 hours. HPLC analysis indicated the disappearance of the starting material and the reaction is considered completed. The reaction mixture was filtered through charcoal, celite and Silicycle to remove most of the Palladium black. Extraction of the filtrate with heptane (2×100 mL) removed the remaining ethyl acetate and triethylamine. The DMF fraction was subjected to Rotovap distillation to remove remaining ethyl acrylate. The remaining DMF solution (~150 mL) was used directly in next step without any purification.

Step 2: Preparation of 2-amino-8-(trans-4-hydroxycyclohexyl)-4-methylpyrido[2,3-d]pyrimidin-7(8H)-one

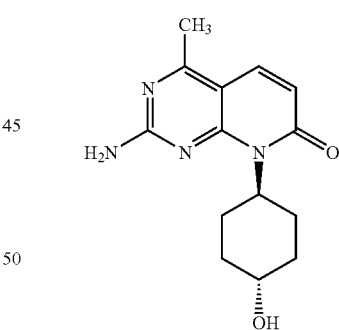

Materials:

| 2-amino-8-(trans-4-hydroxycyclohexyl)-4-methylpyrido[2,3-d]pyrimidin-7(8H)-one solution | 150 mL solution, 1.0 eq. |
| PhSNa (FW = 132) | 13.2 g, 0.1 mol, 1.0 eq. |
| PhSH (FW = 110, d = 1.078) | 11 mL, 0.1 mol, 1.0 eq. |
| DBU (FW = 152, d = 1.018) | 61 mL, 0.4 mol, 4.0 eq. |
| Diisopropylethylamine (FW = 129.24, d = 0.782) | 100 mL, 0.6 mol, 6.0 eq. |
| Dimethylformide | 100 mL |

Procedure:

1. Equip a 500 mL, 3-neck round bottom flask with a mechanical stirrer, thermocouple, addition funnel, nitrogen inlet and distillation set into a heating mantle.
2. Charge the flask with the DMF solution from last step, PhSNa (13.2 g), PhSH (11 mL), DBU (61 mL), Diisopropylethylamine, and DMF (100 mL). The reaction mixture was heated at 110° C. for 3 hours. HPLC analysis indicated the disappearance of the starting material and the reaction was considered completed.
3. The DMF solution was concentrated under high vacuum (5 psi) at 55° C. to give ~150 mL of solution, which was washed with 500 mL of t-butyl methyl ether. The ether layer was separated. 100 mL of MeOH, 600 mL of water, and 300 mL of Toluene were added to the reaction mixture, which was stirred overnight under air. Filtration gave wet crude 2-amino-8-((1r,4r)-4-hydroxycyclohexyl)-4-methylpyrido[2,3-d]pyrimidin-7(8H)-one which was directly used in next step (16 g, 50%, crude)

Step 3: Preparation of 2-amino-6-bromo-8-(trans-4-hydroxycyclohexyl)-4-methylpyrido[2,3-d]pyrimidin-7(8H)-one

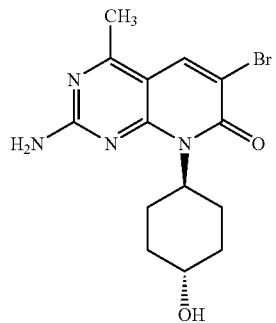

Materials:

| | |
|---|---|
| 2-amino-8-((1r,4r)-4-hydroxycyclohexyl)-4-methylpyrido[2,3-d]pyrimidin-7(8H)-one (FW = 321) | 11.0 g, 34 mmol, 1.0 eq. |
| N-bromosuccinimide (FW = 178) | 9.2 g, 52 mmol, 1.2 eq. |
| Acetonitrile/water (1:1) | 200 mL |

Procedure:

1. Equip a 500 mL, round bottom flask with a mechanical stirrer
2. To a solution of 2-amino-8-((1r,4r)-4-hydroxycyclohexyl)-4-methylpyrido[2,3-d]pyrimidin-7(8H)-one (11.0 g, 34 mmol) in 1:1 acetonitrile/water (200 mL) was added N-bromosuccinimide (9.2 g, 52 mmol). After stirring for 6 hours at room temperature the solution was concentrated. Filtration gave the crude product.
3. The crude product was slurried in 50 mL of t-butyl methyl ether. Filtration gave 2-amino-6-bromo-8-(trans-4-hydroxycyclohexyl)-4-methylpyrido[2,3-d]pyrimidin-7(8H)-one in high purity (~8 g, 70%).

Step 4: Preparation of 2-amino-8-(trans-4-hydroxycyclohexyl)-6-(6-methoxypyridin-3-yl)-4-methylpyrido[2,3-d]pyrimidin-7(8H)-one (Compound 152)

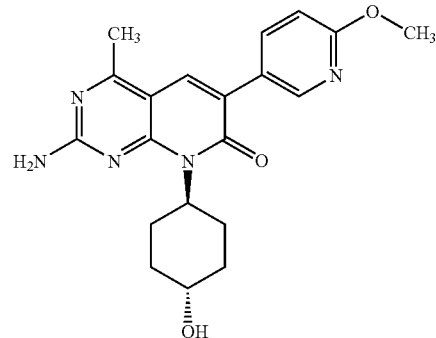

Materials:

| | |
|---|---|
| 2-amino-6-bromo-8-(trans-4-hydroxycyclohexyl)-4-methylpyrido[2,3-d]pyrimidin-7(8H)-one (FW = 353.21) | 13.2 g, 37.38 mmol, 1.0 eq. |
| 6-methoxypyridin-3-ylboronic acid (FW = 152.94) | 7.15 g, 46.7 mol, 1.25 eq. |
| $Cs_2CO_3$ (FW = 325.8) | 36.5 g 112.14 mmol, 3.0 eq. |
| $PdCl_2(PPh_3)_2$ (FW = 816.6) | 916 mg, 1.12 mmol, 0.03 eq. |
| 1,2-dimethoxyethane (DME)/water | 240 mL/50 mL |

Procedure:

1. Equip a 1 L, 3-neck round bottom flask into a heating mantle with a mechanical stirrer, reflux condenser, drying tube, thermocouple and nitrogen inlet.
2. Charge the flask with 2-amino-6-bromo-8-(trans-4-hydroxycyclohexyl)-4-methylpyrido[2,3-d]pyrimidin-7(8H)-one (13.2 g), 6-methoxypyridin-3-ylboronic acid to boronic (7.15 g), $Cs_2CO_3$ (36.5 g), $PdCl_2(PPh_3)_2$ (916 mg), and 1,2-dimethoxyethane (DME)/water (240 mL/50 mL), The reaction mixture was heated to reflux at 80° C. for 2 hours. HPLC analysis indicated the disappearance of the starting material and the reaction was considered completed.
3. The reaction mixture was cooled to room temperature. Filtration removes the insoluble inorganic salts. The inorganic filter cake was vigorously washed with hot THF, combined with filtrate. Aqueous layer was separated and extract THF. THF was evaporated and dry ethanol was added and then evaporated to give a dark solid. The solid were dissolved in 400 mL of THF and heated at 80° C. with 60 g of Silicycle. Filtration and concentration of THF gave the crude final product.
4. The crude product (12.0 g) was slurried in 20 mL of THF and 150 mL of methanol and then heated to reflux for 30 min. The sample was allowed to slowly cool down to 23° C. overnight. The solids were collected by filtration and dried at 55° C. under high vacuum to obtain 9.0 g of 2-amino-8-(trans-4-hydroxycyclohexyl)-6-(6-methoxypyridin-3-yl)-4-methylpyrido[2,3-d]pyrimidin-7(8H)-one (Compound 152). The compound purity was confirmed by HPLC to be 94%.

Example 94 cis-4-(5-Bromo-2-(2,5-dimethyl-1H-pyrrol-1-yl)-6-methylpyrimidin-4-ylamino)cyclohexanol

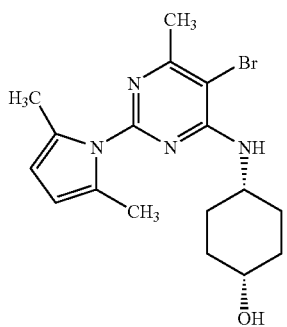

A mixture of 5-bromo-4-chloro-2-(2,5-dimethyl-1H-pyrrol-1-yl)-6-methylpyrimidine (5.00 g, 17.0 mmol), cis-4-aminocyclohexanol hydrochloride (2.77 g, 18.3 mmol), and diisopropylethyl amine (8.69 mL, 49.9 mmol) in dimethylacetamide (60.0 mL) was heated at 160° C. in a sealed tube overnight. The reaction mixture was concentrated and the residue was purified by flash chromatography eluting with chloroform/methanol (0-3%). Combined fractions containing the desired product were concentrated. The resulting gum was dissolved in methyl tert-butyl ether (450 mL) and the solution was washed with 50% brine, dried (MgSO$_4$), filtered and concentrated to afford the title compound as a orange foamy solid (5.53 g, 88%).

(M+H)$^+$379, 381

1H NMR (400 MHz, DMSO-d6) δ ppm 1.46-1.57 (m, 4H) 1.59-1.69 (m, 2H) 1.79-1.90 (m, 2H) 2.25 (s, 6H) 2.41 (s, 3H) 3.77 (d, J=2.27 Hz, 1H) 3.90-4.00 (m, 1H) 4.40 (d, J=2.78 Hz, 1H) 5.75 (s, 2H) 6.74 (d, J=8.08 Hz, 1H)

Example 95

2-cis-4-(5-Bromo-2-(2,5-dimethyl-1H-pyrrol-1-yl)-6-methylpyrimidin-4-ylamino)cyclohexyloxy)ethanol

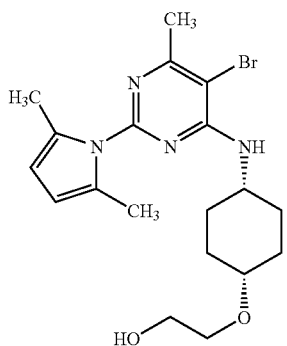

To a cooled (0° C.) solution of cis-4-(5-bromo-2-(2,5-dimethyl-1H-pyrrol-1-yl)-6-methylpyrimidin-4-ylamino)cyclohexanol (2.50 g, 6.59 mmol) in dimethylformamide (17.0 mL) was added sodium hydride (60% dispersion in oil, 527 mg, 13.2 mmol). After 2.5 hr at 0° C. a solution of 1,3,2-dioxathiolane 2,2 dioxane (1.23 g, 9.89 mmol) in dimethylformamide (7.0 mL) was added drop wise over 1 hr. After stirring 0° C. overnight an additional 4 eq sodium hydride was added followed by 1,3,2-dioxathiolane 2,2 dioxane in 0.25 eq portions every 15 min up to 2.25 eq. The reaction was quenched with methanol and concentrated. The residue was then diluted with 1,4 dioxane (200 ml) and water (5.0 ml). p-Toluenesulfonic acid (g mmol) was added and the mixture was heated to 40° C. for 1.5 hour. The solution cooled to 0° C. and saturated with solid sodium bicarbonate. Diluted with water (100 mL) and extracted with dichloromethane (3×500 mL). Combined organics were washed with brine (150 mL), dried (MgSO$_4$), filtered, and concentrated. The crude product was purified by flash chromatography eluting with hexanes/methyl tert-butylether (15-75%) to afford the title compound (1.27 g, 45%).

$^1$H NMR (400 MHz, DMSO-d6) δ ppm 1.40-1.50 (m, 2H) 1.51-1.61 (m, 2H) 1.72-1.80 (m, 2H) 1.80-1.88 (m, 2H) 2.26 (s, 6H) 2.41 (s, 3H) 3.39 (t, J=5.43 Hz, 2H) 3.48-3.57 (m, 3H) 3.94-4.03 (m, 1H) 4.50 (t, J=5.56 Hz, 1H) 5.75 (s, 2H) 6.80 (d, J=8.08 Hz, 1H)

(M+H)$^+$424

Example 96

2-(cis-4-(2-Amino-5-bromo-6-methylpyrimidin-4-ylamino)cyclohexyloxy)ethanol

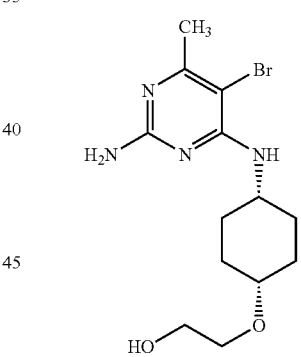

A solution of 2-(cis-4-(5-bromo-2-(2,5-dimethyl-1H-pyrrol-1-yl)-6-methylpyrimidin-4-ylamino)cyclohexyloxy) ethanol (1.23 g, 2.91 mmol) and hydroxylamine hydrochloride (1.01 g, 14.5 mmol) in 10:1 ethanol:water (22.0 mL) was heated to reflux overnight. The reaction mixture was concentrated and the residue was purified by flash chromatography eluting with chloroform/7 N ammonia in methanol (0-4%) to afford the title compound (697 mg, 70%).

(M+H)$^+$345, 347

1H NMR (400 MHz, DMSO-d6) δ ppm 1.41-1.50 (m, 2H) 1.51-1.60 (m, 2H) 1.60-1.70 (m, 2H) 1.72-1.81 (m, 2H) 2.17 (s, 3H) 3.38 (t, J=5.43 Hz, 2H) 3.44-3.47 (m, 1H) 3.49 (q, J=5.39 Hz, 2H) 3.86-3.96 (m, 1H) 4.50 (t, J=5.68 Hz, 1H) 5.76 (d, J=8.08 Hz, 1H) 6.09 (s, 2H)

Example 97

(E)-Ethyl 3-(2-amino-4-(cis-4-(2-hydroxyethoxy)cyclohexylamino)-6-methylpyrimidin-5-yl)acrylate

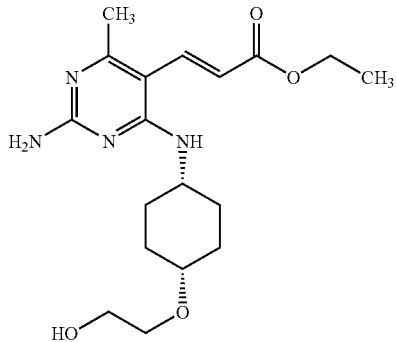

In a sealed tube a solution of 2-(cis-4-(2-amino-5-bromo-6-methylpyrimidin-4-ylamino)cyclohexyloxy)ethanol (695 mg, 4.03 mmol) and ethyl acrylate (438 uL, 4.03 mmol) in triethylamine (10 mL) was bubbled with argon for ~5 minutes. Tetrakis(triphenylphosphin)-palladium (0) (232 mg, 0.201 mmol) was added, the vial was sealed and the mixture was bubbled again with argon (5 minutes). The reaction was heated to 130° C. overnight, cooled to room temperature and concentrated. The residue was dissolved in chloroform (500 mL) and washed with water and brine, dried (MgSO$_4$), filtered and concentrated. The crude product was purified by flash chromatography eluting with chloroform/7 N ammonia in methanol (0-4%) to afford the title compound (615 mg, 84%).

(M+H)$^+$365

1H NMR (400 MHz, DMSO-d6) δ ppm 1.24 (t, J=7.07 Hz, 3H) 1.38-1.48 (m, 2H) 1.51-1.59 (m, 2H) 1.62-1.73 (m, 2H) 1.77-1.86 (m, 2H) 2.21 (s, 3H) 3.39 (t, J=5.43 Hz, 2H) 3.47-3.53 (m, 3H) 3.97-4.06 (m, 1H) 4.15 (q, J=7.07 Hz, 2H) 4.50 (t, J=5.56 Hz, 1H) 5.95 (d, J=15.92 Hz, 1H) 6.30-6.37 (m, 3H) 7.61 (d, J=15.92 Hz, 1H)

Example 98

2-Amino-8-(cis-4-(2-hydroxyethoxy)cyclohexyl)-4-methylpyrido[2,3-d]pyrimidin-7(8H)-one

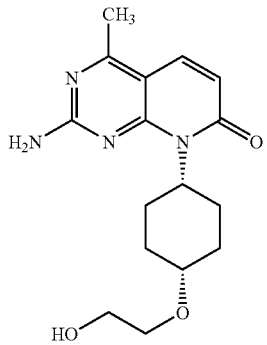

A solution of (E)-ethyl 3-(2-amino-4-(cis-4-(2-hydroxyethoxy)cyclohexylamino)-6-methylpyrimidin-5-yl)acrylate (615 mg, 1.69 mmol), thiophenol (173 ul, 1.69 mmol), benzenethiol, sodium salt (248 mg, 1.69 mmol), 1,5-diazabicyclo5,4,0)undec-5-ene (1.01 mL, 6.75 mmol) and diisopropylethyl amine (1.76 mL, 10.1 mmol) in N',N-dimethylformamide (11.2 mL) was heated to 120° C. overnight. The reaction mixture was concentrated and the residue was partitioned between methyl tert-butylether (500 mL) and saturated sodium bicarbonate (50 mL). The organic layer was separated and washed with 50% brine, dried (Na$_2$SO$_4$), filtered and concentrated. The combined aqueous layers were extracted with chloroform (3×175 mL). Combined extracts were washed with brine (50 mL), dried (Na$_2$SO$_4$), filtered and concentrated. The crude product was purified by flash chromatography eluting with chloroform/7N ammonia in methanol (0-6%) to afford the title compound (411 mg, 77%).

(M+H)$^+$319

1H NMR (300 MHz, DMSO-d6) δ ppm 1.15-1.28 (m, 2H) 1.35-1.50 (m, 2H) 1.91-2.04 (m, 2H) 2.46 (s, 3H) 2.83-3.13 (m, 2H) 3.41 (t, J=5.09 Hz, 2H) 3.50-3.61 (m, 3H) 4.65 (t, J=15.26 Hz, 1H) 5.26-5.43 (m, 1H) 6.14 (d, J=9.42 Hz, 1H) 6.86-7.15 (m, 2H) 7.81 (d, J=9.42 Hz, 1H)

Example 99

2-Amino-6-bromo-8-(cis-4-(2-hydroxyethoxy)cyclohexyl)-4-methylpyrido[2,3-d]pyrimidin-7(8H)-one (Compound 284)

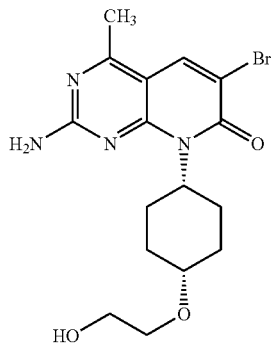

To a solution of 2-amino-8-(cis-4-(2-hydroxyethoxy)cyclohexyl)-4-methylpyrido[2,3-d]pyrimidin-7(8H)-one (411 mg, 1.29 mmol) in dimethylformamide (10 mL) was added N-bromosuccinimide (253 mg, 1.42 mmol). After stirring for 1 hour at room temperature the solution was concentrated. The residue was dissolved in chloroform (250 mL) and washed with 1 N sodium carbonate (2×25 mL) and brine (25 mL). The organic layer was dried (Na$_2$SO$_4$), filtered and concentrated. The crude product was purified by flash chromatography eluting with 1:1 ethyl acetate:chloroform/7N ammonia in methanol (0-4%) to afford the title compound (382 mg, 75%).

(M+H)$^+$397, 399

1H NMR (400 MHz, DMSO-d6) δ ppm 1.22-1.31 (m, 2H) 1.37-1.48 (m, 2H) 1.94-2.04 (m, 2H) 2.49 (s, 3H) 2.78-3.03 (m, 2H) 3.42 (t, J=5.31 Hz, 2H) 3.53-3.61 (m, 3H) 4.53-4.79 (m, 1H) 5.33-5.56 (m, 1H) 7.08-7.32 (m, 2H) 8.33 (s, 1H)

Example 100

2-Amino-8-(cis-4-(2-hydroxyethoxy)cyclohexyl)-6-(6-methoxypyridin-3-yl)-4-methylpyrido[2,3-d]pyrimidin-7(8H)-one (Compound 285)

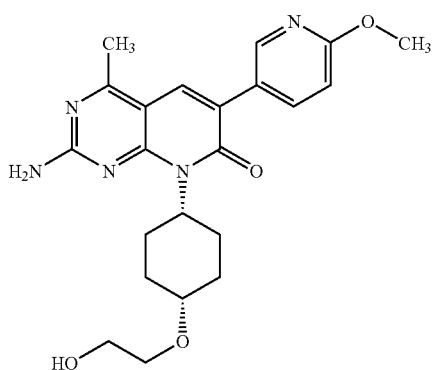

A mixture of 2-amino-6-bromo-8-(cis-4-(2-hydroxyethoxy)cyclohexyl)-4-methylpyrido[2,3-d]pyrimidin-7(8H)-one (50 mg, 0.13 mmol), potassium carbonate (52 mg, 0.38 mmol), and 2-methoxy-5-pyridine boronic acid (38 mg, 0.25 mmol) in 5:1 dimethylformade:water (1.3 mL) was bubbled with argon for 5 minutes. To the mixture was added bis(tripehnylphosphine) palladium (II) chloride (9 mg, 0.13 mmol) and the microwave vial was immediately sealed and the mixture was bubbled again with argon. After heating for 20 min at 100° C. in the microwave, the mixture was concentrated in vacuo. The residue was dissolved in $CHCl_3$ (60 mL) and washed with water (10 mL) and brine (10 mL). The organic layer was dried ($Na_2SO_4$), filtered and concentrated. The crude product was purified by flash chromatography eluting with chloroform/7 N ammonia in methanol (0-5%) to afford the title compound (50 mg, 93%).

$(M+H)^+$ 426

1H NMR (400 MHz, DMSO-d6) δ ppm 1.25-1.33 (m, 2H) 1.39-1.50 (m, 2H) 1.95-2.04 (m, 2H) 2.55 (s, 3H) 2.89-3.12 (m, 2H) 3.42 (t, J=5.18 Hz, 2H) 3.52-3.61 (m, 3H) 3.88 (s, 3H) 4.52-4.79 (m, 1H) 5.37-5.55 (m, 1H) 6.85 (d, J=8.59 Hz, 1H) 6.97-7.20 (m, 2H) 7.97 (s, 1H) 8.00 (dd, J=8.72, 2.40 Hz, 1H) 8.42 (d, J=2.02 Hz, 1H)

TABLE 1

| Compound | Synthetic Method (% Yield) | Structure | Compound Name | LRMS m/z | 1H NMR |
|---|---|---|---|---|---|
| 102 | D | 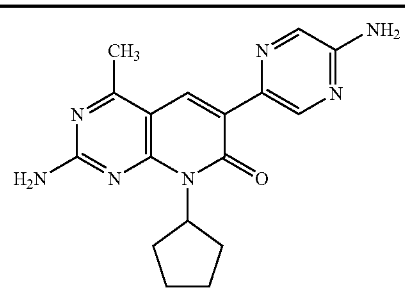 | 2-amino-6-(5-aminopyrazin-2-yl)-8-cyclopentyl-4-methylpyrido[2,3-d]pyrimidin-7(8H)-one | 338 $(M + H)^+$ | 1H NMR ($CDCl_3$, 400 MHz): 8.90 (d, J = 1.52 Hz, 1H), 8.39 (s, 1H), 7.97 (d, J = 1.52 Hz, 1H), 7.18 (s, 2H), 6.56 (s, 2H), 6.11-5.94 (m, 1H), 2.55 (s, 3H), 2.26 (dd, J = 11.12, 7.58 Hz, 2H), 2.11-1.98 (m, 2H), 1.83-1.71 (m, 2H), 1.66-1.54 (m, 2H). |
| 103 | C (20%) | 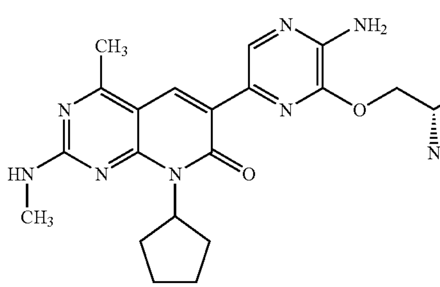 | Chiral 6-(5-amino-6-{[(2S)-2-aminopropyl]oxy}pyrazin-2-yl)-8-cyclopentyl-4-methyl-2-(methylamino)pyrido[2,3-d]pyrimidin-7(8H)-one | 425 $(M + H)^+$ | 1H NMR (DMSO-d6, 400 MHz): 8.65 (1H, s), 8.44 (1H, s), 7.28-7.81 (1H, m), 6.60 (2H, s), 5.78-6.20 (1H, m), 4.32 (1H, dd, J = 10.48, 4.17 Hz), 4.07 (1H, dd, J = 10.36, 7.07 Hz), 2.89 (3H, d, J = 4.55 Hz), 2.53-2.69 (3H, m), 1.52-2.46 (11H, m), 1.14 (3H, d, J = 6.57 Hz). |
| 108 | A (50%) | 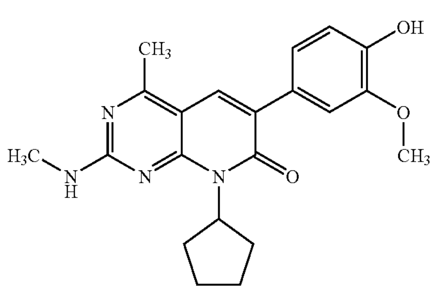 | 8-cyclopentyl-6-(4-hydroxy-3-methoxyphenyl)-4-methyl-2-(methylamino)pyrido[2,3-d]pyrimidin-7(8H)-one | 381 $(M + H)^+$ | 1H NMR (DMSO-$d_6$, 400 MHz): 9.06 (1H, s), 7.84 (1H, s), 7.61 (1H, m), 7.25 (1H, s), 7.10 (1H, m), 6.87-6.88 (1H, m), 5.96 (1H, m), 3.80 (3H, s), 2.88 (3H, m), 2.55 (3H, s), 2.24 (2H, bm), 2.02 (2H, bm), 1.76 (2H, bm), 1.63 (2H, bm). |

TABLE 1-continued

| Compound | Synthetic Method (% Yield) | Structure | Compound Name | LRMS m/z | ¹H NMR |
|---|---|---|---|---|---|
| 110 | E | 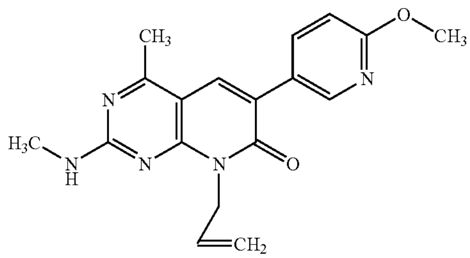 | 8-allyl-6-(6-methoxypyridin-3-yl)-4-methyl-2-(methylamino)pyrido[2,3-d]pyrimidin-7(8H)-one | | (400 MHz, CHLOROFORM-d) δ ppm 2.59 (s, 3H) 3.09 (d, J = 5.05 Hz, 3H) 3.98 (s, 3H) 5.09 (s, 2H) 5.19 (d, J = 9.60 Hz, 1H) 5.24-5.48 (m, 2H) 5.89-6.14 (m, 1H) 6.80 (d, J = 8.84 Hz, 1H) 7.79 (s, 1H) 8.03 (dd, J = 8.72, 2.40 Hz, 1H) 8.35 (d, J = 2.27 Hz, 1H) |
| 111 | A (55%) | 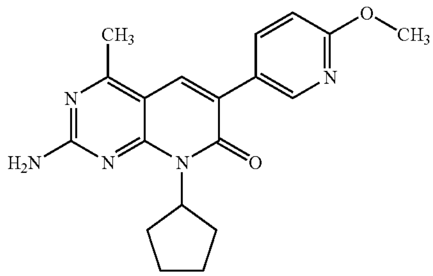 | 2-amino-8-cyclopentyl-6-(6-methoxypyridin-3-yl)-4-methylpyrido[2,3-d]pyrimidin-7(8H)-one | 352 (M + H)⁺ | ¹H NMR (DMSO-d₆, 400 MHz): 8.43 (1H, s), 8.02 (1H, m), 7.99 (1H, s), 7.17 (2H, bs), 6.86-6.84 (1H, m), 6.02-5.98 (1H, m), 3.88 (3H, s), 2.56 (3H, s), 2.24-2.23 (2H, bm), 2.02 (2H, bm), 1.76 (2H, bm), 1.59 (2H, bm). |
| 112 | A (75%) | 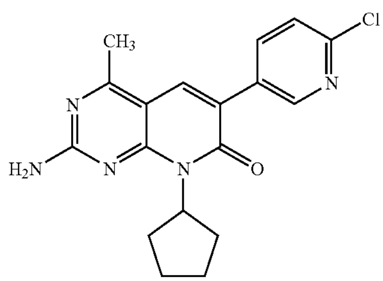 | 2-amino-6-(6-chloropyridin-3-yl)-8-cyclopentyl-4-methylpyrido[2,3-d]pyrimidin-7(8H)-one | 356 (M + H)⁺ | ¹H NMR (DMSO-d₆, 400 MHz): 8.70 (1H, s), 8.15 (1H, s), 7.57 (2H, m), 7.33 (2H, bs), 6.00 (1H, m), 2.59 (3H, s), 2.23 (2H, bm), 2.02 (2H, bm), 1.76 (2H, bm), 1.59 (2H, bm). |
| 115 | A (58%) | 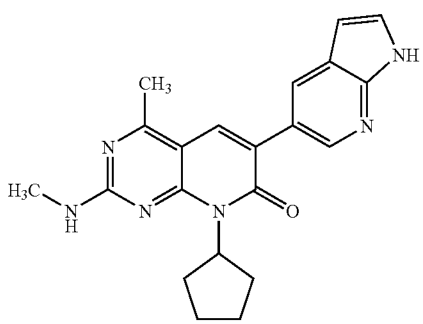 | 8-cyclopentyl-4-methyl-2-(methylamino)-6-(1H-pyrrolo[2,3-b]pyridin-5-yl)pyrido[2,3-d]pyrimidin-7(8H)-one | 375 (M + H)⁺ | ¹H NMR (DMSO-d₆, 400 MHz): 8.47 (1H, s), 8.23 (1H, s), 8.00 (1H, s), 7.49 (1H, d), 7.14 (2H, bs), 6.49 (1H, m), 6.04 (1H, m), 2.98 (3H, s), 2.55 (3H, s), 2.28-2.23 (2H, bm), 2.03 (2H, bm), 1.78 (2H, bm), 1.59 (2H, bm). |
| 117 | B (4.6%) | 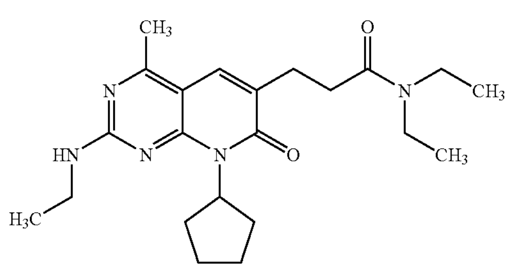 | 3-[8-cyclopentyl-2-(ethylamino)-4-methyl-7-oxo-7,8-dihydropyrido[2,3-d]pyrimidin-6-yl]-N,N-diethylpropanamide | 400 (M + H)⁺ | ¹H NMR (MeOD, 400 MHz) 7.75 (s, 1H) 5.89-6.21 (m, 1H) 3.46 (q, J = 7.30 Hz, 2H) 3.32-3.41 (m, 4H) 2.83 (t, J = 7.30 Hz, 2H) 2.67 (t, J = 7.18 Hz, 2H) 2.54 (s, 3H) 2.29-2.46 (m, 2H) 1.99-2.15 (m, 2H) 1.77-1.89 (m, 2H) 1.61-1.76 (m, 2H) 1.23 (t, J = 7.18 Hz, 3H) 1.14 (t, J = 7.05 Hz, 3H) 1.06 (t, J = 7.05 Hz, 3H). |

TABLE 1-continued

| Compound | Synthetic Method (% Yield) | Structure | Compound Name | LRMS m/z | ¹H NMR |
|---|---|---|---|---|---|
| 118 | B (27%) | 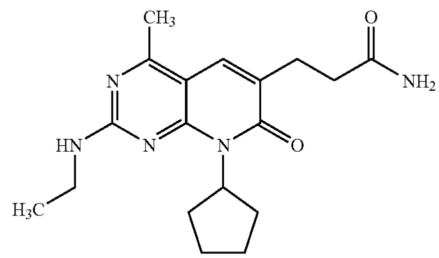 | 3-[8-cyclopentyl-2-(ethylamino)-4-methyl-7-oxo-7,8-dihydropyrido[2,3-d]pyrimidin-6-yl]propanamide | 344 (M + H)⁺ | ¹H NMR (MeOD, 400 MHz) 7.76 (s, 1H) 5.89-6.16 (m, 1H) 3.46 (q, J = 7.30 Hz, 2H) 2.82 (t, J = 7.43 Hz, 2H) 2.54 (s, 3H) 2.51 (t, J = 7.55 Hz, 2H) 2.29-2.44 (m, 2H) 2.01-2.13 (m, 2H) 1.76-1.89 (m, 2H) 1.62-1.75 (m, 2H) 1.23 (t, J = 7.18 Hz, 3H). |
| 119 | B (3.6%) | 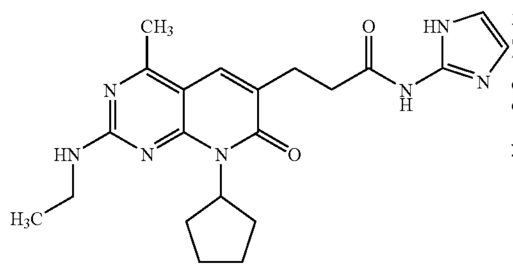 | 3-[8-cyclopentyl-2-(ethylamino)-4-methyl-7-oxo-7,8-dihydropyrido[2,3-d]pyrimidin-6-yl]-N-1H-imidazol-2-ylpropanamide | 410 (M + H)⁺ | ¹H NMR (MeOD, 400 MHz) 7.78 (s, 1H) 6.79 (s, 2H) 5.91-6.16 (m, 1H) 3.42-3.52 (m, 3H) 2.86-2.96 (m, 2H) 2.71 (t, J = 7.55 Hz, 3H) 2.50 (s, 3H) 2.31-2.47 (m, 2H) 2.00-2.14 (m, 2H) 1.84 (d, J = 5.29 Hz, 2H) 1.62-1.76 (m, 2H) 1.23 (t, J = 7.18 Hz, 3H). |
| 122 | B (9.0%) | 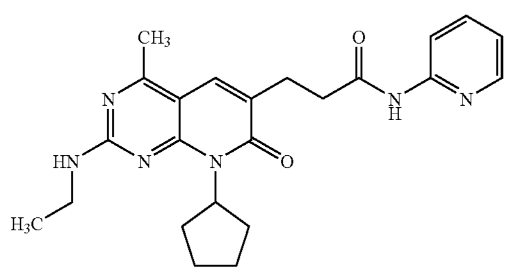 | 3-[8-cyclopentyl-2-(ethylamino)-4-methyl-7-oxo-7,8-dihydropyrido[2,3-d]pyrimidin-6-yl]-N-pyridin-2-ylpropanamide | 421 (M + H)⁺ | ¹H NMR (MeOD, 400 MHz) 8.26 (dd, J = 4.78, 1.01 Hz, 1H) 8.07 (d, J = 8.31 Hz, 1H) 7.79 (s, 1H) 7.71-7.78 (m, 1H) 7.04-7.12 (m, 1H) 5.98-6.15 (m, 1H) 3.40-3.51 (m, 2H) 2.92 (t, J = 7.43 Hz, 2H) 2.73 (t, J = 7.43 Hz, 2H) 2.50 (s, 3H) 2.38 (s, 2H) 1.99-2.14 (m, 2H) 1.77-1.90 (m, 2H) 1.61-1.76 (m, 2H) 1.23 (t, J = 7.30 Hz, 3H). |
| 124 | A (35%) | 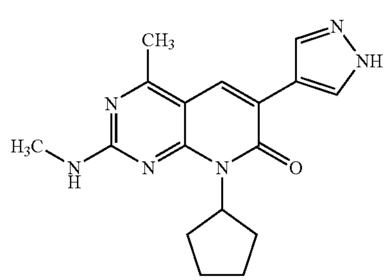 | 8-cyclopentyl-4-methyl-2-(methylamino)-6-(1H-pyrazol-4-yl)pyrido[2,3-d]pyrimidin-7(8H)-one | 325 (M + H)⁺ | ¹H NMR (DMSO-d₆, 400 MHz): 8.26 (2H, bs), 8.13 (1H, s), 7.09 (2H, bs), 6.02-5.99 (1H, m), 2.87 (3H, s), 2.59 (3H, s), 2.27-2.23 (2H, bm), 2.01 (2H, bm), 1.77-1.74 (2H, bm), 1.63 (2H, bm). |
| 125 | A (88%) | 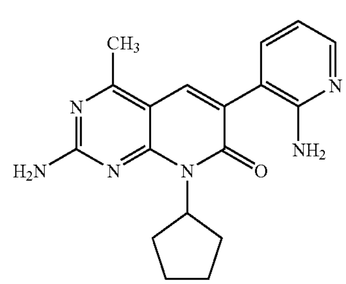 | 2-amino-6-(2-aminopyridin-3-yl)-8-cyclopentyl-4-methylpyrido[2,3-d]pyrimidin-7(8H)-one | 352 (M + H)⁺ | ¹H NMR (CDCl₃, 400 MHz): 7.98-7.96 (1H, m), 7.96 (1H, s), 7.71-7.69 (1H, m), 6.86-6.82 (1H, m), 6.00-5.96 (1H, m), 2.51 (3H, s), 2.25-2.18 (2H, bm), 1.98 (2H, bm), 1.75-1.71 (2H, bm), 1.56-1.54 (2H, bm). |

TABLE 1-continued

| Compound | Synthetic Method (% Yield) | Structure | Compound Name | LRMS m/z | ¹H NMR |
|---|---|---|---|---|---|
| 126 | A (40%) | 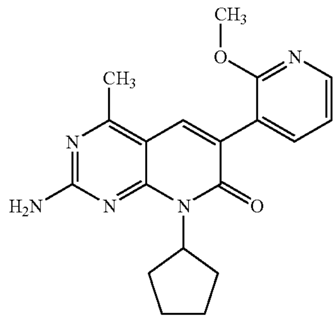 | 2-amino-8-cyclopentyl-6-(2-methoxypyridin-3-yl)-4-methylpyrido[2,3-d]pyrimidin-7(8H)-one | 352 (M + H)⁺ | ¹H NMR (CDCl₃, 400 MHz): 8.09-8.08 (1H, m), 7.75 (1H, s), 7.45-7.43 (1H, m), 6.78-6.75 (1H, m), 6.08 (1H, bs), 5.11 (1H, bs), 3.09 (3H, s), 2.55 (3H, s), 2.41 (2H, bm), 2.08 (2H, bm), 1.90-1.85 (2H, bm), 1.69-1.66 (2H, bm). |
| 127 | A (60%) | 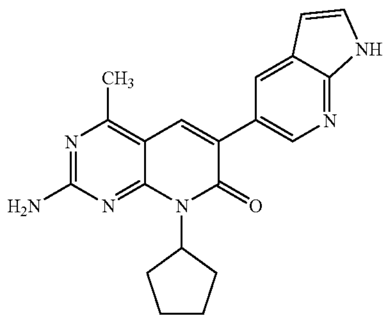 | 2-amino-8-cyclopentyl-4-methyl-6-(1H-pyrrolo[2,3-b]pyridin-5-yl)pyrido[2,3-d]pyrimidin-7(8H)-one | 361 (M + H)⁺ | ¹H NMR (DMSO-d₆, 400 MHz): 8.46 (1H, s), 8.23 (1H, s), 8.00 (1H, s), 7.49 (1H, d), 7.14 (2H, bs), 6.49 (1H, m), 6.04 (1H, m), 2.58 (3H, s), 2.28-2.23 (2H, bm), 2.03 (2H, bm), 1.78 (2H, bm), 1.59 (2H, bm). |
| 128 | A (85%) | 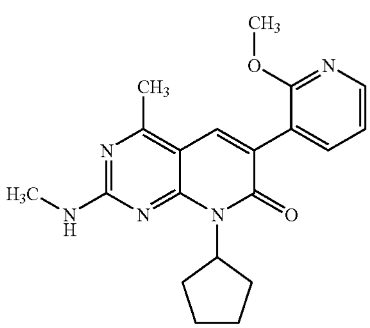 | 8-cyclopentyl-6-(2-methoxypyridin-3-yl)-4-methyl-2-(methylamino)pyrido[2,3-d]pyrimidin-7(8H)-one | 366 (M + H)⁺ | ¹H NMR (CDCl₃, 400 MHz): 8.17-8.15 (1H, m), 7.80 (1H, s), 7.74-7.72 (1H, m), 6.98-6.94 (1H, m), 6.04 (1H, bs), 3.95 (3H, s), 3.09-3.07 (3H, m), 2.55 (3H, s), 2.41 (2H, bm), 2.01 (2H, bm), 1.90-1.85 (2H, bm), 1.69-1.66 (2H, bm). |
| 131 | A (65%) | 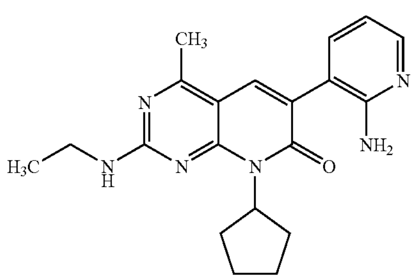 | 6-(2-aminopyridin-3-yl)-8-cyclopentyl-2-(ethylamino)-4-methylpyrido[2,3-d]pyrimidin-7(8H)-one | 365 (M + H)⁺ | ¹H NMR (CDCl₃, 400 MHz): 7.98-7.96 (1H, m), 7.94 (1H, s), 7.63 (1H, m), 6.82-6.79 (1H, m), 5.93 (1H, m), 3.34 (2H, m), 2.51 (3H, s), 2.35-2.34 (2H, bm), 1.95 (2H, bm), 1.91 (2H, bm), 1.61 (2H, bm), 1.15 (3H, t). |
| 134 | A | 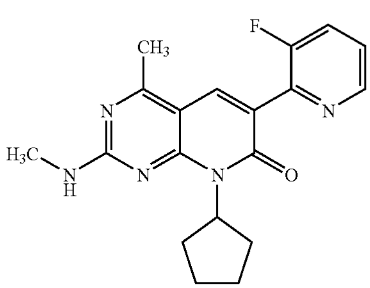 | 8-cyclopentyl-6-(3-fluoropyridin-2-yl)-4-methyl-2-(methylamino)pyrido[2,3-d]pyrimidin-7(8H)-one | 354 (M + H)⁺ | ¹H NMR (CDCl₃, 400 MHz): 8.49-8.48 (1H, m), 8.06 (1H, s), 7.84 (0.7H, b) 7.76 (1H, m), 7.65 (0.3H, b), 7.54-7.48 (1H, m), 6.03-5.90 (1H, m), 2.90 (3H, d, J = 4.3 Hz), 2.60-2.50 (4H, burried m), 2.40-2.10 (2H, bm), 2.00-1.91 (2H, bm), 1.85-1.75 (2H, bm), 1.67-1.54 (2H, bm). |

TABLE 1-continued

| Compound | Synthetic Method (% Yield) | Structure | Compound Name | LRMS m/z | ¹H NMR |
|---|---|---|---|---|---|
| 135 | A (18%) | 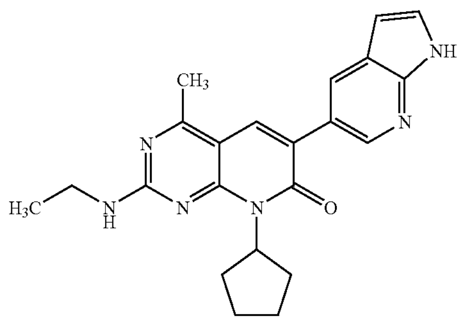 | 8-cyclopentyl-2-(ethylamino)-4-methyl-6-(1H-pyrrolo[2,3-b]pyridin-5-yl)pyrido[2,3-d]pyrimidin-7(8H)-one | 389 (M + H)⁺ | ¹H NMR (DMSO-$d_6$, 400 MHz): 8.46 (1H, s), 8.22 (1H, s), 7.99 (1H, s), 7.47 (1H, d), 6.49-6.47 (1H, m), 6.00 (1H, m), 3.34 (2H, m), 2.51 (3H, s), 2.28-2.23 (2H, bm), 1.99 (2H, bm), 1.79 (2H, bm), 1.64 (2H, bm), 1.17 (3H, t). |
| 136 | A (51%) | 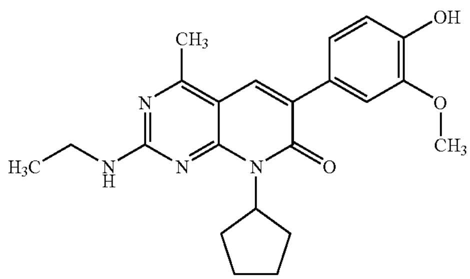 | 8-cyclopentyl-2-(ethylamino)-6-(4-hydroxy-3-methoxyphenyl)-4-methylpyrido[2,3-d]pyrimidin-7(8H)-one | 396 (M + H)⁺ | ¹H NMR (DMSO-$d_6$, 400 MHz): 9.07 (1H, s), 7.84 (1H, s), 7.71 (1H, m), 7.25 (1H, s), 7.10 (1H, m), 6.80-6.78 (1H, m), 5.96 (1H, m), 3.80 (3H, s), 3.35 (2H, m), 2.55 (3H, s), 2.36 (2H, bm), 2.02 (2H, bm), 1.76 (2H, bm), 1.64 (2H, bm), 1.16 (3H, t). |
| 137 | A (55%) | 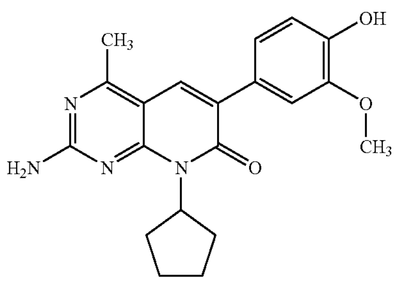 | 2-amino-8-cyclopentyl-6-(4-hydroxy-3-methoxyphenyl)-4-methylpyrido[2,3-d]pyrimidin-7(8H)-one | 367 (M + H)⁺ | ¹H NMR (DMSO-$d_6$, 400 MHz): 9.07 (1H, s), 7.83 (1H, s), 7.65-7.57 (1H, m), 7.24 (1H, s), 7.08 (1H, m), 6.80-6.78 (1H, m), 6.02-5.97 (1H, m), 3.80 (3H, s), 2.55 (3H, s), 2.24 (2H, bm), 2.02 (2H, bm), 1.76 (2H, bm), 1.59 (2H, bm). |
| 138 | A (45%) | 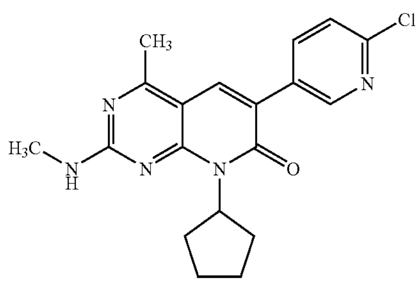 | 6-(6-chloropyridin-3-yl)-8-cyclopentyl-4-methyl-2-(methylamino)pyrido[2,3-d]pyrimidin-7(8H)-one | 370 (M + H)⁺ | ¹H NMR (DMSO-$d_6$, 400 MHz): 8.71 (1H, s), 8.20 (1H, m), 8.15 (1H, s), 7.82 (1H, m), 7.57 (1H, m), 5.99 (1H, m), 2.58 (3H, s), 2.51 (3H, s), 2.37 (2H, bm), 2.00 (2H, bm), 1.79 (2H, bm), 1.63 (2H, bm). |
| 139 | A (61%) | 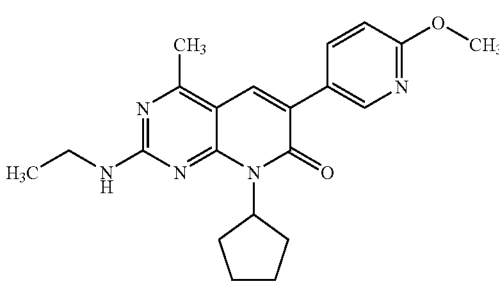 | 8-cyclopentyl-2-(ethylamino)-6-(6-methoxypyridin-3-yl)-4-methylpyrido[2,3-d]pyrimidin-7(8H)-one | 380 (M + H)⁺ | ¹H NMR (DMSO-$d_6$, 400 MHz): 8.43 (1H, s), 8.02 (1H, m), 7.99 (1H, s), 7.80 (1H, bs), 6.86-6.84 (1H, m), 5.96 (1H, m), 3.88 (3H, s), 3.34 (2H, m), 2.55 (3H, s), 2.36 (2H, bm), 1.97 (2H, bm), 1.78 (2H, bm), 1.64 (2H, bm), 1.16 (3H, t). |

TABLE 1-continued

| Compound | Synthetic Method (% Yield) | Structure | Compound Name | LRMS m/z | ¹H NMR |
|---|---|---|---|---|---|
| 140 | A (71%) | 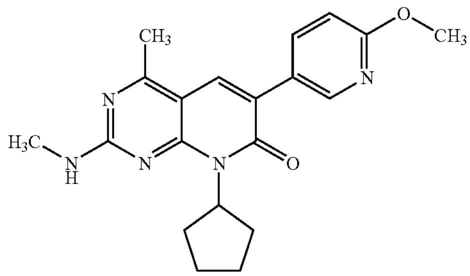 | 8-cyclopentyl-6-(6-methoxypyridin-3-yl)-4-methyl-2-(methylamino)pyrido[2,3-d]pyrimidin-7(8H)-one | 366 (M + H)⁺ | ¹H NMR (DMSO-d$_6$, 400 MHz): 8.43 (1H, s), 8.02 (1H, m), 7.99 (1H, s), 7.17 (2H, bs), 6.86-6.84 (1H, m), 6.02-5.98 (1H, m), 3.88 (3H, s), 2.86 (3H, s), 2.56 (3H, s), 2.24-2.23 (2H, bm), 2.02 (2H, bm), 1.76 (2H, bm), 1.59 (2H, bm). |
| 141 | A | 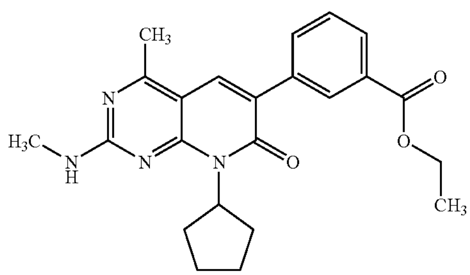 | ethyl 3-[8-cyclopentyl-4-methyl-2-(methylamino)-7-oxo-7,8-dihydropyrido[2,3-d]pyrimidin-6-yl]benzoate | 284 (M + H)⁺ | ¹H NMR (DMSO-d$_6$, 400 MHz): δ ppm 1.34 (q, J = 6.91 Hz, 3H), 1.57-1.68 (m, 2H), 1.78 (d, J = 6.06 Hz, 2H), 1.99 (s, 2H), 2.35-2.43 (m, 1H), 2.56-2.59 (m, 2H), 2.89 (d, J = 4.55 Hz, 3H), 4.35 (q, J = 7.07 Hz, 2H), 5.94-6.05 (m, 1H), 7.56 (t, J = 7.71 Hz, 1H), 7.73 (s, 1H), 7.88-7.94 (m, 2H), 7.99-8.03 (m, 1H), 8.26 (s, 1H). |
| 142 | A (73%) | 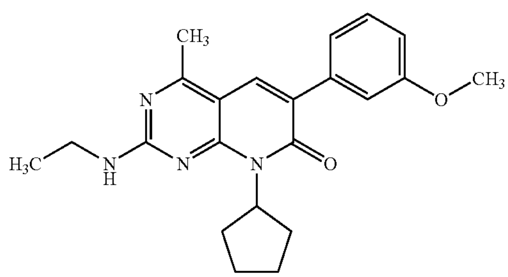 | 8-cyclopentyl-2-(ethylamino)-6-(3-methoxyphenyl)-4-methylpyrido[2,3-d]pyrimidin-7(8H)-one | 379 (M + H)⁺ | ¹H NMR (DMSO-d$_6$, 400 MHz): 8.03 (1H, s), 7.41 (1H, m), 7.33-7.31 (4H, m), 7.03-7.00 (1H, m), 6.11 (1H, m), 3.89 (3H, s), 3.34 (2H, m), 2.55 (3H, s), 2.34 (2H, bm), 2.14 (2H, bm), 1.87 (2H, bm), 1.69 (2H, bm), 1.17 (3H, m). |
| 143 | A (62%) | 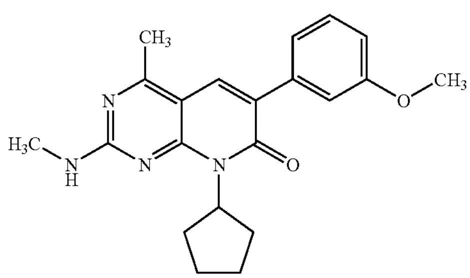 | 8-cyclopentyl-6-(3-methoxyphenyl)-4-methyl-2-(methylamino)pyrido[2,3-d]pyrimidin-7(8H)-one | 365 (M + H)⁺ | ¹H NMR (DMSO-d$_6$, 400 MHz): 8.03 (1H, s), 7.41 (1H, m), 7.33-7.31 (4H, m), 7.03-7.00 (1H, m), 6.11 (1H, m), 3.89 (3H, s), 2.86 (3H, s), 2.66 (3H, s), 2.34 (2H, bm), 2.14 (2H, bm), 1.87 (2H, bm), 1.69 (2H, bm). |
| 144 | A (45%) | 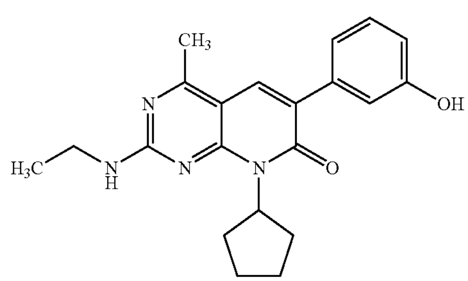 | 8-cyclopentyl-2-(ethylamino)-6-(3-hydroxyphenyl)-4-methylpyrido[2,3-d]pyrimidin-7(8H)-one | 351 (M + H)⁺ | ¹H NMR (DMSO-d$_6$, 400 MHz): 9.36 (1H, s), 7.87 (1H, s), 7.20-7.15 (1H, m), 7.11 (1H, m), 7.05-7.03 (1H, s), 6.74-6.71 (1H, m), 5.98 (1H, m), 3.36 (2H, m), 2.54 (3H, s), 2.37 (2H, m), 2.02 (2H, m), 1.76 (2H, m), 1.64 (2H, m), 1.16 (3H, m). |

TABLE 1-continued

| Compound | Synthetic Method (% Yield) | Structure | Compound Name | LRMS m/z | $^1$H NMR |
|---|---|---|---|---|---|
| 145 | A (70%) | 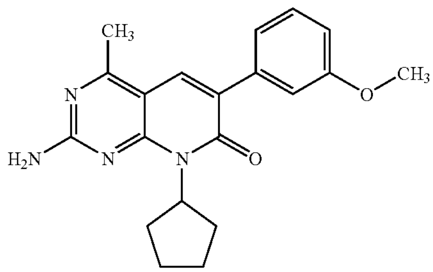 | 2-amino-8-cyclopentyl-6-(3-methoxyphenyl)-4-methylpyrido[2,3-d]pyrimidin-7(8H)-one | 351 (M + H)$^+$ | $^1$H NMR (DMSO-d$_6$, 400 MHz): 8.03 (1H, s), 7.41 (1H, m), 7.33-7.31 (4H, m), 7.03-7.00 (1H, m), 6.11 (1H, m), 3.89 (3H, s), 2.66 (3H, s), 2.34 (2H, bm), 2.14 (2H, bm), 1.87 (2H, bm), 1.69 (2H, bm). |
| 146 | A (56%) | 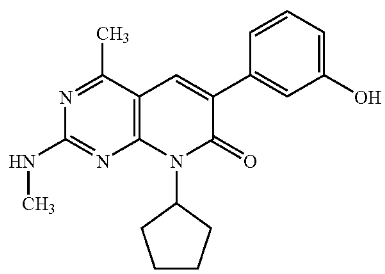 | 8-cyclopentyl-6-(3-hydroxyphenyl)-4-methyl-2-(methylamino)pyrido[2,3-d]pyrimidin-7(8H)-one | 351 (M + H)$^+$ | $^1$H NMR (DMSO-d$_6$, 400 MHz): 9.37 (1H, s), 7.88 (1H, s), 7.69 (1H, m), 7.19 (1H, m), 7.17 (1H, s), 7.05 (1H, d), 6.74-6.71 (1H, m), 6.04-5.99 (1H, m), 2.89 (3H, s), 2.54 (3H, s), 2.36 (2H, m), 2.02 (2H, m), 1.77-1.75 (2H, m), 1.60-1.58 (2H, m). |
| 154 | F | 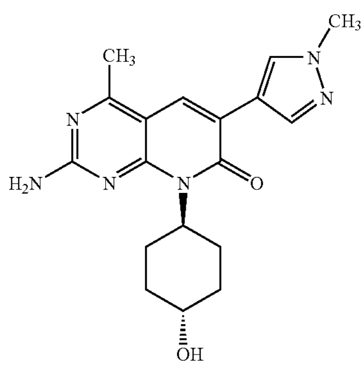 | 2-amino-8-(trans-4-hydroxycyclohexyl)-4-methyl-6-(1-methyl-1H-pyrazol-4-yl)pyrido[2,3-d]pyrimidin-7(8H)-one | 355 | (400 MHz, DMSO-d6) δ ppm 1.23-1.35 (m, 2H) 1.42-1.53 (m, 2H) 1.89-1.97 (m, 2H) 2.56 (s, 3H) 2.72-2.84 (m, 2H) 3.49-3.60 (m, 1H) 3.85 (s, 3H) 4.62 (d, J = 4.29 Hz, 1H) 5.23-5.72 (m, 1H) 7.05 (s, 2H) 8.08 (d, J = 7.58 Hz, 2H) 8.34 (s, 1H) |
| 155 | F | 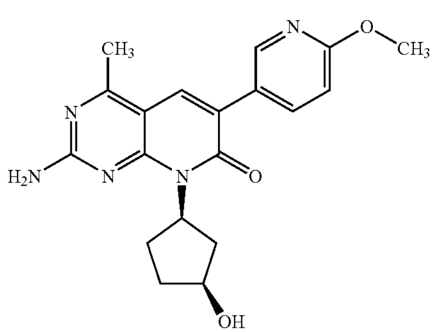 | 2-amino-8-[(1R,3S)-3-hydroxycyclopentyl]-6-(6-methoxypyridin-3-yl)-4-methylpyrido[2,3-d]pyrimidin-7(8H)-one | 368 | (400 MHz, DMSO-d6) δ ppm 1.70-1.81 (m, 2H) 1.92-2.03 (m, 2H) 2.24-2.36 (m, 2H) 2.57 (s, 3H) 3.88 (s, 3H) 4.03-4.12 (m, 1H) 4.97 (d, J = 6.82 Hz, 1H) 5.98-6.08 (m, 1H) 6.86 (d, J = 8.59 Hz, 1H) 7.21 (s, 2H) 7.99-8.02 (m, 1H) 8.03 (s, 1H) 8.43 (d, J = 2.02 Hz, 1H) |

TABLE 1-continued

| Compound | Synthetic Method (% Yield) | Structure | Compound Name | LRMS m/z | ¹H NMR |
|---|---|---|---|---|---|
| 156 | F | 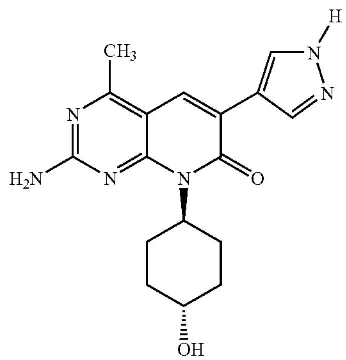 | 2-amino-8-(trans-4-hydroxycyclohexyl)-4-methyl-6-(1H-pyrazol-4-yl)pyrido[2,3-d]pyrimidin-7(8H)-one | 341 | (400 MHz, DMSO-d6) δ ppm 1.21-1.36 (m, 2H) 1.43-1.53 (m, 2H) 1.89-1.98 (m, 2H) 2.56 (s, 3H) 2.72-2.84 (m, 2H) 3.50-3.62 (m, 1H) 4.61 (d, J = 4.04 Hz, 1H) 5.23-5.65 (m, 1H) 7.03 (s, 2H) 8.11 (s, 1H) 8.13 (s, 1H) 8.34 (s, 1H) 12.85 (s, 1H) |
| 157 | F | 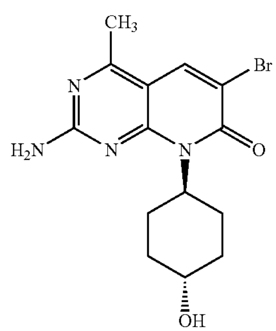 | 2-amino-6-bromo-8-(trans-4-hydroxycyclohexyl)-4-methylpyrido[2,3-d]pyrimidin-7(8H)-one | 354 | (400 MHz, DMSO-d6) δ ppm 1.21-1.32 (m, 2H) 1.43-1.53 (m, 2H) 1.86-1.96 (m, 2H) 2.48 (s, 3H) 2.59-2.71 (m, 2H) 3.46-3.57 (m, 1H) 4.62 (d, J = 3.03 Hz, 1H) 5.08-5.76 (m, 1H) 7.26 (s, 2H) 8.34 (s, 1H) |
| 158 | F | 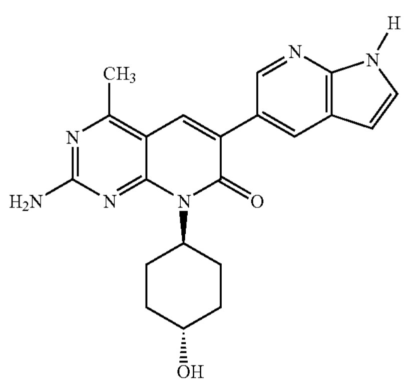 | 2-amino-8-(trans-4-hydroxycyclohexyl)-4-methyl-6-(1H-pyrrolo[2,3-b]pyridin-5-yl)pyrido[2,3-d]pyrimidin-7(8H)-one | 391 | (400 MHz, DMSO-d6) δ ppm 1.24-1.35 (m, 2H) 1.48-1.58 (m, 2H) 1.90-1.99 (m, 2H) 2.56 (s, 3H) 2.74-2.85 (m, 2H) 3.48-3.60 (m, 1H) 4.61 (d, J = 4.29 Hz, 1H) 5.25-5.69 (m, 1H) 6.47 (dd, J = 3.54, 1.77 Hz, 1H) 7.12 (s, 2H) 7.45-7.51 (m, 1H) 7.97 (s, 1H) 8.21 (d, J = 1.77 Hz, 1H) 8.44 (d, J = 2.02 Hz, 1H) 11.66 (s, 1H) |
| 159 | F | 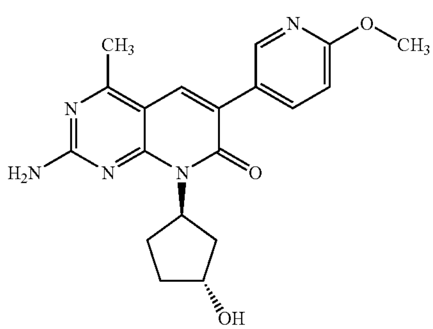 | 2-amino-8-[(1R,3R)-3-hydroxycyclopentyl]-6-(6-methoxypyridin-3-yl)-4-methylpyrido[2,3-d]pyrimidin-7(8H)-one | 368 | (400 MHz, DMSO-d6) δ ppm 1.54-1.63 (m, 1H) 1.63-1.71 (m, 1H) 1.91-2.01 (m, 1H) 2.03-2.13 (m, 1H) 2.21-2.30 (m, 1H) 2.38-2.46 (m, 1H) 2.55 (s, 3H) 3.88 (s, 3H) 4.40-4.46 (m, 1H) 4.53 (d, J = 3.28 Hz, 1H) 6.21-6.30 (m, 1H) 6.85 (d, J = 8.59 Hz, 1H) 7.17 (s, 2H) 7.99 (s, 1H) 7.99-8.02 (m, 1H) 8.42 (d, J = 2.02 Hz, 1H) |

TABLE 1-continued

| Compound | Synthetic Method (% Yield) | Structure | Compound Name | LRMS m/z | ¹H NMR |
|---|---|---|---|---|---|
| 160 | F | 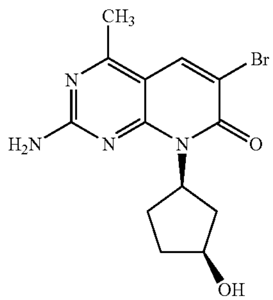 | 2-amino-6-bromo-8-[(1R,3S)-3-hydroxycyclopentyl]-4-methylpyrido[2,3-d]pyrimidin-7(8H)-one | 340 | (400 MHz, DMSO-d$_6$) δ ppm 1.70-1.80 (m, 2H) 1.90-2.01 (m, 2H) 2.18-2.28 (m, 2H) 2.49 (s, 3H) 4.01-4.12 (m, 1H) 4.89 (d, J = 6.32 Hz, 1H) 5.93-6.03 (m, 1H) 7.30 (s, 2H) 8.39 (s, 1H) |
| 161 | F | 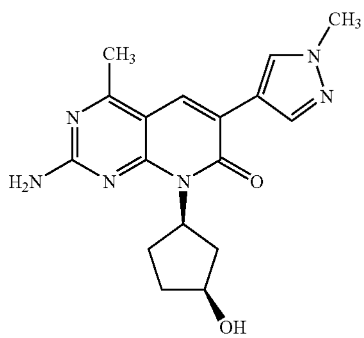 | 2-amino-8-[(1R,3S)-3-hydroxycyclopentyl]-4-methyl-6-(1-methyl-1H-pyrazol-4-yl)pyrido[2,3-d]pyrimidin-7(8H)-one | 341 | (400 MHz, DMSO-d6) δ ppm 1.71-1.81 (m, 2H) 1.93-2.04 (m, 2H) 2.24-2.35 (m, 2H) 2.58 (s, 3H) 3.87 (s, 3H) 4.04-4.14 (m, 1H) 5.03 (d, J = 6.82 Hz, 1H) 6.00-6.10 (m, 1H) 7.10 (s, 2H) 8.09 (s, 1H) 8.15 (s, 1H) 8.34 (s, 1H) |
| 162 | F | 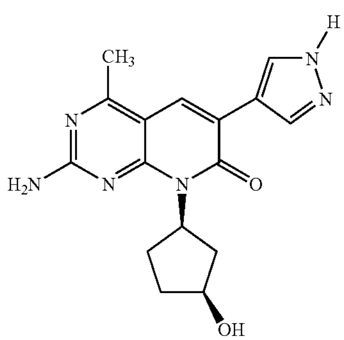 | 2-amino-8-[(1R,3S)-3-hydroxycyclopentyl]-4-methyl-6-(1H-pyrazol-4-yl)pyrido[2,3-d]pyrimidin-7(8H)-one | 327 | (400 MHz, DMSO-d6) δ ppm 1.71-1.81 (m, 2H) 1.94-2.04 (m, 2H) 2.26-2.36 (m, 2H) 2.59 (s, 3H) 4.05-4.14 (m, 1H) 5.04 (d, J = 6.82 Hz, 1H) 5.99-6.09 (m, 1H) 7.09 (s, 2H) 8.15 (s, 1H) 8.16 (s, 1H) 8.35 (s, 1H) 12.88 (s, 1H) |
| 163 | F | 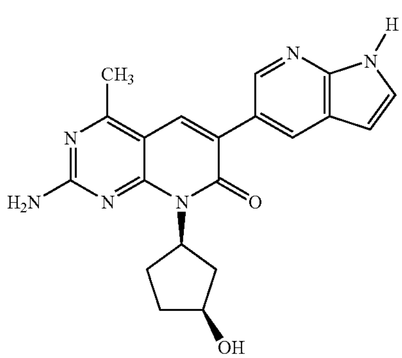 | 2-amino-8-[(1R,3S)-3-hydroxycyclopentyl]-4-methyl-6-(1H-pyrrolo[2,3-b]pyridin-5-yl)pyrido[2,3-d]pyrimidin-7(8H)-one | 377 | (400 MHz, DMSO-d6) δ ppm 1.71-1.83 (m, 2H) 1.94-2.05 (m, 2H) 2.26-2.38 (m, 2H) 2.59 (s, 3H) 4.05-4.13 (m, 1H) 5.01 (d, J = 7.07 Hz, 1H) 6.02-6.11 (m, 1H) 6.49 (dd, J = 3.41, 1.89 Hz, 1H) 7.18 (s, 2H) 7.45-7.53 (m, 1H) 8.03 (s, 1H) 8.22 (d, J = 1.77 Hz, 1H) 8.46 (d, J = 2.27 Hz, 1H) 11.68 (s, 1H) |

TABLE 1-continued

| Compound | Synthetic Method (% Yield) | Structure | Compound Name | LRMS m/z | $^1$H NMR |
|---|---|---|---|---|---|
| 164 | F | 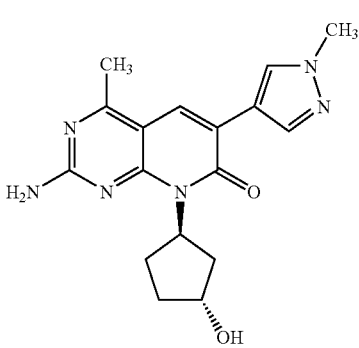 | 2-amino-8-[(1R,3R)-3-hydroxycyclopentyl]-4-methyl-6-(1-methyl-1H-pyrazol-4-yl)pyrido[2,3-d]pyrimidin-7(8H)-one | 341 | (400 MHz, DMSO-d6) δ ppm 1.56-1.62 (m, 1H) 1.62-1.70 (m, 1H) 1.91-2.01 (m, 1H) 2.03-2.13 (m, 1H) 2.24-2.34 (m, 1H) 2.38-2.46 (m, 1H) 2.57 (s, 3H) 3.86 (s, 3H) 4.43-4.51 (m, 1H) 4.54 (d, J = 3.28 Hz, 1H) 6.24-6.33 (m, 1H) 7.07 (s, 2H) 8.08 (s, 1H) 8.11 (s, 1H) 8.33 (s, 1H) |
| 165 | F | 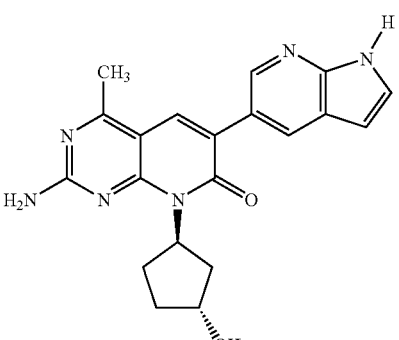 | 2-amino-8-[(1R,3R)-3-hydroxycyclopentyl]-4-methyl-6-(1H-pyrrolo[2,3-b]pyridin-5-yl)pyrido[2,3-d]pyrimidin-7(8H)-one | 377 | (400 MHz, DMSO-d6) δ ppm 1.55-1.64 (m, 1H) 1.65-1.73 (m, 1H) 1.93-2.03 (m, 1H) 2.06-2.16 (m, 1H) 2.22-2.33 (m, 1H) 2.40-2.47 (m, 1H) 2.57 (s, 3H) 4.41-4.47 (m, 1H) 4.53 (d, J = 3.03 Hz, 1H) 6.24-6.34 (m, 1H) 6.48 (dd, J = 3.28, 1.77 Hz, 1H) 7.14 (s, 2H) 7.46-7.49 (m, 1H) 7.99 (s, 1H) 8.21 (d, J = 2.02 Hz, 1H) 8.45 (d, J = 2.02 Hz, 1H) 11.66 (s, 1H) |
| 166 | F | 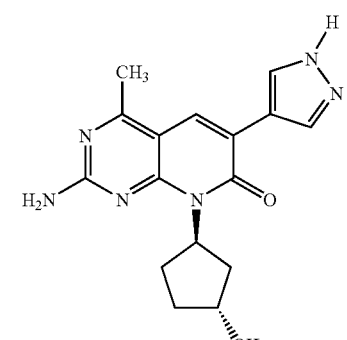 | 2-amino-8-[(1R,3R)-3-hydroxycyclopentyl]-4-methyl-6-(1H-pyrazol-4-yl)pyrido[2,3-d]pyrimidin-7(8H)-one | 327 | (400 MHz, DMSO-d6) δ ppm 1.56-1.63 (m, 1H) 1.63-1.69 (m, 1H) 1.90-2.00 (m, 1H) 2.05-2.14 (m, 1H) 2.25-2.34 (m, 1H) 2.40-2.46 (m, 1H) 2.58 (s, 3H) 4.43-4.50 (m, 1H) 4.53 (d, J = 3.03 Hz, 1H) 6.23-6.32 (m, 1H) 7.05 (s, 2H) 8.12 (s, 1H) 8.13 (s, 1H) 8.34 (s, 1H) 12.86 (s, 1H) |
| 167 | F | 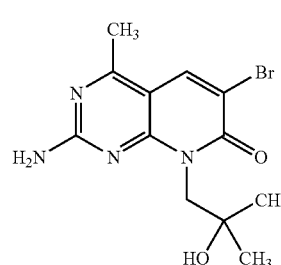 | 2-amino-6-bromo-8-(2-hydroxy-2-methylpropyl)-4-methylpyrido[2,3-d]pyrimidin-7(8H)-one | 328 | (400 MHz, DMSO-d6) δ ppm 1.09 (s, 6H) 2.52 (s, 3H) 4.41 (s, 2H) 4.65 (s, 1H) 7.34 (s, 2H) 8.41 (s, 1H) |

TABLE 1-continued

| Compound | Synthetic Method (% Yield) | Structure | Compound Name | LRMS m/z | $^1$H NMR |
|---|---|---|---|---|---|
| 168 | F | 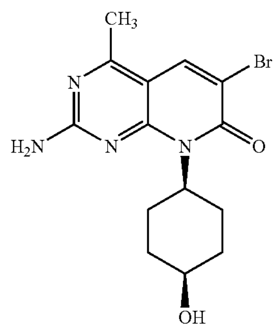 | 2-amino-6-bromo-8-(cis-4-hydroxycyclohexyl)-4-methylpyrido[2,3-d]pyrimidin-7(8H)-one | | (400 MHz, DMSO-d6) δ ppm 1.20-1.27 (m, 2H) 1.43-1.55 (m, 2H) 1.74-1.83 (m, 2H) 2.49 (s, 3H) 2.88-3.00 (m, 2H) 3.83-3.90 (m, 1H) 4.31 (d, J = 2.78 Hz, 1H) 5.39-5.50 (m, 1H) 7.16-7.27 (m, 2H) 8.33 (s, 1H) |
| 169 | F | 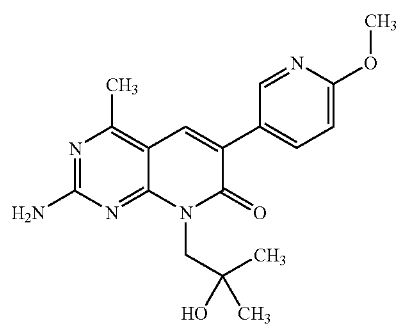 | 2-amino-8-(2-hydroxy-2-methylpropyl)-6-(6-methoxypyridin-3-yl)-4-methylpyrido[2,3-d]pyrimidin-7(8H)-one | 356 | (400 MHz, DMSO-d6) δ ppm 1.12 (s, 6H) 2.58 (s, 3H) 3.88 (s, 3H) 4.46 (s, 2H) 4.79 (s, 1H) 6.87 (d, J = 8.59 Hz, 1H) 7.27 (s, 2H) 8.02 (dd, J = 8.59, 2.53 Hz, 1H) 8.07 (s, 1H) 8.47 (d, J = 2.27 Hz, 1H) |
| 170 | F | 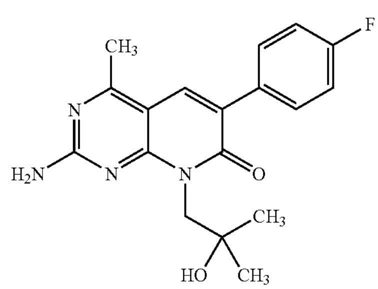 | 2-amino-6-(4-fluorophenyl)-8-(2-hydroxy-2-methylpropyl)-4-methylpyrido[2,3-d]pyrimidin-7(8H)-one | 343 | (400 MHz, DMSO-d$_6$) δ ppm 1.13 (s, 6H) 2.58 (s, 3H) 4.46 (s, 2H) 4.81 (s, 1H) 7.20-7.27 (m, 2H) 7.27 (s, 2H) 7.70-7.77 (m, 2H) 8.02 (s, 1H) |
| 171 | F | 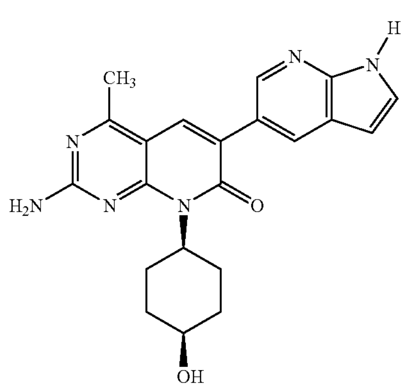 | 2-amino-8-(cis-4-hydroxycyclohexyl)-4-methyl-6-(1H-pyrrolo[2,3-b]pyridin-6-yl)pyrido[2,3-d]pyrimidin-7(8H)-one | 391 | (400 MHz, DMSO-d$_6$) δ ppm 1.23-1.34 (m, 2H) 1.46-1.57 (m, 2H) 1.76-1.86 (m, 2H) 2.57 (s, 3H) 3.00-3.12 (m, 2H) 3.85-3.95 (m, 1H) 4.30 (d, J = 2.78 Hz, 1H) 5.43-5.55 (m, 1H) 6.47 (dd, J = 3.28, 1.77 Hz, 1H) 7.07 (s, 2H) 7.43-7.53 (m, 1H) 7.97 (s, 1H) 8.22 (d, J = 1.77 Hz, 1H) 8.46 (d, J = 2.02 Hz, 1H) 11.66 (s, 1H) |

TABLE 1-continued

| Compound | Synthetic Method (% Yield) | Structure | Compound Name | LRMS m/z | ¹H NMR |
|---|---|---|---|---|---|
| 172 | F | 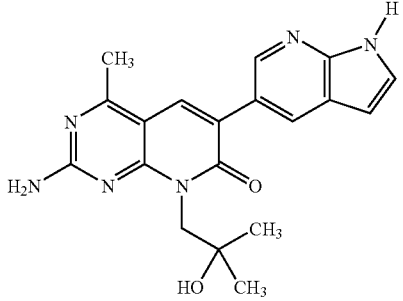 | 2-amino-8-(2-hydroxy-2-methylpropyl)-4-methyl-6-(1H-pyrrolo[2,3-b]pyridin-5-yl)pyrido[2,3-d]pyrimidin-7(8H)-one | 365 | (400 MHz, DMSO-d6) δ ppm 1.15H) 2.60 (s, 3H) 4.49 (s, 2H) 4.85 (s, 1H) 6.49 (dd, J = 3.41, 1.89 Hz, 1H) 7.24 (s, 2H) 7.46-7.51 (m, 1H) 8.08 (s, 1H) 8.24 (d, J = 1.77 Hz, 1H) 8.49 (d, J = 2.02 Hz, 1H) 11.69 (s, 1H) |
| 173 | F | 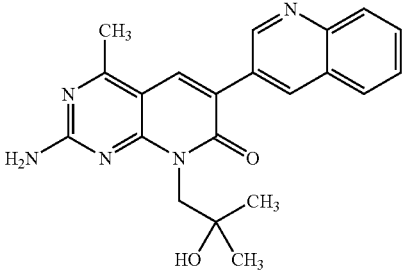 | 2-amino-8-(2-hydroxy-2-methylpropyl)-4-methyl-6-quinolin-3-ylpyrido[2,3-d]pyrimidin-7(8H)-one | 376 | (400 MHz, DMSO-d6) δ ppm 1.16 (s, 6H) 2.63 (s, 3H) 4.50 (s, 2H) 4.81 (s, 1H) 7.36 (s, 2H) 7.61-7.68 (m, 1H) 7.77 (ddd, J = 8.34, 6.95, 1.39 Hz, 1H) 8.00-8.07 (m, 2H) 8.32 (s, 1H) 8.67 (d, J = 2.27 Hz, 1H) 9.20 (d, J = 2.02 Hz, 1H) |
| 174 | F | 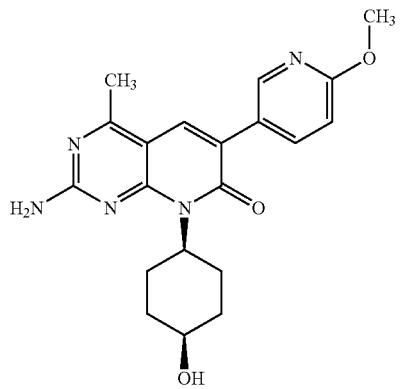 | 2-amino-8-(cis-4-hydroxycyclohexyl)-6-(6-methoxypyridin-3-yl)-4-methylpyrido[2,3-d]pyrimidin-7(8H)-one | 382 | (400 MHz, CHLOROFORM-d) δ ppm 1.48-1.58 (m, 2H) 1.63-1.74 (m, 2H) 1.89-1.96 (m, 2H) 1.96-2.00 (m, 1H) 2.60 (s, 3H) 3.01-3.13 (m, 2H) 3.97 (s, 3H) 4.06-4.15 (m, 1H) 5.21 (s, 2H) 5.46-5.58 (m, 1H) 6.80 (d, J = 8.59 Hz, 1H) 7.74 (s, 1H) 7.98 (dd, J = 8.59, 2.53 Hz, 1H) 8.31 (d, J = 2.27 Hz, 1H) |
| 175 | F | 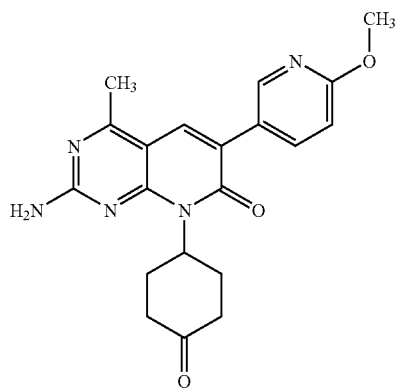 | 2-amino-6-(6-methoxypyridin-3-yl)-4-methyl-8-(4-oxocyclohexyl)pyrido[2,3-d]pyrimidin-7(8H)-one | 380 | 400 MHz, DMSO-d6) δ ppm 1.84-1.93 (m, 2H) 2.34-2.42 (m, 2H) 2.51-2.55 (m, 2H) 2.56 (s, 3H) 2.99-3.10 (m, 2H) 3.88 (s, 3H) 5.86-5.98 (m, 1H) 6.85 (d, J = 8.59 Hz, 1H) 7.21 (s, 2H) 7.99-8.04 (m, 2H) 8.45 (d, J = 2.27 Hz, 1H) |

TABLE 1-continued

| Compound | Synthetic Method (% Yield) | Structure | Compound Name | LRMS m/z | ¹H NMR |
|---|---|---|---|---|---|
| 176 | F | 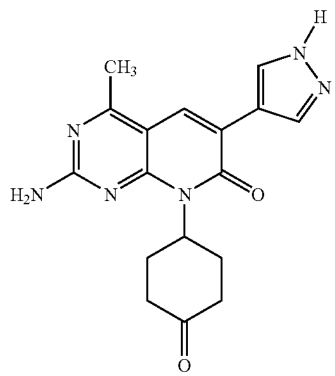 | 2-amino-4-methyl-8-(4-oxocyclohexyl)-6-(1H-pyrazol-4-yl)pyrido[2,3-d]pyrimidin-7(8H)-one | 338 | (400 MHz, DMSO-d6) δ ppm 1.82-1.92 (m, 2H) 2.35-2.42 (m, 2H) 2.51-2.56 (m, 2H) 2.58 (s, 3H) 3.02-3.14 (m, 2H) 5.90-6.01 (m, 1H) 7.08 (s, 2H) 8.15 (s, 1H) 8.19 (s, 1H) 8.34 (s, 1H) 12.87 (s, 1H) |
| 177 | F | 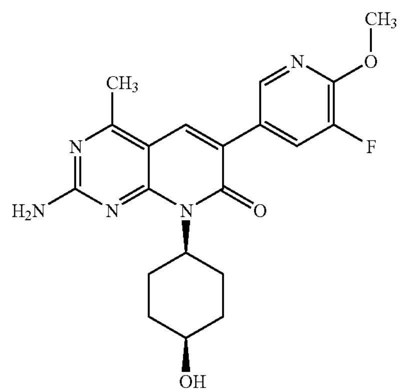 | 2-amino-6-(5-fluoro-6-methoxypyridin-3-yl)-8-(cis-4-hydroxycyclohexyl)-4-methylpyrido[2,3-d]pyrimidin-7(8H)-one | 399 | (400 MHz, DMSO-d6) δ ppm 1.20-1.29 (m, 2H) 1.45-1.56 (m, 2H) 1.75-1.84 (m, 2H) 2.56 (s, 3H) 2.97-3.08 (m, 2H) 3.84-3.90 (m, 1H) 3.98 (s, 3H) 4.30 (d, J = 2.78 Hz, 1H) 5.40-5.52 (m, 1H) 7.10-7.21 (m, 2H) 8.01 (dd, J = 12.25, 1.89 Hz, 1 |
| 178 | F | 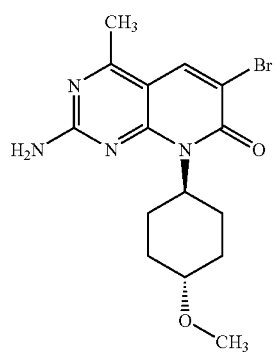 | 2-amino-6-bromo-8-(trans-4-methoxycyclohexyl)-4-methylpyrido[2,3-d]pyrimidin-7(8H)-one | 367 | (400 MHz, DMSO-d6) δ ppm 1.15-1.26 (m, 2H) 1.49-1.59 (m, 2H) 2.06-2.15 (m, 2H) 2.49 (s, 3H) 2.61-2.73 (m, 2H) 3.17-3.26 (m, 1H) 3.27 (s, 3H) 5.15-5.67 (m, 1H) 7.26 (s, 2H) 8.34 (s, 1H) |
| 180 | F | 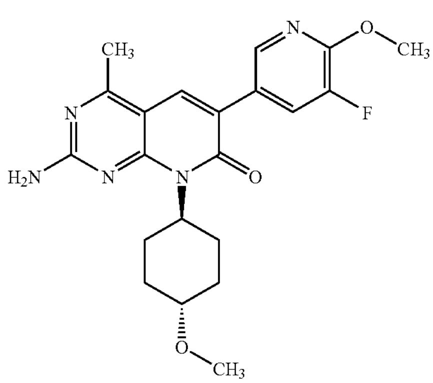 | 2-amino-6-(5-fluoro-6-methoxypyridin-3-yl)-8-(trans-4-methoxycyclohexyl)-4-methylpyrido[2,3-d]pyrimidin-7(8H)-one | 413 | (400 MHz, DMSO-d6) δ ppm 1.16-1.28 (m, 2H) 1.51-1.61 (m, 2H) 2.07-2.16 (m, 2H) 2.56 (s, 3H) 2.71-2.82 (m, 2H) 3.27 (s, 3H) 3.30-3.32 (m, 1H) 3.98 (s, 3H) 5.07-5.75 (m, 1H) 7.22 (s, 2H) 8.01 (dd, J = 12.25, 1.89 Hz, 1H) 8.07 (s, 1H) 8 |

TABLE 1-continued

| Compound | Synthetic Method (% Yield) | Structure | Compound Name | LRMS m/z | ¹H NMR |
|---|---|---|---|---|---|
| 181 | F | 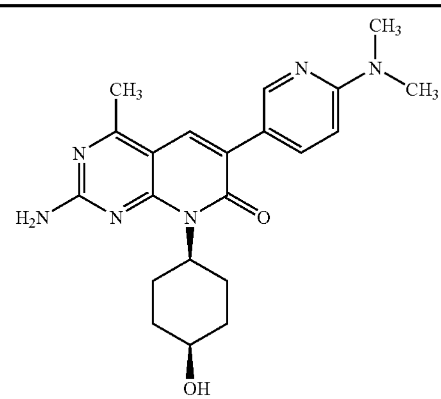 | 2-amino-6-[6-(dimethylamino)pyridin-3-yl]-8-(cis-4-hydroxycyclohexyl)-4-methylpyrido[2,3-d]pyrimidin-7(8H)-one | 394 | (400 MHz, DMSO-d6) δ ppm 1.20-1.29 (m, 2H) 1.45-1.55 (m, 2H) 1.75-1.84 (m, 2H) 2.54 (s, 3H) 3.05 (s, 6H) 3.85-3.91 (m, 1H) 4.30 (d, J = 2.78 Hz, 1H) 5.40-5.51 (m, 1H) 6.65 (d, J = 8.84 Hz, 1H) 7.02 (s, 2H) 7.83-7.87 (m, 2H) 8.38 (d, J = 2 |
| 182 | F | 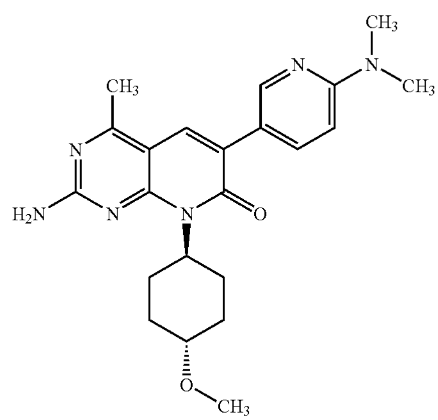 | 2-amino-6-[6-(dimethylamino)pyridin-3-yl]-8-(trans-4-methoxycyclohexyl)-4-methylpyrido[2,3-d]pyrimidin-7(8H)-one | 409 | (400 MHz, DMSO-d6) δ ppm 1.15-1.27 (m, 2H) 1.51-1.61 (m, 2H) 2.07-2.16 (m, 2H) 2.53 (s, 3H) 2.73-2.84 (m, 2H) 3.05 (s, 6H) 3.27 (s, 3H) 3.30-3.32 (m, 1H) 5.02-5.65 (m, 1H) 6.65 (d, J = 9.09 Hz, 1H) 7.09 (s, 2H) 7.84 (dd, J = 8.84, 2.27H |
| 183 | F | 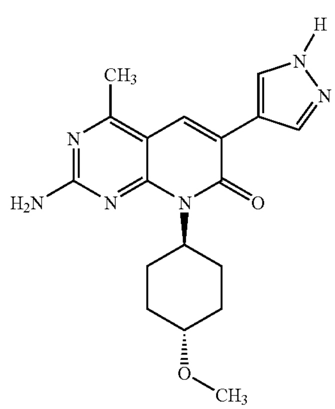 | 2-amino-8-(trans-4-methoxycyclohexyl)-4-methyl-6-(1H-pyrazol-4-yl)pyrido[2,3-d]pyrimidin-7(8H)-one | 354 | (400 MHz, DMSO-d6) δ ppm 1.17-1.29 (m, 2H) 1.50-1.59 (m, 2H) 2.08-2.16 (m, 2H) 2.57 (s, 3H) 2.75-2.87 (m, 2H) 3.28 (s, 3H) 3.30-3.33 (m, 1H) 5.17-5.73 (m, 1H) 7.05 (s, 2H) 8.11 (s, 1H) 8.14 (s, 1H) 8.34 (s, 1H) 12.86 (s, 1H) |
| 184 | F | 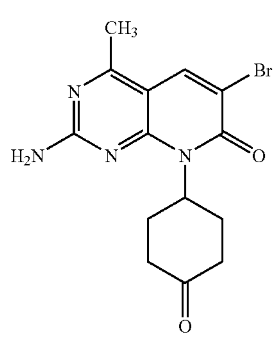 | 2-amino-6-bromo-4-methyl-8-(4-oxocyclohexyl)pyrido[2,3-d]pyrimidin-7(8H)-one | 351 | (400 MHz, CHLOROFORM-d) δ ppm 1.63-1.74 (m, 2H) 1.92-2.04 (m, 2H) 2.48-2.57 (m, 2H) 2.59 (s, 3H) 3.04-3.15 (m, 2H) 5.33 (s, 2H) 5.91-6.03 (m, 1H) 8.13 (s, 1H |

TABLE 1-continued

| Compound | Synthetic Method (% Yield) | Structure | Compound Name | LRMS m/z | ¹H NMR |
|---|---|---|---|---|---|
| 185 | F | 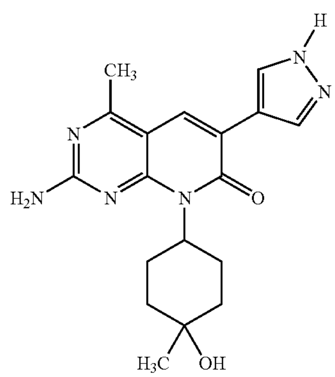 | 2-amino-8-(4-hydroxy-4-methylcyclohexyl)-4-methyl-6-(1H-pyrazol-4-yl)pyrido[2,3-d]pyrimidin-7(8H)-one | 355 | (400 MHz, DMSO-d6) δ ppm 1.15 (s, 3H) 1.20-1.30 (m, 2H) 1.36-1.47 (m, 2H) 1.63-1.72 (m, 2H) 2.57 (s, 3H) 2.98-3.10 (m, 2 H) 4.05 (s, 1H) 5.40-5.52 (m, 1H) 6.98 (s, 2H) 8.10 (s, 1H) 8.16 (s, 1H) 8.33 (s, 1H) 12.86 (s, 1H) |
| 187 | F | 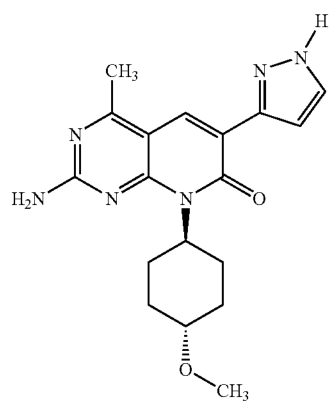 | 2-amino-8-(trans-4-methoxycyclohexyl)-4-methyl-6-(1H-pyrazol-3-yl)pyrido[2,3-d]pyrimidin-7(8H)-one | 355 | (400 MHz, DMSO-d6) δ ppm 1.17-1.29 (m, 2H) 1.51-1.61 (m, 2H) 2.08-2.17 (m, 2H) 2.56 (s, 3H) 2.76-2.87 (m, 2H) 3.28 (s, 3H) 3.28-3.31 (m, 1H) 5.16-5.83 (m, 1H) 6.93 (s, 1H) 7.14-7.26 (m, 2H) 7.40-7.90 (m, 1H) 8.35 (s, 1H) 12.62-13.24 (m, 1H) |
| 188 | F | 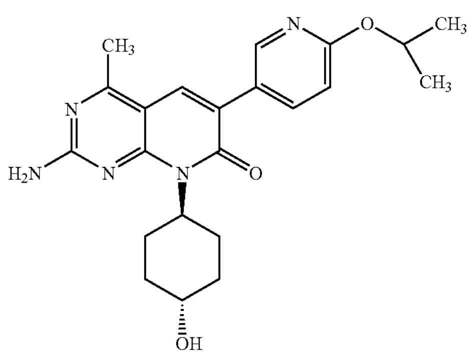 | 2-amino-8-(trans-4-hydroxycyclohexyl)-6-(6-isopropoxypyridin-3-yl)-4-methylpyrido[2,3-d]pyrimidin-7(8H)-one | 410 | (400 MHz, DMSO-d6) δ ppm 1.08-1.17 (m, 8H) 1.34 (d, J = 10.86 Hz, 2H) 1.76 (d, J = 10.11 Hz, 2H) 2.38 (s, 3H) 2.50-2.61 (m, 2H) 3.37 (bs, 1H) 4.45 (bs, 1H) 5.11 (dt, J = 12.38, 6.19 Hz, 1H) 6.59 (d, J = 8.84 Hz, 1H) 6.99 (s, 2H) 7.76-7.84 (m, 2H) 8.22 (d, J = 2.02 Hz, 1H) |
| 189 | F | 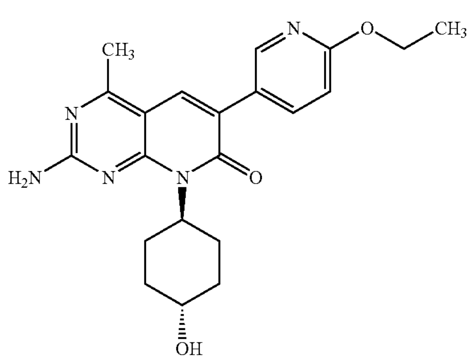 | 2-amino-6-(6-ethoxypyridin-3-yl)-8-(trans-4-hydroxycyclohexyl)-4-methylpyrido[2,3-d]pyrimidin-7(8H)-one | 396 | (400 MHz, DMSO-d6) δ ppm 1.22-1.31 (m, 2H) 1.34 (t, J = 7.07 Hz, 3H) 1.45-1.50 (m, 2H) 1.90-1.95 (m, 2H) 2.55 (s, 3H) 2.70-2.79 (m, 2H) 3.54 (s, 1H) 4.33 (q, J = 6.99 Hz, 2H) 4.62 (d, J = 4.29 Hz, 1H) 6.81 (d, J = 8.59 Hz, 1H) 7.16 (s, 2H) 7.95-8.01 (m, 2H) 8.40 (d, J = 2.27 Hz, 1H) |

TABLE 1-continued

| Compound | Synthetic Method (% Yield) | Structure | Compound Name | LRMS m/z | ¹H NMR |
|---|---|---|---|---|---|
| 190 | F | 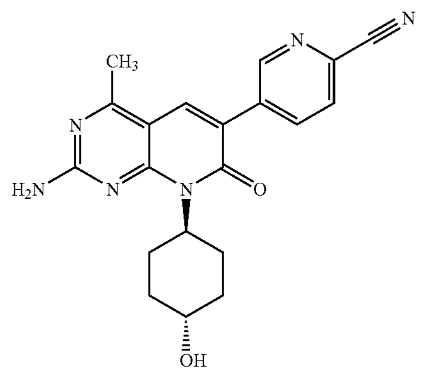 | 5-[2-amino-8-(trans-4-hydroxycyclohexyl)-4-methyl-7-oxo-7,8-dihydropyrido[2,3-d]pyrimidin-6-yl]pyridine-2-carbonitrile | 377 | (400 MHz, DMSO-d6) δ ppm 1.22-1.34 (m, 2H) 1.50-1.53 (m, 2H) 1.93 (d, J = 9.60 Hz, 2H) 2.57 (s, 3H) 2.71-2.83 (m, 2H) 3.50 (bs, 1H) 4.62 (d, J = 4.04 Hz, 1H) 7.36 (s, 2H) 8.07 (d, J = 8.08 Hz, 1H) 8.24 (s, 1H) 8.37 (dd, J = 8.08, 2.27 Hz, 1H) 9.06 (s, 1H) |
| 191 | F | 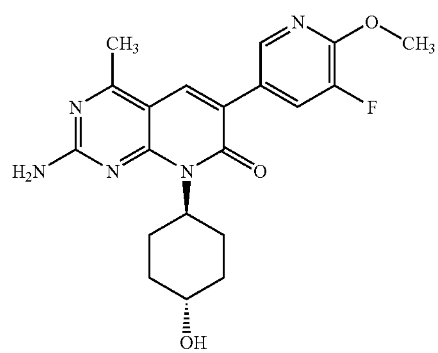 | 2-amino-6-(5-fluoro-6-methoxypyridin-3-yl)-8-(trans-4-hydroxycyclohexyl)-4-methylpyrido[2,3-d]pyrimidin-7(8H)-one | 399 | (400 MHz, DMSO-d6) δ ppm 1.18-1.27 (m, 2H) 1.52-1.55 (m, 2H) 1.90-1.95 (m, 2H) 2.53 (s, 3H) 2.76 (bs, 2H) 3.54 (bs, 1H) 3.98 (s, 3H) 4.62 (d, J = 4.29 Hz, 1H) 7.22 (s, 2H) 8.01 (dd, J = 12.25, 1.89 Hz, 1H) 8.06 (s, 1H) 8.30 (d, J = 2.02 Hz, 1H) |
| 194 | F | 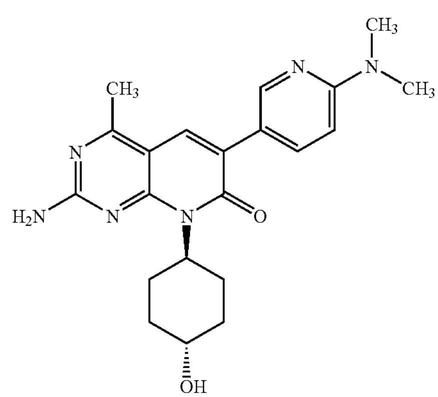 | 2-amino-6-[6-(dimethylamino)pyridin-3-yl]-8-(trans-4-hydroxycyclohexyl)-4-methylpyrido[2,3-d]pyrimidin-7(8H)-one | 395 | (400 MHz, DMSO-d6) δ ppm 1.23-1.34 (m, 2H) 1.48 (d, J = 1.01 Hz, 2H) 1.91 (m, 2H) 2.51 (s, 3H) 2.68-2.78 (m, 2H) 3.03 (s, 6H) 3.53 (s, 1H) 4.61 (s, 1H) 5.38 (s, 1H) 6.65 (d, J = 8.84 Hz, 1H) 7.08 (s, 2H) 7.80-7.88 (m, 2H) 8.36 (d, J = 2.27 Hz, 1H) |
| 195 | Similar to Example 78 | 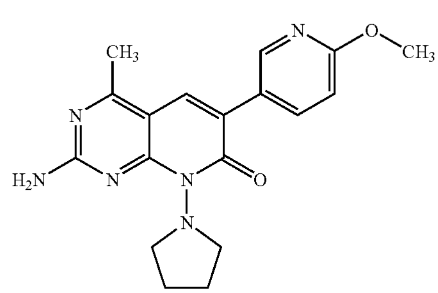 | 2-amino-6-(6-methoxypyridin-3-yl)-4-methyl-8-(pyrrolidin-1-yl)pyrido[2,3-d]pyrimidin-7(8H)-one | 353 | (400 MHz, MeOD) δ ppm 2.03-2.18 (m, 4H) 2.64 (s, 3H) 3.36-3.46 (m, 4H) 3.96 (s, 3H) 6.86 (d, J = 8.59 Hz, 1H) 7.97-8.03 (m, 2H) 8.42 (d, J = 2.53 Hz, 1H) |

TABLE 1-continued

| Compound | Synthetic Method (% Yield) | Structure | Compound Name | LRMS m/z | ¹H NMR |
|---|---|---|---|---|---|
| 196 | Similar to Example 78 | 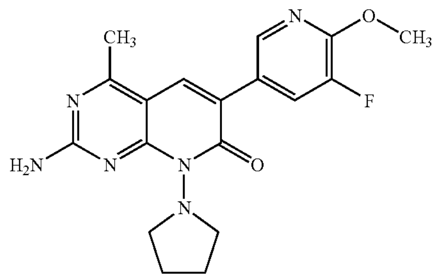 | 2-amino-6-(5-fluoro-6-methoxypyridin-3-yl)-4-methyl-8-(pyrrolidin-1-yl)pyrido[2,3-d]pyrimidin-7(8H)-one | 371 | (400 MHz, MeOD) δ ppm 2.05-2.12 (m, 4H) 2.62 (s, 3H) 3.35-3.43 (m, 4H) 4.02 (s, 3H) 7.85 (dd, J = 11.62, 2.02 Hz, 1H) 8.02 (s, 1H) 8.21 (d, J = 2.02 Hz, 1H) |
| 197 | F | 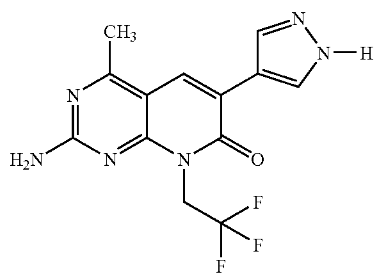 | 2-amino-4-methyl-6-(1H-pyrazol-4-yl)-8-(2,2,2-trifluoroethyl)pyrido[2,3-d]pyrididin-7(8H)-one | 325 | (400 MHz, DMSO-$d_6$) δ ppm 2.62 (s, 3H) 5.19 (q, J = 9.01 Hz, 2H) 7.25 (s, 2H) 8.18 (s, 1H) 8.25 (s, 1H) 8.38 (s, 1H) 12.93 (s, 1H) |
| 198 | F | 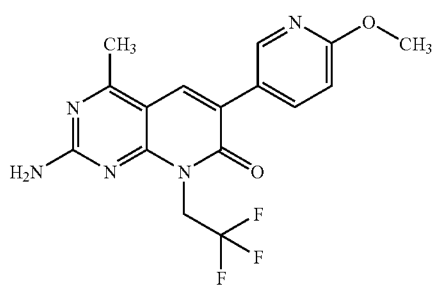 | 2-amino-6-(6-methoxypyridin-3-yl)-4-methyl-8-(2,2,2-trifluoroethyl)pyrido[2,3-d]pyrimidin-7(8H)-one | 366 | (400 MHz, DMSO-$d_6$) δ ppm 2.60 (s, 3H) 3.89 (s, 3H) 5.16 (q, J = 8.93 Hz, 2H) 6.89 (d, J = 8.84 Hz, 1H) 7.39 (s, 2H) 8.03 (dd, J = 8.59, 2.53 Hz, 1H) 8.13 (s, 1H) 8.49 (d, J = 2.27 Hz, 1H) |
| 199 | F | 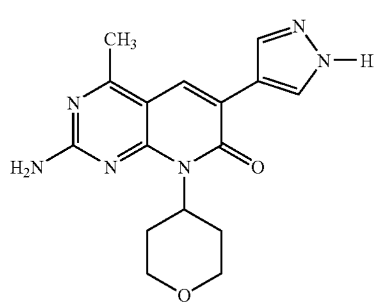 | 2-amino-4-methyl-6-(1H-pyrazol-4-yl)-8-(tetrahydro-2H-pyran-4-yl)pyrido[2,3-d]pyrimidin-7(8H)-one | 327 | (400 MHz, DMSO-d6) δ ppm: 12.86 (1H, s), 8.35 (1H, s), 8.15 (1H, s), 8.13 (1H, s), 7.07 (2H, s), 5.72 (1H, s), 4.00 (2H, dd, J = 11.24, 3.92 Hz), 3.35-3.48 (2H, m), 2.89-3.10 (2H, m), 2.58 (3H, s), 1.46 (2H, dd, J = 11.62, 2.53 Hz) |
| 200 | F | 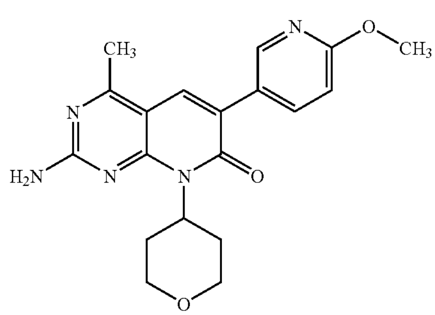 | 2-amino-6-(6-methoxypyridin-3-yl)-4-methyl-8-(tetrahydro-2H-pyran-4-yl)pyrido[2,3-d]pyrimidin-7(8H)-one | 368 | (400 MHz, DMSO-d6) δ ppm: 8.43 (1H, d, J = 2.53 Hz), 7.92-8.06 (2H, m), 7.19 (2H, s), 6.85 (1H, d, J = 8.59 Hz), 5.58-5.84 (1H, m), 3.99 (2H, dd, J 11.24, 4.17 Hz), 3.88 (3H, s), 3.36-3.47 (2H, m), 2.86-3.09 (2H, m), 2.55 (3H, s), 1.48 (2H, dd, J = 11.24, 2.40 Hz) |

TABLE 1-continued

| Compound | Synthetic Method (% Yield) | Structure | Compound Name | LRMS m/z | ¹H NMR |
|---|---|---|---|---|---|
| 201 | F | 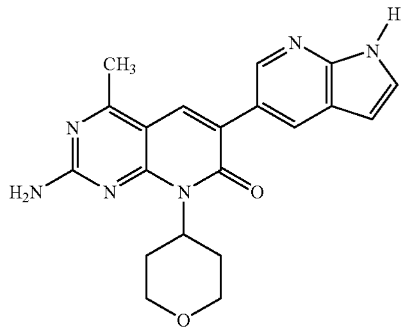 | 2-amino-4-methyl-6-(1H-pyrrolo[2,3-b]pyridin-5-yl)-8-(tetrahydro-2H-pyran-4-yl)pyrido[2,3-d]pyrimidin-7(8H)-one | 377 | (400 MHz, DMSO-d6) δ ppm: 11.66 (1H, s), 8.46 (1H, s), 8.22 (1H s), 8.00 (1H, s), 7.48 (1H, s), 7.15 (2H, s), 6.48 (1H, s), 5.73 (1H, t, J = 11.12 Hz), 4.00 (2H, d, J = 7.83 Hz), 3.41 (2H, t, J = 11.75 Hz), 2.89-3.10 (2H, m), 2.57 (3H, s), 1.50 (2H, d, J = 11.12 Hz) |
| 202 | F | 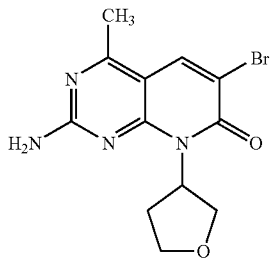 | 2-amino-6-bromo-4-methyl-8-(tetrahydrofuran-3-yl)pyrido[2,3-d]pyrimidin-7(8H)-one | 325 | (400 MHz, DMSO-d6) δ ppm: 8.38 (1H, s), 7.32 (2H, s), 6.08-6.32 (1H, m), 4.20 (1H, q, J = 7.58 Hz), 3.75-3.97 (3H, m), 3.36 (3H, s), 2.26-2.41 (1H, m), 1.95-2.13 (1H, m) |
| 203 | F | 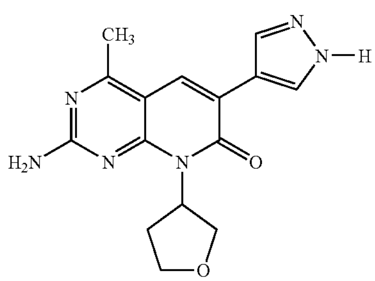 | 2-amino-4-methyl-6-(1H-pyrazol-4-yl)-8-(tetrahydrofuran-3-yl)pyrido[2,3-d]pyrimidin-7(8H)-one | 313 | (400 MHz, DMS0-d6) δ ppm: 12.87 (1H, s), 8.35 (1H, s), 8.15 (2H, s), 7.10 (2H, s), 6.17-6.34 (1H, m), 4.28 (1H, q, J = 7.58 Hz), 3.80-4.04 (3H, m), 2.59 (3H, s), 2.35-2.47 (1H, m), 1.97-2.15 (1H, m) |
| 204 | F | 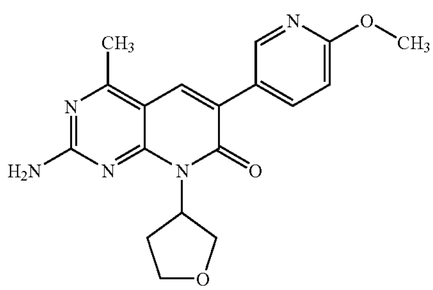 | 2-amino-6-(6-methoxypyridin-3-yl)-4-methyl-8-(tetrahydro-2H-pyran-4-yl)pyrido[2,3-d]pyrimidin-7(8H)-one | 354 | (400 MHz, CDCl₃) δ ppm: 8.32 (1H, d, J = 2.27 Hz), 7.97 (1H, dd, J = 8.59, 2.53 Hz), 7.77 (1H, s), 6.82 (1H, d, J = 8.59 Hz), 6.24-6.43 (1H, m), 5.26 (2H, s), 4.39 (1H, q, J = 7.66 Hz), 4.16 (1H, t, J = 7.71 Hz), 4.00-4.10 (2H, m), 3.98 (3H, s), 2.62 (3H, s), 2.48-2.59 (1H, m), 2.13-2.29 (1H, m) |
| 205 | F | 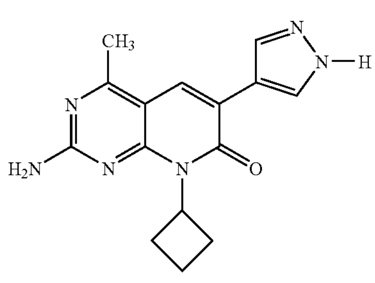 | 2-amino-8-cyclobutyl-4-methyl-6-(1H-pyrazol-4-yl)pyrido[2,3-d]pyrimidin-7(8H)-one | 297 | (400 MHz, DMSO-d6) δ ppm: 12.87 (1H, s), 8.25 (2H, br. s.), 8.11 (1H, s), 7.07 (2H, s), 5.88-6.06 (1H, m), 3.04-3.23 (2H, m), 2.57 (3H, s), 2.11-2.28 (2H, m), 1.89-2.04 (1H, m), 1.68-1.84 (1H, m) |

TABLE 1-continued

| Compound | Synthetic Method (% Yield) | Structure | Compound Name | LRMS m/z | ¹H NMR |
|---|---|---|---|---|---|
| 206 | F | 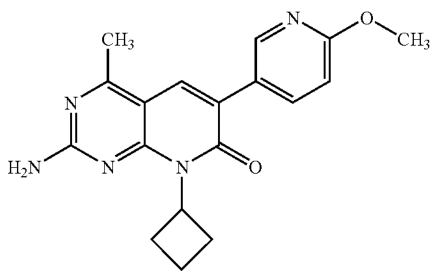 | 2-amino-8-cyclobutyl-6-(6-methoxypyridin-3-yl)-4-methylpyrido[2,3-d]pyrimidin-7(8H)-one | 338 | (400 MHz, DMSO-d6) δ ppm: 8.43 (1H, d, J = 2.27 Hz), 8.01 (1H, dd, J = 8.59, 2.53 Hz), 7.98 (1H, s), 7.18 (2H, s), 6.85 (1H, d, J = 8.59 Hz), 5.84-6.00 (1H, m), 3.88 (3H, s), 3.02-3.19 (2H, m), 2.55 (3H, s), 2.13-2.29 (2H, m), 1.87-2.01 (1H, m), 1.66-1.84 (1H, m) |
| 207 | F | 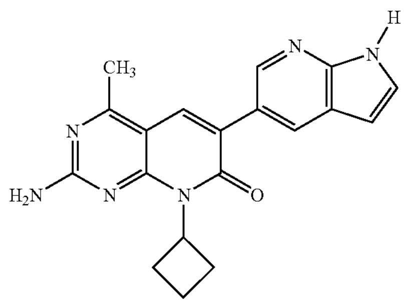 | 2-amino-8-cyclobutyl-4-methyl-6-(1H-pyrrolo[2,3-b]pyridin-5-yl)pyrido[2,3-d]pyrimidin-7(8H)-one | 347 | (400 MHz, DMSO-d6) δ ppm: 11.67 (s, 1H) 8.46 (1H, d, J = 2.02 Hz), 8.22 (1H, d, J = 2.02 Hz), 7.99 (1H, s), 7.45-7.51 (1H, m), 7.15 (2H, s), 6.48 (1H, dd, J = 3.28, 1.77 Hz), 5.87-6.04 (1H, m), 3.05-3.22 (2H, m), 2.56 (3H, s), 2.16-2.30 (2H, m), 1.88-2.04 (1H, m), 1.67-1.83 (1H, m) |
| 208 | E | 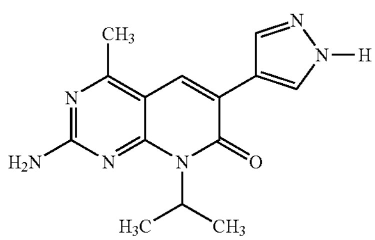 | 2-amino-8-isopropyl-4-methyl-6-(1H-pyrazol-4-yl)pyrido[2,3-d]pyrimidin-7(8H)-one | 285 | (400 MHz, DMSO-d6) δ ppm: 12.86 (1H, br. s.), 8.35 (1H, br. s.), 8.12-8.24 (1H, m), 8.11 (1H, s), 7.04 (2H, s), 5.86 (1H, br. s.), 2.57 (3H, s), 1.53 (6H, d, J = 7.07 Hz) |
| 209 | E | 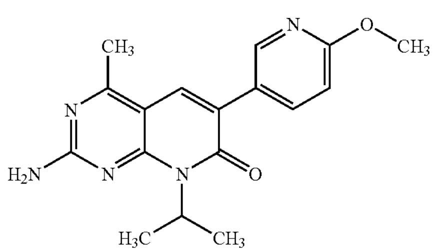 | 2-amino-8-isopropyl-6-(6-methoxypyridin-3-yl)-4-methylpyrido[2,3-d]pyrimidin-7(8H)-one | 326 | (400 MHz, DMSO-d6) δ ppm: 8.43 (1H, d, J = 2.27 Hz), 8.01 (1H, dd, J = 8.59, 2.53 Hz), 7.98 (1H, s), 7.17 (2H, s), 6.85 (1H, d, J = 8.59 Hz), 5.84 (1H, br. s.), 3.88 (3H, s), 2.55 (3H, s), 1.53 (6H, d, J = 7.07 Hz) |
| 210 | E | 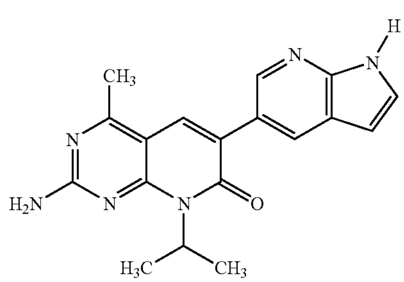 | 2-amino-8-isopropyl-4-methyl-6-(1H-pyrrolo[2,3-b]pyridin-5-yl)pyrido[2,3-d]pyrimidin-7(8H)-one | 335 | (400 MHz, DMSO-d6) δ ppm: 11.67 (1H, br. s.), 8.46 (1H, d, J = 2.02 Hz), 8.22 (1H, d, J = 2.02 Hz), 7.98 (1H, s), 7.48 (1H, t, J = 2.78 Hz), 7.14 (2H, s), 6.48 (1H, dd, J = 3.16, 1.89 Hz), 5.87 (1H, br. s.), 2.57 (3H, s), 1.55 (6H, d, J = 6.82 Hz) |

TABLE 1-continued

| Compound | Synthetic Method (% Yield) | Structure | Compound Name | LRMS m/z | ¹H NMR |
|---|---|---|---|---|---|
| 211 | F | 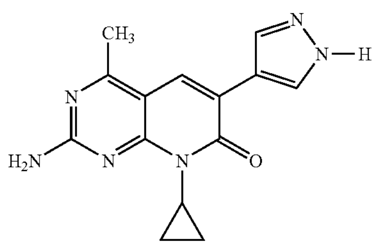 | 2-amino-8-cyclopropyl-4-methyl-6-(1H-pyrazol-4-yl)pyrido[2,3-d]pyrimidin-7(8H)-one | 283 | (400 MHz, DMSO-d6) δ ppm: 12.85 (1H, s), 8.33 (1H, s), 8.14 (1H, s), 8.10 (1H, s), 6.98 (2H, s), 2.79-2.94 (1H, m), 2.55 (3H, s), 1.09-1.25 (2H, m), 0.71-0.86 (2H, m) |
| 212 | F | 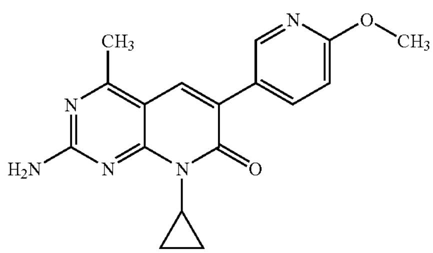 | 2-amino-8-cyclopropyl-6-(6-methoxypyridin-3-yl)-4-methylpyrido[2,3-d]pyrimidin-7(8H)-one | 324 | (400 MHz, DMSO-d6) δ ppm: 8.44 (1H, d, J = 2.53 Hz), 8.00 (1H, dd, J = 8.59, 2.53 Hz), 7.97 (1H, s), 7.10 (2H, s), 6.85 (1H, d, J = 8.59 Hz), 3.88 (3H, s), 2.80-2.92 (1H, m), 2.54 (3H, s), 1.11-1.18 (2H, m), 0.74-0.83 (2H, m) |
| 213 | F | 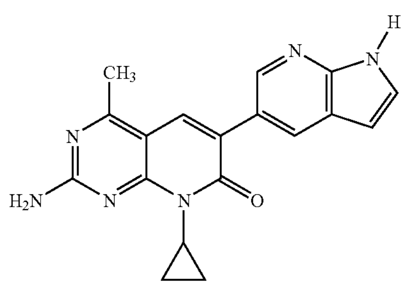 | 2-amino-8-cyclopropyl-4-methyl-6-(1H-pyrrolo[2,3-b]pyridin-5-yl)pyrido[2,3-d]pyrimidin-7(8H)-one | 333 | (400 MHz, DMSO-d6) δ ppm: 11.67 (1H, s), 8.46 (1H, d, J = 2.02 Hz), 8.21 (1H, d, J = 1.77 Hz), 7.98 (1H, s), 7.42-7.53 (1H, m), 7.06 (2H, s), 6.48 (1H, dd, J = 3.41, 1.89 Hz), 2.80-2.95 (1H, m), 2.55 (3H, s), 1.17 (2H, q, J = 7.16 Hz), 0.75-0.88 (2H, m) |
| 214 | E | 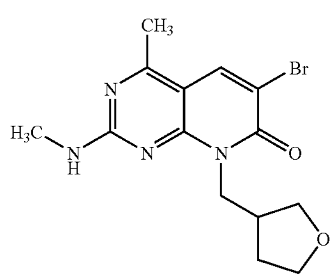 | 6-bromo-4-methyl-2-(methylamino)-8-((tetrahydrofuran-3-yl)methyl)pyrido[2,3-d]pyrimidin-7(8H)-one | 353 | (400 MHz, CDCl₃) δ ppm: 8.11 (1H, s), 5.54 (1H, br. s.), 4.33-4.68 (2H, m), 3.91-4.03 (1H, m), 3.72-3.87 (2H, m), 3.68 (1H, dd, J = 8.59, 6.06 Hz), 3.06 (3H, d, J = 4.80 Hz), 2.79-2.97 (1H, m), 2.54 (3H, s), 1.90-2.03 (1H, m), 1.74-1.88 (1H, m) |
| 215 | E | 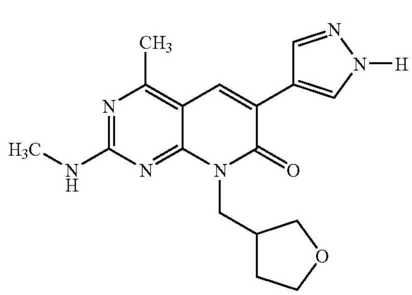 | 4-methyl-2-(methylamino)-6-(1H-pyrazol-4-yl)-8-((tetrahydrofuran-3-yl)methyl)pyrido[2,3-d]pyrimidin-7(8H)-one | 341 | (400 MHz, DMSO-d6) δ ppm: 12.88 (1H, s), 8.38 (1H, s), 8.19 (1H, s), 8.18 (1H, s), 7.64 (1H, d, J = 4.80 Hz), 4.24-4.55 (2H, m), 3.76-.89 (1H, m), 3.51-3.70 (3H, m), 2.87 (3H, d, J = 4.80 Hz), 2.74-2.84 (1H, m), 2.59 (3H, s), 1.79-1.96 (1H, m), 1.59-1.77 (1H, m) |

TABLE 1-continued

| Compound | Synthetic Method (% Yield) | Structure | Compound Name | LRMS m/z | ¹H NMR |
|---|---|---|---|---|---|
| 216 | E | 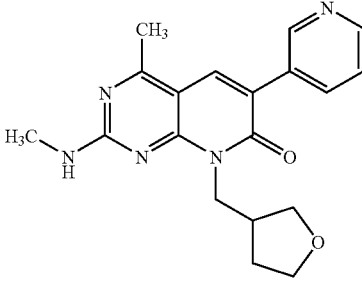 | 6-(6-methoxypyridin-3-yl)-4-methyl-2-(methylamino)-8-((tetrahydrofuran-3-yl)methyl)pyrido[2,3-d]pyrimidin-7(8H)-one | 382 | (400 MHz, DMSO-d6) δ ppm: 8.48 (1H, d, J = 1.77 Hz), 8.06 (1H, s), 8.03 (1H, d, J = 2.27 Hz), 7.50-7.82 (1H, m), 6.86 (1H, d, J = 8.59 Hz), 4.23-4.55 (2H, m), 3.88 (3H, s), 3.76-3.85 (1H, m), 3.50-3.69 (3H, m), 2.88 (3H, d, J = 4.80 Hz), 2.72-2.84 (1H, m), 2.57 (3H, s), 1.79-1.95 (1H, m), 1.59-1.78 (1H, m) |
| 217 | E | 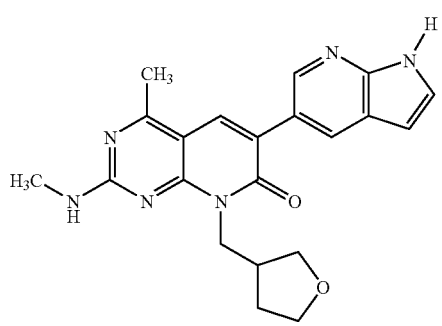 | 4-methyl-2-(methylamino)-6-(1H-pyrrolo[2,3-b]pyridin-5-yl)-8-((tetrahydrofuran-3-yl)methyl)pyrido[2,3-d]pyrimidin-7(8H)-one | 391 | (400 MHz, DMSO-d6) δ ppm: 11.67 (1H, s), 8.50 (1H, s), 8.25 (1H, s), 8.06 (1H, s), 7.51-7.78 (1H, m), 7.44-7.50 (1H, m), 6.48 (1H, dd, J = 3.28, 1.77 Hz), 4.31-4.56 (2H, m), 3.77-3.90 (1H, m), 3.52-3.73 (3H, m), 2.89 (3H, d, J = 4.80 Hz), 2.74-2.86 (1H, m), 2.58 (3H, s), 1.81-1.96 (1H, m), 1.62-1.80 (1H, m) |
| 218 | E | 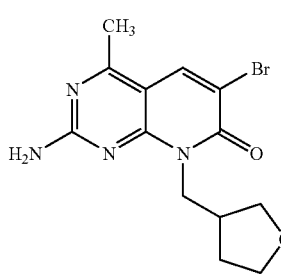 | 2-amino-6-bromo-4-methyl-8-((tetrahydrofuran-3-yl)methyl)pyrido[2,3-d]pyrimidin-7(8H)-one | 339 | (400 MHz, DMSO-d6) δ ppm: 8.40 (1H, s), 7.31 (2H, s), 4.39 (1H, dd, J = 12.63, 7.83 Hz), 4.23 (1H, dd, J = 12.63, 7.07 Hz), 3.82 (1H, dt, J = 7.89, 5.68 Hz), 3.57-3.68 (2H, m), 3.51 (1H, dd, J = 8.46, 5.68 Hz), 3.3 (3H, s), 2.67-2.82 (1H, m), 1.76-1.89 (1H, m), 1.54-1.68 (1H, m) |
| 219 | E | 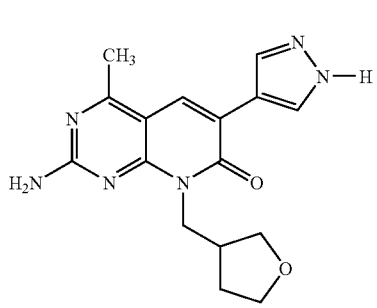 | 2-amino-4-methyl-6-(1H-pyrazol-4-yl)-8-((tetrahydrofuran-3-yl)methyl)pyrido[2,3-d]pyrimidin-7(8H)-one | 327 | (400 MHz, DMSO-d6) δ ppm: 12.87 (1H, s), 8.37 (1H, s), 8.18 (2H, s), 7.07 (2H, s), 4.45 (1H, dd, J = 12.63, 7.83 Hz), 4.28 (1H, dd, J = 12.63, 7.07 Hz), 3.84 (1H, dt J = 7.83, 5.81 Hz), 3.58-3.70 (2H, m), 3.55 (1H, dd, J = 8.34, 5.81 Hz), 2.72-2.85 (1H, m), 2.59 (3H, s), 1.77-1.90 (1H, m), 1.58-1.72 (1H, m) |
| 220 | E | 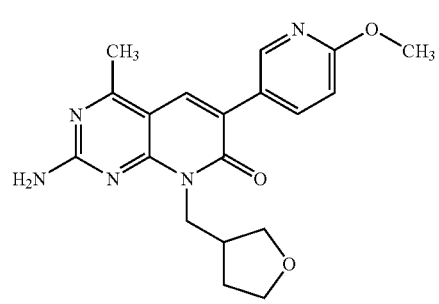 | 2-amino-6-(6-methoxypyridin-3-yl)-4-methyl-8-((tetrahydrofuran-3-yl)methyl)pyrido[2,3-d]pyrimidin-7(8H)-one | 368 | (400 MHz, DMSO-d6) δ ppm: 8.47 (1 H, d, J = 2.27 Hz), 8.00-8.08 (2H, m), 7.21 (2H, s), 6.86 (1H, d, J = 8.59 Hz), 4.43 (1H, dd, J = 12.51, 7.71 Hz), 4.26 (1H, dd, J = 12.63, 7.07 Hz), 3.88 (3H, m), 3.78-3.86 (1H, m), 3.58-3.70 (2H, m), 3.55 (1H, dd, J = 8.46, 5.68 Hz), 2.71-2.85 (1H, m), 2.57 (3H, s), 1.78-1.91 (1H, m), 1.59-1.73 (1H, m) |

TABLE 1-continued

| Compound | Synthetic Method (% Yield) | Structure | Compound Name | LRMS m/z | $^1$H NMR |
|---|---|---|---|---|---|
| 221 | E | 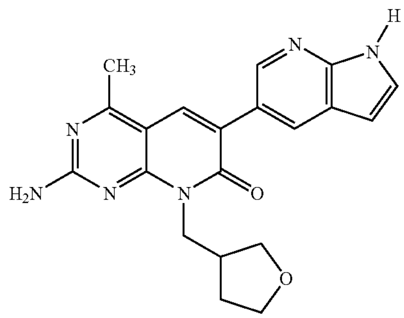 | 2-amino-4-methyl-6-(1H-pyrrolo[2,3-b]pyridin-5-yl)-8-(((tetrahydrofuran-3-yl)methyl)pyrido[2,3-d]pyrimidin-7(8H)-one | 377 | (400 MHz, DMSO-d6) δ ppm: 11.68 (1H, s), 8.49 (1H, d, J = 2.02 Hz), 8.25(1H, d, J = 1.77 Hz), 8.05 (1H, s), 7.45-7.52 (1H, m), 7.17 (2H, s), 6.48 (1H, dd, J = 3.41, 1.89 Hz), 4.46 (1H, dd, J = 12.51, 7.71 Hz), 4.29 (1H, dd J = 12.63, 6.82 Hz), 3.79-3.90 (1H, m), 3.52-3.72 (3H, m), 2.73-2.88 (1H, m), 2.59 (3H, s), 1.80-1.92 (1H, m), 1.62-1.74 (1H, m). |
| 222 | E | 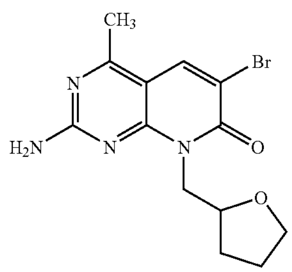 | 2-amino-6-bromo-4-methyl-8-((tetrahydrofuran-2-yl)methyl)pyrido[2,3-d]pyrimidin-7(8H)-one | 339 | (400 MHz, DMSO-d6) δ ppm: 8.39 (1H, s), 7.30 (2H, s), 4.47 (1H, dd, J = 12.38, 7.83 Hz), 4.24-4.37 (1H, m), 4.16 (1H, dd, J = 12.38, 5.56 Hz), 3.74-3.84 (1H, m), 3.55-3.65 (1H, m), 2.51 (3H, s), 1.73-2.02 (3H, m), 1.60-1.70 (1H, m) |
| 223 | E | 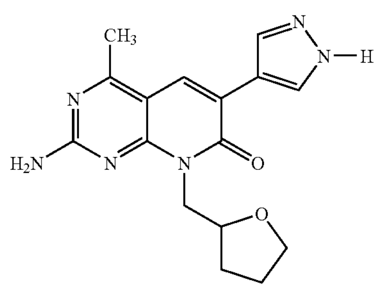 | 2-amino-4-methyl-6-(1H-pyrazol-4-yl)-8-((tetrahydrofuran-2-yl)methyl)pyrido[2,3-d]pyrimidin-7(8H)-one | 327 | (400 MHz, DMSO-d6) δ ppm: 12.87 (1H, br. s.), 8.35 (2H, br. s.), 8.17 (1H, s), 7.06 (2H, s), 4.51 (1H, dd, J = 12.38, 7.58 Hz), 4.28-4.41 (1H, m), 4.23 (1H, dd, J = 12.38, 6.06 Hz), 3.75-3.88 (1H, m), 3.53-3.66 (1H, m), 2.58 (3H, s), 1.89-2.06 (1H, m), 1.74-1.88 (2H, m), 1.60-1.74 (1H, m) |
| 224 | E | 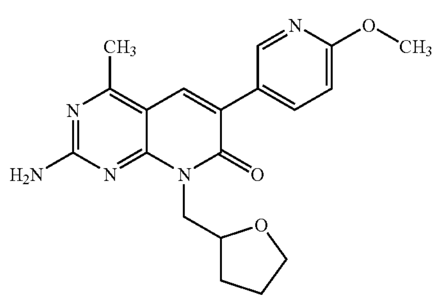 | 2-amino-6-(6-methoxypyridin-3-yl)-4-methyl-8-((tetrahydrofuran-2-yl)methyl)pyrido[2,3-d]pyrimidin-7(8H)-one | 368 | (400 MHz, DMSO-d6) δ ppm: 8.47 (1H, d, J = 2.02 Hz), 7.98-8.08 (2H, m), 7.19 (2H, s), 6.86 (1H, d, J = 8.59 Hz), 4.50 (1H, dd, J = 12.13, 7.58 Hz), 4.28-4.39 (1H, m), 4.20 (1H, dd, J = 12.25, 5.94 Hz), 3.89 (3H, s), 3.81 (1 H, td, J = 7.77, 5.68 Hz), 3.53-3.66 (1H, m), 2.57 (3H, s), 1.91-2.04 (1H, m), 1.62-1.90 (3H, m) |
| 225 | E | 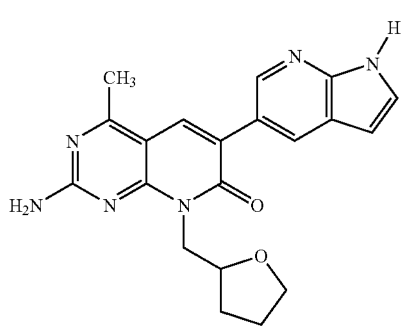 | 2-amino-4-methyl-6-(1H-pyrrolo[2,3-b]pyridin-5-yl)-8-((tetrahydrofuran-2-yl)methyl)pyrido[2,3-d]pyrimidin-7(8H)-one | 377 | (400 MHz, DMSO-d6) δ ppm: 11.67 (1H, br. s.), 8.49 (1H, d, J = 2.02 Hz), 8.24 (1H, d, J = 2.02 Hz), 8.05 (1H, s), 7.44-7.55 (1H, m), 7.15 (2H, br. s.), 6.49 (1H, dd, J = 3.41, 1.89 Hz), 4.52 (1H, dd, J = 12.38, 7.58 Hz), 4.30-4.45 (1H, m), 4.23 (1H, dd, J = 12.38, 5.81 Hz), 3.76-3.91 (1H, m), 3.54-3.68 (1H, m), 2.58 (3H, s), 1.62-2.10 (4H, m) |

TABLE 1-continued

| Compound | Synthetic Method (% Yield) | Structure | Compound Name | LRMS m/z | ¹H NMR |
|---|---|---|---|---|---|
| 226 | F | 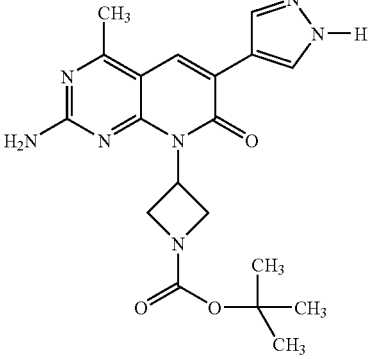 | tert-butyl 3-(2-amino-4-methyl-7-oxo-6-(1H-pyrazol-4-yl)pyrido[2,3-d]pyrimidin-8(7H)-yl)azetidine-1-carboxylate | 398 | (400 MHz, DMSO-d6) δ ppm: 12.90 (1H, s), 8.33 (1H, s), 8.16 (2H, s), 7.08 (2H, s), 5.51-5.69 (1H, m), 4.30 (2H, t, J = 7.96 Hz), 4.22 (2H, t, J = 8.34 Hz), 2.58 (3H, s), 1.41 (9H, s) |
| 227 | F | 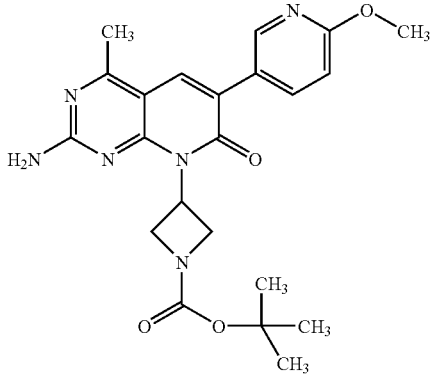 | tert-butyl 3-(2-amino-6-(6-methoxypyridin-3-yl)-4-methyl-7-oxopyrido[2,3-d]pyrimidin-8(7H)-yl)azetidine-1-carboxylate | 439 | (400 MHz, DMSO-d6) δ ppm: 8.45 (1H, s), 8.03 (1H, s), 8.01 (1H, s), 7.18 (2H, s), 6.86 (1H, d, J = 8.34 Hz), 5.38-5.65 (1H, m), 4.12-4.38 (4H, m), 3.88 (3H, s), 2.56 (3H, s), 1.39 (9H, s) |
| 228 | F | 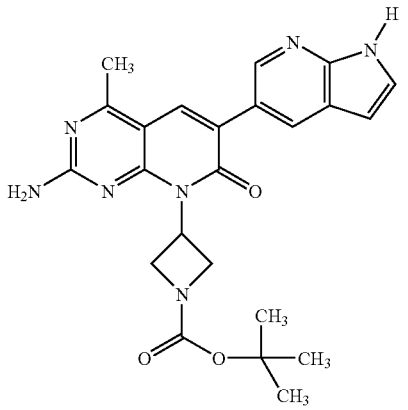 | tert-butyl 3-(2-amino-4-methyl-7-oxo-6-(1H-pyrrolo[2,3-b]pyridin-5-yl)pyrido[2,3-d]pyrimidin-8(7H)-yl)azetidine-1-carboxylate | 448 | (400 MHz, DMSO-d6) δ ppm: 11.69 (1H, s), 8.48 (1H, d, J = 2.02 Hz), 8.24 (1H, d, J = 2.02 Hz), 8.04 (1H, s), 7.44-7.53 (1H, m), 7.17 (2H, s), 6.48 (1H, dd, J = 3.28, 1.77 Hz), 5.47-5.63 (1H, m), 4.32 (2H, t, J = 7.71 Hz), 4.23 (2H, t, J = 8.34 Hz), 2.58 (3H, s), 1.39 (9H, s). |
| 229 | A | 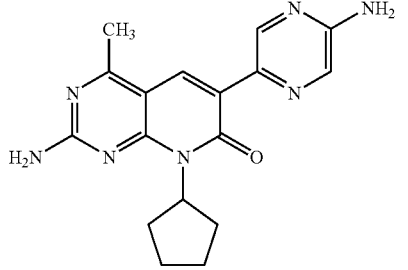 | 2-amino-6-(5-aminopyrazin-2-yl)-8-cyclopentyl-4-methylpyrido[2,3-d]pyrimidin-7(8H)-one | 338 | (400 MHz, DMSO-d6) δ ppm 1.54-1.66 (m, 2H) 1.71-1.83 (m, 2H) 1.98-2.11 (m, 2H) 2.26 (dd, J = 11.12, 7.58 Hz, 2H) 2.55 (s, 3H) 5.94-6.11 (m, 1H) 6.56 (s, 2H) 7.18 (s, 2H) 7.97 (d, J = 1.52 Hz, 1H) 8.39 (s, 1H) 8.90 (d, J = 1.52 Hz, 1H) |

TABLE 1-continued

| Compound | Synthetic Method (% Yield) | Structure | Compound Name | LRMS m/z | $^1$H NMR |
|---|---|---|---|---|---|
| 230 | A | 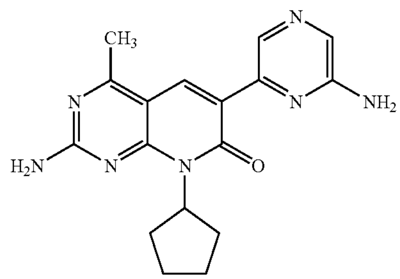 | 2-amino-6-(6-aminopyrazin-2-yl)-8-cyclopentyl-4-methylpyrido[2,3-d]pyrimidin-7(8H)-one | 338 | (400 MHz, DMSO-d6) δ ppm 8.90 (1H, d, J = 1.26 Hz) 8.39 (1H, s) 7.97 (1H, d, J = 1.52 Hz) 7.18 (2H, s) 6.57 (2H, s) 5.95-6.11 (1H, m) 2.55 (3H, s) 2.25 (2H, dd, J = 11.12, 7.58 Hz) 1.95-2.11 (2H, m) 1.71-1.83 (2H, m) 1.59 (2H, dd, J = 9.98, 5.18 Hz) |
| 231 | A | 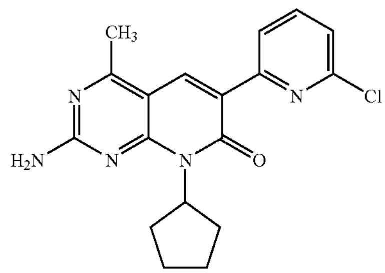 | 2-Amino-6-(6-chloro-pyridin-2-yl)-8-cyclopentyl-4-methyl-8H-pyrido[2,3-d]pyrimidin-7-one | 356 | (400 MHz, CHLOROFORM-d) δ ppm 8.56 (1H, s) 8.29 (1H, d, J = 7.83 Hz) 7.61 (1H, t, J = 7.83 Hz) 7.16 (1H, s) 5.80-6.02 (1H, m) 5.09-5.25 (2H, m) 2.61 (3H, s) 2.25 (2H, dd, J = 11.62, 7.58 Hz) 2.02 (2H, dd, J = 7.71, 4.93 Hz) 1.71-1.86 (2H, m) 1.55-1.66 (2H, m). |
| 232 | A | 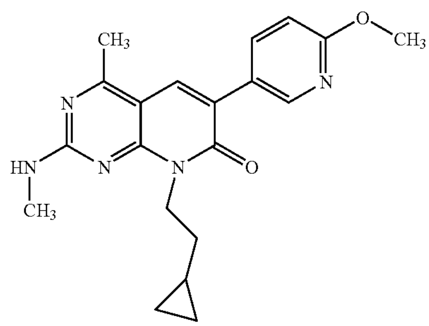 | 8-(2-Cyclopropyl-ethyl)-6-(6-methoxy-pyridin-3-yl)-4-methyl-2-methylamino-8H-pyrido[2,3-d]pyrimidin-7-one | 366 | (400 MHz, CHLOROFORM-d) δ ppm 10.27 (1H, s) 8.35 (1H, d, J = 2.27 Hz) 7.92 (1H, dd, J = 8.59, 2.53 Hz) 7.65 (1H, s) 6.83 (1H, d, J = 8.84 Hz) 4.42-4.61 (2H, m) 3.99 (3H, s) 3.13 (3H, d, J = 4.29 Hz) 2.77 (3H, s) 1.65 (2H, q, J = 7.16 Hz) 0.68-0.89 (1H, m) 0.38-0.55 (2H, m) 0.08 (2H, q, J = 4.88 Hz) |
| 233 | A | 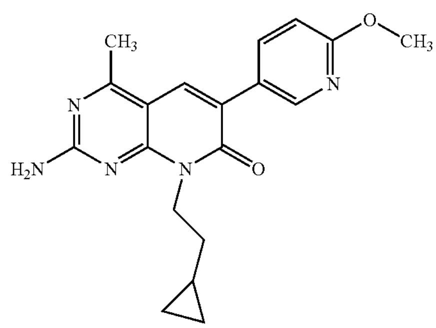 | 2-Amino-8-(2-cyclopropyl-ethyl)-6-(6-methoxy-pyridin-3-yl)-4-methyl-8H-pyrido[2,3-d]pyrimidin-7-one | 352 | (400 MHz, DMSO-d6) δ ppm 8.40 (1H, d, J = 2.02 Hz) 7.91-8.05 (2H, m) 7.09 (2H, s) 6.79 (1H, d, J = 8.59 Hz) 4.24-4.40 (2H, m) 3.82 (3H, s) 2.50 (3H, s) 1.46 (2H, q, J = 7.07 Hz) 0.59-0.77 (1H, m) 0.27-0.39 (2H, m) -0.01 (2H, d, J = 4.55 Hz) |
| 234 | A | 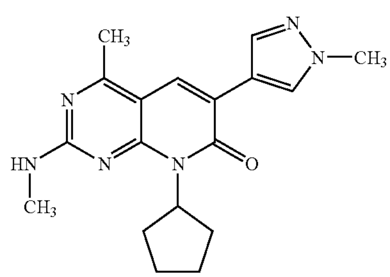 | 8-Cyclopentyl-4-methyl-2-methylamino-6-(1-methyl-1H-pyrazol-4-yl)-8H-pyrido[2,3-d]pyrimidin-7-one | 339 | (400 MHz, CHLOROFORM-d) δ ppm 8.28 (1H, s) 7.87 (2H, s) 5.99-6.26 (1H, m) 5.24 (1H, d, J = 3.03 Hz) 3.95 (3H, s) 3.08 (3H, d, J = 5.05 Hz) 2.62 (3H, s) 2.44 (2H, s) 2.02-2.21 (2H, m) 1.78-1.95 (2H, m) 1.65-1.77 (2H, m) |

TABLE 1-continued

| Compound | Synthetic Method (% Yield) | Structure | Compound Name | LRMS m/z | ¹H NMR |
|---|---|---|---|---|---|
| 235 | A | 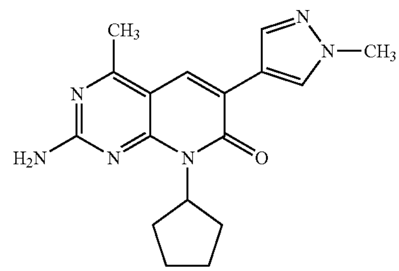 | 2-Amino-8-cyclopentyl-4-methyl-6-(1-methyl-1H-pyrazol-4-yl)-8H-pyrido[2,3-d]pyrimidin-7-one | 325 | (400 MHz, CHLOROFORM-d) δ ppm 8.28 (1H, s) 7.87 (2H, s) 6.04 (1H, d, J = 8.59 Hz) 5.11 (2H, s) 3.95 (3H, s) 2.64 (3H, s) 2.34 (2H, dd, J = 11.49, 7.20 Hz) 2.03-2.17 (2H, m) 1.80-1.96 (2H, m) 1.65-1.77 (2H, m) |
| 236 | A | 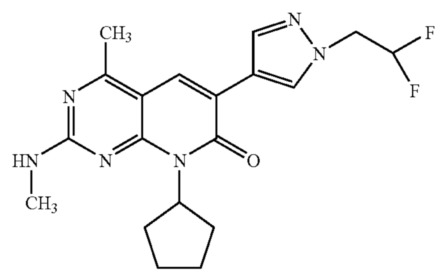 | 8-Cyclopentyl-6-[1-(2,2-difluoro-ethyl)-1H-pyrazol-4-yl]-4-methyl-2-methylamino-8H-pyrido[2,3 d]pyrimidin-7-one | 389 | (400 MHz, CHLOROFORM-d) δ ppm 8.30 (1H, s) 7.88 (1H, s) 7.80 (1H, s) 5.84-6.30 (2H, m) 5.19 (1H, s) 4.29-4.55 (2H, m) 3.00 (3H, d, J = 5.05 Hz) 2.54 (3H, s) 2.37 (2H, s) 1.94-2.09 (2H, m) 1.74-1.89 (2H, m) 1.58-1.69 (2H, m) |
| 237 | A | 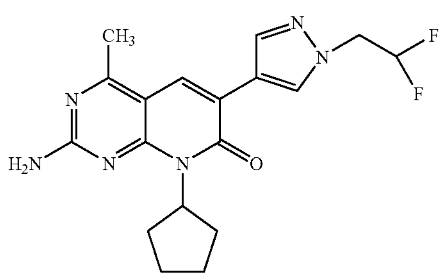 | 2-Amino-8-cyclopentyl-6-[1-(2,2-difluoro-ethyl)-1H-pyrazol-4-yl]-4-methyl-8H-pyrido[2,3-d]pyrimidin-7-one | 375 | (400 MHz, CHLOROFORM-d) δ ppm 8.38 (1H, s) 7.97 (1H, s) 7.89 (1H, s) 5.89-6.34 (2H, m) 5.13 (2H, s) 4.35-4.60 (2H, m) 2.64 (3H, s) 2.24-2.45 (2H, m) 2.04-2.21 (2H, m) 1.80-1.96 (2H, m) 1.66-1.79 (2H, m) |
| 238 | E | 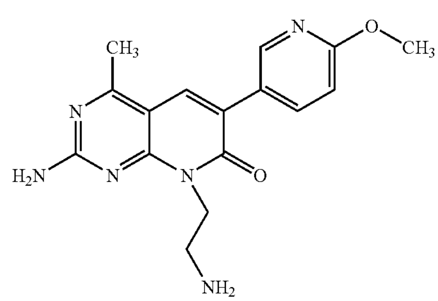 | 2-Amino-8-(2-amino-ethyl)-6-(6-methoxy-pyridin-3-yl)-4-methyl-8H-pyrido[2,3-d]pyrimidin-7-one | 327 | (400 MHz, DMSO-d6) δ ppm 8.48 (1H, d, J = 2.27 Hz) 7.92-8.08 (2H, m) 7.17 (2H, s) 6.86 (1H, d, J = 8.59 Hz) 4.33 (2H, t, J = 6.82 Hz) 3.88 (3H, s) 2.84 (2H, t, J = 6.82 Hz) 2.57 (2H, s) 1.88 (3H, s) |
| 239 | E | 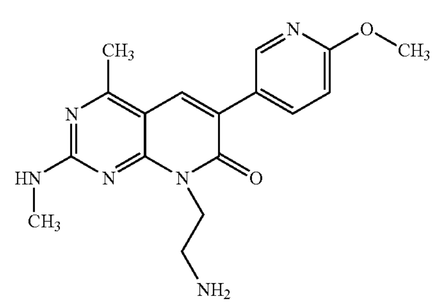 | 8-(2-Amino-ethyl)-6-(6-methoxy-pyridin-3-yl)-4-methyl-2-methylamino-8H-pyrido[2,3-d]pyrimidin-7-one | 341 | (400 MHz, DMSO-d6) δ ppm 8.48 (1H, s) 7.94-8.10 (2H, m) 7.70 (1H, s) 6.85 (1H, d, J = 8.59 Hz) 4.25-4.49 (2H, m) 3.88 (3H, s) 2.89 (5H, d, J = 4.80 Hz) 2.54-2.66 (3H, m) |

TABLE 1-continued

| Compound | Synthetic Method (% Yield) | Structure | Compound Name | LRMS m/z | $^1$H NMR |
|---|---|---|---|---|---|
| 240 | Similar to Example 31 | 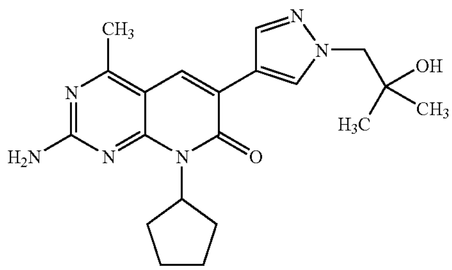 | 2-Amino-8-cyclopentyl-6-[1-(2-hydroxy-2-methyl-propyl)-1H-pyrazol-4-yl]-4-methyl-8H-pyrido[2,3-d]pyrimidin-7-one | 383 | (400 MHz, DMSO-d6) δ ppm 8.37 (1H, s) 8.12 (1H, s) 8.09 (1H, s) 7.05 (2H, s) 5.96-6.11 (1H, m) 4.72 (1H, s) 4.03 (2H, s) 2.58 (3H, s) 2.15-2.31 (2H, m) 1.96-2.09 (2H, m) 1.68-1.82 (2H, m) 1.54-1.65 (2H, m) 1.07 (6H, s) |
| 241 | E | 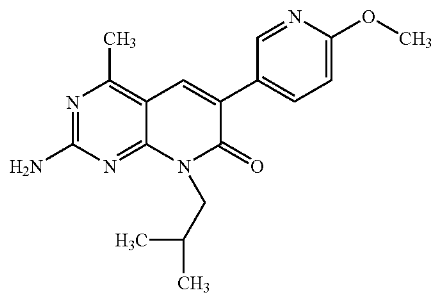 | 2-Amino-8-isobutyl-6-(6-methoxy-pyridin-3-yl)-4-methyl-8H-pyrido[2,3-d]pyrimidin-7-one | 340 | (400 MHz, DMSO-d6) δ ppm 8.47 (1H, d, J = 2.53 Hz) 7.98-8.07 (2H, m) 7.15 (2H, br. s.) 6.86 (1H, d, J = 8.59 Hz) 4.17 (2H, d, J = 7.33 Hz) 3.88 (3H, s) 2.57 (3H, s) 2.16-2.30 (1H, m) 0.87 (6H, d, J = 6.82 Hz) |
| 242 | E | 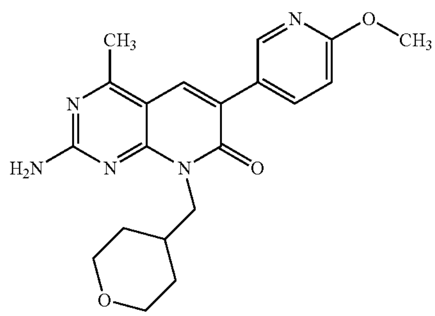 | 2-Amino-6-(6-methoxy-pyridin-3-yl)-4-methyl-8-(tetrahydro-pyran-4-ylmethyl)-8H-pyrido[2,3-d]pyrimidin-7-one | 382 | (400 MHz, DMSO-d6) δ ppm 8.47 (1H, d, J = 2.53 Hz) 7.99-8.09 (2H, m) 7.18 (2H, s) 6.86 (1H, d, J = 8.59 Hz) 4.24 (2H, d, J = 7.07 Hz) 3.88 (3H, s) 3.77-3.86 (2H, m) 3.20 (2H, td, J = 11.43, 2.15 Hz) 2.56 (3H, s) 2.05-2.17 (1H, m) 1.30-1.51 (4H, m) |
| 243 | E | 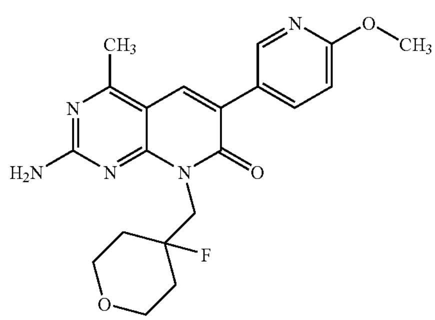 | 2-Amino-8-(4-fluoro-tetrahydro-pyran-4-ylmethyl)-6-(6-methoxy-pyridin-3-yl)-4-methyl-8H-pyrido[2,3-d]pyrimidin-7-one | 400 | (400 MHz, DMSO-d6) δ ppm 8.47 (1H, d, J = 2.53 Hz) 8.06 (1H, s) 8.03 (1H, dd, J = 8.59, 2.53 Hz) 7.22 (2H, br. s.) 6.87 (1H, d, J = 8.59 Hz) 4.66 (2H, d, J = 18.19 Hz) 3.89 (3H, s) 3.69-3.76 (2H, m) 3.45-3.54 (2H, m, J = 11.37, 11.37, 1.52 Hz) 2.57 (3H, s) 1.74-1.94 (2H, m) 1.59-1.73 (2H, m) |
| 244 | E | 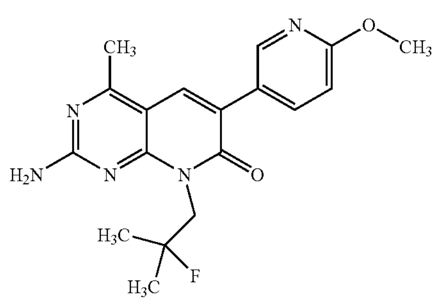 | 2-Amino-8-(2-fluoro-2-methyl-propyl)-6-(6-methoxy-pyridin-3-yl)-4-methyl-8H-pyrido[2,3-d]pyrimidin-7-one | 358 | (400 MHz, DMSO-d6) δ ppm 8.47 (1H, d, J = 2.02 Hz) 8.06 (1H, s) 8.02 (1H, dd, J = 8.72, 2.40 Hz) 7.19 (2H, s) 6.86 (1H, d, J = 8.84 Hz) 4.64 (2H, d, J = 17.94 Hz) 3.88 (3H, s) 2.57 (3H, s) 1.37 (3H, s) 1.31 (3H, s) |

TABLE 1-continued

| Compound | Synthetic Method (% Yield) | Structure | Compound Name | LRMS m/z | 1H NMR |
|---|---|---|---|---|---|
| 245 | C | 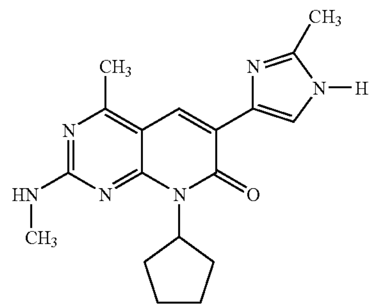 | 8-Cyclopentyl-4-methyl-2-methylamino-6-(2-methyl-1H-imidazol-4-yl)-8H-pyrido[2,3-d]pyrimidin-7-one | 339 | (400 MHz, ETHANOL-d6) δ ppm 8.41 (1H, s) 7.74 (1H, s) 6.09-6.22 (1H, m) 5.50 (1H, s) 3.01 (3H, s) 2.65 (3H, s) 2.47 (5H, s) 2.12 (2H, dd, J = 7.96, 5.43 Hz) 1.82-1.94 (2H, m) 1.67-1.79 (2H, m) |
| 246 | F | 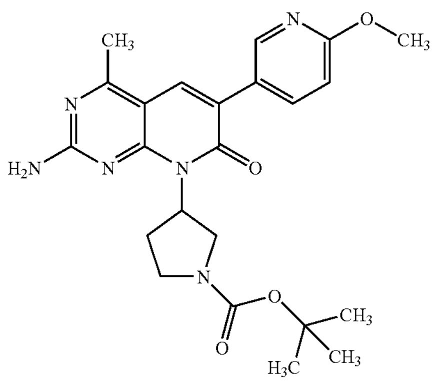 | 3-[2-Amino-6-(6-methoxy-pyridin-3-yl)-4-methyl-7-oxo-7H-pyrido[2,3-d]pyrimidin-8-yl]-pyrrolidine-1-carboxylic acid tert-butyl ester | | (400 MHz, DMSO-d6) δ ppm 8.43 (1H, d, J = 2.53 Hz) 7.94-8.07 (2H, m) 7.21 (2H, br. s.) 6.85 (1H, d, J = 8.59 Hz) 6.16-6.31 (1H, m) 3.88 (3H, s) 3.76 (1H, t, J = 9.09 Hz) 3.59-3.71 (1H, m) 3.51 (1H, t, J = 9.60 Hz) 2.63-2.76 (1H, m) 2.56 (3H, s) 2.06 (1H, d, J = 14.15 Hz) 1.40 (9H, d, J = 12.13 Hz) (one proton is under water peak) |
| 253 | G | 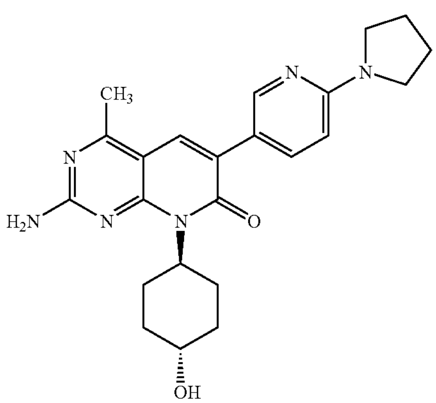 | 2-amino-8-(trans-4-hydroxycyclohexyl)-4-methyl-6-(6-pyrrolidin-1-ylpyridin-3-yl)pyrido[23-d]pyrimidin-7(8H)-one | 421 | (500 MHz, DMSO-d6) δ ppm 1.24-1.35 (m, 2H) 1.48 (d, J = 11.81 Hz, 2H) 1.88-1.98 (m, 6H) 3.33-3.43 (m, 4H) 4.80-4.88 (m, 1H) 6.46 (d, J = 8.52 Hz, 1H) 6.92 (br. s., 2H) 7.78 (dd, J = 8.93, 2.33 Hz, 1H) 7.80 (s, 1H) 8.30 (d, J = 1.65 Hz, 1H). Three aliphatic and one methyl residue not visible due to overlap with solvent and water resonances. |
| 254 | G | 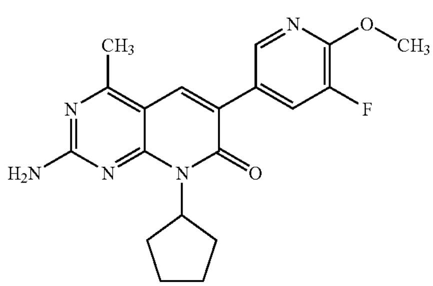 | 2-amino-8-cyclopentyl-6-(5-fluoro-6-methoxypyridin-3-yl)-4-methylpyrido[23-d]pyrimidin-7(8H)-one | 370 | (500 MHz, DMSO-d6) δ ppm 1.51-1.62 (m, 2H) 1.69-1.82 (m, 2H) 1.92-2.06 (m, 2H) 2.14-2.25 (m, 2H) 3.96 (s, 3H) 5.96 (d, J = 8.79 Hz, 1H) 7.04 (br. s., 2H) 7.96 (d, J = 11.81 Hz, 1H) 8.02 (s, 1H) 8.26 (d, J = 1.65 Hz, 1H). One methyl residue not visible due to overlap with solvent resonance |

TABLE 1-continued

| Compound | Synthetic Method (% Yield) | Structure | Compound Name | LRMS m/z | ¹H NMR |
|---|---|---|---|---|---|
| 255 | G | 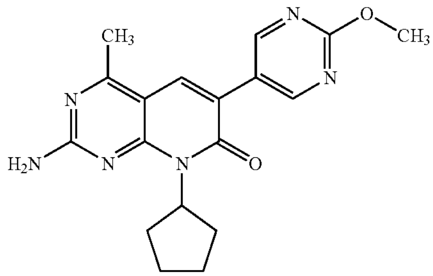 | 2-amino-8-cyclopentyl-6-(2-methoxypyrimidin-5-yl)-4-methylpyrido[23-d]pyrimidin-7(8H)-one | 353 | (500 MHz, DMSO-d6) δ ppm 1.51-1.63 (m, 2H) 1.69-1.81 (m, 2H) 1.93-2.06 (m, 2H) 2.12-2.26 (m, 2H) 3.94 (s, 3H) 5.91-5.99 (m, 1H) 7.05 (br. s., 2H) 8.08 (s, 1H) 8.84 (s, 2H). One methyl residue not visible due to overlap with solvent resonance. |
| 256 | G | 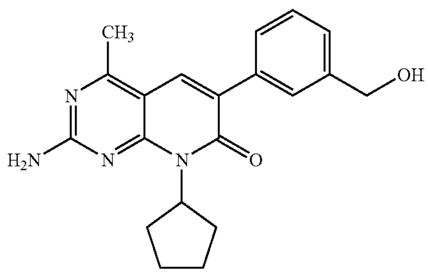 | 2-amino-8-cyclopentyl-6-[3-(hydroxymethyl)phenyl]-4-methylpyrido[23-d]pyrimidin-7(8H)-one | 351 | (500 MHz, DMSO-d6) δ ppm 1.58 (br. s., 2H) 1.75 (d, J = 9.61 Hz, 2H) 1.99 (br. s., 2H) 2.14-2.26 (m, 2H) 4.53 (d, J = 5.49 Hz, 2H) 5.31-5.38 (m, 1H) 5.90-6.03 (m, 1H) 6.98 (br. s., 2H) 7.27 (d, J = 7.69 Hz, 1H) 7.35 (t, J = 7.69 Hz, 1H) 7.48 (d, J = 7.42 Hz, 1H) 7.55 (s, 1H) 7.87 (s, 1H). One methyl residue not visible due to overlap with solvent resonance. |
| 257 | G | 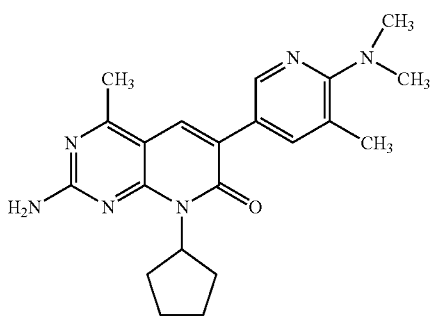 | 2-amino-8-cyclopentyl-6-[6-(dimethylamino)-5-methylpyridin-3-yl]-4-methylpyrido[23-d]pyrimidin-7(8H)-one | 379 | (500 MHz, DMSO-d6) δ ppm 1.52-1.63 (m, 2H) 1.69-1.80 (m, 2H) 1.93-2.04 (m, 2H) 2.14-2.24 (m, 2H) 2.27 (s, 3H) 2.80 (s, 6H) 5.95 (quin, 1H) 6.96 (d, J = 1.37 Hz, 2H) 7.72 (d, J = 1.92 Hz, 1H) 7.89 (s, 1H) 8.27 (d, J = 2.20 Hz, 1H). One methyl residue not visible due to overlap with solvent resonance. |
| 258 | G | 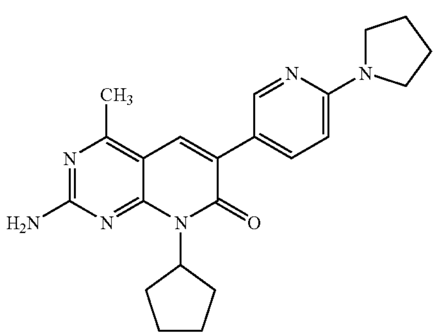 | 2-amino-8-cyclopentyl-4-methyl-6-(6-pyrrolidin-1-ylpyridin-3-yl)pyrido[23-d]pyrimidin-7(8H)-one | 391 | (500 MHz, DMSO-d6) δ ppm 1.52-1.63 (m, 2H) 1.69-1.80 (m, 2H) 1.88-1.98 (m, 4H) 1.96-2.05 (m, 2H) 2.16-2.25 (m, 2H) 3.37 (br. s., 2H) 5.95 (m, 1H) 6.47 (d, J = 9.06 Hz, 1H) 6.89 (br. s., 2H) 7.80 (d, J = 9.06 Hz, 1H) 8.23 (s, 1H) 8.30 (s, 1H). Two aliphatic protons and one methyl residue not visible due to overlap with solvent and water resonances. |

TABLE 1-continued

| Compound | Synthetic Method (% Yield) | Structure | Compound Name | LRMS m/z | ¹H NMR |
|---|---|---|---|---|---|
| 259 | G | 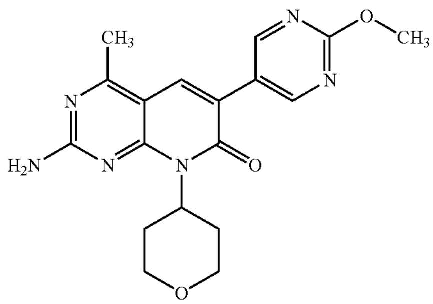 | 2-amino-6-(2-methoxypyrimidin-5-yl)-4-methyl-8-(tetrahydro-2H-pyran-4-yl)pyrido[23-d]pyrimidin-7(8H)-one | 369 | (500 MHz, DMSO-d6) δ ppm 1.49 (d, J = 13.46 Hz, 2H) 2.99 (m, 2H) 3.96 (s, 3H) 3.97-4.02 (m, 2H) 5.60-5.78 (m, 1H) 7.19 (s, 2H) 8.13 (s, 1H) 8.88 (s, 2H). One methyl residue and two aliphatic protons not visible due to overlap with solvent resonace. |
| 260 | G | 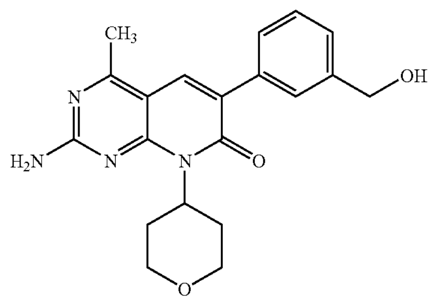 | 2-amino-6-[3-(hydroxymethyl)phenyl]-4-methyl-8-(tetrahydro-2H-pyran-4-yl)pyrido[23-d]pyrimidin-7(8H)-one | 367 | (500 MHz, DMSO-d6) δ ppm 1.48 (d, J = 11.26 Hz, 2H) 2.87-3.07 (m, 2H) 4.00 (dd, J = 11.54, 4.12 Hz, 2H) 4.54 (d, J = 5.22 Hz, 2H) 5.12-5.30 (m, 1H) 5.66-5.73 (m, 1H) 7.10 (s, 2H) 7.29 (d, J = 7.69 Hz, 1H) 7.35 (t, J = 7.55 Hz, 1H) 7.50 (d, J = 7.69 Hz, 1H) 7.58 (s, 1H) 7.89 (s, 1H). One methyl residue and two aliphatic protons not visible due to overlap with solvent resonance. |
| 261 | G | 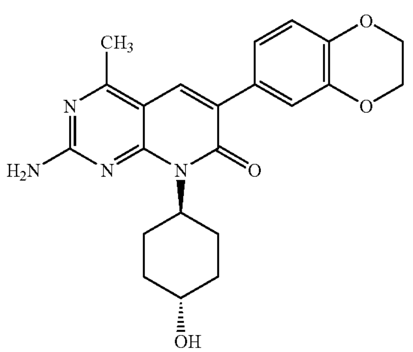 | 2-amino-6-(2,3-dihydro-1,4-benzodioxin-6-yl)-8-(trans-4-hydroxycyclohexyl)-4-methylpyrido[2,3-d]pyrimidin-7(8H)-one | 409 | (500 MHz, DMSO-d6) δ ppm 1.29 (q, J = 13.00 Hz, 2H) 1.48 (d, J = 10.16 Hz, 2H) 1.92 (d, J = 12.36 Hz, 2H) 4.24 (s, 4H) 4.84 (br. s., 1H) 5.37 (br. s., 1H) 6.85 (d, J = 8.52 Hz, 1H) 6.96 (br. s., 2H) 7.09 (dd, J = 8.52, 1.92 Hz, 1H) 7.16 (d, J = 1.92 Hz, 1H) 7.79 (s, 1H). One methyl residue and three aliphatic protons not visible due to overlap with solvent resonance. |
| 262 | G | 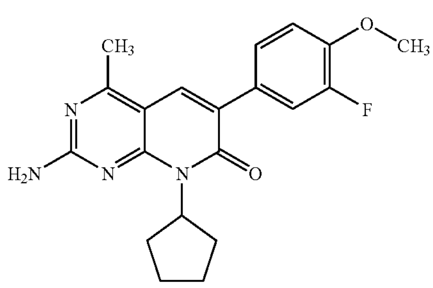 | 2-amino-8-cyclopentyl-6-(3-fluoro-4-methoxyphenyl)-4-methylpyrido[23-d]pyrimidin-7(8H)-one | 369 | (500 MHz, DMSO-d6) δ ppm 1.48-1.65 (m, 2H) 1.68-1.82 (m, 2H) 1.91-2.09 (m, 2H) 2.12-2.28 (m, 2H) 3.85 (s, 3H) 5.92-5.98 (m, 1H) 6.98 (br. s., 2H) 7.16 (t, J = 8.93 Hz, 1H) 7.45 (d, J = 7.97 Hz, 1H) 7.54 (dd, J = 13.19, 1.92 Hz, 1H) 7.90 (s, 1H). One methyl residue not visible due to overlap with solvent and water resonances. |

TABLE 1-continued

| Compound | Synthetic Method (% Yield) | Structure | Compound Name | LRMS m/z | ¹H NMR |
|---|---|---|---|---|---|
| 265 | F | 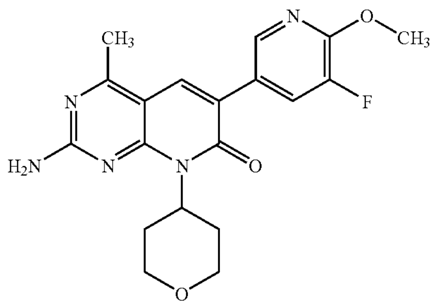 | 2-amino-6-(5-fluoro-6-methoxypyridin-3-yl)-4-methyl-8-(tetrahydro-2H-pyran-4-yl)pyrido[2,3-d]pyrimidin-7(8H)-one | 386 | (400 MHz, DMSO-d6) δ ppm 8.28-8.36 (1H, m) 8.08 (1H, s) 8.01 (1H, dd, J = 12.13, 2.02 Hz) 7.25 (2H, s) 5.57-5.82 (1H, m) 4.00-4.05 (2H, m) 3.98 (3H, s) 3.40 (2H, t, J = 11.37 Hz) 2.87-3.07 (2H, m) 2.57 (3H, s) 1.48 (2H, d, J = 9.60 Hz |
| 266 | E | 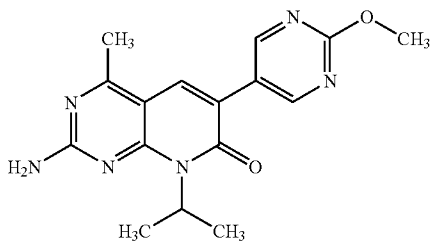 | 2-amino-8-isopropyl-6-(2-methoxypyrimidin-5-yl)-4-methylpyrido[2,3-d]pyrimidin-7(8H)-one | 327 | (400 MHz, CHLOROFORM-d) δ ppm 8.80 (2H, s) 7.75 (1H, s) 5.75-6.00 (1H, m) 5.58 (2H, br. s.) 4.06 (3H, s) 2.66 (3H, s) 1.61 (6H, d, J = 6.82 Hz) |
| 268 | Similar to Example 60 | 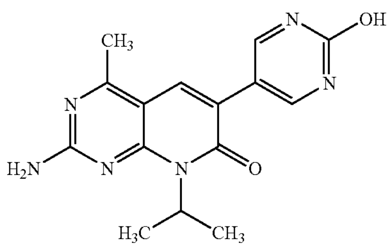 | 2-amino-6-(2-hydroxypyrimidin-5-yl)-8-isopropyl-4-methylpyrido[2,3-d]pyrimidin-7(8H)-one | 313 | (400 MHz, DMSO-d₆) δ ppm 12.12 (1H, br. s.) 8.63 (2H, br. s.) 8.09 (1H, s) 7.19 (2H, br. s.) 5.48-6.13 (1H, m) 2.55 (3H, s) 1.51 (6H, d, J = 6.82 Hz) |
| 271 | F | 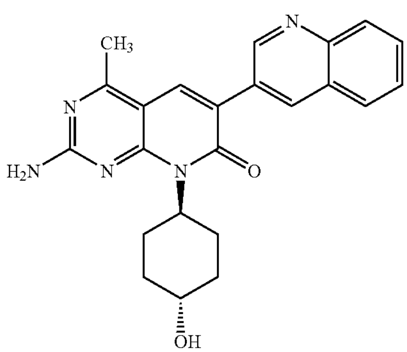 | 2-amino-8-(trans-4-hydroxycyclohexyl)-4-methyl-6-(quinolin-3-yl)pyrido[2,3-d]pyrimidin-7(8H)-one | 402 | (400 MHz, DMSO-d6) d ppm 1.24-1.38 (m, 2H) 1.51-1.60 (m, 2H) 1.92-1.99 (m, 2H) 2.59 (s, 3H) 2.68-2.92 (m, 2H) 3.49-3.66 (m, 1H) 4.47-4.85 (m, 1H) 5.24-5.68 (m, 1H) 7.25 (br. s., 2H) 7.60-7.67 (m, 1H) 7.73-7.79 (m, 1H) 8.00-8.06 (m, 2H) 8.23 (s, 1H) 8.64 (d, J = 1.77 Hz, 1H) 9.16 (d, J = 2.27 Hz, 1H) |
| 272 | F | 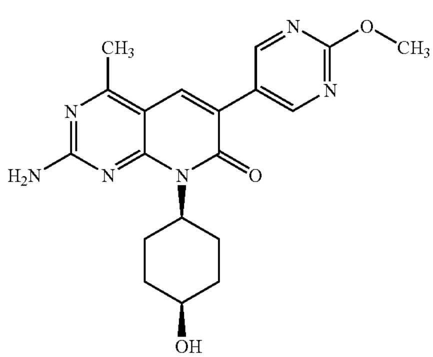 | 2-amino-8-(cis-4-hydroxycyclohexyl)-6-(2-methoxypyrimidin-5-yl)-4-methylpyrido[2,3-d]pyrimidin-7(8H)-one | 383 | (400 MHz, DMSO-d6) δ ppm 1.21-1.31 (m, 2H) 1.45-1.56 (m, 2H) 1.75-1.84 (m, 2H) 2.56 (s, 3H) 2.96-3.08 (m, 2H) 3.85-3.91 (m, 1H) 3.95 (s, 3H) 4.32 (d, J = 2.27 Hz, 1H) 5.41-5.52 (m, 1H) 7.19 (s, 2H) 8.12 (s, 1H) 8.89 (s, 2H) |

TABLE 1-continued

| Compound | Synthetic Method (% Yield) | Structure | Compound Name | LRMS m/z | ¹H NMR |
|---|---|---|---|---|---|
| 273 | F | 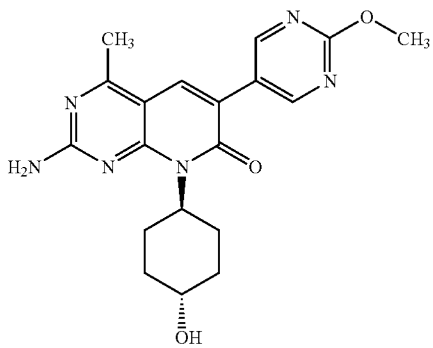 | 2-amino-8-(trans-4-hydroxycyclohexyl)-6-(2-methoxypyrimidin-5-yl)-4-methylpyrido[2,3-d]pyrimidin-7(8H)-one | 383 | (400 MHz, DMSO-d6) δ ppm 1.23-1.34 (m, 2H) 1.47-1.57 (m, 2H) 1.88-1.98 (m, 2H) 2.55 (s, 3H) 2.71-2.82 (m, 2H) 3.47-3.59 (m, 1H) 3.95 (s, 3H) 4.60 (d, J = 4.04 Hz, 1H) 5.17-5.73 (m, 1H) 7.22 (s, 2H) 8.12 (s, 1H) 8.87 (s, 2H) |
| 274 | A | 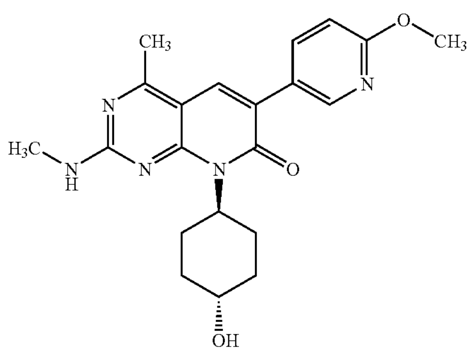 | 8-(trans-4-hydroxycyclohexyl)-6-(6-methoxypyridin-3-yl)-4-methyl-2-(methylamino)pyrido[2,3-d]pyrimidin-7(8H)-one | 396 | (400 MHz, DMSO-d6) δ ppm 1.25-1.35 (m, 2H) 1.47-1.59 (m, 2H) 1.89-2.00 (m, 2H) 2.54 (s, 3H) 2.69-2.79 (m, 2H) 2.85-2.95 (m, 3H) 3.43-3.52 (m, 1H) 3.88 (s, 3H) 4.63 (d, J = 4.29 Hz, 1H) 5.04-5.91 (m, 1H) 6.84 (d, J = 8.59 Hz, 1H) 7.70 (d, J = 4.55 Hz, 1H) 7.97 (s, 1H) 7.98-8.03 (m, 1H) 8.43 (s, 1H) |
| 276 | A | 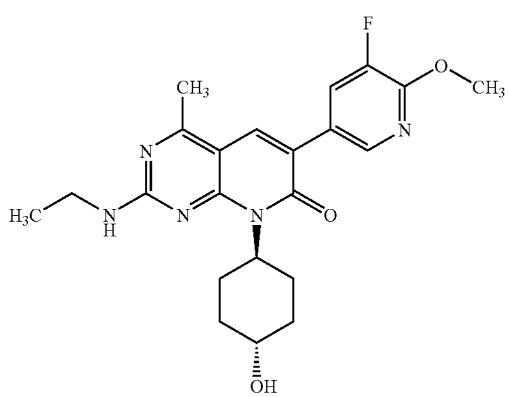 | 2-(ethylamino)-6-(5-fluoro-6-methoxypyridin-3-yl)-8-(trans-4-hydroxycyclohexyl)-4-methylpyrido[2,3-d]pyrimidin-7(8H)-one | 428 | (400 MHz, DMSO-d6) δ ppm 1.15-1.21 (m, 3H) 1.23-1.35 (m, 2H) 1.49-1.60 (m, 2H) 1.90-1.99 (m, 2H) 2.55 (s, 3H) 2.69-3.03 (m, 2H) 3.34-3.42 (m, 2H) 3.43-3.54 (m, 1H) 3.98 (s, 3H) 4.64 (d, J = 4.04 Hz, 1H) 5.11-5.66 (m, 1H) 7.85 (t, J = 5.68 Hz, 1H) 8.02 (d, J = 12.13 Hz, 1H) 8.06 (s, 1H) 8.31 (s, 1H) |
| 277 | A | 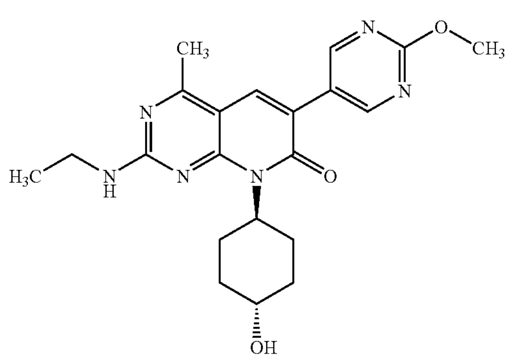 | 2-(ethylamino)-8-(trans-4-hydroxycyclohexyl)-6-(2-methoxypyrimidin-5-yl)-4-methylpyrido[2,3-d]pyrimidin-7(8H)-one | 411 | (300 MHz, DMSO-d6) δ ppm 1.18 (t, J = 6.97 Hz, 3H) 1.23-1.38 (m, 2H) 1.45-1.61 (m, 2H) 1.88-2.03 (m, 2H) 2.55 (s, 3H) 2.67-3.06 (m, 2H) 3.35-3.44 (m, 2H) 3.44-3.58 (m, 1H) 3.95 (s, 3H) 4.64 (d, J = 4.14 Hz, 1H) 5.15-5.56 (m, 1H) 7.84-7.92 (m, 1H) 8.13 (s, 1H) 8.89 (s, 2H) |

TABLE 1-continued

| Compound | Synthetic Method (% Yield) | Structure | Compound Name | LRMS m/z | $^1$H NMR |
|---|---|---|---|---|---|
| 278 | Similar to Example 85 | 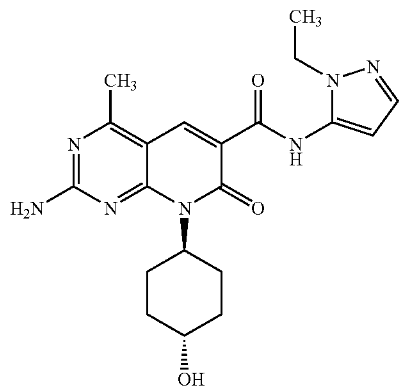 | 2-amino-N-(1-ethyl-1H-pyrazol-5-yl)-8-(trans-4-hydroxycyclohexyl)-4-methyl-7-oxo-78-dihydropyrido[23-d]pyrimidine-6-carboxamide | 412 | (400 MHz, DMSO-d 6) ppm 1.31 (d, J = 14.65 Hz, 4H), 1.38 (t, J = 7.20 Hz, 3H), 1.57 (d, J = 11.87 Hz, 2H), 1.96 (d, J = 12.13 Hz, 2H), 2.62 (s, 3H), 3.13-3.23 (m, 1H), 4.05-4.16 (m, 2H), 4.64 (s, 1H), 6.43 (d, J = 1.26 Hz, 1H), 7.39 (d, J = 1.77 Hz, 1H), 7.75 (d, J = 14.65 Hz, 2H), 8.79 (s, 1H), 12.01 (s, 1H) |
| 279 | Similar to Example 85 | 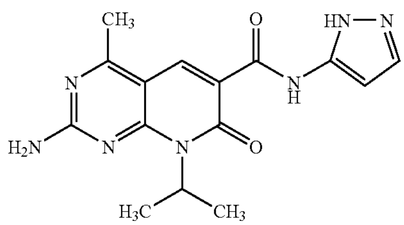 | 2-amino-8-isopropyl-4-methyl-7-oxo-N-1H-pyrazol-5-yl-7,8-dihydropyrido[2,3-d]pyrimidine-6-carboxamide | 328 | (400 MHz, DMSO-d 6 ) δ ppm 1.57 (d, J = 6.82 Hz, 6H) 2.62 (s, 3H) 5.90 (br. s., 1H) 6.66 (t, J = 2.02 Hz, 1H) 7.67 (s, 1H) 7.71 (br. s., 2H) 8.80 (s, 1H) 11.92 (s, 1H) 12.48 (br. s., 1H) |
| 280 | Similar to Example 85 | 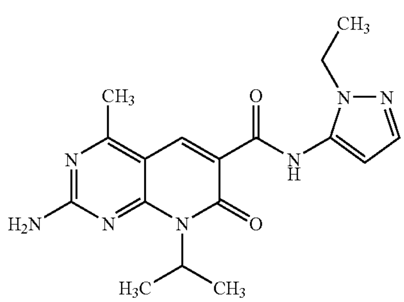 | 2-amino-N-(1-ethyl-1H-pyrazol-5-yl)-8-isopropyl-4-methyl-7-oxo-7,8-dihydropyrido[2,3-d]pyrimidine-6-carboxamide | 356 | (400 MHz, DMSO-d 6) δ ppm 1.38 (t, J = 7.20 Hz, 3H) 1.58 (d, J = 6.82 Hz, 6H) 2.63 (s, 3H) 4.10 (q, J = 7.33 Hz, 2H) 5.89 (br. s., 1H) 6.45 (d, J = 1.77 Hz, 1H) 7.38 (d, J = 1.77 Hz, 1H) 7.77 (d, J = 15.41 Hz, 2H) 8.80 (s, 1H) 12.14 (s, 1H) |
| 281 | Similar to Example 85 | 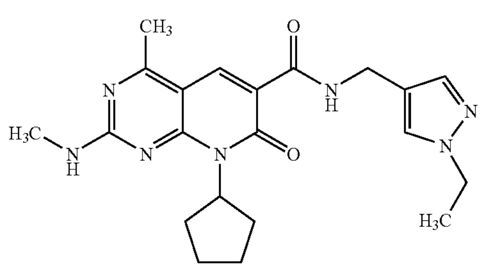 | 8-cyclopentyl-N-[(1-ethyl-1H-pyrazol-4-yl)methyl]-4-methyl-2-(methylamino)-7-oxo-7,8-dihydropyrido[2,3-d]pyrimidine-6-carboxamide | 410 | (400 MHz, DMSO-d 6 ) δ ppm 1.35 (t, J = 7.20 Hz, 3H) 1.48-1.69 (m, 2H) 1.71-1.86 (m, 2H) 1.89-2.09 (m, 2H) 2.12-2.39 (m, 2H) 2.59 (s, 2H) 2.64 (s, 1H) 2.91 (s, 3H) 4.09 (q, J = 7.33 Hz, 2H) 4.35 (d, J = 5.56 Hz, 2H) 5.88-6.06 (m, 1H) 7.40 (s, 1H) 7.69 (s, 1H) 7.84-7.97 (m, 0.3H) 8.14 (q, J = 4.38 Hz, 0.7H) 8.71 (s, 1H) 9.48-9.73 (m, 1H) |
| 282 | Similar to Example 85 | 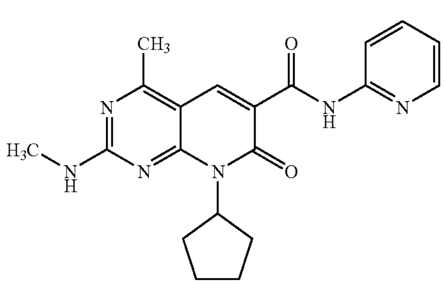 | 8-cyclopentyl-4-methyl-2-(methylamino)-7-oxo-N-pyridin-2-yl-7,8-dihydropyrido[2,3-d]pyrimidine-6-carboxamide | 379 | (400 MHz, DMSO-d 6 ) d ppm 1.62-1.79 (m, 2H) 1.82-1.95 (m, 2H) 1.99-2.18 (m, 2H) 2.23-2.47 (m, 2H) 2.68 (s, 2H) 2.74 (s, 1H) 2.96-3.03 (m, 3H) 5.99-6.26 (m, 1H) 7.12-7.28 (m, 1H) 7.90 (s, 1H) 8.08-8.17 (m, 0.3H) 8.22-8.37 (m, 1.7H) 8.41 (d, J = 4.04 Hz, 1H) 8.88 (s, 1H) 12.23 (s, 1H) |

TABLE 1-continued

| Compound | Synthetic Method (% Yield) | Structure | Compound Name | LRMS m/z | $^1$H NMR |
|---|---|---|---|---|---|
| 283 | Similar to Example 85 | 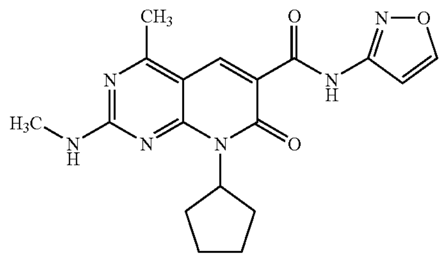 | 8-cyclopentyl-N-isoxazol-3-yl-4-methyl-2-(methylamino)-7-oxo-7,8-dihydropyrido[2,3-d]pyrimidine-6-carboxamide | 369 | (400 MHz, DMSO-d 6 ) d ppm 1.49-1.73 (m, 2H) 1.76-1.90 (m, 2H) 1.95-2.12 (m, 2H) 2.18-2.39 (m, 2H) 2.63 (s, 2H) 2.68 (s, 1H) 2.91-2.98 (m, 3H) 5.94-6.12 (m, 1H) 7.08 (d, J = 1.77 Hz, 1H) 8.13 (m, 0.3H) 8.35 (q, J = 4.38 Hz, 0.7H) 8.81 (s, 1H) 8.88 (d, J = 1.77 Hz, 1H) 12.31 (s, 1H) |
| 286 | I | 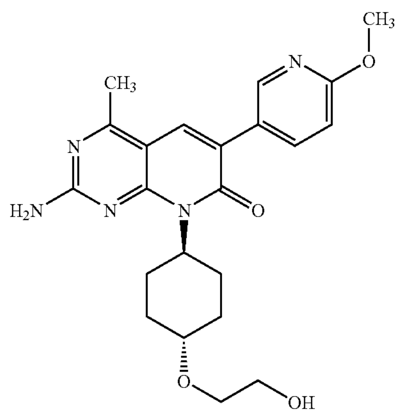 | 2-amino-8-[trans-4-(2-hydroxyethoxy)cyclohexyl]-6-(6-methoxypyridin-3-yl)-4-methylpyrido[2,3-d]pyrimidin-7(8H)-one | 426 | (400 MHz, DMSO-d$_6$) δ ppm 1.21-1.31 (m, 2H) 1.53-1.60 (m, 2H) 2.07-2.14 (m, 2H) 2.55 (s, 3H) 2.69-2.90 (m, 2H) 3.45-3.50 (m, 5H) 3.88 (s, 3H) 4.56 (t, J = 5.43 Hz, 1H) 5.32-5.53 (m, 1H) 6.84 (d, J = 9.09 Hz, 1H) 7.15 (br. s., 2H) 7.97 (s, 1H) 8.00 (dd, J = 8.59, 2.53 Hz, 1H) 8.42 (d, J = 2.27 Hz, 1H) |
| 287 | I | 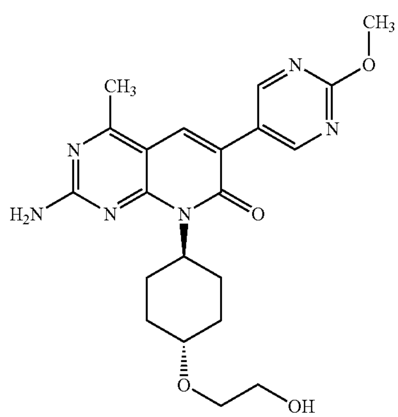 | 2-amino-8-[trans-4-(2-hydroxyethoxy)cyclohexyl]-6-(2-methoxypyrimidin-5-yl)-4-methylpyrido[2,3-d]pyrimidin-7(8H)-one | 427 | (400 MHz, DMSO-d$_6$) δ ppm 1.20-1.31 (m, 2H) 1.53-1.60 (m, 2H) 2.06-2.14 (m, 2H) 2.56 (s, 3H) 2.66-2.86 (m, 2H) 3.45-3.56 (m, 5H) 3.95 (s, 3H) 4.54 (t, 1H) 5.31-5.53 (m, 1H) 7.22 (br. s., 2H) 8.13 (s, 1H) 8.88 (s, 2H) |
| 288 | I | 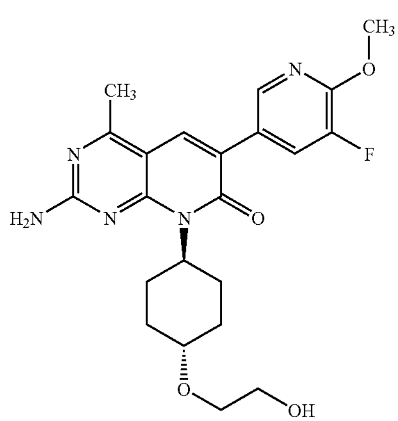 | 2-amino-6-(5-fluoro-6-methoxypyridin-3-yl)-8-[trans-4-(2-hydroxyethoxy)cyclohexyl]-4-methylpyrido[2,3-d]pyrimidin-7(8H)-one | 444 | (300 MHz, DMSO-d$_6$) δ ppm 1.15-1.35 (m, 2H) 1.49-1.63 (m, 2H) 2.06-2.16 (m, 2H) 2.56 (s, 3H) 2.70-2.92 (m, 2H) 3.34-3.43 (m, 1H) 3.43-3.53 (m, 4H) 3.98 (s, 3H) 4.56 (t, 1H) 5.30-5.58 (m, 1H) 7.21 (br. s., 2H) 8.00 (dd, J = 12.34, 1. Hz, 1H) 8.06 (s, 1H) 8.31 (d, J = 1.88 Hz, 1H) |

TABLE 1-continued

| Compound | Synthetic Method (% Yield) | Structure | Compound Name | LRMS m/z | $^1$H NMR |
|---|---|---|---|---|---|
| 289 | I | 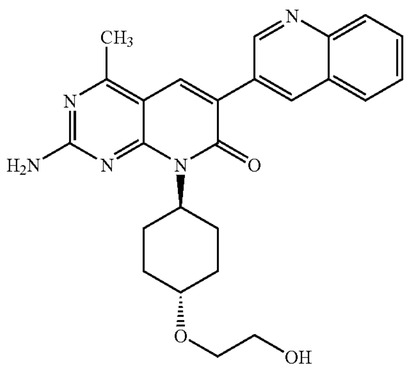 | 2-amino-8-[trans-4-(2-hydroxyethoxy)cyclohexyl]-4-methyl-6-quinolin-3-ylpyrido[2,3-d]pyrimidin-7(8H)-one | 446 | (400 MHz, DMSO-d$_6$) δ ppm 1.21-1.35 (m, 2H) 1.57-1.66 (m, 2H) 2.07-2.18 (m, 2H) 2.60 (s, 3H) 2.73-2.95 (m, 2H) 3.40-3.53 (m, 5H) 4.57 (t, J = 5.18 Hz, 1H) 5.37-5.60 (m, 1H) 7.25 (br. s., 2H) 7.63 (t, J = 6.95 Hz, 1H) 7.76 (t, J = 7.71 Hz, 1H) 8.03 (t, J = 7.07 Hz, 2H) 8.24 (s, 1H) 8.65 (d, J = 2.02 Hz, 1H) 9.17 (d, J = 2.27 Hz, 1H) |
| 290 | I | 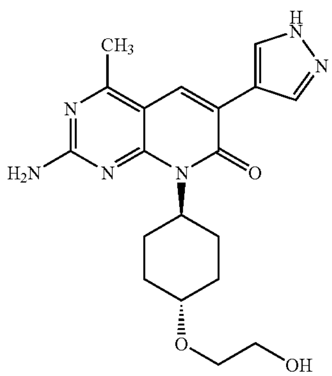 | 2-amino-8-[trans-4-(2-hydroxyethoxy)cyclohexyl]-4-methyl-6-(1H-pyrazol-4-yl)pyrido[2,3-d]pyrimidin-7(8H)-one | 385 | (400 MHz, DMSO-d6) δ ppm 1.20-1.37 (m, 2H) 1.50-1.61 (m, 2H) 2.07-2.18 (m, 2H) 2.57 (s, 3H) 2.69-2.93 (m, 2H) 3.36-3.45 (m, 1H) 3.45-3.54 (m, 4H) 4.56 (t, J = 5.31 Hz, 1H) 5.35-5.58 (m, 1H) 7.03 (br. s., 2H) 8.11 (s, 1H) 8.13 (br. s., 1H) 8.34 (br. s., 1H) 12.85 (br. s., 1H) |
| 291 | I | 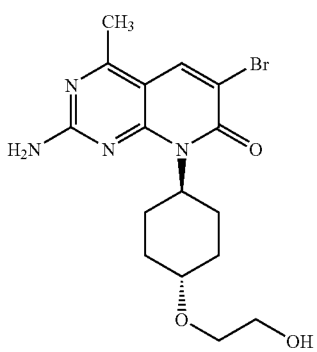 | 2-amino-6-bromo-8-[trans-4-(2-hydroxyethoxy)cyclohexyl]-4-methylpyrido[2,3-d]pyrimidin-7(8H)-one | 397, 399 | (400 MHz, DMSO-d$_6$) δ ppm 1.17-1.30 (m, 2H) 1.51-1.59 (m, 2H) 2.07-2.14 (m, 2H) 2.49 (br. s., 3H) 2.63-2.76 (m, 2H) 3.35-3.41 (m, 1H) 3.45-3.52 (m, 4H) 4.56 (t, 1H) 5.33-5.55 (m, 1H) 7.26 (br. s., 2H) 8.35 (s, 1H) |
| 292 | I | 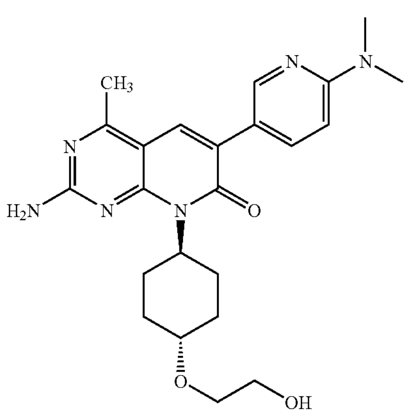 | 2-amino-6-[6-(dimethylamino)pyridin-3-yl]-8-[trans-4-(2-hydroxyethoxy)cyclohexyl]-4-methylpyrido[2,3-d]pyrimidin-7(8H)-one | 439 | (400 MHz, DMSO-d$_6$) δ ppm 1.19-1.32 (m, 2H) 1.51-1.60 (m, 2H) 2.06-2.15 (m, 2H) 2.54 (s, 3H) 2.67-2.88 (m, 2H) 3.05 (s, 6H) 3.40-3.52 (m, 5H) 4.56 (t, J = 5.43 Hz, 1H) 5.31-5.54 (m, 1H) 6.65 (d, J = 8.84 Hz, 1H) 7.07 (br. s., 2H) 7.84 (dd, J = 8.84, 2.53 Hz, 1H) 7.86 (s, 1H) 8.37 (d, J = 2.53 Hz, 1H) |

| Compound | Synthetic Method (% Yield) | Structure | Compound Name | LRMS m/z | ¹H NMR |
|---|---|---|---|---|---|
| 293 | I | 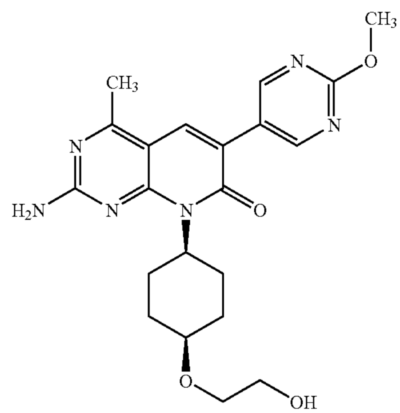 | 2-amino-8-[cis-4-(2-hydroxyethoxy)cyclohexyl]-6-(2-methoxypyrimidin-5-yl)-4-methylpyrido[2,3-d]pyrimidin-7(8H)-one | 427 | (400 MHz, DMSO-d6) δ ppm 1.21-1.34 (m, 2H) 1.38-1.50 (m, 2H) 1.90-2.05 (m, 2H) 2.56 (s, 3H) 2.88-3.12 (m, 2H) 3.42 (t, J = 5.18 Hz, 2H) 3.58 (d, J = 5.81 Hz, 3H) 3.95 (s, 3H) 4.54-4.76 (m, 1H) 5.36-5.59 (m, 1H) 7.04-7.38 (m, 2H) 8.12 (s, 1H) 8.88 (s, 2H) |
| 294 | I | 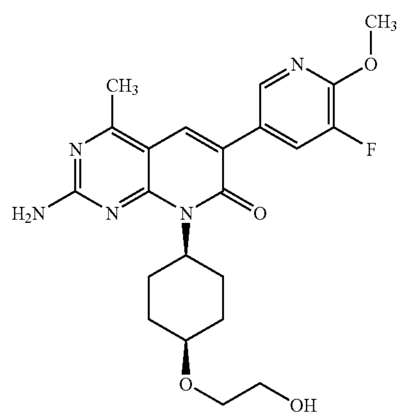 | 2-amino-6-(5-fluoro-6-methoxypyridin-3-yl)-8-[cis-4-(2-hydroxyethoxy)cyclohexyl]-4-methylpyrido[2,3-d]pyrimidin-7(8H)-one | 444 | (400 MHz, DMSO-d6) δ ppm 1.22-1.35 (m, 2H) 1.37-1.51 (m, 2H) 1.96-2.05 (m, 2H) 2.56 (s, 3H) 2.88-3.12 (m, 2H) 3.43 (t, J = 5.18 Hz, 2H) 3.51-3.63 (m, 3H) 3.98 (s, 3H) 4.54-4.78 (m, 1H) 5.35-5.57 (m, 1H) 7.04-7.27 (m, 2H) 8.01 (dd, J = 12.25, 1.89 Hz, 1H) 8.06 (s, 1H) 8.31 (d, J = 1.77 Hz, 1H) |
| 295 | I | 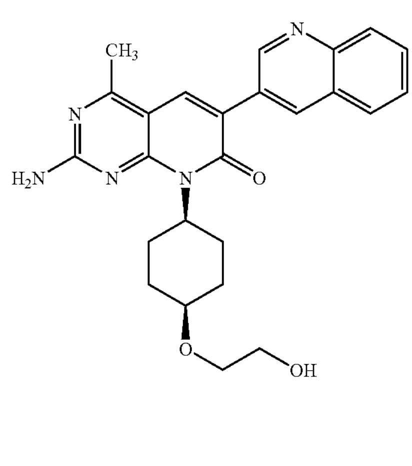 | 2-amino-8-[cis-4-(2-hydroxyethoxy)cyclohexyl]-4-methyl-6-quinolin-3-ylpyrido[2,3-d]pyrimidin-7(8H)-one | 446 | (400 MHz, DMSO-d6) δ ppm 1.22-1.38 (m, 2H) 1.39-1.52 (m, 2H) 1.96-2.08 (m, 2H) 2.59 (s, 3H) 2.91-3.14 (m, 2H) 3.43 (t, J = 5.05 Hz, 2H) 3.52-3.65 (m, 3H) 4.51-4.75 (m, 1H) 5.41-5.61 (m, 1H) 7.07-7.31 (m, 2H) 7.62 (t, J = 7.96 Hz, 1H) 7.76 (td, J = 7.64, 1.39 Hz, 1H) 8.03 (d, J = 8.34 Hz, 2H) 8.22 (s, 1H) 8.63 (d, J = 2.02 Hz, 1H) 9.16 (d, J = 2.02 Hz, 1H) |

TABLE 1-continued

| Compound | Synthetic Method (% Yield) | Structure | Compound Name | LRMS m/z | ¹H NMR |
|---|---|---|---|---|---|
| 296 | I | 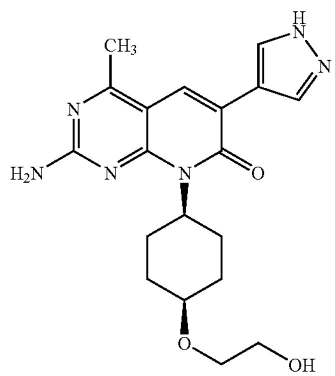 | 2-amino-8-[cis-4-(2-hydroxyethoxy)cyclohexyl]-4-methyl-6-(1H-pyrazol-4-yl)pyrido[2,3-d]pyrimidin-7(8H)-one | 385 | (400 MHz, DMSO-d6) δ ppm 1.22-1.31 (m, 2H) 1.41-1.51 (m, 2H) 1.96-2.05 (m, 2H) 2.57 (s, 3H) 2.91-3.13 (m, 2H) 3.44 (t, J = 5.18 Hz, 2H) 3.57-3.62 (m, 3H) 4.57-4.79 (m, 1H) 5.37-5.56 (m, 1H) 6.83-7.06 (m, 2H) 8.10 (s, 1H) 8.13 (s, 1H) 8.34 (s, 1H) 12.85 (br. s., 1H) |
| 297 | I | 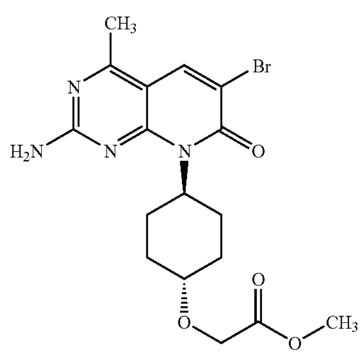 | methyl 2-(trans-amino-6-bromo-4-methyl-7-oxopyrido[2,3-d]pyrimidin-8(7H)-yl)cyclohexyloxy)acetate | 425 | (400 MHz, DMSO-d 6) ppm 1.18-1.35 (m, 2H) 1.55 (d, J = 11.37 Hz, 2H) 2.13 (d, J = 10.36 Hz, 2H) 3.67 (s, 3H) 4.18 (s, 2H) 5.47 (br. s., 1H) 7.27 (br. s., 2H) 8.35 (s, 1H) |
| 298 | I | 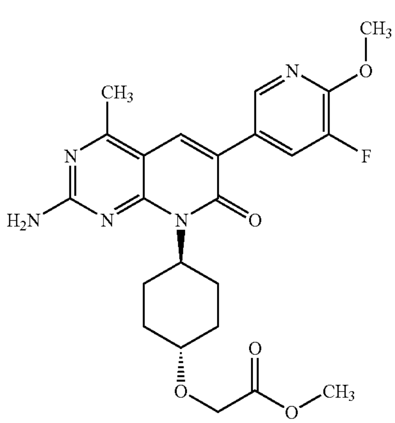 | methyl ({trans-4-[2-amino-6-(5-fluoro-6-methoxypyridin-3-yl)-4-methyl-7-oxopyrido[2,3-d]pyrimidin-8(7H)-yl[cyclohexyl}oxy)acetate | 472.2 | (400 MHz, DMSO-d 6) ppm 1.21-1.40 (m, 2H) 1.58 (d, J = 10.36 Hz, 2H) 2.14 (d, J = 9.85 Hz, 2H) 2.57 (s, 3H) 2.69-2.87 (m, 2H) 3.46 (dd, J = 13.26, 8.97 Hz, 1H) 3.67 (s, 3H) 3.99 (s, 3H) 4.18 (s, 2H) 5.47 (br. s., 1H) 7.22 (br. s., 2H) 8.01 (dd, J = 12.25, 1.89 Hz, 1H) 8.07 (s, 1H) 8.32 (d, J = 2.02 Hz, 1H) |

TABLE 1-continued

| Compound | Synthetic Method (% Yield) | Structure | Compound Name | LRMS m/z | ¹H NMR |
|---|---|---|---|---|---|
| 299 | I | 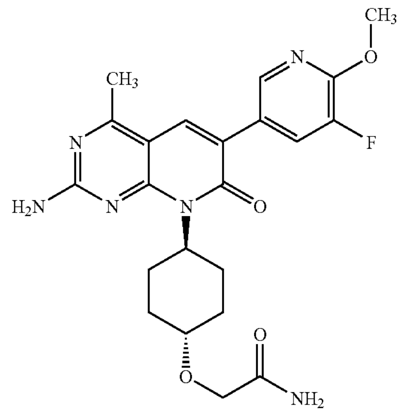 | 2-({trans-4-[2-amino-6-(5-fluoro-6-methoxypyridin-3-yl)-4-methyl-7-oxopyrido[2,3-d]pyrimidin-8(7H)-yl]cyclohexyl}oxy)acetamide | 457.2 | (400 MHz, DMSO-d 6) ppm 1.27-1.46 (m, 2H) 1.64 (d, J = 10.61 Hz, 2H) 2.22 (d, J = 10.61 Hz, 2H) 2.63 (s, 3H) 2.85 (br. s., 2H) 3.44-3.64 (m, 1H) 3.91 (s, 2H) 4.05 (s, 3H) 5.52 (br. s., 1H) 7.15 (br. s., 1H) 7.28 (br. s., 2H) 7.38 (br. s., 1H) 8.07 (dd, J = 12.25, 1.89 Hz, 1H) 8.13 (s, 1H) 8.38 (d, J = 2.02 Hz, 1H) |
| 300 | I | 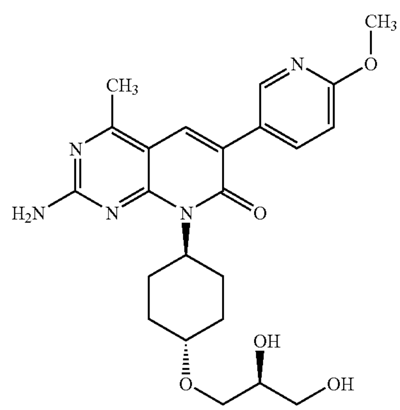 | 2-amino-8-(trans-4-{[(2S)-2,3-dihydroxypropyl]oxy}cyclohexyl)-6-(6-methoxypyridin-3-yl)-4-methylpyrido[2,3-d]pyrimidin-7(8H)-one | 456 | (400 MHz, CHLOROFORM-d) δ ppm 1.45 (m, 2H) 1.71 (m, 2H) 2.15-2.26 (m, 3H) 2.60 (s, 3H) 2.68 (d, J = 5.05 Hz, 1H) 2.82 (bs, 2H) 3.44 (m, 1H) 3.57-3.75 (m, 4H) 3.87 (m, 1H) 3.98 (s, 3H) 5.22 (s, 2H) 5.51 (bs, 1H) 6.80 (d, J = 8.84 Hz, 1H) 7.71-7.78 (m, 1H) 7.96 (dd, J = 8.72, 2.40 Hz, 1H) 8.30 (d, J = 2.02 Hz, 1H) |
| 301 | I | 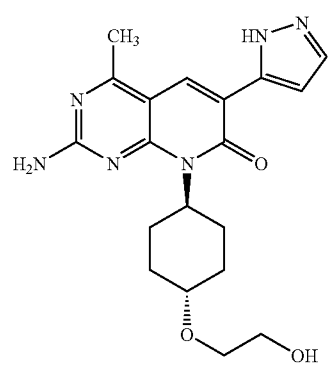 | 2-amino-8-[trans-4-(2-hydroxyethoxy)cyclohexyl]-4-methyl-6-(1H-pyrazol-3-yl)pyrido[2,3-d]pyrimidin-7(8H)-one | 385 | (400 MHz, DMSO-d6) d ppm 1.20-1.35 (m, 2H) 1.54-1.61 (m, 2H) 2.09-2.16 (m, 2H) 2.57 (s, 3H) 2.71-2.93 (m, 2H) 3.46-3.53 (m, 5H) 4.57 (t, 1H) 5.33-5.56 (m, 1H) 6.94 (s, 1H) 7.19 (s, 2H) 7.49-7.66 (m, 1H) 8.35 (s, 1H) 12.95-13.12 (m, 1H) |

| Compound | Synthetic Method (% Yield) | Structure | Compound Name | LRMS m/z | 1H NMR |
|---|---|---|---|---|---|
| 302 | I | 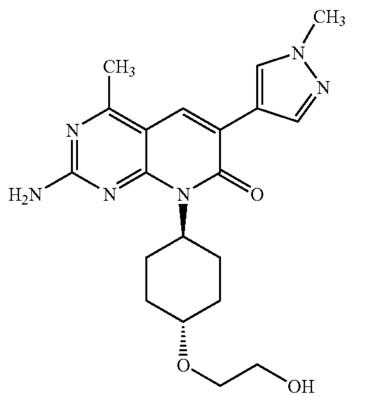 | 2-amino-8-[trans-4-(2-hydroxyethoxy)cyclohexyl]-4-methyl-6-(1-methyl-1H-pyrazol-4-yl)pyrido[2,3-d]pyrimidin-7(8H)-one | 399 | (400 MHz, DMSO-$d_6$) δ ppm 1.18-1.34 (m, 2H) 1.47-1.59 (m, 2H) 2.06-2.16 (m, 2H) 2.56 (s, 3H) 2.69-2.92 (m, 2H) 3.44-3.53 (m, 5H) 3.86 (s, 3H) 4.58 (t, J = 5.18 Hz, 1H) 5.34-5.57 (m, 1H) 7.05 (br. s., 2H) 8.07 (s, 1H) 8.09 (s, 1H) 8.33 (s, 1H) |
| 303 | I | 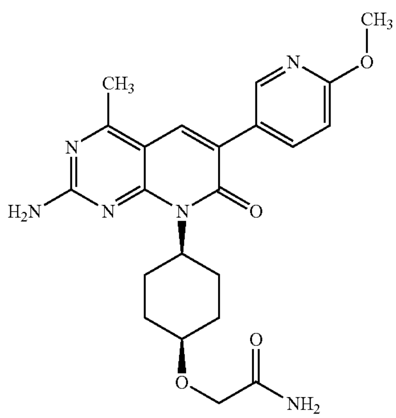 | 2-({cis-4-[2-amino-6-(6-methoxypyridin-3-yl)-4-methyl-7-oxopyrido[2,3-d]pyrimidin-8(7H)-yl]cyclohexyl}oxy)acetamide | 439 | (400 MHz, DMSO-d6) δ ppm 1.29-1.37 (m, 2H) 1.38-1.51 (m, 2H) 1.99-2.11 (m, 2H) 2.55 (s, 3H) 2.83-3.08 (m, 2H) 3.58-3.67 (m, 1H) 3.82 (s, 2H) 3.88 (s, 3H) 5.41-5.66 (m, 1H) 6.84 (d, J = 8.84 Hz, 1H) 7.06-7.24 (m, 3H) 7.38 (br. s., 1H) 7.98 (s, 1H) 8.00 (dd, J = 8.59, 2.53 Hz, 1H) 8.42 (d, J = 2.53 Hz, 1H) |
| 304 | I | 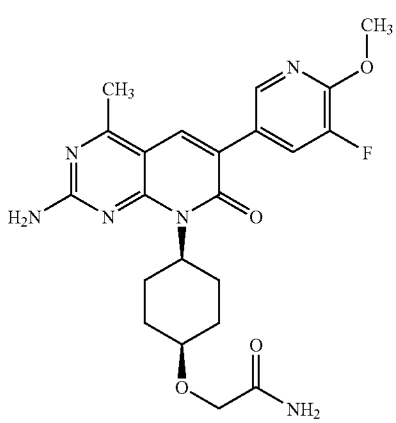 | 2-({cis-4-[2-amino-6-(5-fluoro-6-methoxypyridin-3-yl)-4-methyl-7-oxopyrido[2,3-d]pyrimidin-8(7H)-yl]cyclohexyl}oxy)acetamide | 457 | (400 MHz, DMSO-d6) δ ppm 1.24-1.39 (m, 2H) 1.39-1.53 (m, 2H) 1.95-2.15 (m, 2H) 2.57 (s, 3H) 2.81-3.12 (m, 2H) 3.56-3.69 (m, 1H) 3.82 (s, 2H) 3.98 (s, 3H) 5.36-5.67 (m, 1H) 7.02-7.29 (m, 3H) 7.38 (br. s., 1H) 8.00 (dd, J = 12.13, 1.77 Hz, 1H) 8.06 (s, 1H) 8.30 (d, J = 2.02 Hz, 1H) |

TABLE 1-continued

| Compound | Synthetic Method (% Yield) | Structure | Compound Name | LRMS m/z | ¹H NMR |
|---|---|---|---|---|---|
| 305 | I | 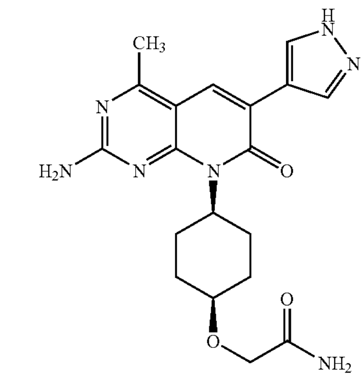 | 2-({cis-4-[2-amino-4-methyl-7-oxo-6-(1H-pyrazol-4-yl)pyrido[2,3-d]pyrimidin-8(7H)-yl]cyclohexyl}oxy)acetamide | 398 | (400 MHz, DMSO-d6) δ ppm 1.26-1.37 (m, 2H) 1.39-1.52 (m, 2H) 2.00-2.11 (m, 2H) 2.58 (s, 3H) 2.89-3.09 (m, 2H) 3.62-3.69 (m, 1H) 3.85 (s, 2H) 5.46-5.68 (m, 1H) 7.01 (br. s., 2H) 7.31 (br. s., 1H) 7.49 (br. s., 1H) 8.12 (s, 1H) 8.16 (br. s., 1H) 8.34 (br. s., 1H) 12.85 (br. s., 1H) |
| 306 | I | 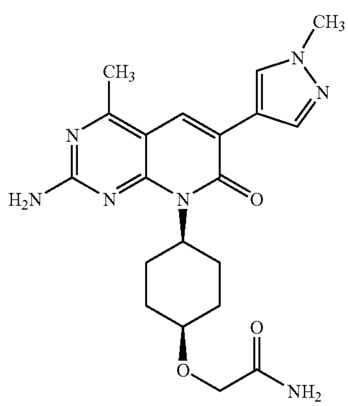 | 2-({cis-4-[2-amino-4-methyl-6-(1-methyl-1H-pyrazol-4-yl)-7-oxopyrido[2,3-d]pyrimidin-8(7H)-yl]cyclohexyl}oxy)acetamide | 412 | (400 MHz, DMSO-d6) δ ppm 1.27-1.35 (m, 2H) 1.40-1.50 (m, 2H) 1.99-2.10 (m, 2H) 2.57 (s, 3H) 2.86-3.07 (m, 2H) 3.63-3.70 (m, 1H) 3.85 (s, 2H) 3.87 (s, 3H) 5.45-5.73 (m, 1H) 7.03 (br. s., 2H) 7.37 (s, 1H) 7.55 (s, 1H) 8.10 (d, J = 12.13 Hz, 2H) 8.31 (s, 1H) |
| 307 | I | 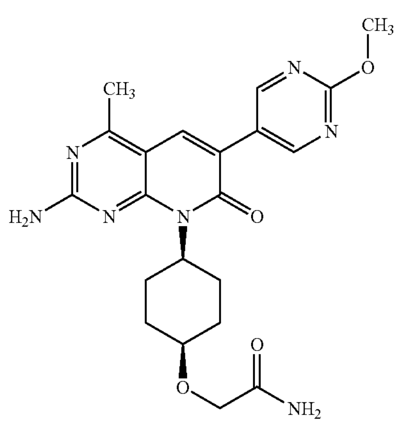 | 2-({cis-4-[2-amino-6-(2-methoxypyrimidin-5-yl)-4-methyl-7-oxopyrido[2,3-d]pyrimidin-8(7H)-yl]cyclohexyl}oxy)acetamide | 440 | (400 MHz, DMSO-d6) δ ppm 1.28-1.38 (m, 2H) 1.38-1.51 (m, 2H) 1.98-2.12 (m, 2H) 2.56 (s, 3H) 2.84-3.06 (m, 2H) 3.57-3.67 (m, 1H) 3.82 (s, 2H) 3.96 (s, 3H) 5.41-5.63 (m, 1H) 7.00-7.29 (m, 3H) 7.39 (br. s., 1H) 8.13 (s, 1H) 8.88 (s, 2H) |

| Compound | Synthetic Method (% Yield) | Structure | Compound Name | LRMS m/z | ¹H NMR |
|---|---|---|---|---|---|
| 308 | I | 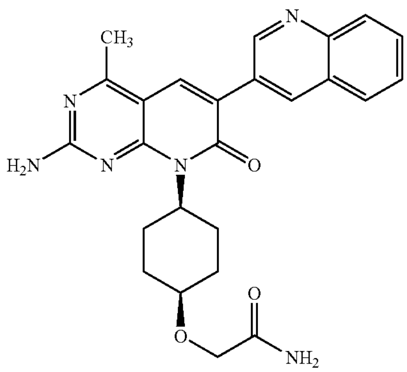 | 2-{[cis-4-(2-amino-4-methyl-7-oxo-6-quinolin-3-ylpyrido[2,3-d]pyrimidin-8(7H)-yl)cyclohexyl]oxy}acetamide | 459 | (400 MHz, DMSO-d6) δ ppm 1.33-1.41 (m, 2H) 1.41-1.53 (m, 2H) 2.07 (dd, J = 12.51, 0.88 Hz, 2H) 2.60 (s, 3H) 2.90-3.11 (m, 2H) 3.61-3.69 (m, 1H) 3.83 (s, 2H) 5.48-5.69 (m, 1H) 7.10-7.32 (m, 3H) 7.39 (br. s., 1H) 7.63 (t, J = 7.33 Hz, 1H) 7.76 (ddd, J = 8.40, 7.01, 1.26 Hz, 1H) 8.04 (t, J = 6.95 Hz, 2H) 8.23 (s, 1H) 8.64 (d, J = 2.02 Hz, 1H) 9.16 (d, J = 2.02 Hz, 1H) |
| 309 | I | 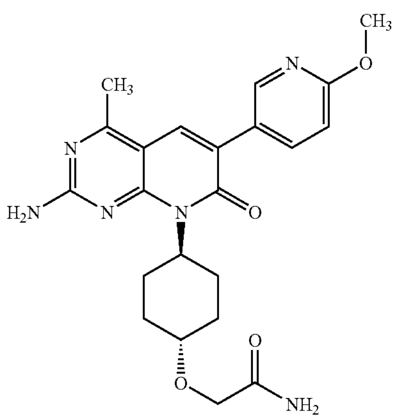 | 2-({trans-4-[2-amino-6-(6-methoxypyridin-3-yl)-4-methyl-7-oxopyrido[2,3-d]pyrimidin-8(7H)-yl]cyclohexyl}oxy)acetamide | 439 | (400MHz, DMSO-d6) d ppm 1.25-1.39 (m, 2H) 1.50-1.62 (m, 2H) 2.10-2.20 (m, 2H) 2.39-2.45 (m, 2H) 2.55 (s, 3H) 3.38-3.50 (m, 1H) 3.84 (s, 2H) 3.88 (s, 3H) 5.30-5.53 (m, 1H) 6.84 (d, J = 8.59 Hz, 1H) 7.08 (br. s., 1H) 7.16 (br. s., 2H) 7.26 (br. s., 1H) 7.98(s, 1H) 7.98-8.02 (m, 1H) 8.41-8.45 (m, 1H) |
| 310 | I | 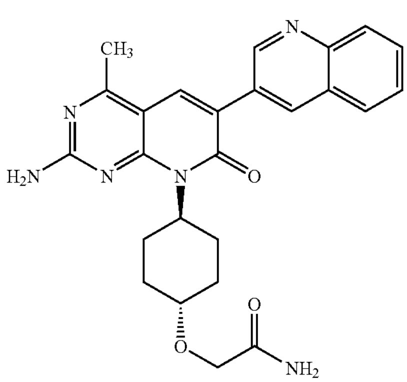 | 2-{[trans-4-(2-amino-4-methyl-7-oxo-6-quinolin-3-ylpyrido[2,3-d]pyrimidin-8(7H)-yl)cyclohexyl]oxy}acetamide | 459 | (400 MHz, DMSO-d₆) δ ppm 1.27-1.41 (m, 2H) 1.58-1.68 (m, 2H) 2.10-2.23 (m, 2H) 2.29-2.38 (m, 2H) 2.61 (s, 3H) 3.58-3.69 (m, 1H) 3.86 (s, 2H) 5.37-5.60 (m, 1H) 7.10 (br. s., 1H) 7.26 (br. s., 3H) 7.64 (t, J = 7.45 Hz, 1H) 7.77 (t, J = 8.08 Hz, 1H) 8.04 (t, J = 7.45 Hz, 2H) 8.24 (s, 1H) 8.65 (s, 1H) 9.17 (s, 1H) |

TABLE 1-continued

| Compound | Synthetic Method (% Yield) | Structure | Compound Name | LRMS m/z | ¹H NMR |
|---|---|---|---|---|---|
| 311 | I | 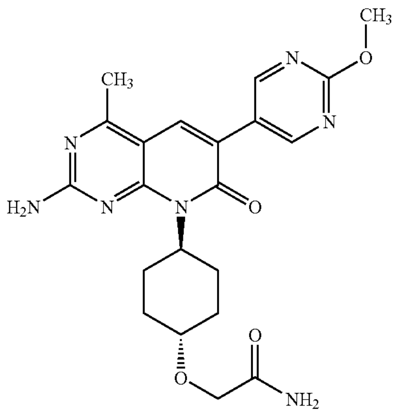 | 2-({trans-4-[2-amino-6-(2-methoxypyrimidin-5-yl)-4-methyl-7-oxopyrido[2,3-d]pyrimidin-8(7H)-yl]cyclohexyl}oxy)acetamide | 440.2 | (400 MHz, DMSO-$d_6$) δ ppm 1.34-1.46 (m, 2H) 1.61-1.72 (m, 2H) 2.16-2.28 (m, 2H) 2.64 (s, 3H) 2.80-3.02 (m, 2H) 3.45-3.60 (m, 1H) 3.93 (s, 2H) 4.04 (s, 3H) 5.39-5.61 (m, 1H) 7.17 (br. s., 1H) 7.28-7.39 (m, 3H) 8.21 (s, 1H) 8.97 (s, 2H) |
| 312 | I | 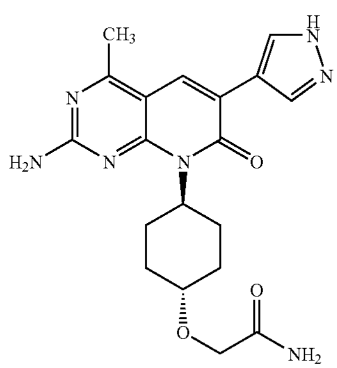 | 2-({trans-4-[2-amino-4-methyl-7-oxo-6-(1H-pyrazol-4-yl)pyrido[2,3-d]pyrimidin-8(7H)-yl]cyclohexyl}oxy)acetamide | 398.2 | (400 MHz, DMSO-$d_6$) δ ppm 1.27-1.40 (m, 2H) 1.50-1.61 (m, 2H) 2.08-2.20 (m, 2H) 2.57 (s, 3H) 2.72-2.88 (m, 2H) 3.39-3.54 (m, 1H) 3.86 (s, 2H) 5.48 (br. s., 2H) 7.05 (br. s., 2H) 7.41 (br. s., 2H) 8.12 (s, 2H) 8.34 (br. s., 1H) |
| 313 | I | 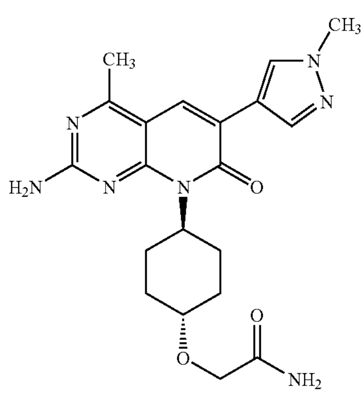 | 2-({trans-4-[2-amino-4-methyl-6-(1-methyl-1H-pyrazol-4-yl)-7-oxopyrido[2,3-d]pyrimidin-8(7H)-yl]cyclohexyl}oxy)acetamide | 412.2 | (400 MHz, DMSO-$d_6$) δ ppm 1.26-1.39 (m, 2H) 1.47-1.61 (m, 2H) 2.09-2.19 (m, 2H) 2.56 (s, 3H) 2.71-2.91 (m, 2H) 3.37-3.55 (m, 1H) 3.85 (s, 5H) 5.17-5.88 (m, 1H) 7.01-7.14 (m, 3H) 7.27 (br. s., 1H) 8.08 (d, J = 8.84 Hz, 2H) 8.33 (s, 1H) |

TABLE 1-continued

| Compound | Synthetic Method (% Yield) | Structure | Compound Name | LRMS m/z | ¹H NMR |
|---|---|---|---|---|---|
| 314 | I | 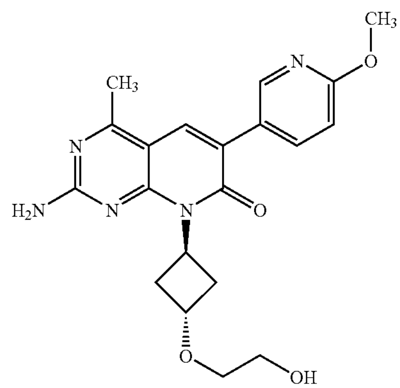 | 2-amino-8-[trans-3-(2-hydroxyethoxy)cyclobutyl]-6-(6-methoxypyridin-3-yl)-4-methylpyrido[2,3-d]pyrimidin-7(8H)-one | 398.2 | (300 MHz, DMSO-d6) δppm 2.18-2.33 (m, J = 10.46, 10.46 Hz, 2H) 2.56 (s, 3H) 3.12-3.25 (m, 2H) 3.36 (q, J = 5.34 Hz, 2H) 3.54 (q, J = 5.34 Hz, 2H) 3.89 (s, 3H) 4.35-4.45 (m, 1H) 4.63 (t, J = 5.37 Hz, 1H) 6.15-6.31 (m, J = 8.67, 8.67 Hz, 1H) 6.86 (d, J = 8.67 Hz, 1H), 7.22 (s, 2H), 7.96-8.07 (m, 2H), 8.44 (d, J = 2.45 Hz, 1H) |
| 315 | I | 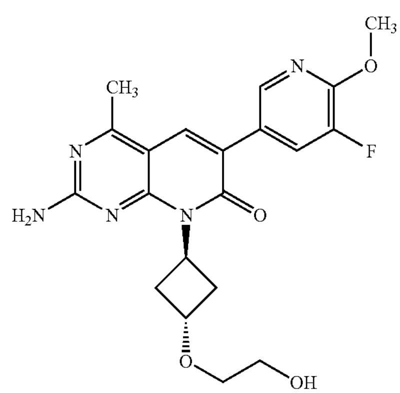 | 2-amino-6-(5-fluoro-6-methoxypyridin-3-yl)-8-[trans-3-(2-hydroxyethoxy)cyclobutyl]-4-methylpyrido[2,3-d]pyrimidin-7(8H)-one | 416.2 | (300 MHz, DMSO-d6) δppm 2.27 (t, J = 10.46 Hz, 2H) 2.56 (s, 3H) 3.10-3.26 (m, 2H) 3.36 (q, J = 5.18 Hz, 2H) 3.54 (q, J = 5.40 Hz, 2H) 3.98 (s, 3H) 4.33-4.44 (m, 1H) 4.63 (t, J = 5.46 Hz, 1H) 6.13-6.31 (m, 1H, J = 8.85 Hz, 1H) 7.27 (s, 2H) 8.02 (dd, J = 12.15, 1.98 Hz, 1H) 8.08 (s, 1H) 8.31 (d, J = 1.88 Hz, 1H) |
| 316 | I | 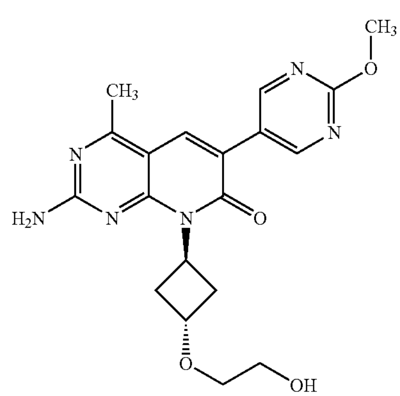 | 2-amino-8-[trans-3-(2-hydroxyethoxy)cyclobutyl]-6-(2-methoxypyrimidin-5-yl)-4-methylpyrido[2,3-d]pyrimidin-7(8H)-one | 399.2 | (300 MHz, DMSO-d6) δppm 2.18-2.32 (m, 2H) 2.55 (s, 3H) 3.12-3.24 (m, 2H) 3.33-3.36 (m, 2H) 3.47-3.58 (m, 2H) 3.95 (s, 3H) 4.33-4.47 (m, 1H) 4.58-4.70 (m, 1H) 6.15-6.31 (m, 1H) 7.28 (s, 2H), 8.14 (s, 1H), 8.89 (s, 2H) |

TABLE 1-continued

| Compound | Synthetic Method (% Yield) | Structure | Compound Name | LRMS m/z | $^1$H NMR |
|---|---|---|---|---|---|
| 317 | I | 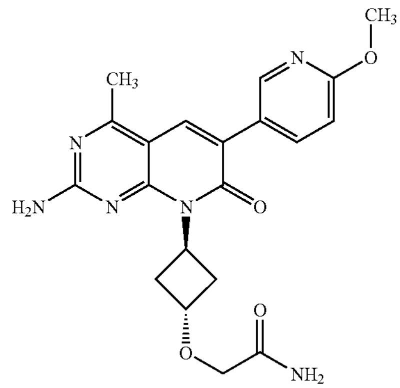 | 2-({trans-3-[2-amino-6-(6-methoxypyridin-3-yl)-4-methyl-7-oxopyrido[2,3-d]pyrimidin-8(7H)-yl]cyclobutyl}oxy)acetamide | 411.2 | (300 MHz, DMSO-d6) δppm 2.28-2.39 (m, 2H) 2.55 (s, 3H) 3.08-3.25 (m, 2H) 3.75 (s, 2H) 3.89 (s, 3H) 4.41-4.57 (m, 1H) 6.17-6.31 (m, 1H) 6.86 (d, J = 8.67 Hz, 1H) 7.13 7.37 (m, 4H), 7.95-8.08 (m, 2H), 8.44 (d, J = 2.45 Hz, 1H) |
| 318 | I | 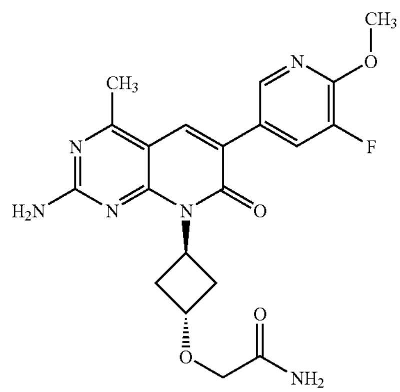 | 2-({trans-3-[2-amino-6-(5-fluoro-6-methoxypyridin-3-yl)-4-methyl-7-oxopyrido[2,3-d]pyrimidin-8(7H)-yl]cyclobutyl}oxy)acetamide | 429.2 | (300 MHz, DMSO-d6) δppm 2.32-2.39 (m, 2H) 2.56 (s, 3H) 3.10-3.24 (m, 2H) 3.75 (s, 2H) 3.98 (s, 3H) 4.39-4.56 (m, 1H) 6.18-6.30 (m, 1H) 7.08-7.35 (m, 4H), 8.02 (dd, J = 12.24, 1.88 Hz, 1H) 8.08 (s, 1H), 8.31 (d, J = 1.88 Hz, 1H) |
| 319 | I | 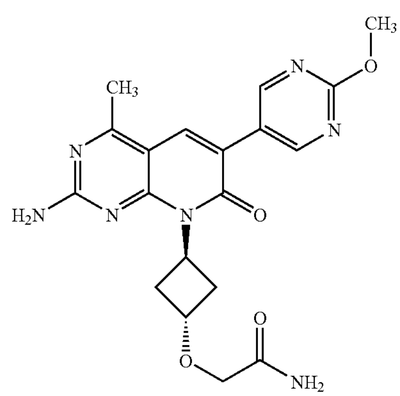 | 2-({trans-3-[2-amino-6-(2-methoxypyrimidin-5-yl)-4-methyl-7-oxopyrido[2,3-d]pyrimidin-8(7H)-yl]cyclobutyl}oxy)acetamide | 412.2 | (300 MHz, DMSO-d6) δppm 2.24-2.41 (m, 2H) 2.57 (s, 3H) 3.09-3.25 (m, 2H) 3.76 (s, 2H) 3.96 (s, 3H) 4.42-4.54 (m, 1H) 6.13-6.35 (m, 1H) 7.19-7.38 (m, 4H), 8.16 (s, 1H), 8.90 (s, 2H) |

Example 101

PI3-Kα Biochemical Assay

Compounds of the present invention were evaluated for potency against PI3-Kα using an in vitro kinase assay. PI3-Kα activity is measured in vitro by determining the level of phosphorylation of the substrate PI(4,5)P$_2$. The formation of product PI(3,4,5)P$_3$ is monitored by binding to the Grip1 PH domain in a ligand displacement fluorescence polarization (FP) assay, in which the TAMRA-labeled PI(3,4,5)P$_3$ complexed with Grip1 PH domain is displaced by PI(3,4,5)P$_3$ formed in the PI3-Kα reaction resulting in a decrease in FP signal. Mouse PI3-Kα P110 and P85 subunits were co-expressed in insect cells and co-purified to homogeneity. PI(4,5)P$_2$ were obtained from Cayman. TAMRA-labeled PI(3,4,5)P$_3$ were from Echelon, Grip1 PH domain from Dundee and other reagents were from Sigma.

All assays were performed in a Corning solid black 96-well half area plate using LJL Analyst (Molecular Devices) at room temperature. The assay buffer contained 50 mM HEPES, pH 7.4, 150 mM NaCl, 5 mM DTT, and 0.05% CHAPS. Dry powder PI(4,5)P$_2$ was dissolved in 50 mM TRIS, pH 8 to make 1 mM stock solution. The PI(4,5)P$_2$ stock solution was then diluted in the assay buffer to 60 μM, and sonicated for 30 sec before use. To the assay plate, the following reagents were added in sequence: 10 μL of 60 μM PI(4,5)P$_2$, 5 μL of 4 nM PI3-Kα, 2 μL of compound in 25% DMSO, 3 μL of mixture containing 200 μM ATP and 33 mM MgCl$_2$. The final volume for the reaction was 20 μL. The reaction mixture was incubated at room temperature for 35 min. The reaction was then stopped by 20 μL of 20 mM EDTA. After the reaction was stopped, 15 μL of the assay mixture was transferred to a 96-well half area plate containing 15 μL detection mixture of 480 nM Grip1 PH domain and 12 nM TAMRA-labeled PI(3,4,5)P$_3$. The FP signal was allowed to develop for 40 min before reading on a LJL analyst at excitation 535 nm and emission 580 nm.

The percentage of inhibition was calculated based on the following equation

% inhibition=[1−(FP$_{compound}$−FP$_{max}$)/(FP$_{min}$−FP$_{max}$)]×100, where FP$_{compound}$ is the FP reading at a given compound concentration, FP$_{min}$ is the FP signal of the PI3-Kα reaction in the absence of a compound, and FP$_{max}$ is the background FP signal in the absence of PI3-Kα and a compound. The IC$_{50}$ was determined by fitting the FP signal vs. compound concentration to a sigmoidal dose response equation using GraphPad Prism curve fitting program.

Example 102

PI3-Kα Cellular Assay

Compounds of the present invention were evaluated for potency against PI3-K using a cellular assay as follows. The activity of PI3-K in cells is determined by measuring the level of phosphorylation of AKT at serine 473. AKT Ser phosphorylation is measured using anti-phospho-AKT (Ser473) antibodies (Cell Signaling #4058) in an ELISA format.

Healthy growing human breast cancer cells BT20 (PI3K mutated) are used for the assay. BT20 cells are grown in 10% FBS+GLN (1:100)+PS (1:100)+1 mM Sodium Pyruvate+0.1 mM Sodium Bicarbonate+Non-Essential Amino Acids Solution (1:100) MEM medium (MEM+all). When the cells are near 85%+confluence, the cells are rinsed with PBS once and are trypsinized with trypsin EDTA for 3 minutes. The cells are re-suspended in 10% FBS MEM all and are centrifuged down at 1400 rpm for 5 minutes. The cells are re-suspended in 0.5% FBS MEM all and are counted on a cell counter. The cells are seeded at 25,000 cells/well in volume of 100 μL/well in 0.5% FBS MEM all in a 96 well flat-bottom plate. The negative control wells receive only 100 μL of 0.5% FBS MEM all medium without cells. The plate is incubated overnight in a cell culture incubator with 5% CO$_2$ at 37° C.

On day 2, testing compounds are prepared in 0.5% FBS MEM all medium and serially diluted at 1:3 for 11 test concentrations. Each concentration of the compounds is tested in duplicate. The compound solutions are added at 25 μL/well to the corresponded wells in cell plate, and 25 μL/well of the vehicle (0.5% DMSO in 0.5% FBS MEM all) is added to the negative control wells (no cells) and the positive control wells (cells without compounds). The plate is incubated for 1 hour in a cell culture incubator with 5% CO$_2$ at 37° C. After 1 hour of incubation, the medium is removed, 100 μL/well of cell lysis buffer is added into the cell plate, and shake for 15 minutes at room temperature. After 15 minutes, the cell lysates are transferred to ELISA plate [pre-coated with anti-phospho-AKT (Ser473) rabbit monoclonal antibody, Cell signaling, catalog #4058], and the plate is incubated with gentle shaking for 2 hours at room temperature. After 2 hours, empty the contents of the wells, wash plate 4 times with the wash buffer, and add 100 μL of anti-AKT1 mouse monoclonal detection antibody (Cell signaling, catalog #2967) into each well, incubate with gentle shaking for 1 hour at room temperature. After 1 hour, empty the contents of the wells and wash the plate 4 times with the wash buffer, and add 100 μL of anti-mouse IgG HRP-linked antibody (Cell Signaling, catalog #7076) into each well, and incubate the plate with gentle shaking for 1 hour at room temperature. After 1 hour, empty the contents of the wells, wash the plate 4 times with the wash buffer, and add 100 μL of TMB substrate solution (catalog #T0440, Sigma) into each well, and incubate with gentle shaking at room temperature for 20 minutes. After 15 minutes of color development, add 100 μL of stop solution (1N hydrochloric acid) to each well, and read the plate at 450 nm on ELISA plate reader.

TABLE 2

PI3-Kα Biochemical and Cellular Activity Data

| COMPOUND NUMBER | PI3-Kα Cellular Assay IC$_{50}$ μM | PI3-Kα Biochemical Assay IC$_{50}$ μM | PI3-Kα Biochemical Assay % Inhibition |
|---|---|---|---|
| 101 | 0.00349 | 0.011 | |
| 102 | 0.0179 | 0.015 | |
| 103 | 2.33 | 0.4 | |
| 104 | 10 | | 43 at 10 μM |
| 105 | 0.234 | 0.024 | |
| 106 | 0.495 | 0.045 | |
| 107 | 0.305 | 0.023 | |
| 108 | 0.00382 | 0.00157 | 99 at 10 μM |
| 109 | 0.0584 | 0.0063 | 99 at 10 μM |
| 110 | 0.106 | 0.017 | |
| 111 | 0.0161 | 0.00296 | |
| 112 | 0.0742 | 0.0391 | |
| 113 | 0.0952 | 0.021 | |
| 114 | 1.18 | 0.11 | |
| 115 | 0.00382 | 0.00075 | |
| 116 | 5.75 | 0.83 | |
| 117 | 10 | | 32 at 10 μM |
| 118 | 8.37 | 1.1 | |
| 119 | 5.71 | 0.31 | |
| 120 | 0.896 | 0.042 | |
| 121 | 10 | | 27 at 50 μM |
| 122 | 10 | | |
| 123 | 0.65 | 0.068 | |
| 124 | 0.00258 | 0.008 | |
| 125 | 9.01 | 1.43 | |
| 126 | 5.48 | 0.856 | |
| 127 | 0.00276 | 0.00048 | |
| 128 | 3.53 | 0.275 | |
| 129 | 2.75 | 0.004 | |
| 130 | 10 | 0.054 | |
| 131 | 7.98 | 3.4 | |
| 132 | 10 | 5.5 | |
| 133 | 0.603 | 0.06 | |
| 134 | 8.3 | 2.1 | |
| 135 | 0.0461 | 0.00177 | |
| 136 | 0.0263 | 0.00308 | |
| 137 | 0.019 | 0.000989 | |
| 138 | 0.146 | 0.0297 | |
| 139 | 0.017 | 0.00503 | |
| 140 | 0.000793 | 0.00103 | |
| 141 | 10 | 7.08 | |
| 142 | 1.39 | 0.792 | |
| 143 | 0.669 | 0.244 | |
| 144 | 0.00305 | 0.00101 | |
| 145 | 0.622 | 0.168 | |
| 146 | 0.00176 | 0.000731 | |
| 147 | 0.00484 | 0.000524 | |
| 148 | 0.0147 | 0.00478 | |
| 149 | >10 | 0.31 | |
| 150 | >10 | 1.4 | |
| 151 | >10 | 4.9 | |
| 152 | 0.0036 | 0.024 | |
| 153 | 2.76 | 0.46 | |

TABLE 2-continued

PI3-Kα Biochemical and Cellular Activity Data

| COMPOUND NUMBER | PI3-Kα Cellular Assay IC$_{50}$ μM | PI3-Kα Biochemical Assay IC$_{50}$ μM | PI3-Kα Biochemical Assay % Inhibition |
|---|---|---|---|
| 154 | 0.475 | 0.018 | |
| 155 | 0.0829 | 0.011 | |
| 156 | 0.169 | 0.0067 | |
| 157 | 0.305 | 0.044 | |
| 158 | 0.0319 | 0.0013 | |
| 159 | 0.0876 | 0.0046 | |
| 160 | 1.04 | 0.15 | |
| 161 | 0.934 | 0.055 | |
| 162 | 0.0472 | 0.014 | |
| 163 | 0.0204 | 0.0012 | |
| 164 | 1.3 | 0.036 | |
| 165 | 0.0558 | 0.0012 | |
| 166 | 0.262 | 0.0095 | |
| 167 | 2.36 | 0.68 | |
| 168 | 0.228 | 0.13 | |
| 169 | 0.34 | 0.088 | |
| 170 | 10 | 3.4 | |
| 171 | 0.0254 | 0.0016 | |
| 172 | 0.116 | 0.015 | |
| 173 | 0.322 | 0.27 | |
| 174 | 0.019 | 0.0076 | |
| 175 | 0.0193 | 0.0043 | |
| 176 | 0.00466 | 0.012 | |
| 177 | 0.00802 | 0.0024 | |
| 178 | 0.064 | 0.031 | |
| 179 | 0.00737 | 0.0039 | |
| 180 | 0.00339 | 0.0016 | |
| 181 | 0.0176 | 0.012 | |
| 182 | 0.0101 | 0.0062 | |
| 183 | 0.00469 | 0.009 | |
| 184 | 0.211 | 0.11 | |
| 185 | 0.0152 | 0.018 | |
| 186 | 0.0252 | 0.01 | |
| 187 | 0.0172 | 0.0095 | |
| 188 | 0.0718 | 0.0094 | |
| 189 | 0.0212 | 0.0027 | |
| 190 | 2.69 | 0.47 | |
| 191 | 0.0031 | 0.0011 | |
| 192 | 0.00508 | 0.093 | |
| 193 | 0.00701 | 0.028 | |
| 194 | 0.00597 | 0.0059 | |
| 195 | 0.0757 | 0.023 | |
| 196 | 0.0366 | 0.0045 | |
| 197 | 0.236 | 0.188 | |
| 198 | 0.262 | 0.13 | |
| 199 | 0.0199 | 0.0185 | |
| 200 | 0.0714 | 0.0066 | |
| 201 | 0.0153 | 0.0037 | |
| 202 | 1.67 | 0.23 | |
| 203 | 0.0258 | 0.02 | |
| 204 | 0.143 | 0.0075 | |
| 205 | 0.0167 | 0.015 | |
| 206 | 0.0265 | 0.0082 | |
| 207 | 0.0119 | 0.002 | |
| 208 | 0.00964 | 0.0294 | |
| 209 | 0.064 | 0.011 | |
| 210 | 0.00677 | 0.0023 | |
| 211 | 0.399 | 0.078 | |
| 212 | 0.176 | 0.056 | |
| 213 | 0.138 | 0.017 | |
| 214 | 0.594 | 0.048 | |
| 215 | 0.0221 | 0.006 | |
| 216 | 0.0456 | 0.0046 | |
| 217 | 0.0135 | 0.0016 | |
| 218 | 1.02 | 0.094 | |
| 219 | 0.0949 | 0.014 | |
| 220 | 0.145 | 0.0077 | |
| 221 | 0.0578 | 0.0028 | |
| 222 | 2.13 | 0.1 | |
| 223 | 0.249 | 0.022 | |
| 224 | 0.12 | 0.021 | |
| 225 | 0.0366 | 0.0054 | |
| 226 | 0.0415 | 0.12 | |
| 227 | 0.318 | 0.029 | |
| 228 | 0.256 | 0.038 | |
| 229 | 0.0179 | 0.015 | |
| 230 | 0.0339 | 0.02 | |
| 231 | 3.45 | 0.17 | |
| 232 | 0.0414 | 0.0089 | |
| 233 | 0.0942 | 0.011 | |
| 234 | 0.314 | 0.039 | |
| 235 | 0.623 | 0.032 | |
| 236 | 10 | 0.046 | |
| 237 | 0.397 | 0.012 | |
| 238 | 4.53 | 0.34 | |
| 239 | 1.27 | 0.3 | |
| 240 | 0.101 | 0.089 | |
| 241 | 0.0793 | 0.01 | |
| 242 | 0.0884 | 0.015 | |
| 243 | 0.316 | 0.018 | |
| 244 | 0.437 | 0.03 | |
| 245 | 0.181 | 0.067 | |
| 246 | 0.172 | 0.027 | |
| 247 | 0.671 | 0.2 | |
| 248 | 0.127 | 0.007 | |
| 249 | 0.121 | 0.0063 | |
| 250 | 0.0164 | 0.00234 | |
| 251 | 0.0283 | 0.00059 | |
| 252 | 0.055 | 0.0029 | |
| 253 | 0.00492 | 0.019 | |
| 254 | 0.00792 | 0.0017 | |
| 255 | 0.00957 | 0.002 | |
| 256 | 0.0202 | 0.0031 | |
| 257 | 0.0231 | 0.011 | |
| 258 | 0.0265 | 0.088 | |
| 259 | 0.0267 | 0.045 | |
| 260 | 0.0332 | 0.0039 | |
| 261 | 0.0348 | 0.004 | |
| 262 | 0.0459 | 0.015 | |
| 263 | 10 | 3.3 | |
| 264 | 0.556 | 0.062 | |
| 265 | | 0.00143 | |
| 266 | 0.0493 | 0.0022 | |
| 267 | 10 | 0.81 | |
| 268 | 2.52 | 0.3 | |
| 269 | 2.09 | 0.095 | |
| 270 | 0.657 | 0.11 | |
| 271 | 0.042 | 0.0082 | |
| 272 | 0.0437 | 0.0044 | |
| 273 | 0.0251 | 0.0023 | |
| 274 | 0.00781 | 0.0018 | |
| 275 | 0.0468 | 0.012 | |
| 276 | 0.0051 | 0.000788 | |
| 277 | 0.0206 | 0.00159 | |
| 278 | 0.0505 | 0.00130 | |
| 279 | 0.0305 | 0.0029 | |
| 280 | | 0.0039 | |
| 281 | >10 | 1.2 | |
| 282 | 0.265 | 0.017 | |
| 283 | 0.0722 | 0.005 | |
| 285 | 0.018 | 0.0099 | |
| 286 | 0.0131 | 0.00485 | |
| 287 | 0.0389 | 0.0022 | |
| 288 | 0.0053 | 0.00144 | |
| 289 | 0.0295 | 0.0176 | |
| 290 | 0.0335 | 0.00758 | |
| 291 | 0.0965 | 0.0552 | |
| 292 | 0.0121 | 0.00928 | |
| 293 | 0.0153 | 0.00531 | |
| 294 | | 0.0026 | |
| 295 | 0.0962 | 0.0529 | |
| 296 | 0.0091 | 0.0297 | |
| 299 | 0.00735 | 0.000686 | |
| 300 | 0.0132 | 0.00682 | |
| 301 | 0.137 | 0.0146 | |
| 302 | 0.226 | 0.0223 | |

TABLE 2-continued

PI3-Kα Biochemical and Cellular Activity Data

| COMPOUND NUMBER | PI3-Kα Cellular Assay IC$_{50}$ μM | PI3-Kα Biochemical Assay IC$_{50}$ μM | PI3-Kα Biochemical Assay % Inhibition |
|---|---|---|---|
| 303 | 0.0205 | 0.00387 | |
| 304 | 0.00768 | 0.00158 | |
| 305 | 0.148 | 0.0148 | |
| 306 | 0.998 | 0.0581 | |
| 307 | 0.0829 | 0.00362 | |
| 308 | 0.116 | 0.0177 | |
| 309 | 0.0193 | 0.00579 | |
| 310 | 0.0555 | 0.0113 | |
| 311 | 0.0519 | 0.00411 | |
| 312 | 0.256 | 0.0135 | |
| 313 | 0.376 | 0.0479 | |
| 314 | 0.0508 | 0.0102 | |
| 315 | 0.0146 | 0.00311 | |
| 316 | 0.0935 | 0.00665 | |
| 317 | 0.0335 | 0.00472 | |
| 318 | 0.0126 | 0.00214 | |
| 319 | 0.11 | 0.00591 | |

Example 103

Mouse Xenograft Efficacy Studies

Figure 2:
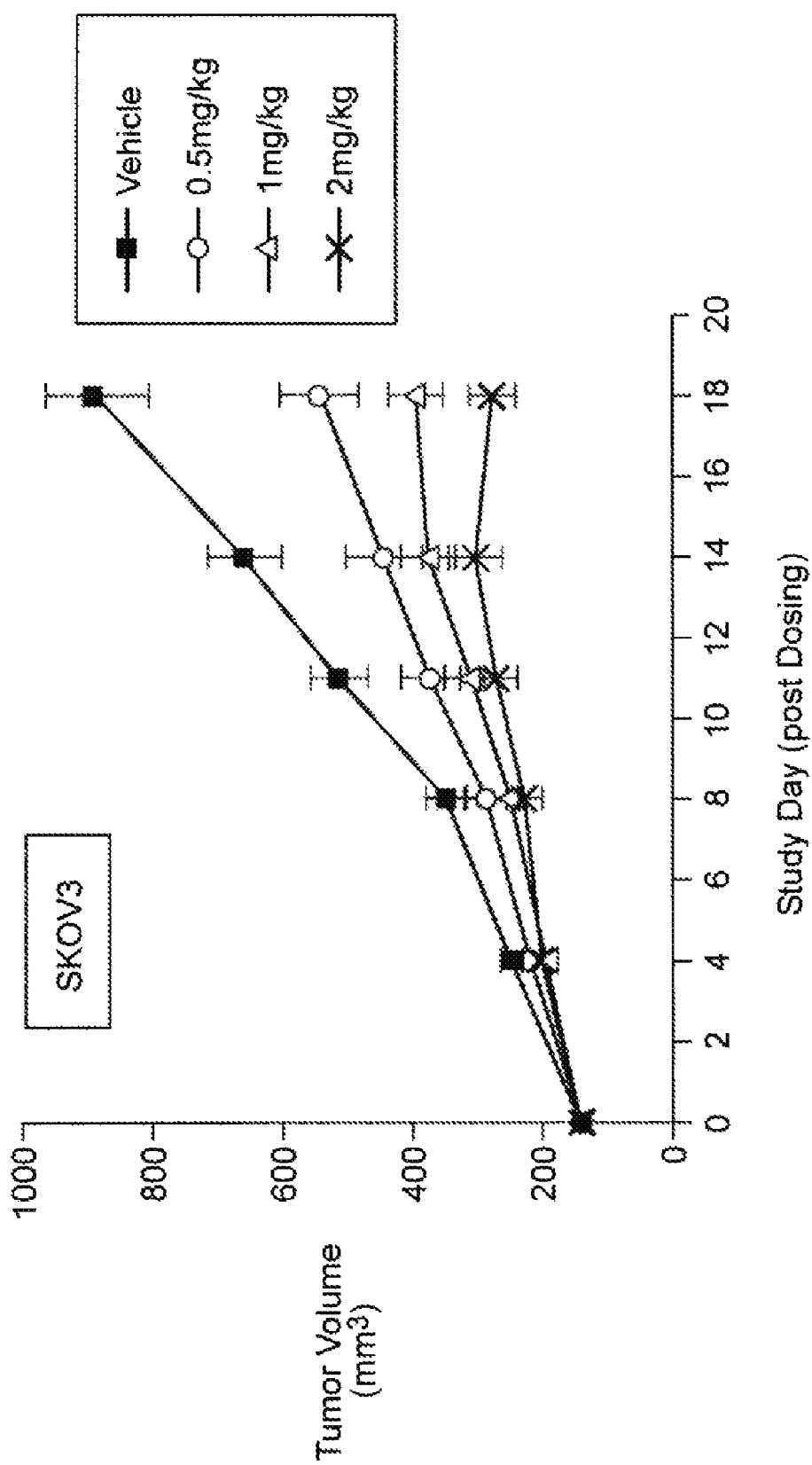
FIG. 2 shows an example of dose-dependent anti-tumor efficacy of Compound 152 in the SKOV3 tumor model.
Figure 3:
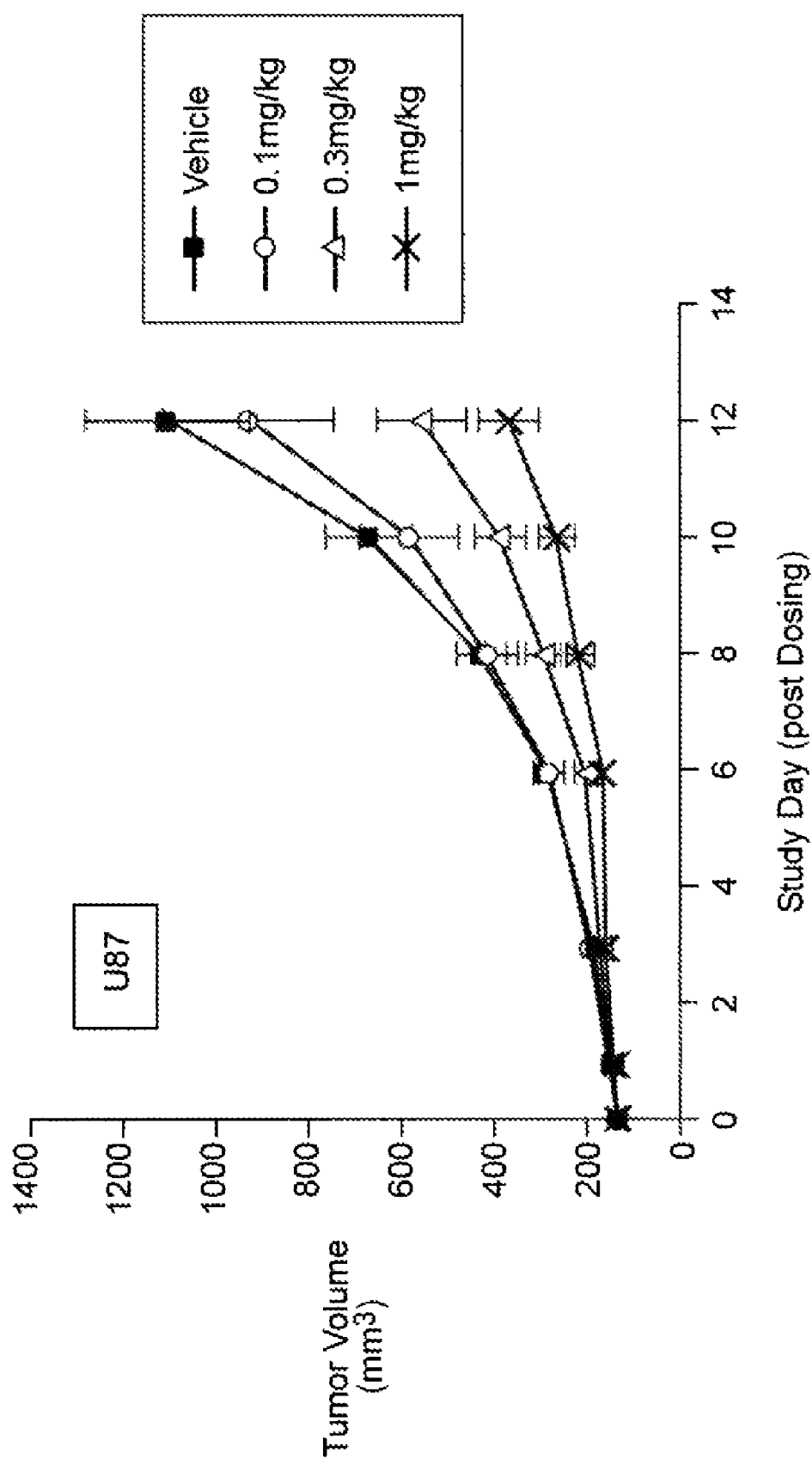
FIG. 3 shows an example of dose-dependent anti-tumor efficacy of Compound 152 in the U87MG tumor model.

The in vivo efficacy of 2-amino-8-(trans-4-hydroxycyclohexyl)-6-(6-methoxypyridin-3-yl)-4-methylpyrido[2,3-d]pyrimidin-7(8H)-one (Compound 152) disclosed in Example 53 was examined in s.c. xenograft model. Human tumor cell lines PC3 (PTEN deletion)), U87MG (PTEN deletion) and SKOV3 (PI3Kα H1047K) were chosen for in vivo efficacy studies due to their different genetic background and relatively high levels of phospho AKT S473 signal. Cells were implanted in the hind flank of athymic mice and tumors grew in size to 100-200 mm$^3$ before daily oral treatment with Compound 152 was initiated. Compound 152 exhibited dose-dependent anti-tumor efficacy in each tumor model, resulting in regression of PC3, growth inhibition of SKOV3 and U87MG tumors. Data are summarized in Table 3 and representative examples are shown in FIGS. 1-3. For all models tested 1 mg/kg was an efficacious dose.

Animal Care: Female and male athymic mice (6-8 weeks old) weighing ~22 g were obtained from Charles River Laboratory. Animal were housed on a 12 h light/dark cycle in the Pfizer vivarium and all procedures are conducted in accordance with the Pfizer Institutional Animal Care and Use Committee (IACUC). Animals are provided free access to rodent chow and water ad libitum and maintained under clean room conditions. Prior to study start animals acclimate for at least 48 h.

Cell lines: All cell lines were cultured at 37° C. in humidified 5% CO$_2$ incubator. U87 MG glioblastoma tumor cell line was obtained from American Type Culture Collection (ATCC) and cultured with DMEM supplemented with 15% FBS and 2 mM glutamine. PC3 prostate cancer cell line were obtained from National Cancer Institute and cultured in RPMI media supplemented with 10% FBS and 2 mM glutamine. SKOV3 ovarian cancer cells were obtained from ATCC and passaged multiple times through mice, and cultured in McCoy's 5A media supplemented with 10% FBS and 2 mM glutamine. All cell lines were tested by University of Missouri Research Animal Diagnostic Laboratory for known species of murine viruses and mycoplasma contamination.

Mouse Xenograft Models: U87MG (glioblastoma), PC3 (prostate cancer) and SKOV3 (ovarian cancer) cell lines in culture were harvested by trypsinisation. Briefly, 2.5-4×10$^6$ tumor cells were suspended in the medium used to culture each cell line without serum and implanted sub-cutaneously (s.c) into the hind flank region of mice on day 0. Daily treatment with Compound 152, formulated in 10% ethanol, 40% PEG and 50% sodium citrate buffer or vehicle alone commenced 10-14 d after implantation when average tumors were 100-200 mm$^3$ in size.

Tumors were measured twice weekly and tumor volume was calculated as a product of (length×width$^2$)/2. Studies were typically terminated when the tumor in the vehicle treated animals reached a size of >1500 mm3 or when judged to adversely affect the well being of the animal. At the end of the study percentage of tumor growth inhibition values were calculated as 100×(1−[(tumor volume$_{final}$−tumor volume$_{initial}$ for the compound-treated group)/(tumor volume$_{final}$−tumor volume$_{initial}$ for the vehicle-treated group)]). Where applicable, percent tumor regression for each group was calculated as 100×(tumor volume$_{initial}$−tumor volume$_{final}$)/(tumor volume$_{initial}$). A cohort of 12 animals was used for each dose group for efficacy studies. A representative cohort of animals were sacrificed at the times indicated, tumors resected, and a blood sample taken from the cardiac left ventricle and immediately placed in a vial primed with heparin sulfate. Typically one half of the tumor was fixed in 10% neutral buffered formalin, paraffin embedded, and sectioned for immunohistochemistry. The other half was frozen in liquid nitrogen and later processed to generate cell lysates for target modulation studies.

TABLE 3

Mouse Xenograft Efficacy Data

| Cell line | Tumor Type | Initial tumor volume (mm3) | Dose mg/kg/day | Growth Inhibition (%) | Regressionn (%) |
|---|---|---|---|---|---|
| PC3 | Prostate | 126 | 0.25 | 45 | |
| | | 126 | 0.5 | 62 | |
| | | 124 | 1 | 89 | |
| | | 125 | 2 | | 19 |
| SKOV3 | Ovarian | 146 | 0.5 | 46 | |
| | | 146 | 1 | 66 | |
| | | 146 | 2 | 82 | |
| U87 MG | Glioma | 134 | 0.1 | 18 | |
| | | 135 | 0.3 | 56 | |
| | | 135 | 1.0 | 76 | |

Example 104

In Vivo Target Modulation Studies

In vivo target modulation studies to determine the effect of Compound 152 treatment on the phosphorylation of AKT on S473 by ELISA and S6 on S235/S236 by IHC were performed. Resected tumors were frozen on dry ice and pulverized using the FAST PREP instrument (Qbiogene). Briefly, frozen tumors were placed in Fast Prep matrix tubes, cold lysis buffer [20 mM HEPES (pH 7.5), 150 mM NaCl, 1.0 mM sodium EDTA, 1% Triton X-100, 2.5 mM sodium pyrophosphate, 1 mM sodium orthovanadate, 1 μg/ml leupeptin, and 1 mM PMSF] was added and samples were centrifuged for 5 sec, mixed and process repeated two more times. Samples were centrifuged in a cold refrigerated Eppendorf centrifuge at 14,000 RPM for 20 min. Supernatant was collected and total and phosphoAKT (S473) protein levels determined by ELISA. The extent of phosphorylation in tumors resected from treated animals was compared with that in tumors resected from vehicle-treated animals at the same time point. Plasma samples, obtained by centrifuging individual blood samples at 3000×g for 5 min at 4° C. in an Eppendorf 5417R centrifuge, were stored at −80° C. until they could be analyzed for drug concentration. Briefly, plasma samples (50 µl) or Compound 152 standards in mouse plasma were mixed with acetonitrile 3 µl) and injected onto a LC/MS/MS system where separation occurred on a C-18 SB phenyl (5 µM, 2.1× 50 mm, Agilent) reverse-phase high-performance liquid chromatography column. The amount of inhibitor and the internal standard (0.5 µM buspirone) in each mouse plasma sample was quantified based on standard curves generated using known amounts of compound. Compound 152 treatment resulted in dose dependent inhibition of pAKT at S473 in all 3 models discussed above. Time course and dose response of in vivo target modulation and plasma inhibitor concentrations were determined post last dose at the end of the efficacy study described above and data are summarized in Table 4. For the U87MG model the $EC_{50}$ Compound 152 plasma concentration for pAKT S473 target modulation was calculated as 24 nM and correlated to 50% tumor growth inhibition.

TABLE 4

Pharmacokinetic and Pharmacodynamic (PK-PD) correlation in xenograft models

| Cell Line | p-Akt/Akt (%) | | | | Free plasma conc (nM) | | | |
|---|---|---|---|---|---|---|---|---|
| | 1 h | 3 h | 7 h | 24 h | 1 h | 3 h | 7 h | 24 h |
| PC3 | | | | | | | | |
| 0.25 mg/kg | | 42 ± 14 | 82 ± 18 | 137 ± 23 | 29 | 14 | 0 | |
| 0.5 mg/kg | | 32 ± 4 | 38 ± 5 | 107 ± 6 | 59 | 37 | 0 | |
| 1 mg/kg | | 23 ± 10 | 27 ± 9 | 113 ± 15 | 118 | 86 | 0 | |
| 2 mg/kg | | 21 ± 5 | 17 ± 7 | 78 ± 9 | 189 | 185 | 8 | |
| SKOV3 | | | | | | | | |
| 0.5 mg/kg | | 30 ± 3 | 55 ± 4 | 147 ± 21 | 74 | 49 | 0 | |
| 1 mg/kg | | 27 ± 6 | 48 ± 17 | 124 ± 10 | 158 | 95 | 0 | |
| 2 mg/kg | | 23 ± 5 | 30 ± 13 | 126 ± 20 | 298 | 214 | 8 | |
| U87 | | | | | | | | |
| 0.1 mg/kg | 44 | | | | 26 | | | |
| 0.3 mg/kg | 27 | | | | 85 | | | |
| 1 mg/kg | 11 | | | | 238 | | | |

We claim:

1. A compound of Formula (I)

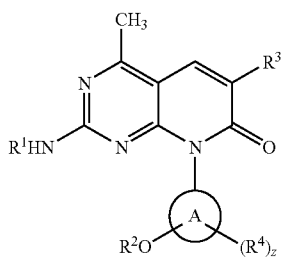

(I)

or a salt thereof,
wherein:
$R^1$ is H or ($C_1$ to $C_6$) alkyl optionally substituted with at least one $R^5$ group;
A is a 3 to 10 membered cycloalkyl group;
$R^2$ is ($C_1$ to $C_6$) alkyl substituted with at least one $R^6$ group, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$NR^{7a}R^{7b}$, or —N═$CR^{8a}R^{8b}$ wherein each of the said ($C_3$ to $C_{10}$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^9$ group;
$R^3$ is ($C_1$ to $C_6$) alkyl, ($C_3$ to $C_{10}$) cycloalkyl, ($C_2$ to $C_9$) cycloheteroalkyl, ($C_2$ to $C_8$) alkenyl, ($C_2$ to $C_8$) alkynyl, halogen, cyano, —$(CH_2)_nC(O)OR^{10}$, —$(CH_2)_nC(O)N(R^{11a}R^{11b})$, $COR^{12}$, ($C_6$ to $C_{14}$) aryl, or ($C_2$ to $C_9$) heteroaryl, wherein said ($C_1$ to $C_6$) alkyl, ($C_3$ to $C_{10}$) cycloalkyl, ($C_2$ to $C_9$) cycloheteroalkyl, ($C_2$ to $C_8$) alkenyl, ($C_2$ to $C_8$) alkynyl, ($C_6$ to $C_{14}$) aryl and ($C_2$ to $C_9$) heteroaryl is optionally substituted with at least one $R^9$ group;
each $R^4$ is independently —OH, halogen, $CF_3$, —$NR^{11a}R^{11b}$, ($C_1$ to $C_6$) alkyl, ($C_2$ to $C_6$) to alkenyl, ($C_2$ to $C_6$) alkynyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$C(O)R^{12}$, —$C(O)NR^{11a}R^{11b}$, —$S(O)_mR^{12}$, —$S(O)_mNR^{11a}R^{11b}$, —$NR^{11a}S(O)_mR^{12}$, —$(CH_2)_nC(O)OR^{10}$, —$(CH_2)_nC(O)N(R^{11a}R^{11b})$, —$OC(O)R^{12}$, —$NR^{11a}C(O)R^{12}$ or —$NR^{11a}C(O)N(R^{11a}R^{11b})$ wherein each of the said ($C_1$ to $C_6$) alkyl, ($C_2$ to $C_6$) alkenyl, ($C_2$ to $C_6$) alkynyl, ($C_1$ to $C_6$) alkoxy, ($C_3$ to $C_{10}$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^{13}$ group;
each $R^5$ is independently —OH, halogen, $CF_3$, —$NR^{11a}R^{11b}$, ($C_1$ to $C_6$) alkyl, ($C_1$ to $C_6$) alkoxy, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$S(O)_mR^{12}$, —$S(O)_mNR^{11a}R^{11b}$, —$C(O)R^{12}$ or —$C(O)NR^{11a}R^{11b}$ wherein each of the said ($C_1$ to $C_6$) alkyl, ($C_1$ to $C_6$) alkoxy, ($C_3$ to $C_{10}$) cycloalkyl, ($C_2$ to $C_9$) cycloheteroalkyl, ($C_6$ to $C_{14}$) aryl, and ($C_2$ to $C_9$) heteroaryl is optionally substituted with at least one $R^9$ group;
each $R^6$ is independently —OH, ($C_2$ to $C_6$) alkynyl, cyano, ($C_3$ to $C_{10}$) cycloalkyl, ($C_2$ to $C_9$) cycloheteroalkyl, ($C_6$ to $C_{14}$) aryl, ($C_2$ to $C_9$) heteroaryl, —$C(O)R^{12}$, —$C(O)NR^{11a}R^{11b}$, —$S(O)_mR^{12}$, —$S(O)_mNR^{11a}R^{11b}$, —$NR^{11a}S(O)_mR^{12}$, —$(CH_2)_nC(O)OR^{10}$, —$(CH_2)_nC(O)N(R^{11a}R^{11b})$, —$OC(O)R^{12}$, —NR$^{11a}$C(O)R$^{12}$ or —NR$^{11a}$C(O)N(R$^{11a}$R$^{11b}$) wherein each of the said (C$_2$ to C$_6$) alkynyl, (C$_3$ to C$_{10}$) cycloalkyl, (C$_2$ to C$_9$) cycloheteroalkyl, (C$_6$ to C$_{14}$) aryl, and (C$_2$ to C$_9$) heteroaryl is optionally substituted with at least one R$^{13}$ group;

R$^{7a}$ and R$^{7b}$ are each independently H, (C$_1$ to C$_6$) alkyl, (C$_2$ to C$_6$)alkenyl, (C$_2$ to C$_6$)alkynyl, (C$_3$ to C$_{10}$) cycloalkyl, or (C$_6$ to C$_{10}$)aryl, wherein each of the said (C$_1$ to C$_6$) alkyl, (C$_2$ to C$_6$)alkenyl, (C$_2$ to C$_6$)alkynyl, (C$_3$ to C$_{10}$) cycloalkyl, and (C$_6$ to C$_{10}$)aryl is optionally substituted with at least one R$^9$ group; or R$^{7a}$ and R$^{7b}$ may be taken together with the nitrogen atom to form a 5 to 8 membered cycloheteroalkyl ring, wherein said heterocyclyl ring has 1 to 3 ring heteroatoms selected from the group consisting of N, O, and S and wherein the said 5 to 8 membered cycloheteroalkyl ring is optionally substituted with at least one R$^9$ group;

R$^{8a}$ and R$^{8b}$ are each independently H, (C$_1$ to C$_6$) alkyl, or (C$_3$ to C$_{10}$) cycloalkyl wherein each of the said (C$_1$ to C$_6$) alkyl, and (C$_3$ to C$_{10}$) cycloalkyl, is optionally substituted with at least one R$^9$ group;

each R$^9$ is independently —OH, halogen, CF$_3$, —NR$^{11a}$R$^{11b}$, (C$_1$ to C$_6$) alkyl, (C$_2$ to C$_6$) alkenyl, (C$_2$ to C$_6$) alkynyl, (C$_1$ to C$_6$) alkoxy, cyano, (C$_3$ to C$_{10}$) cycloalkyl, (C$_2$ to C$_9$) cycloheteroalkyl, (C$_6$ to C$_{14}$) aryl, (C$_2$ to C$_9$) heteroaryl, —C(O)R$^{12}$, —C(O)NR$^{11a}$R$^{11b}$, —S(O)$_m$R$^{12}$, —S(O)$_m$NR$^{11a}$R$^{11b}$, —NR$^{11a}$S(O)$_m$R$^{12}$, —(CH$_2$)$_n$C(O)OR$^{10}$, —(CH$_2$)$_n$C(O)N(R$^{11a}$R$^{11b}$), —OC(O)R$^{12}$, —NR$^{11a}$C(O)R$^{12}$ or —NR$^{11a}$C(O)N(R$^{11a}$R$^{11b}$) wherein each of the said (C$_1$ to C$_6$) alkyl, (C$_2$ to C$_6$) alkenyl, (C$_2$ to C$_6$) alkynyl, (C$_1$ to C$_6$) alkoxy, (C$_3$ to C$_{10}$) cycloalkyl, (C$_2$ to C$_9$) cycloheteroalkyl, (C$_6$ to C$_{14}$) aryl, and (C$_2$ to C$_9$) heteroaryl is optionally substituted with at least one R$^{13}$ group;

each R$^{10}$ is independently H, or (C$_1$ to C$_6$) alkyl;

R$^{11a}$ and R$^{11b}$ are each independently H, (C$_1$ to C$_6$) alkyl, (C$_2$ to C$_9$) cycloheteroalkyl, (C$_2$ to C$_9$) heteroaryl, or (C$_6$ to C$_{12}$) aryl wherein each of the said (C$_1$ to C$_6$) alkyl, (C$_2$ to C$_9$) cycloheteroalkyl, (C$_2$ to C$_9$) heteroaryl, and (C$_6$ to C$_{12}$) aryl is optionally substituted with at least one R$^{13}$ group;

each R$^{12}$ is independently (C$_1$ to C$_6$) alkyl, (C$_3$ to C$_{10}$) cycloalkyl, (C$_2$ to C$_9$) cycloheteroalkyl, (C$_2$ to C$_9$) heteroaryl, or (C$_6$ to C$_{14}$) aryl wherein each of the said (C$_1$ to C$_6$) alkyl, (C$_3$ to C$_{10}$) cycloalkyl, (C$_2$ to C$_9$) cycloheteroalkyl, (C$_2$ to C$_9$) heteroaryl, and (C$_6$ to C$_{14}$) aryl is optionally substituted with at least one R$^{13}$ group;

each R$^{13}$ is independently —OH, halogen, CF$_3$, (C$_1$ to C$_6$) alkyl, (C$_2$ to C$_6$) alkenyl, (C$_2$ to C$_6$) alkynyl, (C$_1$ to C$_6$) alkoxy, cyano, (C$_3$ to C$_{10}$) cycloalkyl, (C$_2$ to C$_9$) cycloheteroalkyl, (C$_6$ to C$_{14}$) aryl, (C$_2$ to C$_9$) heteroaryl, amino, C-amido, S-sulfonamido, C-carboxyl, N-amido, or N-carbamyl;

each m is independently 1 or 2;
each n is independently 0, 1, 2, 3, or 4; and
each z is independently 0, 1, 2, 3, 4, 5, 6, 7, or 8.

2. The compound or salt according to claim 1, wherein A is cyclohexyl.

3. The compound or salt according to claim 1, wherein R$^3$ is (C$_6$ to C$_{14}$) aryl or (C$_2$ to C$_9$) heteroaryl, wherein said (C$_6$ to C$_{14}$) aryl or (C$_2$ to C$_9$) heteroaryl is optionally substituted with at least one R$^9$ group.

4. A pharmaceutical composition, comprising at least one compound or salt according to claim 1 and a pharmaceutically acceptable carrier or diluent.

5. The compound or salt according to claim 1, wherein A is selected from the group consisting of cyclobutyl, cyclopentyl, and cyclohexyl.

6. The compound or salt according to 1, wherein A is selected from the group consisting of cyclobutyl, cyclopentyl, and cyclohexyl; and R$^3$ is (C$_6$ to C$_{14}$) aryl or (C$_2$ to C$_9$) heteroaryl, wherein said (C$_6$ to C$_{14}$) aryl or (C$_2$ to C$_9$) heteroaryl is optionally substituted with at least one R$^9$ group.

7. The compound or salt according to claim 6, wherein R$^3$ is (C$_2$ to C$_9$) heteroaryl, wherein said (C$_2$ to C$_9$) heteroaryl is optionally substituted with at least one R$^9$ group.

8. The compound or salt according to claim 7, wherein A is cyclohexyl.

9. The compound or salt according to claim 6, wherein and R$^3$ is (C$_6$ to C$_{14}$) aryl, wherein said (C$_6$ to C$_{14}$) aryl is optionally substituted with at least one R$^9$ group.

10. The compound or salt according to claim 9, wherein A is cyclohexyl.

11. The compound or salt according to claim 1, wherein:
R$^1$ is H;
A is selected from the group consisting of cyclobutyl, cyclopentyl, and cyclohexyl;
R$^3$ is (C$_6$ to C$_{14}$) aryl or (C$_2$ to C$_9$) heteroaryl, wherein said (C$_6$ to C$_{14}$) aryl or (C$_2$ to C$_9$) heteroaryl is optionally substituted with at least one R$^9$ group; and
z is 0.

12. The compound or salt according to claim 11, wherein R$^3$ is (C$_6$ to C$_{14}$) aryl, wherein said (C$_6$ to C$_{14}$) aryl is optionally substituted with at least one R$^9$ group.

13. The compound or salt according to claim 12, wherein A is cyclohexyl.

14. The compound or salt according to claim 11, wherein R$^3$ is (C$_2$ to C$_9$) heteroaryl, wherein said (C$_2$ to C$_9$) heteroaryl is optionally substituted with at least one R$^9$ group.

15. The compound or salt according to claim 14, wherein A is cyclohexyl.

* * * * *